(12) United States Patent
Morin et al.

(10) Patent No.: US 7,279,294 B2
(45) Date of Patent: Oct. 9, 2007

(54) TUMOR MARKERS IN OVARIAN CANCER

(75) Inventors: Patrice J. Morin, Perry Hall, MD (US); Cheryl A. Sherman-Baust, Laurel, MD (US); Ellen S. Pizer, Bellevue, WA (US); Colleen D. Hough, South Jordan, UT (US)

(73) Assignee: The United States of America as represented by the Secretary, Dept. of Health and Human Services, NIH, Rockville, MD (US)

( * ) Notice: Subject to any disclaimer, the term of this patent is extended or adjusted under 35 U.S.C. 154(b) by 610 days.

(21) Appl. No.: 10/257,021

(22) PCT Filed: Apr. 3, 2001

(86) PCT No.: PCT/US01/10947

§ 371 (c)(1), (2), (4) Date: Oct. 3, 2002

(87) PCT Pub. No.: WO01/75177

PCT Pub. Date: Oct. 11, 2001

(65) Prior Publication Data

US 2003/0211498 A1    Nov. 13, 2003

Related U.S. Application Data

(60) Provisional application No. 60/194,336, filed on Apr. 3, 2000.

(51) Int. Cl.
    *G01N 33/574*    (2006.01)
(52) U.S. Cl. .................. 435/7.23; 530/350; 530/387.7; 436/64
(58) Field of Classification Search ............... 435/7.23; 436/501, 64; 424/138.1, 1.37, 178.1; 530/350, 530/387.7
    See application file for complete search history.

(56) References Cited

U.S. PATENT DOCUMENTS 5,356,817 A * 10/1994 Cole ........................... 436/64

FOREIGN PATENT DOCUMENTS

WO    WO99/53040    10/1999

OTHER PUBLICATIONS

Morin. Cancer Res. Nov. 1, 2005; 65 (21):9603-9606.*
Tsukita et al. J. Cell Biol. Apr. 3, 2000; 149 (1): 13-16.*
Swisshelm et al. (Adv. Drug Delivery Rev. 2005; 57; 919-928).*
Rae et al. (International Journal of Cancer. 2000; 88: 726-732).*
Alon et al., "Broad patterns of gene expression revealed by clustering analysis of tumor and normal colon tissues probed by oligonucleotide arrays." *Proc Natl Acad Sci USA* 96:6745-6750 (Jun. 1999).
Auersperg et al., "E-cadherin induces mesenchymal-to-epithelial transition in human ovarian surface epithelium." *Proc Natl Acad Sci USA* 96:6249-6254 (May 1999).
Bast et al., "Reactivity of a monoclonal antibody with human ovarian carcinoma." *J Clin Invest* 68(5):1331-1337 (Nov. 1981).
Berezowski et al., "Cytokeratins 7 and 20 and carcinoembryonic antigen in ovarian and colonic carcinoma." *Mod Pathol* 9(4):426-429 (1996).
Datson et al., "MicroSAGE: a modified procedure for serial analysis of gene expression in limited amounts of tissue." *Nucl Acids Res* 27(5):1300-1307 (1999).
DePasquale et al., "Differential expression of the pRb2 tumor suppressor gene in human epithelial ovarian carcinoma compared to ovarian tumors of low malignant potential and normal ovaries." *Proc Am Assoc Cancer Res Ann* 38:109 (1997) (Abstract).
Eisen et al., "Cluster analysis and display of genome-wide expression patterns." *Proc Natl Acad Sci USA* 95:14863-14868 (Dec. 1998).
Goodman et al., "Recombinant Adeno-Associated Virus-Mediated Gene Transfer Into Hematopoietic Progenitor Cells." *Blood* 84(5):1492-1500 (Sep. 1, 1994).
Hough et al., "Comparison of Sage-Generated Expression Profiles Between Ovarian Cancer and Human Ovarian Surface Epithelium." *Proc Am Assoc Cancer Res Ann* 41:310-311 (Mar. 2000) (Abstract).
Hough et al., "Large-Scale Serial Analysis of Gene Expression Reveals Genes Differentially Expressed in Ovarian Cancer." *Cancer Res* 60(22):6281-6287 (Nov. 15, 2000).
Hough et al., "Use of SAGE to study gene expression in ovarian cancer." *Proc Am Assoc Cancer Res Ann* 40:34 (Mar. 1999) (Abstract).
Lagendijk et al., "Tracing the origin of adenocarcinomas with unknown primary using immunohistochemistry: differential diagnosis between colonic and ovarian carcinomas as primary sites." *Hum Pathol* 29(5):491-497 (May 1, 1998).
Lal et al., "A Public Database for Gene Expression in Human Cancers." *Cancer Res* 59:5403-5407 (Nov. 1, 1999).

(Continued)

Primary Examiner—Stephen L. Rawlings
(74) Attorney, Agent, or Firm—Needle & Rosenberg, P.C.

(57) ABSTRACT

The present invention features methods of diagnosing and prognosticating ovarian tumors by detecting increased expression of an ovarian tumor marker gene in a subject or in a sample from a subject. Also featured are kits for the aforementioned diagnostic and prognostic methods. In addition, the invention features methods of treating and preventing ovarian tumors, and methods of inhibiting the growth or metastasis of ovarian tumors, by modulating the production or activity of an ovarian tumor marker polypeptide. Further featured are methods of inhibiting the growth or metastasis of an ovarian tumor by contacting an ovarian tumor cell with an antibody that specifically binds an ovarian tumor marker polypeptide.

4 Claims, No Drawings

OTHER PUBLICATIONS

Luo et al., "Establishment of long-term in vitro cultures of human ovarian cystadenomas and LMP tumors and examination of their spectrum of expression of matrix-degrading proteinases." *Gynecol Oncol* 67(3):277-284 (Dec. 1997).

Maines-Bandiera et al., "Increased E-cadherin expression in ovarian surface epithelium: an early step in metaplasia and dysplasia." *Int J Gynecol Pathol* 16(3):250-255 (Jul. 1, 1997).

Mok et al., "Molecular Cloning of Differentially Expressed Genes in Human Epithelial Ovarian Cancer." *Gynecol Oncol* 52(2):247-252 (Feb. 1994).

Ross et al., "Systematic variation in gene expression patterns in human cancer cell lines." *Nat Genet* 24(3):227-235 (Mar. 1, 2000).

Schink, "Current initial therapy of stage III and IV ovarian cancer: challenges for managed care." *Semin Oncol* 26(1Suppl 1):2-7 (Feb. 1, 1999).

Scully, "Pathology of ovarian cancer precursors." *J Cell Biochem* Suppl 23:208-218 (Jan. 1, 1995).

Velculescu et al., "Serial Analysis of Gene Expression." *Science* 270(5235):484-487 (Oct. 20, 1995).

Zhang et al., "Gene expression profiles in normal and cancer cells," *Science* 276(5316):1268-1272 (May 23, 1997).

* cited by examiner

TUMOR MARKERS IN OVARIAN CANCER

CROSS-REFERENCE TO RELATED APPLICATIONS

The present application is a 35 U.S.C. § 371 national phase application filed from, and claiming priority to, international application PCT/US01/10947, filed Apr. 3, 2001 (published under PCT Article 21(2) in English), which claims priority to U.S. provisional patent application Ser. No. 60/194,336, filed Apr. 3, 2000, which applications are herein incorporated by reference in their entireties.

This invention was made with intramural support from the National Institutes of Health. The government has certain rights in the invention.

FIELD OF THE INVENTION

This invention relates generally to the identification of ovarian tumor markers and diagnostic, prognostic, and therapeutic methods for their use, as well as kits for use in the aforementioned methods.

BACKGROUND OF THE INVENTION

Ovarian cancer is one of the most common forms of neoplasia in women. Early diagnosis and treatment of any cancer ordinarily improves the likelihood of survival. However, ovarian cancer is difficult to detect in its early stages, and remains the leading cause of death among women with cancer of the female reproductive tract.

The low survival rate of ovarian cancer patients is in part due to the lack of good diagnostic markers for the detection of early stage neoplasms, and in part due to a deficit in the general understanding of ovarian cancer biology, which would facilitate the development of effective anti-tumor therapies. The present invention overcomes these shortcomings by providing much-needed improvements for the diagnosis, treatment, and prevention ovarian tumors, based on the identification of a series of ovarian tumor marker genes that are highly expressed in ovarian epithelial tumor cells and are minimally expressed in normal ovarian epithelial cells. Over 75% of all ovarian tumors, and about 95% of all malignant ovarian tumors, arise from the ovarian surface epithelium (OSE). Because the tumor marker genes are broadly expressed in various types of ovarian epithelial tumors, the present invention should greatly improve the diagnosis and treatment of most ovarian cancers.

SUMMARY OF THE INVENTION

In a first aspect, the invention features a method of detecting an ovarian tumor in a subject. The method includes the step of measuring the expression level of an ovarian tumor marker gene in the subject, wherein an increase in the expression level of the ovarian tumor marker gene in the subject, relative to the expression level of the ovarian tumor marker gene in a reference subject not having an ovarian tumor, detects an ovarian tumor in the subject.

In a second aspect, the invention features a method of identifying a subject at increased risk for developing ovarian cancer. The method includes the step of measuring the expression level of an ovarian tumor marker gene in the subject, wherein an increase in the expression level of the ovarian tumor marker gene in the subject, relative to the expression level of the ovarian tumor marker gene in a reference subject not at increased risk for developing ovarian cancer, identifies an individual at increased risk for developing ovarian cancer.

In a preferred embodiment of the second aspect of the invention, the expression level of the ovarian tumor marker gene in the subject is compared to the expression level of the tumor marker gene in a reference subject that is identified as having an increased risk for developing ovarian cancer.

In a third aspect, the invention features a method of determining the effectiveness of an ovarian cancer treatment in a subject. The method includes the step of measuring the expression level of an ovarian tumor marker gene in the subject after treatment of the subject, wherein a modulation in the expression level of the ovarian tumor marker gene in the subject, relative to the expression level of the ovarian tumor marker gene in the subject prior to treatment, indicates an effective ovarian cancer treatment in the subject.

In a preferred embodiment of the first three aspects of the invention, the expression level of the ovarian tumor marker gene is determined in the subject by measuring the expression level of the tumor marker gene in a sample from the subject. The sample may be, for example, a tissue biopsy, ovarian epithelial cell scrapings, peritoneal fluid, blood, urine, or serum. In another preferred embodiment of the first three aspects of the invention, the expression level of the tumor marker gene is measured in vivo in the subject.

In yet another preferred embodiment of the first three aspects of the invention, the expression level of more than one ovarian tumor marker gene is measured. For example, the expression level of two, three, four, five, or more tumor marker genes may be measured.

In various other embodiments of the first three aspects of the invention, the expression level of the tumor marker gene may be determined by measuring the level of ovarian tumor marker mRNA. For example, the level of ovarian tumor marker mRNA may be measured using RT-PCR, Northern hybridization, dot-blotting, or in situ hybridization. In addition, or alternatively, the expression level of the ovarian tumor marker gene may be determined by measuring the level of ovarian tumor marker polypeptide encoded by the ovarian tumor marker gene. For example, the level of ovarian tumor marker polypeptide may be measured by ELISA, immunoblotting, or immunohistochemistry. The level of ovarian tumor marker polypeptide may also be measured in vivo in the subject using an antibody that specifically binds an ovarian tumor marker polypeptide, coupled to a paramagnetic label or other label used for in vivo imaging, and visualizing the distribution of the labeled antibody within the subject using an appropriate in vivo imaging method, such as magnetic resonance imaging.

In still another embodiment of the first three aspects of the invention, the expression level of the tumor marker gene may be compared to the expression level of the tumor marker gene in a reference subject diagnosed with ovarian cancer.

In a fourth aspect, the invention features a method of identifying a tumor as an ovarian tumor. The method includes the step of measuring the expression level of an ovarian tumor marker gene in a tumor cell from the tumor, wherein an increase in the expression level of the ovarian tumor marker gene in the tumor cell, relative to the expression level of the ovarian tumor marker gene in a noncancerous ovarian cell, identifies the tumor as an ovarian tumor.

In a fifth aspect, the invention features a method of treating or preventing an ovarian tumor in a subject. The method includes the step of modulating production or activity of a polypeptide encoded by an ovarian tumor marker gene in an ovarian epithelial cell in the subject.

In a sixth aspect, the invention features a method of inhibiting the growth or metastasis of an ovarian tumor cell in a subject. The method includes the step of modulating production or activity of a polypeptide encoded by an ovarian tumor marker gene in the ovarian tumor cell in the subject.

In a seventh aspect, the invention features a method of inhibiting the growth or metastasis of an ovarian tumor in a subject. The method includes the step of contacting an ovarian tumor cell with an antibody that specifically binds an ovarian tumor marker polypeptide encoded by an ovarian tumor marker gene, wherein the binding of the antibody to the ovarian tumor marker polypeptide inhibits the growth or metastasis of the ovarian tumor in the subject.

In various preferred embodiments of the seventh aspect of the invention, the ovarian tumor marker polypeptide may be on the surface of the ovarian tumor cell, and the antibody may be coupled to a radioisotope or to a toxic compound.

In an eighth aspect, the invention features a kit including an antibody for measuring the expression level of an ovarian tumor marker gene in a subject.

In a ninth aspect, the invention features a kit including a nucleic acid for measuring the expression level of an ovarian tumor marker gene in a subject.

In a tenth aspect, the invention features a method of diagnosing ovarian cancer in a subject. The method includes the step of measuring the amount of an ovarian tumor marker polypeptide in the subject, wherein an amount of ovarian tumor marker polypeptide that is greater than the amount of ovarian tumor marker polypeptide measured in a subject not having ovarian cancer diagnoses an ovarian cancer in the subject.

In various embodiments of the tenth aspect of the invention, the ovarian tumor marker polypeptide can be present at the surface of a cell (e.g., a cell-surface-localized polypeptide such as a cell adhesion molecule), or the ovarian tumor marker polypeptide may be in soluble form (e.g., secreted from a cell, released from a lysed cell, or otherwise detectable in a fluid-based assay).

In a preferred embodiment of all of the above aspects of the invention, the ovarian tumor may be an epithelial ovarian tumor. The epithelial ovarian tumor may be, for example, a serous cystadenoma, a borderline serous tumor, a serous cystadenocarcinoma, a mucinous cystadenoma, a borderline mucinous tumor, a mucinous cystadenocarcinoma, an endometrioid carcinoma, an undifferentiated carcinoma, a cystadenofibroma, an adenofibroma, or a Brenner tumor. The epithelial ovarian tumor may also be a clear cell adenocarcinoma.

In preferred embodiments of all of the above aspects of the invention, the ovarian tumor marker gene can be, but is not limited to, alpha prothymosin; beta polypeptide 2-like G protein subunit 1; tumor rejection antigen-1 (gp96)1; HSP90; Hepatoma-Derived Growth Factor (HGDF); DKFZp586O031; CD63 antigen (melanoma 1 antigen); protein kinase C substrate 80K-H; Polymerase II cofactor 4 (PC4); mitochondrial Tu translation elongation factor; hNRP H1; Solute carrier family 2; KIAA0591 protein; X-ray repair protein; DKFZP564M2423 protein; growth factor-regulated tyrosine kinase substrate; and eIF-2-associated $p^{67}$. The ovarian tumor marker gene may also be HSP60 or Lutheran blood group (3-CAM). In other preferred embodiments of all aspects of the invention, the ovarian tumor marker gene may also be HLA-DR alpha chain; cysteine-rich protein 1; claudin 4; claudin 3; ceruloplasmin (ferroxidase), glu-tathione perroxidase 3; secretory leukocyte protease inhibitor; HOST-1 (FLI4303 fis); interferon-induced transmembrane protein 1; apolipoprotein J/clusterin; serine protease inhibitor, Kunitz type 2; apoplipoprotein E; complement component 1, r subcomponent; G1P3/IFI-6-16; Lutheran blood group (BCAM); collagen type III, alpha-1; Mal (T cell differentiation protein); collagen type I, alpha-2; HLA-DPB1; bone marrow stroma antigen 2 (BST-2); or HLA-Cw.

The ovarian tumor marker gene may also be HOST-3 (Claudin-16) (e.g., Genbank® Accession No. XM_003150; SEQ ID NOs: 141 and 142); HOST-4 (e.g., a gene that comprises SEQ ID NO: 144); or HOST-5 (sodium dependent transporter isoform NaPi-Iib) (e.g., Genbank® Accession No. AF146796; SEQ ID NOs: 146 and 147).

In other preferred embodiments of all aspects of the invention, the ovarian tumor marker gene comprises a nucleotide sequence set forth in one of SEQ ID NOs: 84-102.

In still other preferred embodiments of all aspects of the invention, the ovarian tumor marker gene comprises a nucleotide sequence set forth in one of SEQ ID NOs: 103-129.

In yet other preferred embodiments of all aspects of the invention, the ovarian tumor marker gene comprises a nucleotide sequence set forth in one of SEQ ID NOs: 141, 143, or 145.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE INVENTION

The low survival rate of ovarian cancer patients is in part due to the lack of good diagnostic markers allowing early detection of the disease. Further compounding this difficulty in early diagnosis is the lack of effective treatments for ovarian cancer, development of which has been impeded by a deficit in the general understanding of ovarian cancer biology. The present invention overcomes these deficits in the art by providing ovarian tumor markers that are expressed at elevated levels in ovarian epithelial tumor cells, relative to their expression in normal ovarian epithelial cells.

To identify marker genes that are up-regulated in ovarian tumor cells, SAGE (Serial Analysis of Gene Expression; Velculescu et al., Science 270:484-487, 1995) was employed to obtain global gene expression profiles of three ovarian tumors, five ovarian tumor cell lines of various histological types, a pool of ten ovarian tumor cell lines of various histological types, and normal human ovarian surface epithelium (HOSE). The expression patterns were generated by acquiring thousands of short sequence tags that contain sufficient information to uniquely identify transcripts due to the unique position of each tag within the transcript. Comparing the SAGE-generated expression profiles between ovarian cancer and HOSE revealed an abundance of genes that are expressed at elevated levels in ovarian tumor cells, relative to their expression in normal HOSE.

Selected SAGE results were further validated through immunohistochemical analysis of archival ovarian serous carcinoma samples. Ovarian tumor marker genes implicated in immune response pathways, regulation of cell proliferation, and protein folding were identified, many of which are membrane-localized or secreted. The ovarian tumor marker genes identified from these SAGE profiles are useful both as diagnostic and prognostic markers to detect and monitor a broad variety of ovarian cancers, and as therapeutic targets for the treatment of such ovarian cancers.

Definitions

In this specification and in the claims that follow, reference is made to a number of terms that shall be defined to have the following meanings.

As used in the specification and in the appended claims, the singular forms "a," "an," and "the" include plural referents unless the context clearly dictates otherwise. For example, "a cell" can mean a single cell or more than one cell.

By "ovarian cell" is meant a cell that is of ovarian origin or that is a descendent of a cell of ovarian origin (e.g., a metastatic tumor cell in the liver that is derived from a tumor originating in the ovary), irrespective of whether the cell is physically within the ovary at the time at which it is subjected to a diagnostic test or an anti-tumor treatment. For example, the ovarian cell may be a normal ovarian cell or an ovarian tumor cell, either within the ovary or at another location within the body. The ovarian cell may also be outside the body (for example, in a tissue biopsy). A preferred ovarian cell is an ovarian cell of epithelial origin.

By "ovarian tumor marker gene" is meant a gene of the invention, for which expression is increased (as described below) in ovarian tumor cells relative to normal ovarian cells. Preferably, an ovarian tumor marker gene has been observed to display increased expression in at least two ovarian tumor SAGE libraries (relative to a HOSE library), more preferably in at least three SAGE libraries, and most preferably in at least four SAGE libraries (relative to a HOSE library). Examples of ovarian tumor marker genes are provided in Tables 2 and 4 hereinbelow.

By "ovarian tumor marker polypeptide" is meant a polypeptide that is encoded by an ovarian tumor marker gene and is produced at an increased level in an ovarian tumor cell due to the increased expression of the ovarian tumor marker gene that encodes the polypeptide.

By "sample" is meant any body fluid (e.g., but not limited to, blood, serum, urine, cerebrospinal fluid, semen, sputum, saliva, tears, joint fluids, body cavity fluids (e.g., peritoneal fluid), or washings), tissue, or organ obtained from a subject; a cell (either within a subject, taken directly from a subject, or a cell maintained in culture or from a cultured cell line); a lysate (or lysate fraction) or extract derived from a cell; or a molecule derived from a cell or cellular material.

By "modulate" is meant to alter, by increase or decrease.

By "increase in gene expression level," "expressed at an increased level," "increased expression," and similar phrases is meant a rise in the relative amount of mRNA or protein, e.g., on account of an increase in transcription, translation, mRNA stability, or protein stability, such that the overall amount of a product of the gene, i.e., an mRNA or polypeptide, is augmented. Preferably the increase is by at least about 3-fold, more preferably, by at least about: 4-fold, 5-fold, 7-fold, 10-fold, 15-fold, 20-fold, 30-fold, 40-fold, 50-fold, 70-fold, or more. For example, as described herein, the expression level of the ovarian tumor marker genes of the invention is generally increased by at least 3-fold in ovarian tumor cells, relative to normal ovarian surface epithelial cells.

By "decrease in gene expression level" is meant a reduction in the relative amount of mRNA or protein transcription, translation, mRNA stability, or protein stability, such that the overall amount of a product of the gene, i.e., an mRNA or polypeptide, is reduced. Preferably the decrease is by at least about 20%-25%, more preferably by at least about 26%-50%, still more preferably by at least about 51%-75%, even more preferably by at least about 76%-95%, and most preferably, by about 96%-100%.

By "about" is meant ±10% of a recited value.

By "modulating production or activity of a polypeptide encoded by an ovarian tumor marker gene" is meant to increase or decrease gene expression level, as described above, or to stimulate or inhibit the ability of an ovarian tumor marker polypeptide to perform its intrinsic biological function (examples of such functions include, but are not limited to, enzymatic activity, e.g., kinase activity or GTPase activity; cell-signaling activity, e.g., activation of a growth factor receptor; or cell adhesion activity. The modulation may be an increase in the amount of the polypeptide produced or an increase in the activity of the polypeptide, of at least about: 2-fold, 4-fold, 6-fold, or 10-fold, or the modulation may be a decrease in the amount of the polypeptide produced or a decrease in the activity of the polypeptide, of at least about: 20%-25%, 26%-50%, 51%-75%, 76%-95%, or 96%-100%. These increases and/or decreases are compared with the amount of production and/or activity in a normal cell, sample, or subject.

By "effective amount" of a compound as provided herein is meant a nontoxic but sufficient amount of the compound to provide the desired effect, e.g., modulation of ovarian tumor marker gene expression or modulation of ovarian tumor marker polypeptide activity. As will be pointed out below, the exact amount required will vary from subject to subject, depending on the species, age, and general condition of the subject, the severity and type of disease that is being treated, the particular compound used, its mode of administration, and the like. Thus, it is not possible to specify an exact "effective amount." However, an appropriate "effective amount" may be determined by one of ordinary skill in the art using only routine experimentation.

By "pharmaceutically acceptable" is meant a material that is not biologically or otherwise undesirable, i.e., the material may be administered to an individual along with a molecule or compound of the invention (e.g., an antibody or nucleic acid molecule) without causing any undesirable biological effects or interacting in a deleterious manner with any of the other components of the pharmaceutical composition in which it is contained.

By "having an increased risk" is meant a subject that is identified as having a higher than normal chance of developing an ovarian tumor, compared to the general population. Such subjects include, for example, women that have a hereditary disposition to develop ovarian cancer, for example, those identified as harboring one or more genetic mutations (e.g., a mutation in the BRCA-1 gene) that are known indicators of a greater than normal chance of developing ovarian cancer, or who have a familial history of ovarian cancer. In addition, a subject who has had, or who currently has, an ovarian tumor is a subject who has an increased risk for developing an ovarian tumor, as such a subject may continue to develop new tumors. Subjects who currently have, or who have had, an ovarian tumor also have an increased risk for ovarian tumor metastases.

By "treat" is meant to administer a compound or molecule of the invention to a subject in order to: eliminate an ovarian tumor or reduce the size of an ovarian tumor or the number of ovarian tumors in a subject; arrest or slow the growth of an ovarian tumor in a subject; inhibit or slow the development of a new ovarian tumor or an ovarian tumor metastasis in a subject; or decrease the frequency or severity of symptoms and/or recurrences in a subject who currently has or who previously has had an ovarian tumor.

By "prevent" is meant to minimize the chance that a subject will develop an ovarian tumor or to delay the development of an ovarian tumor. For example, a woman at increased risk for an ovarian tumor, as described above, would be a candidate for therapy to prevent an ovarian tumor.

By "specifically binds" is meant that an antibody recognizes and physically interacts with its cognate antigen and does not significantly recognize and interact with other antigens.

By "probe," "primer," or "oligonucleotide" is meant a single-stranded DNA or RNA molecule of defined sequence that can base-pair to a second DNA or RNA molecule that contains a complementary sequence (the "target"). The stability of the resulting hybrid depends upon the extent of the base-pairing that occurs. The extent of base-pairing is affected by parameters such as the degree of complementarity between the probe and target molecules, and the degree of stringency of the hybridization conditions. The degree of hybridization stringency is affected by parameters such as temperature, salt concentration, and the concentration of organic molecules such as formamide, and is determined by methods known to one skilled in the art. Probes or primers specific for ovarian tumor marker nucleic acids (e.g., genes and/or mRNAs) preferably have at least 50%-55% sequence complementarity, more preferably at least 60%-75% sequence complementarity, even more preferably at least 80%-90% sequence complementarity, yet more preferably at least 91%-99% sequence complementarity, and most preferably 100% sequence complementarity to the ovarian tumor marker nucleic acid to be detected. Probes, primers, and oligonucleotides may be detectably-labeled, either radioactively, or non-radioactively, by methods well-known to those skilled in the art. Probes, primers, and oligonucleotides are used for methods involving nucleic acid hybridization, such as: nucleic acid sequencing, reverse transcription and/or nucleic acid amplification by the polymerase chain reaction, single stranded conformational polymorphism (SSCP) analysis, restriction fragment polymorphism (RFLP) analysis, Southern hybridization, Northern hybridization, in situ hybridization, electrophoretic mobility shift assay (EMSA).

By "specifically hybridizes" is meant that a probe, primer, or oligonucleotide recognizes and physically interacts (i.e., base-pairs) with a substantially complementary nucleic acid (e.g., an ovarian tumor marker mRNA of the invention) under high stringency conditions, and does not substantially base pair with other nucleic acids.

By "high stringency conditions" is meant conditions that allow hybridization comparable with the hybridization that occurs using a DNA probe of at least 500 nucleotides in length, in a buffer containing 0.5 M $NaHPO_4$, pH 7.2, 7% SDS, 1 mM EDTA, and 1% BSA (fraction V), at a temperature of 65° C., or a buffer containing 48% formamide, 4.8×SSC, 0.2 M Tris-Cl, pH 7.6, 1× Denhardt's solution, 10% dextran sulfate, and 0.1% SDS, at a temperature of 42° C. (these are typical conditions for high stringency Northern or Southern hybridizations). High stringency hybridization is relied upon for the success of numerous techniques routinely performed by molecular biologists, such as high stringency PCR, DNA sequencing, single strand conformational polymorphism analysis, and in situ hybridization. In contrast to Northern and Southern hybridizations, these techniques are usually performed with relatively short probes (e.g., usually 16 nucleotides or longer for PCR or sequencing, and 40 nucleotides or longer for in situ hybridization). The high stringency conditions used in these techniques are well known to those skilled in the art of molecular biology, and may be found, for example, in F. Ausubel et al., *Current Protocols in Molecular Biology*, John Wiley & Sons, New York, N.Y., 1997, herein incorporated by reference.

Examples of Ovarian Tumor Marker Genes

Examples of ovarian tumor marker genes of the invention include alpha prothymosin (e.g., Genbank® Accession No. M14483; SEQ ID NOs: 1 and 2); beta polypeptide 2-like G protein subunit 1 (e.g., Genbank® Accession No. M24194; SEQ ID NOs: 3 and 4); tumor rejection antigen-1 (gp96)1 (e.g., Genbank® Accession No. NM_003299; SEQ ID NOs: 7 and 8); HSP90 (e.g., Genbank® Accession No. AA071048; SEQ ID NOs: 9 and 10); Hepatoma-Derived Growth Factor (HGDF) (e.g., Genbank® Accession No. D16431; SEQ ID NOs: 13 and 14); DKFZp5860031 (e.g., Genbank® Accession No. AL117237; SEQ ID NOs: 15 and 16); CD63 antigen (melanoma 1 antigen) (e.g., Genbank® Accession No. AA041408; SEQ ID NOs: 17 and 18); protein kinase C substrate 80K-H (e.g., Genbank® Accession No. J03075; SEQ ID NOs: 19 and 20); Polymerase II cofactor 4 (PC4) (e.g., Genbank® Accession No. X79805; SEQ ID NOs: 21 and 22); mitochondrial Tu translation elongation factor (e.g., Genbank® Accession No. L38995; SEQ ID NOs: 23 and 24); hHRP H1 (e.g., Genbank® Accession No. L22009; SEQ ID NOs: 25 and 26); Solute carrier family 2 (e.g., Genbank® Accession No. AF070544; SEQ ID NOs: 27 and 28); KIAA0591 protein (e.g., Genbank® Accession No. AB011163; SEQ ID NOs: 29 and 30); X-ray repair protein (e.g., Genbank® Accession No. AF035587; SEQ ID Nos: 31 and 32); DKFZP564M2423 protein (e.g., Genbank® Accession No. BC003049; SEQ ID NOs: 35 and 139); growth factor-regulated tyrosine kinase substrate (e.g., Genbank® Accession No. D84064; SEQ ID NOs: 36 and 37); and/or eIF-2-associated p67 (e.g., Genbank® Accession No. U29607; SEQ ID NOs: 38 and 39). The ovarian tumor marker gene may also be HSP60 (e.g., Genbank® Accession No. M22382; SEQ ID NOs: 11 and 12) and Lutheran blood group protein (B-CAM) (e.g., Genbank® Accession No. NM_005581; SEQ ID NOs: 5 and 6).

Other examples of ovarian tumor marker genes of the invention include HLA-DR alpha chain (e.g., Genbank® Accession No. K01171; SEQ ID NOs: 40 and 41); cysteine-rich protein 1 (e.g., Genbank® Accession No. NM_001311; SEQ ID NOs: 42 and 43); claudin 4 (e.g., Genbank® Accession No. NM_001305; SEQ ID NOs: 44 and 45); HOST-2 (e.g., SEQ ID NO: 46); claudin 3 (e.g., Genbank® Accession No. NM_001306; SEQ ID NOs: 47 and 48); ceruloplasmin (ferroxidase) (e.g., Genbank® Accession No. M13699; SEQ ID NOs: 49 and 50); glutathione perroxidase 3 (e.g., Genbank® Accession No. D00632; SEQ ID NOs: 51 and 52); secretory leukocyte protease inhibitor (e.g., Genbank® Accession No. M114471; SEQ ID NOs: 53 and 54); HOST-1 (FLJ14303 fis) (e.g., Genbank® Accession No. AK024365; SEQ ID NOs: 55 and 56); interferon-induced transmembrane protein 1 (e.g., Genbank® Accession No. J04164; SEQ ID NOs: 57 and 58); apolipoprotein J/clusterin (e.g., Genbank® Accession No. J02908; SEQ ID NOs: 59 and 60); serine protease inhibitor, Kunitz type 2 (e.g., Genbank® Accession No. AF027205; SEQ ID NOs: 61 and 62); apoplipoprotein E (e.g., Genbank® Accession No. BC003557; SEQ ID NOs: 63 and 64); complement component 1, r subcomponent (e.g., Genbank® Accession No. M14058; SEQ ID NOs: 65 and 66); G1P3/IIFI-6-16 (e.g., Genbank® Accession No. X02492; SEQ ID NOs: 67 and 68); Lutheran blood group (BCAM) (e.g., Genbank® Accession No. X83425; SEQ ID NOs: 69 and 70); collagen type III, alpha-1 (e.g., Genbank® Accession No. X14420; SEQ ID NOs: 71 and 72); Mal (T cell differentiation protein) (e.g., Genbank® Accession No. M15800; SEQ ID NOs: 73 and 74); collagen type I, alpha-2 (e.g., Genbank® Accession No. J03464; SEQ ID NOs: 75 and 76); HLA-DPB1 (e.g., Genbank® Accession No. J03041: SEQ ID NOs: 77 and 78): bone marrow stroma antigen 2 (BST-2) (e.g., Genbank® Accession No. D28137; SEQ ID NOs: 79 and 80); and HLA-Cw (e.g., Genbank® Accession No. X17093; SEQ ID NOs: 81 and 82).

Still other examples of ovarian tumor marker genes of the invention include HOST-3 (Claudin-16) (e.g., Genbank® Accession No. XM_003150; SEQ If) NOs: 141 and 142); HOST-4 (e.g., a gene that comprises SEQ ID NO: 144); or HOST-5 (sodium dependent transporter isoform NaPi-Iib) (e.g., Genbank® Accession No. AF146796; SEQ ID NOs: 146 and 147).

Ovarian tumor marker genes of the invention may also be described by SAGE tags, as disclosed herein. For example, an ovarian tumor marker genes of the invention can include a nucleotide sequence set forth in one of SEQ ID NOs: 84-102; 103-129; or 141, 143, or 145.

Diagnostic Uses of Ovarian Tumor Marker Genes and Polypeptides

The ovarian tumor marker genes of the invention are overexpressed in a broad variety of ovarian epithelial tumor cells, relative to normal ovarian epithelial cells. This differential expression can be exploited in diagnostic tests for ovarian cancer, in prognostic tests for assessing the relative severity of ovarian cancer, in tests for monitoring a subject in remission from ovarian cancer, and in tests for monitoring disease status in a subject being treated for ovarian cancer. Increased expression of an ovarian tumor marker gene, i.e., detection of elevated levels of ovarian tumor marker mRNA and/or protein in a subject or in a sample from a subject (i.e., levels at least three-fold higher than in a normal subject or in an equivalent sample, e.g., blood, cells, or tissue from a normal subject) is diagnostic of ovarian cancer.

One of ordinary skill in the art will understand that in some instances, higher expression of a given ovarian tumor marker gene will indicate a worse prognosis for a subject having ovarian cancer. For example, relatively higher levels of ovarian tumor marker gene expression may indicate a relative large primary tumor, a higher tumor burden (e.g., more metastases), or a relatively more malignant tumor phenotype.

The diagnostic and prognostic methods of the invention involve using known methods, e.g., antibody-based methods to detect ovarian tumor marker polypeptides and nucleic acid hybridization- and/or amplification-based methods to detect ovarian tumor marker mRNA. One of ordinary skill in the art will understand how to choose the most appropriate method for measuring ovarian tumor marker expression, based upon the combination of the particular ovarian tumor marker to be measured, the information desired, and the particular type of diagnostic test to be used. For example, immunological tests such as enzyme-linked immunosorbent assays (ELISA), radioimmunoassays (RIA), and Western blots may be used to measure the level of an ovarian tumor marker polypeptide in a body fluid sample (such as blood, serum, sputum, urine, or peritoneal fluid). Biopsies, tissue samples, and cell samples (such as ovaries, lymph nodes, ovarian surface epithelial cell scrapings, lung biopsies, liver biopsies, and any fluid sample containing cells (such as peritoneal fluid, sputum, and pleural effusions) may be tested by disaggregating and/or solubilizing the tissue or cell sample and subjecting it to an immunoassay for polypeptide detection, such as ELISA, RIA, or Western blotting. Such cell or tissue samples may also be analyzed by nucleic acid-based methods, e.g., reverse transcription-polymerase chain reaction (RT-PCR) amplification, Northern hybridization, or slot- or dot-blotting. To visualize the three-dimensional distribution of tumor cells within a tissue sample, diagnostic tests that preserve the tissue structure of a sample, e.g., immunohistological staining, in situ RNA hybridization, or in situ RT-PCR may be employed to detect ovarian tumor marker polypeptide or mRNA, respectively. For in vivo localization of tumor masses, imaging tests such as magnetic resonance imaging (MRI) may be employed by introducing into the subject an antibody that specifically binds an ovarian tumor marker polypeptide (particularly a cell surface-localized polypeptide), wherein the antibody is conjugated or otherwise coupled to a paramagnetic tracer (or other appropriate detectable moiety, depending upon the imaging method used); alternatively, localization of an unlabeled tumor marker-specific antibody may be detected using a secondary antibody coupled to a detectable moiety.

The skilled artisan will understand that selection of a particular ovarian tumor marker polypeptide as the target for detection in any diagnostic test and selection of the particular test to be employed will depend upon the type of sample to be tested. For example, measurement of ovarian tumor marker polypeptides that are secreted from a cell (e.g., HDGF) may be preferred for serological tests. Moreover, ovarian tumor marker polypeptides that are not normally actively secreted from cells (e.g., intracellular or membrane-associated polypeptides), but that are found in blood and other fluid samples (e.g., peritoneal fluid or washings) at detectable levels in subjects having tumors (e.g., due to tumor cell lysis) are considered to be soluble ovarian tumor marker polypeptides that may be used in serological and other diagnostic assays of body fluids.

A fluid sample (such as blood, peritoneal fluid, sputum, or pleural effusions) from a subject with ovarian cancer, particularly metastatic cancer, may contain one or more ovarian tumor cells or ovarian tumor cell fragments. The presence of such cells or fragments allows detection of a tumor mRNA using an RT-PCR assay, e.g., but not limited to, real-time quantitative RT-PCR using the Taqman method (Heid and Stevens, *Genome Res.* 6:986-94, 1996).

In addition, since rapid tumor cell destruction often results in autoantibody generation, the ovarian tumor markers of the invention may be used in serological assays (e.g., an ELISA test of a subject's serum) to detect autoantibodies against ovarian tumor markers in a subject. Ovarian tumor marker polypeptide-specific autoantibody levels that are at least about 3-fold higher (and preferably at least 5-fold or 7-fold higher, most preferably at least 10-fold or 20-fold higher) than in a control sample are indicative of ovarian cancer.

Cell-surface localized, intracellular, and secreted ovarian tumor marker polypeptides may all be employed for analysis of biopsies, e.g., tissue or cell samples (including cells obtained from liquid samples such as peritoneal cavity fluid) to identify a tissue or cell biopsy as containing ovarian tumor cells. A biopsy may be analyzed as an intact tissue or as a whole-cell sample, or the tissue or cell sample may be disaggregated and/or solubilized as necessary for the particular type of diagnostic test to be used. For example, biopsies or samples may be subjected to whole-tissue or whole-cell analysis of ovarian tumor marker polypeptide or mRNA levels in situ, e.g., using immunohistochemistry, in situ mRNA hybridization, or in situ RT-PCR. The skilled artisan will know how to process tissues or cells for analysis of polypeptide or mRNA levels using immunological methods such as ELISA, immunoblotting, or equivalent methods, or analysis of mRNA levels by nucleic acid-based analytical methods such as RT-PCR, Northern hybridization, or slot- or dot-blotting.

All of the above methods are well-known in the art. For example, generation of antibodies against a given protein, ELISA, immunoblotting, selection of nucleic acid primers for PCR, RT-PCR, Northern hybridization, in situ hybridization, in situ RT-PCR, and slot- or dot-blotting are all well-described in *Current Protocols in Molecular Biology* (Ausubel et al., eds.), John Wiley and Sons, Inc., 1996.

Kits for Measuring Expression Levels of Ovarian Tumor Marker Genes

The present invention provides kits for detecting an increased expression level of an ovarian tumor marker gene in a subject. A kit for detecting ovarian tumor marker polypeptide will contain an antibody that specifically binds a chosen ovarian tumor marker polypeptide. A kit for detecting ovarian tumor marker mRNA will contain one or more nucleic acids (e.g., one or more oligonucleotide primers or probes, DNA probes, RNA probes, or templates for generating RNA probes) that specifically hybridize with a chosen ovarian tumor marker mRNA.

Particularly, the antibody-based kit can be used to detect the presence of, and/or measure the level of, an ovarian tumor marker polypeptide that is specifically bound by the antibody or an immunoreactive fragment thereof. The kit can include an antibody reactive with the antigen and a reagent for detecting a reaction of the antibody with the antigen. Such a kit can be an ELISA kit and can contain a control (e.g., a specified amount of a particular ovarian tumor marker polypeptide), primary and secondary antibodies when appropriate, and any other necessary reagents such as detectable moieties, enzyme substrates and color reagents as described above. The diagnostic kit can, alternatively, be an immunoblot kit generally comprising the components and reagents described herein.

A nucleic acid-based kit can be used to detect and/or measure the expression level of an ovarian tumor marker gene by detecting and/or measuring the amount of ovarian tumor marker mRNA in a sample, such as a tissue or cell biopsy (e.g., an ovary, ovarian cell scrapings, a bone marrow biopsy, a lung biopsy or lung aspiration, etc.). For example, an RT-PCR kit for detection of elevated expression of an ovarian tumor marker gene will contain oligonucleotide primers sufficient to perform reverse transcription of ovarian tumor marker mRNA to cDNA and PCR amplification of ovarian tumor marker cDNA, and will preferably also contain control PCR template molecules and primers to perform appropriate negative and positive controls, and internal controls for quantitation. One of ordinary skill in the art will understand how to select the appropriate primers to perform the reverse transcription and PCR reactions, and the appropriate control reactions to be performed. Such guidance is found, for example, in F. Ausubel et al., *Current Protocols in Molecular Biology*, John Wiley & Sons, New York, N.Y., 1997. Numerous variations of RT-PCR are known in the art.

One example of a quantitative RT-PCR assay is the real-time quantitative RT-PCR assay described by Heid and Stevens (*Genome Res.* 6:986-94, 1996), in which the primers are labeled by a fluorescent tag, and the amount of amplification product may be measured in a Taqman® apparatus (Perkin-Elmer; Norwal, Conn.).

Targeted Delivery of Immunotoxins to Ovarian Tumor Cells

The tumor marker genes of the invention can be employed as therapeutic targets for the treatment or prevention of ovarian cancer. For example, an antibody molecule that specifically binds a cell surface-localized ovarian tumor marker polypeptide can be conjugated to a radioisotope or other toxic compound. Antibody conjugates are administered to the subject such that the binding of the antibody to its cognate ovarian tumor marker polypeptide results in the targeted delivery of the therapeutic compound to ovarian tumor cells, thereby treating an ovarian cancer.

The therapeutic moiety can be a toxin, radioisotope, drug, chemical, or a protein (see, e.g., Bera et al. "Pharmacokinetics and antitumor activity of a bivalent disulfide-stabilized Fv immunotoxin with improved antigen binding to erbB2" *Cancer Res.* 59:4018-4022 (1999)). For example, the antibody can be linked or conjugated to a bacterial toxin (e.g., diptheria toxin, pseudomonas exotoxin A, cholera toxin) or plant toxin (e.g., ricin toxin) for targeted delivery of the toxin to a cell expressing the ovarian tumor marker. This immunotoxin can be delivered to a cell and upon binding the cell surface-localized ovarian tumor marker polypeptide, the toxin conjugated to the ovarian tumor marker-specific antibody will be delivered to the cell.

In addition, for any ovarian tumor polypeptide for which there is a specific ligand (e.g., a ligand that binds a cell surface-localized protein), the ligand can be used in place of an antibody to target a toxic compound to an ovarian tumor cell, as described above.

Antibodies That Specifically Bind Ovarian Tumor Marker Polypeptides

The term "antibodies" is used herein in a broad sense and includes both polyclonal and monoclonal antibodies. In addition to intact immunoglobulin molecules, also included in the term "antibodies" are fragments or polymers of those immunoglobulin molecules and humanized versions of immunoglobulin molecules, so long as they exhibit any of the desired properties (e.g., specific binding of an ovarian tumor marker polypeptide, delivery of a toxin to an ovarian tumor cell expressing an ovarian tumor marker gene at an increased level, and/or inhibiting the activity of an ovarian tumor marker polypeptide) described herein.

Whenever possible, the antibodies of the invention may be purchased from commercial sources. The antibodies of the invention may also be generated using well-known methods. The skilled artisan will understand that either full length ovarian tumor marker polypeptides or fragments thereof may be used to generate the antibodies of the invention. A polypeptide to be used for generating an antibody of the invention may be partially or fully purified from a natural source, or may be produced using recombinant DNA techniques. For example, a cDNA encoding an ovarian tumor marker polypeptide, or a fragment thereof, can be expressed in prokaryotic cells (e.g., bacteria) or eukaryotic cells (e.g., yeast, insect, or mammalian cells), after which the recombinant protein can be purified and used to generate a monoclonal or polyclonal antibody preparation that specifically bind the ovarian tumor marker polypeptide used to generate the antibody.

In addition, one of skill in the art will know how to choose an antigenic peptide for the generation of monoclonal or polyclonal antibodies that specifically bind ovarian tumor antigen polypeptides. Antigenic peptides for use in generating the antibodies of the invention are chosen from non-helical regions of the protein that are hydrophilic. The PredictProtein Server or an analogous program may be used to select antigenic peptides to generate the antibodies of the invention. In one example, a peptide of about fifteen amino acids may be chosen and a peptide-antibody package may be obtained from a commercial source such as Anaspec (San Jose, Calif.). One of skill in the art will know that the generation of two or more different sets of monoclonal or polyclonal antibodies maximizes the likelihood of obtaining an antibody with the specificity and affinity required for its intended use (e.g., ELISA, immunohistochemistry, in vivo imaging, immunotoxin therapy). The antibodies are tested for their desired activity by known methods, in accordance with the purpose for which the antibodies are to be used (e.g., ELISA, immunohistochemistiy, immunotherapy, etc.; for further guidance on the generation and testing of antibodies, see, e.g., Harlow and Lane, *Antibodies: A Laboratory Manual*, Cold Spring Harbor Laboratory Press, Cold Spring Harbor, N.Y., 1988). For example, the antibodies may be tested in ELISA assays, Western blots, immunohistochemical staining of formalin-fixed ovarian cancers or frozen tissue sections. After their initial in vitro characterization, antibodies intended for therapeutic or in vivo diagnostic use are tested according to known clinical testing methods.

The term "monoclonal antibody" as used herein refers to an antibody obtained from a substantially homogeneous population of antibodies, i.e.; the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity (See, U.S. Pat. No. 4,816,567 and Morrison et al., Proc. Natl. Acad. Sci. USA, 81:6851-6855 (1984)).

Monoclonal antibodies of the invention may be prepared using hybridoma methods, such as those described by Kohler and Milstein, Nature, 256:495 (1975). In a hybridoma method, a mouse or other appropriate host animal, is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies).

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The antibody fragments, whether attached to other sequences or not, can also include insertions, deletions, substitutions, or other selected modifications of particular regions or specific amino acids residues, provided the activity of the fragment is not significantly altered or impaired compared to the nonmodified antibody or antibody fragment. These modifications can provide for some additional property, such as to remove/add amino acids capable of disulfide bonding, to increase its bio-longevity, to alter its secretory characteristics, etc. In any case, the antibody fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody fragment. (Zoller, M. J. Curr. Opin. Biotechnol. 3:348-354, 1992).

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab' or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986), Reichmann et al., Nature, 332:323-327 (1988), and Presta, Curr. Op. Struct. Biol., 2:593-596 (1992)).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525 (1986), Riechmann et al., Nature, 332:323-327 (1988), Verhoeyen et al., Science, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits et al., Proc. Natl. Acad. Sci. USA, 90:2551-255 (1993); Jakobovits et al., Nature, 362:255-258 (1993); Bruggermann et al., Year in Immuno., 7:33 (1993)). Human antibodies can also be produced in phage display libraries (Hoogenboom et al., J. Mol. Biol., 227:381 (1991); Marks et al., J. Mol. Biol., 222:581 (1991)). The techniques of Cote et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)].

Administration of Therapeutic and Diagnostic Antibodies

Antibodies of the invention are preferably administered to a subject in a pharmaceutically acceptable carrier. Suitable carriers and their formulations are described in *Remington's Pharmaceutical Sciences,* 16th ed., 1980, Mack Publishing Co., edited by Oslo et al. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. The antibodies may also be administered by intratumoral or peritumoral routes, to exert local as well as systemic therapeutic effects. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. Guidance in selecting appropriate doses for antibodies is found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

Following administration of an antibody for treating ovarian cancer, the efficacy of the therapeutic antibody can be assessed in various ways well known to the skilled practitioner. For instance, the size, number, and/or distribution of ovarian tumors in a subject receiving treatment may be monitored using standard tumor imaging techniques. A therapeutically-administered antibody that arrests tumor growth, results in tumor shrinkage, and/or prevents the development of new tumors, compared to the disease course that would occurs in the absence of antibody administration, is an efficacious antibody for treatment of ovarian cancer.

Antisense and Gene Therapy Approaches for Inhibiting Ovarian Tumor Marker Gene Function Because the ovarian tumor marker genes of the invention are highly expressed in ovarian tumor cells and are expressed at extremely low levels in normal ovarian cells, inhibition of ovarian tumor marker expression or polypeptide activity may be integrated into any therapeutic strategy for treating or preventing ovarian cancer.

The principle of antisense therapy is based on the hypothesis that sequence-specific suppression of gene expression (via transcription or translation) may be achieved by intracellular hybridization between genomic DNA or mRNA and a complementary antisense species. The formation of such a hybrid nucleic acid duplex interferes with transcription of the target tumor antigen-encoding genomic DNA, or processing/transport/translation and/or stability of the target tumor antigen mRNA.

Antisense nucleic acids can be delivered by a variety of approaches. For example, antisense oligonucleotides or antisense RNA can be directly administered (e.g., by intravenous injection) to a subject in a form that allows uptake into tumor cells. Alternatively, viral or plasmid vectors that encode antisense RNA (or RNA fragments) can be introduced into cells in vivo. Antisense effects can also be induced by sense sequences; however, the extent of phenotypic changes are highly variable. Phenotypic changes induced by effective antisense therapy are assessed according to changes in, e.g., target mRNA levels, target protein levels, and/or target protein activity levels.

In a specific example, inhibition of ovarian tumor marker function by antisense gene therapy may be accomplished by direct administration of antisense ovarian tumor marker RNA to a subject. The antisense tumor marker RNA may be produced and isolated by any standard technique, but is most readily produced by in vitro transcription using an antisense tumor marker cDNA under the control of a high efficiency promoter (e.g., the T7 promoter). Administration of antisense tumor marker RNA to cells can be carried out by any of the methods for direct nucleic acid administration described below.

An alternative strategy for inhibiting ovarian tumor marker polypeptide function using gene therapy involves intracellular expression of an anti-ovarian tumor marker antibody or a portion of an anti-ovarian tumor marker antibody. For example, the gene (or gene fragment) encoding a monoclonal antibody that specifically binds to an ovarian tumor marker polypeptide and inhibits its biological activity is placed under the transcriptional control of a specific (e.g., tissue- or tumor-specific) gene regulatory sequence, within a nucleic acid expression vector. The vector is then administered to the subject such that it is taken up by ovarian tumor cells or other cells, which then secrete the anti-ovarian tumor marker antibody and thereby block biological activity of the ovarian tumor marker polypeptide. Preferably, the ovarian tumor marker polypeptide is present at the extracellular surface of ovarian tumor cells.

Nucleic Acid Delivery

In the methods described above which include the administration and uptake of exogenous DNA into the cells of a subject (i.e., gene transduction or transfection), the nucleic acids of the present invention can be in the form of naked DNA or the nucleic acids can be in a vector for delivering the nucleic acids to the cells for inhibition of ovarian tumor marker protein expression. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system which can package a recombinant retroviral genome (see e.g., Pastan et al., *Proc. Natl. Acad. Sci. U.S.A.* 85:4486, 1988; Miller et al., *Mol. Cell. Biol.* 6:2895, 1986). The recombinant retrovirus can then be used to infect and thereby deliver to the infected cells antisense nucleic acid that inhibits expression of an ovarian tumor marker gene. The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5:941-948, 1994), adeno-associated viral (AAV) vectors (Goodman et al., *Blood* 84:1492-1500, 1994), lentiviral vectors (Naidini et al., *Science* 272:263-267, 1996), pseudotyped retroviral vectors (Agrawal et al., *Exper. Hematol.* 24:738-747, 1996). Physical transduction techniques can also be used, such as liposome delivery and receptor-mediated and other endocytosis mechanisms (see, for example, Schwartzenberger et al., *Blood* 87:472-478, 1996). This invention can be used in conjunction with any of these or other commonly used gene transfer methods.

As one example, if the antisense nucleic acid of this invention is delivered to the cells of a subject in an adenovirus vector, the dosage for administration of adenovirus to humans can range from about $10^7$ to $10^9$ plaque forming units (pfu) per injection but can be as high as $10^{12}$ pfu per injection (Crystal, *Hum. Gene Ther.* 8:985-1001, 1997; Alvarez and Curiel, *Hum. Gene Ther.* 8:597-613, 1997). Ideally, a subject will receive a single injection. If additional injections are necessary, they can be repeated at six month intervals for an indefinite period and/or until the efficacy of the treatment has been established.

Parenteral administration of the nucleic acid or vector of the present invention, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein. For additional discussion of suitable formulations and various routes of administration of therapeutic compounds, see, e.g., *Remington: The Science and Practice of Pharmacy* (19th ed.) ed. A. R. Gennaro, Mack Publishing Company, Easton, Pa. 1995.

EXAMPLE I

Identification of Ovarian Tumor Marker Genes Using SAGE

Serial Analysis of Gene Expression is a method that enables the global analysis of gene expression from a tissue of interest (Velculescu et al., *Science* 270:484487, 1995; Zhang et al., *Science* 276:1268-72, 1997). The advantages of SAGE over cDNA arrays, another method for the global analysis of gene expression, include: 1) the possibility of identifying novel genes, 2) determination of absolute levels of gene expression, which is difficult in hybridization-based techniques, and, 3) examination of gene expression as a whole instead of as a subset of genes.

Construction and Screening of SAGE Libraries

The SAGE technique has been described in detail (Velculescu et al., *Science* 270:484-487, 1995). The SAGE libraries disclosed herein were made as described by Velculescu, supra. First, total RNA was purified from the cells. Poly A+RNA was then isolated and reverse transcription was performed using a biotinylated poly dT primer for first strand synthesis. The cDNA mixture was cut with NlaIII and the biotinylated 3'fragments were collected using streptavidin beads. The beads were divided into two aliquots (A and B) and linkers containing PCR primer sites and a site for class II restriction enzyme BsmFI were ligated to the DNA fragments attached to the beads from samples A and B. The mixture was treated with the restriction enzyme BsmFI, which recognizes the site in the linker but cuts 14 bp downstream. The resulting fragments contained the linker and 10 bp of "cDNA sequence" that is referred to as "tag". The tags from samples A and B were ligated together to form ditags, which were then amplified by PCR. Any repeated ditag (tags containing the same two individual tags) are an indication of PCR bias and were eliminated by the SAGE software (Velculescu et al., *Science* 270:484-487, 1995; Zhang et al., *Science* 276:1268-72, 1997). The tags were concatemerized and cloned into a sequencing vector. Sequencing revealed the identity and frequency of the different tags. As described above, the 10 bp tag is sufficient to identify cDNA and the frequency of a particular tag represents the frequency of a particular message in the population. The SAGE software developed in the laboratories of Bert Vogelstein and Kenneth Kinzler at Johns Hopkins extracts the tags from the raw sequencing data, matches the tags to the corresponding genes (present in Genbank®) and makes frequency comparisons between the tags from an individual library or other libraries.

Verification of Ovarian Tumor Marker Genes Identified by SAGE

The most promising candidates are selected and verified by any expression analysis method, e.g., Northern analysis or reverse transcription-polymerase chain reaction (RT-PCR). For Northern analysis, radioactive probes are generated from expressed sequence tags (ESTs) corresponding to the candidate genes and are used to hybridize to membranes containing total RNA from various ovarian cancers and controls. The candidates may also be verified by real-time PCR using the Taqman® method (Heid and Stevens, *Genome Res.* 6:986-94, 1996). Amplification primers and fluorescent probes are synthesized according to instructions from the manufacturer (Perkin-Elmer; Norwalk, Conn.). Quantitative PCR is performed using a PE 5700 apparatus or an analogous instrument.

Sources of RNA for SAGE Library Construction

Eleven SAGE libraries were constructed, as shown in Table 1. The human ovarian surface epithelial cell (HOSE) library was constructed using RNA from HOSE cells that were obtained by gently scraping the ovarian surface from a hysterectomy patient followed by short-term in vitro culture (three passages) of the cells. Three of the ovarian tumor libraries (designated OVT6, OVT7, and OVT8) were constructed using RNA from one of three primary high grade serous adenocarcinomas libraries from individual ovarian tumor cell lines were generated using RNA from OV1063 (derived from an ovarian papillary adenocarcinoma; obtained from the American Type Culture Collection (ATCC; Manassas, Va.; CRL-2183)); ES-2 (derived from a clear cell adenocarcinoma; from the ATCC; CRL-1978); A2780 (derived from an ovarian cancer; obtained from Dr. Vilhelm Bohr, Baltimore, Md.); OVCA432 (derived from an ovarian serous cystadenocarcinoma; Bast et al., *J. Clin. Invest.* 68:1331-1337, 1981); ML10 (derived from an ovarian cystadenoma; Luo et al. *Gyn. Oncol.,* 67:277-284, 1997); or IOSE29 (simian virus 40-immortalized OSE cells; Auersperg et al., *Proc. Natl. Acad. Sci. USA* 96:6249-6254, 1999).

The pooled library was generated using RNA from a pool of 10 cell lines: A2780; BG-1 (poorly differentiated ovarian cancer; obtained from Dr. Carl Barrett, Durham, N.C.); ES-2; OVCA432; MDAH 2774 (endometrioid adenocarcinoma; obtained from the ATCC); and five cell lines obtained from Dr. Michael Birrer (Rockville, Md.): AD10 (an adriamycin-resistant derivative of A2780); A222 (ovarian carcinoma); UCI101 (papillary ovarian adenocarcinoma); UCI107 (papillary ovarian adenocarcinoma); and A224 (ovarian carcinoma).

TABLE 1

| Library | Seq | Tags (raw) | Tags | Genes | At least 2 |
|---|---|---|---|---|---|
| HOSE | 2,290 | 49,394 | 47,881 | 16,034 | 4,532 |
| OVT6 | 2,104 | 43,891 | 41,620 | 18,476 | 4,799 |
| OVT7 | 2,089 | 57,725 | 53,898 | 19,523 | 5,669 |
| OVT8 | 2,076 | 36,813 | 32,494 | 16,363 | 3,815 |
| OV1063 | 2,146 | 41,131 | 37,862 | 15,231 | 4,746 |
| ES-2 | 1,775 | 36,430 | 35,352 | 14,739 | 3,952 |
| A2780** | 475 | 9,269 | 8,246 | 5,179 | 1,021 |
| OVCA432 | 384 | 3,011 | 2,824 | 1,940 | 310 |
| Pool | 2,201 | 10,952 | 10,554 | 5,956 | 1,627 |
| ML10 | 1,935 | 61,083 | 55,700 | 18,727 | 6,637 |
| IOSE29 | * | * | * | * | * |
| TOTAL | 17,475 | 349,699 | 326,431 | 75,056 | 25,071 |

* To be sequenced
** Incomplete

Results of SAGE

Eleven ovarian SAGE libraries were constructed, ten of which have been sequenced to date. The overall data are summarized in Table 1 above. For each SAGE library, Table 1 shows the number of SAGE library clones sequenced, the number of raw tags sequenced, the number of tags obtained after correction for PCR bias, the total number of genes that are represented by the corrected pool of tags, and the number of genes that were represented at least twice in the corrected pool of tags. For most libraries, 35,000-61,000 tags were obtained, yielding anywhere from 14,000-20,000 genes. In total, 75,056 genes were identified.

In order to identify genes that are up-regulated in ovarian tumors and that may serve as diagnostic markers and therapeutic targets, we compared gene expression between the normal ovarian cells (HOSE) and the cancer cells (OVT6, OVT7, OVT8, OV1063, ES2, A2780, Pool). OVCA432 was not included in this analysis because of the poor number of tags obtained from this library. We looked for genes for which expression was absent or low (frequency smaller or equal to 2 tags per 100,000) in HOSE and at least 7- to 10-fold up-regulated in the majority of the tumor libraries, and detected a number of genes matching these criteria. Table 2 shows the libraries that were screened, the SAGE tags that were identified in the library screens, along with their corresponding genes and Genbank® accession numbers, and the relative expression of each gene in each library. Any one of these ovarian tumor marker genes may be used in the diagnostic and/or therapeutic methods of the invention.

TABLE 2

| SEQ. ID NO. (Tag) | Tag | OVT8 | OVT7 | OVT6 | A2780 | OV1063 | ES2 | Pool | HOSE | Gene Product | Genbank |
|---|---|---|---|---|---|---|---|---|---|---|---|
| 83 | TCAGACGCAG | 52 | 149 | 91 | 97 | 49 | 214 | 82 | 2 | Prothymosin, alpha | M14483 |
| 84 | TTATGGGATC | 57 | 80 | 57 | 140 | 83 | 126 | 274 | 2 | G protein, beta polypeptide 2-like 1 | M24194 |
| 85 | CCCGCCCCCG | 136 | 166 | 52 | 22 | 7 | 0 | 146 | 2 | Lutheran blood group (B-CAM) | NM_005581 |
| 86 | GAGGAAGAAG | 14 | 38 | 57 | 76 | 53 | 80 | 100 | 2 | Tumor rejection antigen-1 (gp96) 1 | NM_003299 |
| 87 | GAAGCTTTGC | 27 | 43 | 43 | 22 | 27 | 66 | 73 | 2 | HSP90 | AA071048 |
| 88 | TACCAGTGTA | 30 | 16 | 14 | 140 | 22 | 30 | 100 | 2 | HSP60 | M22382 |
| 89 | TCTTCTCCCT | 8 | 42 | 32 | 22 | 27 | 25 | 46 | 2 | Hepatoma-Derived Growth Factor (HDGF) | D16431 |
| 90 | TTGGCTTTTC | 14 | 12 | 71 | 32 | 10 | 22 | 18 | 0 | DKFZp5860031 | AL117237 |
| 91 | GGAAGGGAGG | 30 | 14 | 16 | 11 | 12 | 44 | 55 | 2 | CD63 antigen (melanoma 1 antigen) | AA041408 |

TABLE 2-continued

| SEQ. ID NO. (Tag) | Tag | OVT8 | OVT7 | OVT6 | A2780 | OV1063 | ES2 | Pool | HOSE | Gene Product | Genbank |
|---|---|---|---|---|---|---|---|---|---|---|---|
| 92 | AAGCCAGCCC | 19 | 17 | 36 | 22 | 17 | 27 | 18 | 2 | Protein kinase C substrate 80K-H | J03075 |
| 93 | TTTCAGATTG | 16 | 26 | 25 | 32 | 22 | 19 | 18 | 0 | Polymerase II cofactor 4 (PC4) | X79805 |
| 94 | GCATAGGCTG | 11 | 24 | 25 | 22 | 12 | 27 | 9 | 2 | Tu translation elong. factor (mitochondrial) | L38995 |
| 95 | TTTGTTAATT | 30 | 16 | 16 | 43 | 17 | 19 | 18 | 2 | hNRP H1 | L22009 |
| 96 | GAGACTCCTG | 11 | 23 | 23 | 22 | 12 | 3 | 64 | 2 | Solute carrier family 2 | AF070544 |
| 97 | CCTGTAATTC | 19 | 10 | 27 | 32 | 15 | 8 | 27 | 2 | KIAA0591 protein | AB011163 |
| 98 | GTGGTGCGTG | 16 | 10 | 21 | 11 | 15 | 19 | 27 | 2 | X-ray repair protein | AF035587 |
| 99 | TTGGACCTGG | 11 | 19 | 9 | 11 | 27 | 16 | 18 | 2 | ATP synthase (delta subunit) | AA524164 |
| 100 | CTTAAGGATT | 11 | 12 | 18 | 11 | 15 | 27 | 9 | 0 | DKFZP564M2423 protein | BC003049 |
| 101 | GTCTGTGAGA | 8 | 17 | 9 | 22 | 12 | 22 | 18 | 0 | Growth factor-regul. tyr kinase substrate | D84064 |
| 102 | GAAACTGAAC | 16 | 10 | 14 | 32 | 12 | 3 | 9 | 2 | eIF-2-associated p67 | U29607 |

EXAMPLE II

Identification of Additional Ovarian Tumor Marker Genes Using SAGE

Serial Analysis of Gene Expression (SAGE) was used to generate global gene expression profiles from various ovarian cell lines and tissues, including primary cancers, ovarian surface epithelial (OSE) cells and cystadenoma cells. The profiles were used to compare overall patterns of gene expression and identify differentially expressed genes. We have sequenced a total of 385,000 tags, yielding over 56,000 genes expressed in ten different libraries derived from ovarian tissues.

In general, ovarian cancer cell lines showed relatively high levels of similarity to libraries from other cancer cell lines, regardless of the tissue of origin (ovarian or colon), indicating that these lines had lost many of their tissue specific expression patterns. In contrast, immortalized OSE (IOSE) and ovarian cystadenoma cells showed much higher similarity to primary ovarian carcinomas as compared to primary colon carcinomas. Primary tissue specimens therefore appeared to be a better model for gene expression analyses. Using the expression profiles described above and stringent selection criteria, we have identified a number of genes highly differentially expressed between non-transformed ovarian epithelia and ovarian carcinomas. Some of the genes identified are already known to be overexpressed in ovarian cancer but several represent novel candidates. Many of the genes up-regulated in ovarian cancer represent surface or secreted proteins such as Claudin-3 and -4, HE4, Mucin-1, Ep-CAM and Mesothelin. The genes encoding apolipoprotein E (ApoE) and apolipoprotein J (ApoJ), two proteins involved in lipid homeostasis are among the genes highly up-regulated in ovarian cancer. Selected SAGE results were further validated through immunohistochemical analysis of ApoJ, Claudin-3, Claudin-4 and Ep-CAM in archival material. These experiments provided additional evidence of the relevance of our findings in vivo.

A) Methods

Cell Culture and Tissue Samples

Ovarian cancer cell lines OV1063, ES2, and MDAH 2774 were obtained from the American Type Culture Collection (Manassas, Va.). Cell lines A222, AD10, UCI101 and UCI107 were obtained from Dr. Michael Birrer (Rockville, Md.). Cell line A2780 was obtained from Dr. Vilhelm Bohr (Baltimore, Md.). The SV40-immortalized cell lines IOSE29 (Auersperg, N., et al. *Proc. Natl Acad. Sci. USA*, 96:6249-6254, 1999) and ML10 (Luo, M. P., et al. *Gynecol. Oncol.* 67:277-284, 1997) were kindly provided by Dr. Nelly Auersperg (British Columbia, Canada) and Dr. Louis Dubeau (Los Angeles, Calif.), respectively. Except for IOSE29, ML-10 and HOSE-4, all cell lines were cultured in McCoy's 5A growth medium (Life Technologies, Inc, Gaithersburg, Md.) supplemented with 10% fetal bovine serum (FBS) and antibiotics (100 U/ml of Penicillin and 100 ug/ml Streptomycin). IOSE29 was cultivated in Medium 199 (Life Technologies, Inc, Gaithersburg, Md.) supplemented with 5% newborn calf serum (NCS). ML10 was cultivated in MEM (Life Technologies, Inc, Gaithersburg, Md.) supplemented with 10% FBS and antibiotics as above.

Three high-grade serous ovarian cancer specimens, OVT6, OVT7, and OVT8, composed of at least 80% tumor cells as determined by histopathology, were chosen for SAGE. The ovarian tumor samples were frozen immediately after surgical resection and were obtained form the Johns Hopkins gynecological tumor bank in accordance with institutional guidelines on the use of human tissue. Normal human ovarian surface epithelial (HOSE-4) cells were cultured from the right ovary of a patient undergoing hysterectomy and bilateral salpingo-oophorectomy for benign disease. The OSE cells were obtained by gently scraping the surface of the ovary with a cytobrush and grown for 2 passages in RPMI 1640 medium supplemented with 10% FBS and 10 ug/ml insulin-like growth factor (IGF).

Serial Analysis of Gene Expression (SAGE)

Total RNA was obtained from guanidinium isothiocyanate cell lysates by centrifugation on CsCl. Polyadenylated mRNA was purified from total RNA using the Messagemaker® kit (Life Technologies, Gaithersburg, Md.) and the cDNA generated using the cDNA Synthesis System (Life Technologies, Gaithersburg, Md.). For the "Pool" library, 100 ug of total RNA from each of 10 ovarian cancer cell lines (A222, A2780, AD10, BG-1, ES-2, MDAH 2774, OVCA432, OV1063, UCI101 and UCI107) were combined and mRNA purified. SAGE was performed essentially as described (Velculescu, V. E., et al, *Science* 270:484-487, 1995) for all the libraries except HOSE. To create the HOSE library, MicroSAGE, a modified SAGE technique developed for limited sample sizes (Datson, N. A., et al. *Nucleic Acids Res.* 27:1300-1307, 1999), was used. Approximately 1×10$^6$ OSE cells in short-term culture were lysed and the mRNA purified directly using Oligo (dT)$_{25}$ Dynabeads® (Dynal, Norway). As part of the Cancer Genome Anatomy Project (CGAP) SAGE consortium, the SAGE libraries were arrayed at the Lawrence Livermore National Laboratories and sequenced at the Washington University Human Genome Center or NISC (Nil, Bethesda, MD). The data has been posted on the CGAP website as part of the SAGEmap database (Lal, A., et al. Cancer Res. 59:5403-5407, 1999.).

Sequence data from each library were analyzed by the SAGE software (Velculescu, V. E., et al. Science 270:484-487, 1995.) to quantify tags and identify their corresponding transcripts. The data for the colon libraries NC1, NC2, Tu98, Tu102, HCT116 and SW837 were obtained from the SAGEmap database and analyzed in the same way. Because the different libraries contained various numbers of total tags, normalization (to 100,000 tags) was performed to allow meaningful comparisons. The 10,000 most highly expressed genes in each of the 16 SAGE libraries of interest were formatted in a Microsoft Excel spreadsheet and Pearson correlation coefficients were calculated for each pairwise comparison using normalized tag values for each library. The value for the Pearson correlation coefficient (r) represents the degree of similarity (the strength of the relationship) between two libraries and is calculated using the following equation:

$$r = \frac{n(\Sigma xy) - (\Sigma x)(\Sigma y)}{\sqrt{[n\Sigma x^2 - (\Sigma x)^2][n\Sigma y^2 - (\Sigma y)^2]}}$$

where, $x_i$=number of tags per 100,000 for tag i in the first library and $y_i$=number of tags per 100,000 for tag i in the second library. For our purposes n equals 10,000 since 10,000 tags are compared. A dendrogram representing the hierarchical relationships between samples was then generated using hierarchical cluster analysis as described risen, M. B., et al. Proc. Natl Acad. Sci. USA 95:14863-14868, 1998). In addition, the identification of differentially expressed genes was also done using this subset of the SAGE data.

Immunohistochemistry

Deparafinized 5-um sections of formalin-fixed ovarian cancer specimens were submitted to heat-induced antigen retrieval and processed using the LSAB2 system (DAKO, Carpinteria, Calif.) with 3,3'-diaminobenzidine as the chromatogen and a hematoxylin counterstain. Monoclonal antibody against ApoJ/Clusterin (Clone CLJ-9) was obtained from Alexis Corporation (San Diego, Calif.) and used at a 1:500 Dilution. Monoclonal antibody against Ep-CAM (Clone 323/A3) from NeoMarkers® (Fremont, Calif.) was used at a 1:500 dilution. Polyclonal antibodies against Claudin-3 and 4 were a generous gift from Drs. M. Furuse and S. Tsukita (Kyoto, Japan) and were used at a dilution of 1:1000.

B) Results

Ovarian SAGE Library Construction and Analysis

Gene expression alterations that arise during malignant transformation can be identified a number of ways. We chose the unbiased, comprehensive method SAGE to create global gene expression profiles from ten different ovarian sources. The expression patterns are generated by sequencing thousands of short sequence tags that contain sufficient information to uniquely identify the corresponding transcripts (Velculescu, V. E., et al. Science 270:484487, 1995). Ten different SAGE libraries were constructed and sequenced for this study (Table 3). Our libraries included two derived from OSE cells (IOSE29 and HOSE-4), one derived from immortalized cystadenoma cells (ML-10), three primary tumors (OVT-6, -7, -8) and four libraries derived from ovarian cancer cell lines (OV-1063, ES-2, A2780 and a pool of cell lines). Almost 20,000 sequencing reactions were performed yielding a total of 384,497 tags, of which, 82,533 were unique. Accounting for a SAGE tag error rate of 6.8% (due to sequencing errors; see Zhang, L., et al., Science 276: 1268-1272, 1997), we estimate that we have identified a total of 56,387 genes expressed in ovarian tissues. Except for the A2780 cell line and the pooled lines (POOL) samples, a minimum of 12,000 genes were obtained from every library. Typically, for each library, 10% of the genes were expressed at levels of at least 0.01% and, collectively, these genes accounted for more than 50% of all the tags sequenced. Among the tags that appeared more than once, up to 95% matched to known sequences in the current Genbank nr database. For example, of the 6637 tags that appeared more than once in ML10, only 311 had no matches in the current database, excluding the EST databases.

TABLE 3

Summary of SAGE library analyses

| Library[a] | Sequence | Tags[b] | Unique tags[c] | Genes[d] | ≧2 tags[e] |
|---|---|---|---|---|---|
| HOSE | 2,290 | 47,881 | 16,034 | 12,778 | 4,532 |
| IOSE | 1,912 | 47,549 | 18,004 | 14,771 | 5,681 |
| ML10 | 1,935 | 55,700 | 18,727 | 14,939 | 6,637 |
| OVT6 | 2,104 | 41,620 | 18,476 | 15,646 | 4,799 |
| OVT7 | 2,089 | 53,898 | 19,523 | 15,858 | 5,669 |
| OVT8 | 2,076 | 32,494 | 16,363 | 14,153 | 3,815 |
| OV1063 | 2,146 | 37,862 | 15,231 | 12,656 | 4,746 |
| A2780 | 1,332 | 21,587 | 10,717 | 9,249 | 2,761 |
| ES2 | 1,775 | 35,352 | 14,739 | 12,335 | 3,952 |
| POOL | 2,201 | 10,554 | 5,956 | 5,238 | 1,627 |
| TOTAL | 19,860 | 384,497 | 82,533 | 56,387 | 28,219 |

[a]The libraries are: HOSE, human ovarian surface epithelium from short term culture; IOSE, SV40-immortalized ovarian surface epithelium; ML10, SV40-immortalized benign cystadenoma; OVT6, OVT7, and OVT8, primary ovarian serous adenocarcinomas; OV1063, A2780, and ES2, ovarian cancer cell lines; POOL, a pool of ten ovarian cancer cell lines.
[b]Tag numbers after elimination of linker-based tags and duplicate ditags.
[c]The number of unique tags identified in each library.
[d]The number of genes identified after correction for sequencing errors.
[e]The number of genes represented at least twice.

Comparison of Global Gene Expression Between Ovarian Tissue Samples

Although progression to malignancy requires a number of gene expression changes, the transcript levels from the vast majority of genes remain unaltered (Zhang, L., et al., Science 276:1268-1272, 1997; and Alon, U., et al., Proc. Natl Acad. Sci. USA 96:6745-6750, 1999). Similarities between the global expression profiles of two given samples can be readily visualized using scatterplots and quantitated through the calculation of Pearson correlation coefficients. Scatterplots of global gene expression analysis in lOSE (ovarian) vs. ML10 (ovarian), OVT6 (ovarian), or Tu98 (colon) cells were generated using the Spotfire® Pro 4.0 software (Cambridge, Mass.) and the Pearson correlation coefficients for each pair-wise comparison of the 16 ovarian and colon SAGE libraries were calculated.

As expected, the immortalized IOSE29 and ovarian cystadenoma strain ML10 are much more similar to ovarian tumors than to colon tumors (average correlation coefficients of 0.70 vs. 0.51, respectively). In addition, IOSE29 and ML10 are very similar to each other, with a correlation coefficient of 0.82. The primary culture of OSE cells (HOSE-4) exhibited higher similarities to the ovarian tumors than to the colon tumors, although the similarity levels were much lower than those observed for IOSE29. Interestingly, HOSE-4 and IOSE29 appear to be much more distantly related than expected considering the fact that they were both derived from "normal" OSE cells. The differences in gene expression between these cells may be due to a number of factors. The age of the patient, the pathological state of the ovaries, the presence of non-epithelial cells in the culture and the fact that IOSE29 is SV40-immortalized may all contribute to the gene expression differences observed. However, it is unlikely that the main differences are due to SV40-immortalization since IOSE29 is much more similar to normal colon (a non SV40-immortalized epithelium) than HOSE-4. It is, of course, possible that the lower degree of similarity between HOSE-4 and the ovarian tumors compared to IOSE29 and ML-10 reflects the fact that HOSE-4 represents a better approximation of the normal in vivo OSE cell.

Three dendrograms were created from hierarchical cluster analysis of all colon and ovarian SAGE libraries, ovarian samples only, and non-malignant ovarian and colon epithelia as well as ovarian and colon primary tumors, using Cluster software (Eisen, M. B., et al. *Proc. Natl. Acad. Sci USA* 95:14863-14868, 1998). When all the samples were included in the hierarchical clustering analysis, the primary colon tumors clustered with the normal colon epithelium, but colon cell lines clustered with the ovarian specimens. Clearly, the tissue clustering that was readily apparent when comparing primary tissues or immortalized lines was lost when including carcinoma cell lines. For example, A2780, a widely used ovarian cancer cell line was just as similar to colon cancer cell lines as it was to ovarian cancer cell lines. This observation supports the idea that in the process of establishment, cell lines may lose many of the gene expression characteristics of their tissue of origin, although tissue specific expression is clearly not completely lost in cancer cell lines (Ross, D. T., et al. *Nat. Genet.* 24:227-235,2000).

It is widely believed that epithelial ovarian cancer and benign ovarian cysts, while not necessarily part of a progression sequence toward malignancy, are both derived from the ovarian surface epithelium (Scully, R. E. *J. Cell Biochem.* 23, Suppl.: 208-218, 1995). OSE cells themselves are mesodermal in origin and are believed to undergo metaplasia before progressing to neoplasia (Scully, R. E. *J. Cell Biochem.* 23 Suppl.: 208-218, 1995; and Maines-Bandiera, S. L. and Auersperg, N. *Int. J. Gynecol. Pathol.* 16:250-255, 1997). On the other hand, it has also been argued that ovarian cancers are not derived from OSE but rather from the secondary Mullerian system, structures lined by Mullerian epithelium but located outside the uterus, cervix and fallopian tubes (Schink, J. C. *Semin. Oncol.* 26 Suppl. 1: 2-7, 1999). This hypothesis would explain some of the shortcomings of the OSE model, such as the requirement for metaplasia and the lack of well-defined precursors in the ovary. While not wishing to be bound by theory, our results are consistent with the widely accepted dogma of the OSE origin of ovarian cancer. Indeed, IOSE29 showed high degrees of similarity to the ovarian tumors and both IOSE29 and HOSE were much more closely related to ovarian than colon primary cancers.

E-cadherin expression has been proposed to be a major determinant in the formation of metaplastic OSE (Auersperg, N., et al. *Proc. Natl Acad. Sci. USA,* 96:6249-6254, 1999; and Maines-Bandiera, S. L. and Auersperg, N. *Int. J. Gynecol. Pathol.* 16:250-255, 1997). Consistent with this hypothesis, E-cadherin was absent in IOSE29, HOSE and ML10 but was expressed in all three ovarian tumors (Table 4). Other cadherins are also shown for comparison. Interestingly, VE-cadherin is absent in most libraries except in two of the pre-neoplastic ovarian samples, again suggesting metaplasia As expected, LI-Cadherin was expressed exclusively in the colon-derived libraries. Interestingly, vimentin, a mesenchymal marker, was present in essentially all the ovarian libraries but very low in the colon specimens. Although the specificity of vimentin as a mesenchymal marker has been questioned, this suggests that OSE may retain some of their mesenchymal characteristics, even after turning on the expression of E-cadherin.

The cytokeratins (CKs) and carcinoembryonic antigen (CEA) have been used to differentiate between colon cancer and ovarian cancer (Lagendijk, J. H., et al. *Hum. Pathol.* 29:491-497, 1998; and Berezowski, K., et al. *Mod. Pathol.* 9:426-429, 1996). Typically, colon cancer expresses CK20 and CEA while ovarian cancer expresses CK7. The expression patterns in our libraries were consistent with previously reported observations: CK20 and CEA were found in normal colon and colon tumors but absent from all of our ovarian samples (Table 4). Conversely, CK7 was expressed in all three primary ovarian tumors and, while not absent, was much lower in the colon samples. Examination of the differential expression patterns of a variety of established ovarian cancer markers thus provided validation of the SAGE database and cluster analysis.

Differential Gene Expression

The ultimate goal of comparing SAGE libraries is to identify differentially expressed genes. Criteria for differential expression can be determined for each comparison and transcripts within the determined range selected for study. We found a large number of genes that were up-regulated in only one or two of the three tumors on which SAGE was performed. For example, a total of 444 genes were up-regulated more than 10-fold in at least one of the three ovarian primary cancers compared to IOSE29. However, only 45 genes were overexpressed more than 10-fold in all three ovarian tumors analyzed compared to IOSE29.

Our analysis of three different primary ovarian cancers allowed us to reduce the number of candidates by looking for consistency between samples. In order to identify genes that are very likely to be frequently up-regulated during ovarian tumorigenesis we set the following conservative criteria for our analysis. First, the fold induction was calculated by adding the number of normalized tags from the three primary tumors and dividing this number by the total normalized tags in the three non-malignant specimens. Cell lines were not included here for reasons described above. In addition, although HOSE-4 appeared more distantly related to the other non-transformed specimens, we believe that the inclusion of HOSE-4, while possibly eliminating real candidates makes our analysis more conservative and more likely to identify truly overexpressed genes in ovarian cancer. Second, all three primary tumors were required to consistently show elevated levels (>12 tags/100,000) of the gene in question. This eliminated genes that may be very highly overexpressed in one tumor but not in others. Finally, the candidate genes were required to be expressed in at least one ovarian cell line at a level greater than 3 tags/100,000. This last criterion was used to reduce the possibility of identifying genes because of their high level of expression in inflammatory cells or in the stroma of the primary tumors. Using these criteria, the genes that exhibited more than 10-fold overexpression were identified and are shown in Table 4.

Two members of the Claudin family of tight junction proteins, Claudin-3 and 4 were found among the top six differentially expressed genes and likely represent transmembrane receptors. In addition, Apolipoprotein J (ApoJ) and Apolipoprotein E (ApoE) were both overexpressed in ovarian cancer.

Of the 27 overexpressed genes shown in Table 4, ten were relatively specific for the ovary (HLA-DR, two different ESTs, GA733-1, ceruloplasmin, glutathione peroxidase-3, the secretory leukocyte protease inhibitor, ApoJ, ApoE and mesothelin) while the others were also expressed in colon tissues. In any event, it is significant that MUC1, HE4, Ep-CAM and mesothelin, four genes already known to be up-regulated in epithelial ovarian cancer, were identified in this study. This fact validates our approach as well as our set of criteria used to determine the genes differentially expressed.

Similarly, stringent criteria were used to identify genes down-regulated in ovarian tumors compared to IOSE29, HOSE-4 and ML10. Again, the fold difference was calculated by adding tag frequency for all three "normal" specimens and dividing by the total number of tags in the three ovarian tumors. A candidate was required to be expressed at a level of 12 tags/100,000 or greater in all three normal samples. The genes found elevated more than ten-fold in normal tissue compared to tumors are shown in Table 4.

TABLE 4

A subset of genes differentially expressed in ovarian tumors compared to non-malignant ovarian samples

| SEQ ID NO. (TAG) | TAG | GENE | Fold | OSE ML10 | Ovarian Tumors | Colon Epithelium | Colon Tumors | FUNCTION |
|---|---|---|---|---|---|---|---|---|
| | | up-regulated[a] | | | | | | |
| 103 | GGGCATCTCT | HLA-DR α chain | 289 | − | ++ | − | − | Major histocompatibility complex, class II/antigen presentation |
| 104 | TTTGGGCCTA | Cysteine-rich protein 1 | 123 | − | ++ | + | − | LIM/double zinc finger |
| 105 | ATCGTGGCGG | Claudin 4 | 109 | − | + | ++ | + | Tight junction barrier function |
| 106 | TATTATGGTA | ESTs (HOST-2) | 101 | − | + | − | − | Unknown |
| 107 | GCCTACCCGA | Surface marker 1/GA733-1/TROP2 | 93 | − | + | − | − | Tumor Ag/$Ca^{2+}$ signal transducer |
| 108 | CTCGCGCTGG | Claudin 3 | 83 | − | + | ++ | + | Tight junction barrier function |
| 109 | TTGCTTGCCA | Ceruloplasmin (ferroxidase) | 79 | − | + | − | − | Secreted metalloprotein/antioxidant |
| 110 | CCTGCTTGTC | HE4 | 72 | − | ++ | + | − | Secreted protease inhibitor |
| 111 | AGGGAGGGGC | Glutathione peroxidase 3 (plasma) | 69 | − | + | − | − | Secreted selenoprotein/peroxidase |
| 112 | TGTGGGAAAT | Secretory leukocyte protease inhibitor | 60 | − | ++ | − | − | Secreted serine protease inhibitor |
| 113 | CCTGATCTGC | ESTs (HOST-1) | 56 | − | + | − | − | Unknown |
| 114 | ACCATTGGAT | Interferon-induced transmembrane protein 1 | 49 | − | ++ | − | + | Receptor for interferon signaling |
| 115 | AGTTTGTTAG | Ep-CAM/EGP2/TROP1/GA733-2 | 48 | − | + | ++ | + | Tumor Ag/$Ca^{2+}$-independant CAM/proliferation |
| 116 | CCTGGGAAGT | Mucin 1 | 43 | − | ++ | + | + | Tumor Ag/Type-I membrane glycoprotein |
| 117 | CAACTAATTC | Apolipoprotein J/clusterin | 39 | − | ++ | − | − | Secreted chaperone/cytoprotection |
| 118 | GCCTGCAGTC | Serine protease inhibitor, Kunitz type, 2 | 34 | − | ++ | ++ | + | Transmembrane/protease inhibitor |
| 119 | CGACCCCACG | Apolipoprotein E | 34 | − | ++ | − | − | Lipoprotein particle binding, internalization and catabolism |
| 120 | TTCTGTGCTG | Complement component 1, r subcomponent | 24 | − | + | − | − | Serine protease of complement system/autoimmune diseases |
| 121 | CGCCGACGAT | G1P3/IFI-6-16 | 24 | − | ++ | + | + | Interferon primary response/α IFN-inducible |
| 122 | CCCGCCCCCG | Lutheran blood group protein/BCAM | 17 | − | ++ | − | − | Possible cell surface receptor/immunoglobulin superfamily |
| 123 | GATCAGGCCA | Collagen Type III, alpha-1 | 16 | − | ++ | − | + | Unknown |
| 124 | GTGGAAGACG | Mal (T cell differentiation protein) | 16 | − | + | − | − | Trans-Golgi membrane protein (epithelial cells)/T-cell differentiation |

TABLE 4-continued

A subset of genes differentially expressed in ovarian tumors compared to non-malignant ovarian samples

| SEQ ID NO. (TAG) | TAG | GENE | Fold | EXPRESSION[c] OSE ML10 | Ovarian Tumors | Colon Epithelium | Colon Tumors | FUNCTION |
|---|---|---|---|---|---|---|---|---|
| 124 | GATGAGGAGA | ESTs (Collagen Type I, alpha-2 | 13 | + | ++ | − | + | Unknown |
| 126 | TTCCCTTCTT | HLA-DPB1 | 13 | − | + | − | − | Major histocompatibility complex, class II/antigen presentation |
| 127 | CCCCCTGCAG | Mesothelin | 12 | − | ++ | − | − | GPI-anchored/mesothelioma and ovarian cancer antigen/cell adhesion |
| 128 | TGCTGCCTGT | Bone marrow stroma antigen 2/BST-2 | 12 | − | ++ | − | + | Type II transmembrane protein/pre-B-cell growth |
| 129 | TGCAGCACGA | HLA-Cw | 10 | − | ++ | ++ | + | Major histocompatibility complex, class I/antigen presentation |
| down-regulated[b] | | | | | | | | |
| 130 | GGTTATTTTG | Unknown | 99 | + | − | − | − | Unknown |
| 131 | TGTCATCACA | Lysyl oxidase-like 2 | 73 | + | − | − | − | Secreted/collagen and elastin crosslinker |
| 132 | AAAATAAACA | Chloride intracellular channel 4 like | 29 | + | − | − | − | Ion transport |
| 133 | TAAAAATGTT | Plasminogen activator inhibitor, type 1 | 26 | ++ | − | − | − | Serine protease inhibitor family/tPA inhibitor |
| 134 | GAGCTTTTGA | EST | 14 | + | − | − | − | Unknown |
| 135 | GGCTGATGTG | Glycine-t-RNA synthetase | 13 | + | − | − | − | Protein synthesis |
| 136 | CGACGAGGAG | Epithelial membrane protein-3 | 13 | + | − | − | − | Proliferation, differentiation, and apoptosis |
| 137 | GCCCCCAATA | Galectin-1 | 10 | ++ | + | − | − | β-galactoside binding lectin/ECM interaction and proliferation |
| 138 | GCAACTTGGA | Vinexin β | 10 | + | − | − | − | Cell-adhesion and cytoarchitecture |

[a]Candidates up-regulated at least 30-fold in tumors
[b]Candidates down-regulated at least 10-fold in tumors
[c]Expression is defined as: −, 0–9 tags/100,000; +, 10–49 tags/100,000; ++, >49 tags/100,000

In order to validate the candidates identified by SAGE, we performed immunohistochemical analysis of thirteen cases of serous cancer of the ovary using antibodies against four of the genes identified as up-regulated in ovarian cancer (Table 5). This was particularly important since the SAGE analysis was initially performed from primary ovarian cancers, which contain a mixture of cell types. Ep-CAM exhibited diffuse, strong staining of tumor cell membranes in all thirteen tumors, without blood cell or stromal staining. Importantly, only one of six samples of the ovarian surface epithelium present in the cases showed weak focal staining, and the rest were negative. The strong immunoreactivity of all thirteen ovarian tumors confirms the validity of our approach to identify genes highly and consistently up-regulated in ovarian cancer. Similarly, ApoJ was found to be expressed in ovarian cancer cells and absent from the surface epithelium. While some expression was detected in non-tumor stroma and inflammatory cells, most of the immuno-reactivity was in tumor cells, and a majority (nine out of thirteen) of the cases showed staining. This observation represents the first report of ApoJ expression in ovarian cancer and provides a novel target for diagnosis or therapy. Claudin-3 and -4 also exhibited staining limited to the tumor component of the specimens. Most tumor cells showed strong membrane staining with weak cytoplasmic reactivity. Some tumors specimens showed decreased membrane staining with strong cytoplasmic reactivity. The normal surface epithelial component (or mesothelial cells) examined did not stain or only stained weakly with the Claudin-4 antibody, while the determination of Claudin-3 levels in normal epithelium was complicated by a low background reactivity with this antibody.

Incorporation by Reference

Throughout this application, various publications, patents, and/or patent applications are referenced in order to more fully describe the state of the art to which this invention pertains. The disclosures of these publications, patents, and/or patent applications are herein incorporated by reference in their entireties to the same extent as if each independent publication, patent, and/or patent application was specifically and individually indicated to be incorporated by reference.

OTHER EMBODIMENTS

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for detecting an ovarian carcinoma in a subject comprising, acquiring a first sample of ovarian tissue from the subject, measuring the amount of claudin-3 present in the first sample and comparing said measurement from said first sample with a value determined by measuring the amount of claudin-3 in a second sample of non-cancerous ovarian epithelium, wherein an increase in the amount of claudin-3 in the first sample, as compared to the amount of claudin-3 in the second sample indicates the presence of ovarian carcinoma cells in the first sample.

2. The method of claim 1, wherein said first sample is selected from the group consisting of an ovarian tissue biopsy and ovarian epithelial cell scrapings.

3. The method of claim 1, wherein the first sample comprises suspected ovarian carcinoma tissue.

4. The method of claim 1, wherein said second sample is selected from the group consisting of an ovarian tissue biopsy and ovarian epithelial cell scrapings.

* * * * *

SEQUENCE LISTING

<160> NUMBER OF SEQ ID NOS: 147

<210> SEQ ID NO 1
<211> LENGTH: 490
<212> TYPE: DNA
<213> ORGANISM: Homo sapiens

<400> SEQUENCE: 1

| | | | | | |
|---|---|---|---|---|---|
| tccttgcccg | ccgcagtcgc | ctccgccgcg | cgcctcctcc | gccgccgcgg | actccggcag | 60 |
| ctttatcgcc | agagtccctg | aactctcgct | ttcttttttaa | tccctgcat | cggatcaccg | 120 |
| gcgtgcccca | ccatgtcaga | cgcagccgta | gacaccagct | ccgaaatcac | caccaaggac | 180 |
| ttaaaggaga | agaaggaagt | tgtggaagag | gcagaaaatg | gaagagacgc | ccctgctaac | 240 |
| gggaatgcta | atgaggaaaa | cggggagcag | gaggctgaca | atgaggtaga | cgaagaagag | 300 |
| gaagaaggtg | gggaggaaga | ggaggaggaa | gaagaaggtg | atggtgagga | agaggatgga | 360 |
| gatgaagatg | aggaagctga | gtcagctacg | ggcaagcggg | cagctgaaga | tgatgaggat | 420 |
| gacgatgtcg | ataccaagaa | gcagaagacc | gacgaggatg | actagacagc | aaaaaaggaa | 480 |
| aagttaaact | | | | | | 490 |

<210> SEQ ID NO 2
<211> LENGTH: 110
<212> TYPE: PRT
<213> ORGANISM: Homo sapiens

<400> SEQUENCE: 2

Met Ser Asp Ala Ala Val Asp Thr Ser Ser Glu Ile Thr Thr Lys Asp
1               5                   10                  15
Leu Lys Glu Lys Lys Glu Val Val Glu Glu Ala Glu Asn Gly Arg Asp
            20                  25                  30
Ala Pro Ala Asn Gly Asn Ala Asn Glu Glu Asn Gly Glu Gln Glu Ala
        35                  40                  45
Asp Asn Glu Val Asp Glu Glu Glu Glu Gly Gly Glu Glu Glu Glu
    50                  55                  60
Glu Glu Glu Glu Gly Asp Gly Glu Glu Glu Asp Gly Asp Glu Asp
65                  70                  75                  80
Glu Ala Glu Ser Ala Thr Gly Lys Arg Ala Ala Glu Asp Asp Glu Asp
                85                  90                  95
Asp Asp Val Asp Thr Lys Lys Gln Lys Thr Asp Glu Asp Asp
                100                 105                 110

<210> SEQ ID NO 3
<211> LENGTH: 1093
<212> TYPE: DNA
<213> ORGANISM: Homo sapiens

<400> SEQUENCE: 3

| | | | | | |
|---|---|---|---|---|---|
| ctgcaaggcg | gcggcaggag | aggttgtggt | gctagtttct | ctaagccatc | cagtgccatc | 60 |
| ctcgtcgctg | cagcgacacc | gctctcgccg | ccgccatgac | tgagcagatg | acccttcgtg | 120 |
| gcaccctcaa | gggccacaac | ggctgggtaa | cccagatcgc | tactaccccg | cagttcccgg | 180 |
| acatgatcct | ctccgcctct | cgagataaga | ccatcatcat | gtggaaactg | accagggatg | 240 |
| agaccaacta | tggaattcca | cagcgtgctc | tgcgggtca | ctcccacttt | gttagtgatg | 300 |
| tggttatctc | ctcagatggc | cagttttgccc | tctcaggctc | ctgggatgga | accctgcgcc | 360 |
| tctgggatct | cacaacgggc | accaccacga | ggcgatttgt | gggccatacc | aaggatgtgc | 420 |

-continued

```
tgagtgtggc cttctcctct gacaaccggc agattgtctc tggatctcga gataaaacca    480
tcaagctatg gaataccctg ggtgtgtgca atacactgt ccaggatgag agccactcag    540
agtgggtgtc ttgtgtccgc ttctcgccca acagcagcaa ccctatcatc gtctcctgtg    600
gctgggacaa gctggtcaag gtatggaacc tggctaactg caagctgaag accaaccaca    660
ttggccacac aggctatctg aacacggtga ctgtctctcc agatggatcc ctctgtgctt    720
ctggaggcaa ggatggccag gccatgttat gggatctcaa cgaaggcaaa cacctttaca    780
cgctagatgg tggggacatc atcaacgccc tgtgcttcag ccctaaccgc tactggctgt    840
gtgctgccac aggccccagc atcaagatct gggatttaga gggaaagatc attgtagatg    900
aactgaagca agaagttatc agtaccagca gcaaggcaga accacccag tgcacttccc    960 tggcctggtc tgctgatggc cagactctgt tgctggcta cacggacaac ctggtgcgag   1020
tgtggcaggt gaccattggc acacgctaga agtttatggc agagctttac aaataaaaaa   1080
aaaatggctt ttc                                                       1093
```

<210> SEQ ID NO 4
<211> LENGTH: 317
<212> TYPE: PRT
<213> ORGANISM: Homo sapiens

<400> SEQUENCE: 4

```
Met Thr Glu Gln Met Thr Leu Arg Gly Thr Leu Lys Gly His Asn Gly
  1               5                  10                  15

Trp Val Thr Gln Ile Ala Thr Thr Pro Gln Phe Pro Asp Met Ile Leu
             20                  25                  30

Ser Ala Ser Arg Asp Lys Thr Ile Ile Met Trp Lys Leu Thr Arg Asp
         35                  40                  45

Glu Thr Asn Tyr Gly Ile Pro Gln Arg Ala Leu Arg Gly His Ser His
     50                  55                  60

Phe Val Ser Asp Val Val Ile Ser Ser Asp Gly Gln Phe Ala Leu Ser
 65                  70                  75                  80

Gly Ser Trp Asp Gly Thr Leu Arg Leu Trp Asp Leu Thr Thr Gly Thr
                 85                  90                  95

Thr Thr Arg Arg Phe Val Gly His Thr Lys Asp Val Leu Ser Val Ala
            100                 105                 110

Phe Ser Ser Asp Asn Arg Gln Ile Val Ser Gly Ser Arg Asp Lys Thr
        115                 120                 125

Ile Lys Leu Trp Asn Thr Leu Gly Val Cys Lys Tyr Thr Val Gln Asp
    130                 135                 140

Glu Ser His Ser Glu Trp Val Ser Cys Val Arg Phe Ser Pro Asn Ser
145                 150                 155                 160

Ser Asn Pro Ile Ile Val Ser Cys Gly Trp Asp Lys Leu Val Lys Val
                165                 170                 175

Trp Asn Leu Ala Asn Cys Lys Leu Lys Thr Asn His Ile Gly His Thr
            180                 185                 190

Gly Tyr Leu Asn Thr Val Thr Val Ser Pro Asp Gly Ser Leu Cys Ala
        195                 200                 205

Ser Gly Gly Lys Asp Gly Gln Ala Met Leu Trp Asp Leu Asn Glu Gly
    210                 215                 220

Lys His Leu Tyr Thr Leu Asp Gly Gly Asp Ile Ile Asn Ala Leu Cys
225                 230                 235                 240

Phe Ser Pro Asn Arg Tyr Trp Leu Cys Ala Ala Thr Gly Pro Ser Ile
```

-continued

```
               245                 250                 255
Lys Ile Trp Asp Leu Glu Gly Lys Ile Ile Val Asp Glu Leu Lys Gln
            260                 265                 270

Glu Val Ile Ser Thr Ser Ser Lys Ala Glu Pro Gln Cys Thr Ser
        275                 280                 285

Leu Ala Trp Ser Ala Asp Gly Gln Thr Leu Phe Ala Gly Tyr Thr Asp
    290                 295                 300

Asn Leu Val Arg Val Trp Gln Val Thr Ile Gly Thr Arg
305                 310                 315
```

<210> SEQ ID NO 5
<211> LENGTH: 2402
<212> TYPE: DNA
<213> ORGANISM: Homo sapiens

<400> SEQUENCE: 5

| | | | | | |
|---|---|---|---|---|---|
| agtctccgcc | gccgccgtga | acatggagcc | cccggacgca | ccggcccagg | cgcgcgggc | 60 |
| cccgcggctg | ctgttgctcg | cagtcctgct | ggcggcgcac | ccagatgccc | aggcggaggt | 120 |
| gcgcttgtct | gtaccccgc | tggtggaggt | gatgcgagga | aagtctgtca | ttctggactg | 180 |
| caccccctacg | ggaacccacg | accattatat | gctggaatgg | ttccttaccg | accgctcggg | 240 |
| agctcgcccc | cgcctagcct | cggctgagat | gcagggctct | gagctccagg | tcacaatgca | 300 |
| cgacacccgg | gccgcagtc | ccccataccaa | gctggactcc | aggggcgcc | tggtgctggc | 360 |
| tgaggcccag | gtgggcgacg | agcgagacta | cgtgtgcgtg | gtgagggcag | gggcggcagg | 420 |
| cactgctgag | gccactgcgc | ggctcaacgt | gtttgcaaag | ccagaggcca | ctgaggtctc | 480 |
| ccccaacaaa | gggacactgt | ctgtgatgga | ggactctgcc | caggagatcg | ccacctgcaa | 540 |
| cagccggaac | gggaacccgg | cccccaagat | cacgtggtat | cgcaacgggc | agcgcctgga | 600 |
| ggtgcccgta | gagatgaacc | cagagggcta | catgaccagc | cgcacggtcc | gggaggcctc | 660 |
| gggcctgctc | tccctcacca | gcaccctcta | cctgcggctc | cgcaaggatg | accgagacgc | 720 |
| cagcttccac | tgcgccgccc | actacagcct | gcccgagggc | cgccacgcc | gcctggacag | 780 |
| ccccaccttc | cacctcaccc | tgcactatcc | cacggagcac | gtgcagttct | gggtgggcag | 840 |
| cccgtccacc | ccagcaggct | gggtacgcga | gggtgacact | gtccagctgc | tctgccgggg | 900 |
| ggacggcagc | cccagcccgg | agtatacgct | tttccgcctt | caggatgagc | aggaggaagt | 960 |
| gctgaatgtg | aatctcgagg | ggaacttgac | cctggaggga | gtgacccggg | gccagagcgg | 1020 |
| gacctatgc | tgcagagtgg | aggattacga | cgcggcagat | gacgtgcagc | tctccaagac | 1080 |
| gctggagctg | cgcgtggcct | atctggaccc | cctggagctc | agcgagggga | aggtgctttc | 1140 |
| cttacctcta | aacagcagtg | cagtcgtgaa | ctgctccgtg | cacggcctgc | ccacccctgc | 1200 |
| cctacgctgg | accaaggact | ccactcccct | gggcgatggc | ccatgctgt | cgctcagttc | 1260 |
| tatcaccttc | gattccaatg | gcacctacgt | atgtgaggcc | tccctgccca | gtcccggt | 1320 |
| cctcagccgc | acccagaact | tcacgctgct | ggtccaaggc | tcgccagagc | taaagacagc | 1380 |
| ggaaatagag | cccaaggcag | atggcagctg | gagggaagga | gacgaagtca | cactcatctg | 1440 |
| ctctgcccgc | ggccatccag | accccaaact | cagctggagc | caattggggg | cagccccgc | 1500 |
| agagccaatc | cccggacggc | agggttgggt | gagcagctct | ctgaccctga | agtgaccag | 1560 |
| cgccctgagc | cgcgatggca | tctcctgtga | agcctccaac | ccccacggga | caagcgcca | 1620 |
| tgtcttccac | ttcggcgccg | tgagccccca | gacctcccag | gctggagtgg | ccgtcatggc | 1680 |
| cgtggccgtc | agcgtgggcc | tcctgctcct | cgtcgttgct | gtcttctact | gcgtgagacg | 1740 |

-continued

```
caaaggggc ccctgctgcc gccagcggcg ggagaagggg gctccgccgc caggggagcc      1800
agggctgagc cactcggggt cggagcaacc agagcagacc ggccttctca tgggaggtgc      1860
ctccggagga gccaggggtg gcagcggggg cttcggagac gagtgctgag ccaagaacct      1920
cctagaggct gtccctggac ctggagctgc aggcatcaga gaaccagccc tgctcacgcc      1980
atgcccgccc ccgccttccc tcttccctct ccctctcccc tgcccagccc tcccttcctt      2040
cctctgccgg caaggcaggg acccacagtg gctgcctgcc tccgggaggg aaggagaggg      2100
agggtgggtg ggtgggaggg ggccttcctc cagggaatgt gactctccca ggccccagaa      2160
tagctcctgg acccaagccc aaggcccagc ctgggacaag gctccgaggg tcggctggcc      2220
ggagctattt ttacctcccg cctcccctgc tggtccccccc acctgacgtc ttgctgcaga      2280
gtctgacact ggattccccc ccctcacccc gcccctggtc ccactcctgc cccgcccta       2340 cctccgcccc accccatcat ctgtggacac tggagtctgg aataaatgct gtttgtcaca      2400
tc                                                                     2402
```

<210> SEQ ID NO 6
<211> LENGTH: 628
<212> TYPE: PRT
<213> ORGANISM: Homo sapiens

<400> SEQUENCE: 6

```
Met Glu Pro Pro Asp Ala Pro Ala Gln Ala Arg Gly Ala Pro Arg Leu
 1               5                  10                  15

Leu Leu Leu Ala Val Leu Ala Ala His Pro Asp Ala Gln Ala Glu
             20                  25                  30

Val Arg Leu Ser Val Pro Pro Leu Val Glu Val Met Arg Gly Lys Ser
         35                  40                  45

Val Ile Leu Asp Cys Thr Pro Thr Gly Thr His Asp His Tyr Met Leu
     50                  55                  60

Glu Trp Phe Leu Thr Asp Arg Ser Gly Ala Arg Pro Arg Leu Ala Ser
 65                  70                  75                  80

Ala Glu Met Gln Gly Ser Glu Leu Gln Val Thr Met His Asp Thr Arg
                 85                  90                  95

Gly Arg Ser Pro Pro Tyr Gln Leu Asp Ser Gln Gly Arg Leu Val Leu
            100                 105                 110

Ala Glu Ala Gln Val Gly Asp Glu Arg Asp Tyr Val Cys Val Val Arg
        115                 120                 125

Ala Gly Ala Ala Gly Thr Ala Glu Ala Thr Ala Arg Leu Asn Val Phe
    130                 135                 140

Ala Lys Pro Glu Ala Thr Glu Val Ser Pro Asn Lys Gly Thr Leu Ser
145                 150                 155                 160

Val Met Glu Asp Ser Ala Gln Glu Ile Ala Thr Cys Asn Ser Arg Asn
                165                 170                 175

Gly Asn Pro Ala Pro Lys Ile Thr Trp Tyr Arg Asn Gly Gln Arg Leu
            180                 185                 190

Glu Val Pro Val Glu Met Asn Pro Glu Gly Tyr Met Thr Ser Arg Thr
        195                 200                 205

Val Arg Glu Ala Ser Gly Leu Leu Ser Leu Thr Ser Thr Leu Tyr Leu
    210                 215                 220

Arg Leu Arg Lys Asp Asp Arg Asp Ala Ser Phe His Cys Ala Ala His
225                 230                 235                 240

Tyr Ser Leu Pro Glu Gly Arg His Gly Arg Leu Asp Ser Pro Thr Phe
```

```
                245                 250                 255
His Leu Thr Leu His Tyr Pro Thr Glu His Val Gln Phe Trp Val Gly
            260                 265                 270

Ser Pro Ser Thr Pro Ala Gly Trp Val Arg Glu Gly Asp Thr Val Gln
        275                 280                 285

Leu Leu Cys Arg Gly Asp Gly Ser Pro Ser Pro Glu Tyr Thr Leu Phe
    290                 295                 300

Arg Leu Gln Asp Glu Gln Glu Glu Val Leu Asn Val Asn Leu Glu Gly
305                 310                 315                 320

Asn Leu Thr Leu Glu Gly Val Thr Arg Gly Gln Ser Gly Thr Tyr Gly
                325                 330                 335

Cys Arg Val Glu Asp Tyr Asp Ala Ala Asp Asp Val Gln Leu Ser Lys
            340                 345                 350

Thr Leu Glu Leu Arg Val Ala Tyr Leu Asp Pro Leu Glu Leu Ser Glu
        355                 360                 365

Gly Lys Val Leu Ser Leu Pro Leu Asn Ser Ser Ala Val Val Asn Cys
    370                 375                 380

Ser Val His Gly Leu Pro Thr Pro Ala Leu Arg Trp Thr Lys Asp Ser
385                 390                 395                 400

Thr Pro Leu Gly Asp Gly Pro Met Leu Ser Leu Ser Ser Ile Thr Phe
                405                 410                 415

Asp Ser Asn Gly Thr Tyr Val Cys Glu Ala Ser Leu Pro Thr Val Pro
            420                 425                 430

Val Leu Ser Arg Thr Gln Asn Phe Thr Leu Leu Val Gln Gly Ser Pro
        435                 440                 445

Glu Leu Lys Thr Ala Glu Ile Glu Pro Lys Ala Asp Gly Ser Trp Arg
    450                 455                 460

Glu Gly Asp Glu Val Thr Leu Ile Cys Ser Ala Arg Gly His Pro Asp
465                 470                 475                 480

Pro Lys Leu Ser Trp Ser Gln Leu Gly Gly Ser Pro Ala Glu Pro Ile
                485                 490                 495

Pro Gly Arg Gln Gly Trp Val Ser Ser Ser Leu Thr Leu Lys Val Thr
            500                 505                 510

Ser Ala Leu Ser Arg Asp Gly Ile Ser Cys Glu Ala Ser Asn Pro His
        515                 520                 525

Gly Asn Lys Arg His Val Phe His Phe Gly Ala Val Ser Pro Gln Thr
    530                 535                 540

Ser Gln Ala Gly Val Ala Val Met Ala Val Ala Val Ser Val Gly Leu
545                 550                 555                 560

Leu Leu Leu Val Val Ala Val Phe Tyr Cys Val Arg Arg Lys Gly Gly
                565                 570                 575

Pro Cys Cys Arg Gln Arg Arg Glu Lys Gly Ala Pro Pro Gly Glu
            580                 585                 590

Pro Gly Leu Ser His Ser Gly Ser Glu Gln Pro Glu Gln Thr Gly Leu
        595                 600                 605

Leu Met Gly Gly Ala Ser Gly Gly Ala Arg Gly Gly Ser Gly Gly Phe
    610                 615                 620

Gly Asp Glu Cys
625

<210> SEQ ID NO 7
<211> LENGTH: 2780
<212> TYPE: DNA
<213> ORGANISM: Homo sapiens
```

<400> SEQUENCE: 7

```
gtgggcggac cgcgcggctg gaggtgtgag gatccgaacc caggggtggg gggtggaggc      60
ggctcctgcg atcgaagggg acttgagact caccggccgc acgccatgag ggccctgtgg     120
gtgctgggcc tctgctgcgt cctgctgacc ttcgggtcgg tcagagctga cgatgaagtt     180
gatgtggatg gtacagtaga agaggatctg ggtaaaagta gagaaggatc aaggacggat     240
gatgaagtag tacagagaga ggaagaagct attcagttgg atggattaaa tgcatcacaa     300
ataagagaac ttagagagaa gtcggaaaag tttgccttcc aagccgaagt taacagaatg     360
atgaaactta tcatcaattc attgtataaa aataaagaga ttttcctgag agaactgatt     420
tcaaatgctt ctgatgcttt agataagata aggctaatat cactgactga tgaaaatgct     480
ctttctggaa atgaggaact aacagtcaaa attaagtgtg ataaggagaa gaacctgctg     540
catgtcacag acaccggtgt aggaatgacc agagaagagt tggttaaaaa ccttggtacc     600
atagccaaat ctgggacaag cgagttttta aacaaaatga ctgaagcaca ggaagatggc     660
cagtcaactt ctgaattgat tggccagttt ggtgtcggtt tctattccgc cttccttgta     720
gcagataagg ttattgtcac ttcaaaacac aacaacgata cccagcacat ctgggagtct     780
gactccaatg aatttttctgt aattgctgac ccaagaggaa acactctagg acggggaacg     840
acaattaccc ttgtcttaaa agaagaagca tctgattacc ttgaattgga tacaattaaa     900
aatctcgtca aaaatattc acagttcata actttccta tttatgtatg gagcagcaag     960
actgaaactg ttgaggagcc catggaggaa gaagaagcag ccaaagaaga gaagaagaa    1020
tctgatgatg aagctgcagt agaggaagaa gaagaagaaa agaaaccaaa gactaaaaaa    1080
gttgaaaaaa ctgtctggga ctgggaactt atgaatgata tcaaaccaat atggcagaga    1140
ccatcaaaag aagtagaaga agatgaatac aaagctttct acaaatcatt ttcaaaggaa    1200
agtgatgacc ccatggctta tattcacttt actgctgaag gggaagttac cttcaaatca    1260
atttttatttg tacccacatc tgctccacgt ggtctgtttg acgaatatgg atctaaaaag    1320
agcgattaca ttaagctcta tgtgcgccgt gtattcatca cagacgactt ccatgatatg    1380
atgcctaaat acctcaattt tgtcaagggt gtggtggact cagatgatct cccccttgaat    1440
gtttcccgcg agactcttca gcaacataaa ctgcttaagg tgattaggaa gaagcttgtt    1500
cgtaaaacgc tggacatgat caagaagatt gctgatgata aatacaatga tactttttgg    1560
aaagaatttg gtaccaacat caagcttggt gtgattgaag accactcgaa tcgaacacgt    1620
cttgctaaac ttcttaggtt ccagtcttct catcatccaa ctgacattac tagcctagac    1680
cagtatgtgg aaagaatgaa ggaaaaacaa gacaaaatct acttcatggc tgggtccagc    1740
agaaaagagg ctgaatcttc tccatttgtt gagcgacttc tgaaaaaggg ctatgaagtt    1800
atttacctca cagaacctgt ggatgaatac tgtattcagg cccttcccga atttgatggg    1860
aagaggttcc agaatgttgc caaggaagga gtgaagttcg atgaaagtga aaaactaag     1920
gagagtcgtg aagcagttga aaagaatttt gagcctctgc tgaattggat gaaagataaa    1980
gcccttaagg acaagattga aaaggctgtg gtgtctcagc gcctgacaga atctccgtgt    2040
gctttggtgg ccagccagta cggatggtct ggcaacatgg agagaatcat gaaagcacaa    2100
gcgtaccaaa cgggcaagga catctctaca aattactatg cgagtcagaa gaaaacattt    2160
gaaattaatc ccagacaccc gctgatcaga gacatgcttc gacgaattaa ggaagatgaa    2220
gatgataaaa cagttttgga tcttgctgtg gtttttgtttg aaacagcaac gcttcggtca    2280
```

-continued

```
gggtatcttt taccagacac taaagcatat ggagatagaa tagaaagaat gcttcgcctc    2340
agtttgaaca ttgaccctga tgcaaaggtg gaagaagagc ccgaagaaga acctgaagag    2400
acagcagaag acacaacaga agacacagag caagacgaag atgaagaaat ggatgtggga    2460
acagatgaag aagaagaaac agcaaaggaa tctacagctg aaaaagatga attgtaaatt    2520
atactctcac catttggatc ctgtgtggag agggaatgtg aaatttacat catttctttt    2580
tgggagagac ttgttttgga tgcccoctaa tccccttctc ccctgcactg taaaatgtgg    2640
gattatgggt cacaggaaaa agtgggtttt ttagttgaat ttttttttaac attcctcatg    2700 aatgtaaatt tgtactattt aactgactat tcttgatgta aatcttgtc atgtgtataa    2760 aaataaaaaa gatcccaaat                                                2780
```

<210> SEQ ID NO 8
<211> LENGTH: 838
<212> TYPE: PRT
<213> ORGANISM: Homo sapiens

<400> SEQUENCE: 8

```
Val Gly Gly Pro Arg Gly Trp Arg Cys Glu Asp Pro Asn Pro Gly Val
 1               5                  10                  15

Gly Gly Gly Gly Gly Ser Cys Asp Arg Arg Gly Leu Glu Thr His Arg
             20                  25                  30

Pro His Ala Met Arg Ala Leu Trp Val Leu Gly Leu Cys Cys Val Leu
         35                  40                  45

Leu Thr Phe Gly Ser Val Arg Ala Asp Asp Glu Val Asp Val Asp Gly
     50                  55                  60

Thr Val Glu Glu Asp Leu Gly Lys Ser Arg Glu Gly Ser Arg Thr Asp
 65                  70                  75                  80

Asp Glu Val Val Gln Arg Glu Glu Ala Ile Gln Leu Asp Gly Leu
                 85                  90                  95

Asn Ala Ser Gln Ile Arg Glu Leu Arg Glu Lys Ser Glu Lys Phe Ala
            100                 105                 110

Phe Gln Ala Glu Val Asn Arg Met Met Lys Leu Ile Ile Asn Ser Leu
        115                 120                 125

Tyr Lys Asn Lys Glu Ile Phe Leu Arg Glu Leu Ile Ser Asn Ala Ser
    130                 135                 140

Asp Ala Leu Asp Lys Ile Arg Leu Ile Ser Leu Thr Asp Glu Asn Ala
145                 150                 155                 160

Leu Ser Gly Asn Glu Glu Leu Thr Val Lys Ile Lys Cys Asp Lys Glu
                165                 170                 175

Lys Asn Leu Leu His Val Thr Asp Thr Gly Val Gly Met Thr Arg Glu
            180                 185                 190

Glu Leu Val Lys Asn Leu Gly Thr Ile Ala Lys Ser Gly Thr Ser Glu
        195                 200                 205

Phe Leu Asn Lys Met Thr Glu Ala Gln Glu Asp Gly Gln Ser Thr Ser
    210                 215                 220

Glu Leu Ile Gly Gln Phe Gly Val Gly Phe Tyr Ser Ala Phe Leu Val
225                 230                 235                 240

Ala Asp Lys Val Ile Val Thr Ser Lys His Asn Asn Asp Thr Gln His
                245                 250                 255

Ile Trp Glu Ser Asp Ser Asn Glu Phe Ser Val Ile Ala Asp Pro Arg
            260                 265                 270

Gly Asn Thr Leu Gly Arg Gly Thr Thr Ile Thr Leu Val Leu Lys Glu
        275                 280                 285
```

-continued

Glu Ala Ser Asp Tyr Leu Glu Leu Asp Thr Ile Lys Asn Leu Val Lys
    290                 295                 300

Lys Tyr Ser Gln Phe Ile Asn Phe Pro Ile Tyr Val Trp Ser Ser Lys
305                 310                 315                 320

Thr Glu Thr Val Glu Pro Met Glu Glu Glu Ala Ala Lys Glu
                325                 330                 335

Glu Lys Glu Glu Ser Asp Asp Glu Ala Ala Val Glu Glu Glu Glu
        340                 345                 350

Glu Lys Lys Pro Lys Thr Lys Lys Val Glu Lys Thr Val Trp Asp Trp
        355                 360                 365

Glu Leu Met Asn Asp Ile Lys Pro Ile Trp Gln Arg Pro Ser Lys Glu
    370                 375                 380

Val Glu Glu Asp Glu Tyr Lys Ala Phe Tyr Lys Ser Phe Ser Lys Glu
385                 390                 395                 400

Ser Asp Asp Pro Met Ala Tyr Ile His Phe Thr Ala Glu Gly Glu Val
                405                 410                 415

Thr Phe Lys Ser Ile Leu Phe Val Pro Thr Ser Ala Pro Arg Gly Leu
        420                 425                 430

Phe Asp Glu Tyr Gly Ser Lys Lys Ser Asp Tyr Ile Lys Leu Tyr Val
        435                 440                 445

Arg Arg Val Phe Ile Thr Asp Asp Phe His Asp Met Met Pro Lys Tyr
450                 455                 460

Leu Asn Phe Val Lys Gly Val Val Asp Ser Asp Asp Leu Pro Leu Asn
465                 470                 475                 480

Val Ser Arg Glu Thr Leu Gln Gln His Lys Leu Leu Lys Val Ile Arg
                485                 490                 495

Lys Lys Leu Val Arg Lys Thr Leu Asp Met Ile Lys Lys Ile Ala Asp
            500                 505                 510

Asp Lys Tyr Asn Asp Thr Phe Trp Lys Glu Phe Gly Thr Asn Ile Lys
            515                 520                 525

Leu Gly Val Ile Glu Asp His Ser Asn Arg Thr Arg Leu Ala Lys Leu
    530                 535                 540

Leu Arg Phe Gln Ser Ser His His Pro Thr Asp Ile Thr Ser Leu Asp
545                 550                 555                 560

Gln Tyr Val Glu Arg Met Lys Glu Lys Gln Asp Lys Ile Tyr Phe Met
                565                 570                 575

Ala Gly Ser Ser Arg Lys Glu Ala Glu Ser Ser Pro Phe Val Glu Arg
            580                 585                 590

Leu Leu Lys Lys Gly Tyr Glu Val Ile Tyr Leu Thr Glu Pro Val Asp
        595                 600                 605

Glu Tyr Cys Ile Gln Ala Leu Pro Glu Phe Asp Gly Lys Arg Phe Gln
    610                 615                 620

Asn Val Ala Lys Glu Gly Val Lys Phe Asp Glu Ser Glu Lys Thr Lys
625                 630                 635                 640

Glu Ser Arg Glu Ala Val Glu Lys Glu Phe Glu Pro Leu Leu Asn Trp
                645                 650                 655

Met Lys Asp Lys Ala Leu Lys Asp Lys Ile Glu Lys Ala Val Val Ser
            660                 665                 670

Gln Arg Leu Thr Glu Ser Pro Cys Ala Leu Val Ala Ser Gln Tyr Gly
            675                 680                 685

Trp Ser Gly Asn Met Glu Arg Ile Met Lys Ala Gln Ala Tyr Gln Thr
    690                 695                 700

-continued

```
Gly Lys Asp Ile Ser Thr Asn Tyr Tyr Ala Ser Gln Lys Lys Thr Phe
705                 710                 715                 720

Glu Ile Asn Pro Arg His Pro Leu Ile Arg Asp Met Leu Arg Arg Ile
            725                 730                 735

Lys Glu Asp Glu Asp Lys Thr Val Leu Asp Leu Ala Val Val Leu
            740                 745                 750

Phe Glu Thr Ala Thr Leu Arg Ser Gly Tyr Leu Leu Pro Asp Thr Lys
        755                 760                 765

Ala Tyr Gly Asp Arg Ile Glu Arg Met Leu Arg Leu Ser Leu Asn Ile
        770                 775                 780

Asp Pro Asp Ala Lys Val Glu Glu Pro Glu Glu Pro Glu Glu
785                 790                 795                 800

Thr Ala Glu Asp Thr Thr Glu Asp Thr Glu Gln Asp Glu Asp Glu Glu
            805                 810                 815

Met Asp Val Gly Thr Asp Glu Glu Glu Glu Thr Ala Lys Glu Ser Thr
            820                 825                 830

Ala Glu Lys Asp Glu Leu
        835
```

<210> SEQ ID NO 9
<211> LENGTH: 2912
<212> TYPE: DNA
<213> ORGANISM: Homo sapiens

<400> SEQUENCE: 9

```
cagttgcttc agcgtcccgg tgtggctgtg ccgttggtcc tgtgcggtca cttagccaag     60
atgcctgagg aaacccagac ccaagaccaa ccgatggagg aggaggaggt tgagacgttc    120
gcctttcagg cagaaattgc ccagttgatg tcattgatca tcaatacttt ctactcgaac    180
aaagagatct ttctgagaga gctcatttca aattcatcag atgcattgga caaaatccgg    240
tatgaaactt tgacagatcc cagtaaaatta gactctggga agagctgca tattaacctt    300
ataccgaaca acaagatcg aactctcact attgtggata ctggaattgg aatgaccaag    360
gctgacttga tcaataacct tggtactatc gccaagtctg ggaccaaagc gttcatggaa    420
gctttgcagg ctggtgcaga tatctctatg attggccagt tcggtgttgg ttttattct    480
gcttatttgg ttgctgagaa agtaactgtg atcaccaaac ataacgatga tgagcagtac    540
gcttgggagt cctcagcagg ggatcattc acagtgagga cagacacagg tgaacctatg    600
ggtcgtggaa caaagttat cctacacctg aagaagacc aaactgagta cttggaggaa    660
cgaagaataa aggagattgt gaagaaacat tctcagttta ttggatatcc cattactctt    720
tttgtgagaa ggaacgtgaa taagaagta agcgatgatg aggctgaaga aaaggaagac    780
aaagaagaag aaaagaaaa agaagagaaa gagtcggaag acaaacctga aattgaagat    840
gttggttctg atgaggaaga agaaagaag gatggtgaca agaagaagaa gaagaagatt    900
aaggaaaagt acatcgatca agaagagctc aacaaaacaa agcccatctg gaccagaaat    960
cccgacgata ttactaatga ggagtacgga gaattctata gagcttgac caatgactgg   1020
gaagatcact tggcagtgaa gcatttttca gttgaaggac agttggaatt cagagccctt   1080
ctatttgtcc cacgacgtgc tcctttttgat ctgtttgaaa acagaaagaa aaagaacaat   1140
atcaaattgt atgtacgcag agttttcatc atggataact gtgaggagct aatccctgaa   1200
tatctgaact tcattagagg ggtggtagac tcggaggatc tccctctaaa catatcccgt   1260
gagatgttgc aacaaagcaa aattttgaaa gttatcagga gaatttggt caaaaatgc   1320
```

```
ttagaactct ttactgaact ggcggaagat aaagagaact acaagaaatt ctatgagcag    1380
ttctctaaaa acataaagct tggaatacac gaagactctc aaaatcggaa gaagctttca    1440
gagctgttaa ggtactacac atctgcctct ggtgatgaga tggtttctct caaggactac    1500
tgcaccagaa tgaaggagaa ccagaaacat atctattata tcacaggtga gaccaaggac    1560
caggtagcta actcagcctt tgtgaacgt cttcggaaac atggcttaga agtgatctat     1620
atgattgagc ccattgatga gtactgtgtc aacagctga aggaatttga ggggaagact    1680
ttagtgtcag tcaccaaaga aggcctggaa cttccagagg atgaagaaga gaaaagaag    1740 caggaagaga aaaaaacaaa gtttgagaac ctctgcaaaa tcatgaaaga catattggag    1800
aaaaaagttg aaaaggtggt tgtgtcaaac cgattggtga catctccatg ctgtattgtc    1860
acaagcacat atggctggac agcaaacatg gagagaatca tgaaagctca gccctaaga    1920 gacaactcaa caatgggtta catggcagca agaaacacc tggagataaa ccctgaccat     1980
tccattattg agaccttaag gcaaaaggca gaggctgata agaacgacaa gtctgtgaag    2040
gatctggtca tcttgcttta tgaaactgcg ctcctgtctt ctggcttcag tctggaagat    2100
ccccagacac atgctaacag gatctacagg atgatcaaac ttggtctggg tattgatgaa    2160
gatgacccta ctgctgatga taccagtgct gctgtaactg aagaaatgcc accccttgaa    2220
ggagatgacg acacatcacg catggaagaa gtagactaat ctctggctga gggatgactt    2280
acctgttcag tactctacaa ttcctctgat aatatatttt caaggatgtt tttctttatt    2340
tttgttaata ttaaaaagtc tgtatggcat gacaactact ttaaggggaa gataagattt    2400
ctgtctacta agtgatgctg tgataccttag gcactaaag cagagctagt aatgcttttt     2460
gagtttcatg ttggttcttt cacagatggg gtaacgtgca ctgtaagacg tatgtaacat    2520
gatgttaact ttgtgtggtc taaagtgttt agctgtcaag ccggatgcct aagtagacca    2580
aatcttgtta ttgaagtgtt ctgagctgta tcttgatgtt tagaaaagta ttcgttacat    2640
cttgtaggat ctactttttg aacttttcat tccctgtagt tgacaattct gcatgtacta    2700
gtcctctaga aataggttaa actgaagcaa cttgatggaa ggatctctcc acagggcttg    2760
ttttccaaag aaaagtattg tttggaggag caaagttaaa agcctaccta agcatatcgt    2820
aaagctgttc aaatactcga gcccagtctt gtggatggaa atgtagtgct cgagtcacat    2880
tctgcttaaa gttgtaacaa atacagatga gt                                 2912
```

<210> SEQ ID NO 10
<211> LENGTH: 732
<212> TYPE: PRT
<213> ORGANISM: Homo sapiens

<400> SEQUENCE: 10

```
Met Pro Glu Glu Thr Gln Thr Gln Asp Gln Pro Met Glu Glu Glu Glu
 1               5                  10                  15

Val Glu Thr Phe Ala Phe Gln Ala Glu Ile Ala Gln Leu Met Ser Leu
                20                  25                  30

Ile Ile Asn Thr Phe Tyr Ser Asn Lys Glu Ile Phe Leu Arg Glu Leu
            35                  40                  45

Ile Ser Asn Ser Ser Asp Ala Leu Asp Lys Ile Arg Tyr Glu Thr Leu
        50                  55                  60

Thr Asp Pro Ser Lys Leu Asp Ser Gly Lys Glu Leu His Ile Asn Leu
65                  70                  75                  80

Ile Pro Asn Lys Gln Asp Arg Thr Leu Thr Ile Val Asp Thr Gly Ile
                85                  90                  95
```

-continued

```
Gly Met Thr Lys Ala Asp Leu Ile Asn Asn Leu Gly Thr Ile Ala Lys
            100                 105                 110

Ser Gly Thr Lys Ala Phe Met Glu Ala Leu Gln Ala Gly Ala Asp Ile
        115                 120                 125

Ser Met Ile Gly Gln Phe Gly Val Gly Phe Tyr Ser Ala Tyr Leu Val
        130                 135                 140

Ala Glu Lys Val Thr Val Ile Thr Lys His Asn Asp Asp Glu Gln Tyr
145                 150                 155                 160

Ala Trp Glu Ser Ser Ala Gly Gly Ser Phe Thr Val Arg Thr Asp Thr
                165                 170                 175

Gly Glu Pro Met Gly Arg Gly Thr Lys Val Ile Leu His Leu Lys Glu
                180                 185                 190

Asp Gln Thr Glu Tyr Leu Glu Glu Arg Arg Ile Lys Glu Ile Val Lys
            195                 200                 205

Lys His Ser Gln Phe Ile Gly Tyr Pro Ile Thr Leu Phe Val Glu Lys
        210                 215                 220

Glu Arg Asp Lys Glu Val Ser Asp Asp Glu Ala Glu Glu Lys Glu Asp
225                 230                 235                 240

Lys Glu Glu Glu Lys Glu Lys Glu Glu Lys Glu Ser Glu Asp Lys Pro
                245                 250                 255

Glu Ile Glu Asp Val Gly Ser Asp Glu Glu Glu Lys Lys Asp Gly
                260                 265                 270

Asp Lys Lys Lys Lys Lys Ile Lys Glu Lys Tyr Ile Asp Gln Glu
            275                 280                 285

Glu Leu Asn Lys Thr Lys Pro Ile Trp Thr Arg Asn Pro Asp Asp Ile
        290                 295                 300

Thr Asn Glu Glu Tyr Gly Glu Phe Tyr Lys Ser Leu Thr Asn Asp Trp
305                 310                 315                 320

Glu Asp His Leu Ala Val Lys His Phe Ser Val Glu Gly Gln Leu Glu
                325                 330                 335

Phe Arg Ala Leu Leu Phe Val Pro Arg Arg Ala Pro Phe Asp Leu Phe
            340                 345                 350

Glu Asn Arg Lys Lys Lys Asn Asn Ile Lys Leu Tyr Val Arg Arg Val
        355                 360                 365

Phe Ile Met Asp Asn Cys Glu Glu Leu Ile Pro Glu Tyr Leu Asn Phe
        370                 375                 380

Ile Arg Gly Val Val Asp Ser Glu Asp Leu Pro Leu Asn Ile Ser Arg
385                 390                 395                 400

Glu Met Leu Gln Gln Ser Lys Ile Leu Lys Val Ile Arg Lys Asn Leu
                405                 410                 415

Val Lys Lys Cys Leu Glu Leu Phe Thr Glu Leu Ala Glu Asp Lys Glu
            420                 425                 430

Asn Tyr Lys Lys Phe Tyr Glu Gln Phe Ser Lys Asn Ile Lys Leu Gly
        435                 440                 445

Ile His Glu Asp Ser Gln Asn Arg Lys Lys Leu Ser Glu Leu Leu Arg
450                 455                 460

Tyr Tyr Thr Ser Ala Ser Gly Asp Glu Met Val Ser Leu Lys Asp Tyr
465                 470                 475                 480

Cys Thr Arg Met Lys Glu Asn Gln Lys His Ile Tyr Tyr Ile Thr Gly
                485                 490                 495

Glu Thr Lys Asp Gln Val Ala Asn Ser Ala Phe Val Glu Arg Leu Arg
            500                 505                 510
```

```
Lys His Gly Leu Glu Val Ile Tyr Met Ile Glu Pro Ile Asp Glu Tyr
        515                 520                 525

Cys Val Gln Gln Leu Lys Glu Phe Glu Gly Lys Thr Leu Val Ser Val
        530                 535                 540

Thr Lys Glu Gly Leu Glu Leu Pro Glu Asp Glu Glu Lys Lys Lys
545                 550                 555                 560

Gln Glu Glu Lys Lys Thr Lys Phe Glu Asn Leu Cys Lys Ile Met Lys
                565                 570                 575

Asp Ile Leu Glu Lys Lys Val Glu Lys Val Val Ser Asn Arg Leu
            580                 585                 590

Val Thr Ser Pro Cys Cys Ile Val Thr Ser Thr Tyr Gly Trp Thr Ala
        595                 600                 605

Asn Met Glu Arg Ile Met Lys Ala Gln Ala Leu Arg Asp Asn Ser Thr
        610                 615                 620

Met Gly Tyr Met Ala Ala Lys Lys His Leu Glu Ile Asn Pro Asp His
625                 630                 635                 640

Ser Ile Ile Glu Thr Leu Arg Gln Lys Ala Glu Ala Asp Lys Asn Asp
                645                 650                 655

Lys Ser Val Lys Asp Leu Val Ile Leu Leu Tyr Glu Thr Ala Leu Leu
            660                 665                 670

Ser Ser Gly Phe Ser Leu Glu Asp Pro Gln Thr His Ala Asn Arg Ile
        675                 680                 685

Tyr Arg Met Ile Lys Leu Gly Leu Gly Ile Asp Glu Asp Pro Thr
        690                 695                 700

Ala Asp Asp Thr Ser Ala Ala Val Thr Glu Glu Met Pro Pro Leu Glu
705                 710                 715                 720

Gly Asp Asp Asp Thr Ser Arg Met Glu Glu Val Asp
                725                 730

<210> SEQ ID NO 11
<211> LENGTH: 2227
<212> TYPE: DNA
<213> ORGANISM: Homo sapiens

<400> SEQUENCE: 11
gacgacctgt ctcgccgagc gcacgcttgc cgccgccccg cagaaatgct tcggttaccc      60
acagtctttc gccagatgag accggtgtcc agggtactgg ctcctcatct cactcgggct     120
tatgccaaag atgtaaaatt tggtgcagat gcccgagcct aatgcttca aggtgtagac      180 cttttagccg atgctgtggc cgttacaatg gggccaaagg aagaacagt gattattgag      240 cagagttggg gaagtcccaa agtaacaaaa gatggtgtga ctgttgcaaa gtcaattgac     300
ttaaaagata aatacaagaa cattggagct aaacttgttc aagatgttgc caataacaca     360
aatgaagaag ctggggatgg cactaccact gctactgtac tggcacgctc tatagccaag     420
gaaggcttcg agaagattag caaaggtgct aatccagtgg aaatcaggag aggtgtgatg     480
ttagctgttg atgctgtaat tgctgaactt aaaaagcagt ctaaacctgt gaccaccct      540 gaagaaattg cacaggttgc tacgatttct gcaacggag acaaagaaat tggcaatatc      600
atctctgatg caatgaaaaa agttggaaga agggtgtca tcacagtaaa ggatggaaaa     660
acactgaatg atgaattaga aattattgaa ggcatgaagt tgatcgagg ctatatttct     720 ccatacttta ttaatacatc aaaaggtcag aaatgtgaat tccaggatgc ctatgttctg     780
ttgagtgaaa agaaaatttc tagtatccag tccattgtac ctgctcttga aattgccaat     840
gctcaccgta agccttttggt cataatcgct gaagatgttg atggagaagc tctaagtaca     900
```

-continued

```
ctcgtcttga ataggctaaa ggttggtctt caggttgtgg cagtcaaggc tccagggttt      960
ggtgacaata gaaagaacca gcttaaagat atggctattg ctactggtgg tgcagtgttt     1020
ggagaagagg gattgaccct gaatcttgaa gacgttcagc ctcatgactt aggaaaagtt     1080
ggagaggtca ttgtgaccaa agacgatgcc atgctcttaa aggaaaaggg tgacaaggct     1140
caaattgaaa aacgtattca agaaatcatt gagcagttag atgtcacaac tagtgaatat     1200
gaaaaggaaa aactgaatga acggcttgca aaactttcag atggagtggc tgtgctgaag     1260
gttggtggga caagtgatgt tgaagtgaat gaaaagaaag acagagttac agatgccctt     1320
aatgctacaa gagctgctgt tgaagaaggc attgttttgg gagggggttg tgccctcctt     1380
cgatgcattc cagccttgga ctcattgact ccagctaatg aagatcaaaa aattggtata     1440
gaaattatta aagaacact caaaattcca gcaatgacca ttgctaagaa tgcaggtgtt      1500
gaaggatctt tgatagttga gaaaattatg caaagttcct cagaagttgg ttatgatgct     1560
atggctggag attttgtgaa tatggtggaa aaaggaatca ttgacccaac aaaggttgtg     1620
agaactgctt tattggatgc tgctggtgtg gcctctctgt taactacagc agaagttgta     1680
gtcacagaaa ttcctaaaga agagaaggac cctggaatgg gtgcaatggg tggaatggga     1740
ggtggtatgg gaggtggcat gttctaactc ctagactagt gctttacctt tattaatgaa     1800
ctgtgacagg aagcccaagg cagtgttcct caccaataac ttcagagaag tcagttggag     1860
aaaatgaaga aaaaggctgg ctgaaaatca ctataaccat cagttactgg tttcagttga     1920
caaaatatat aatggtttac tgctgtcatt gtccatgcct acagataatt tattttgtat     1980
ttttgaataa aaacatttg tacattcctg atactgggta caagagccat gtaccagtgt      2040
actgctttca acttaaatca ctgaggcatt tttactacta ttctgttaaa atcaggattt     2100
tagtgcttgc caccaccaga tgagaagtta agcagccttt ctgtggagag tgagaataat     2160
tgtgtacaaa gtagagaagt atccaattat gtgacaacct ttgtgtaata aaaatttgtt     2220
taaagtt                                                              2227
```

<210> SEQ ID NO 12
<211> LENGTH: 573
<212> TYPE: PRT
<213> ORGANISM: Homo sapiens

<400> SEQUENCE: 12

```
Met Leu Arg Leu Pro Thr Val Phe Arg Gln Met Arg Pro Val Ser Arg
 1               5                  10                  15

Val Leu Ala Pro His Leu Thr Arg Ala Tyr Ala Lys Asp Val Lys Phe
            20                  25                  30

Gly Ala Asp Ala Arg Ala Leu Met Leu Gln Gly Val Asp Leu Leu Ala
        35                  40                  45

Asp Ala Val Ala Val Thr Met Gly Pro Lys Gly Arg Thr Val Ile Ile
    50                  55                  60

Glu Gln Ser Trp Gly Ser Pro Lys Val Thr Lys Asp Gly Val Thr Val
65                  70                  75                  80

Ala Lys Ser Ile Asp Leu Lys Asp Lys Tyr Lys Asn Ile Gly Ala Lys
                85                  90                  95

Leu Val Gln Asp Val Ala Asn Asn Thr Asn Glu Glu Ala Gly Asp Gly
            100                 105                 110

Thr Thr Thr Ala Thr Val Leu Ala Arg Ser Ile Ala Lys Glu Gly Phe
        115                 120                 125
```

-continued

```
Glu Lys Ile Ser Lys Gly Ala Asn Pro Val Glu Ile Arg Arg Gly Val
    130                 135                 140

Met Leu Ala Val Asp Ala Val Ile Ala Glu Leu Lys Lys Gln Ser Lys
145                 150                 155                 160

Pro Val Thr Thr Pro Glu Glu Ile Ala Gln Val Ala Thr Ile Ser Ala
                    165                 170                 175

Asn Gly Asp Lys Glu Ile Gly Asn Ile Ile Ser Asp Ala Met Lys Lys
                180                 185                 190

Val Gly Arg Lys Gly Val Ile Thr Val Lys Asp Gly Lys Thr Leu Asn
            195                 200                 205

Asp Glu Leu Glu Ile Ile Glu Gly Met Lys Phe Asp Arg Gly Tyr Ile
    210                 215                 220

Ser Pro Tyr Phe Ile Asn Thr Ser Lys Gly Gln Lys Cys Glu Phe Gln
225                 230                 235                 240

Asp Ala Tyr Val Leu Leu Ser Glu Lys Lys Ile Ser Ser Ile Gln Ser
                245                 250                 255

Ile Val Pro Ala Leu Glu Ile Ala Asn Ala His Arg Lys Pro Leu Val
                260                 265                 270

Ile Ile Ala Glu Asp Val Asp Gly Glu Ala Leu Ser Thr Leu Val Leu
            275                 280                 285

Asn Arg Leu Lys Val Gly Leu Gln Val Val Ala Val Lys Ala Pro Gly
    290                 295                 300

Phe Gly Asp Asn Arg Lys Asn Gln Leu Lys Asp Met Ala Ile Ala Thr
305                 310                 315                 320

Gly Gly Ala Val Phe Gly Glu Glu Gly Leu Thr Leu Asn Leu Glu Asp
                325                 330                 335

Val Gln Pro His Asp Leu Gly Lys Val Gly Glu Val Ile Val Thr Lys
                340                 345                 350

Asp Asp Ala Met Leu Leu Lys Gly Lys Gly Asp Lys Ala Gln Ile Glu
            355                 360                 365

Lys Arg Ile Gln Glu Ile Ile Glu Gln Leu Asp Val Thr Thr Ser Glu
    370                 375                 380

Tyr Glu Lys Glu Lys Leu Asn Glu Arg Leu Ala Lys Leu Ser Asp Gly
385                 390                 395                 400

Val Ala Val Leu Lys Val Gly Gly Thr Ser Asp Val Glu Val Asn Glu
                405                 410                 415

Lys Lys Asp Arg Val Thr Asp Ala Leu Asn Ala Thr Arg Ala Ala Val
                420                 425                 430

Glu Glu Gly Ile Val Leu Gly Gly Gly Cys Ala Leu Leu Arg Cys Ile
            435                 440                 445

Pro Ala Leu Asp Ser Leu Thr Pro Ala Asn Glu Asp Gln Lys Ile Gly
    450                 455                 460

Ile Glu Ile Ile Lys Arg Thr Leu Lys Ile Pro Ala Met Thr Ile Ala
465                 470                 475                 480

Lys Asn Ala Gly Val Glu Gly Ser Leu Ile Val Glu Lys Ile Met Gln
                485                 490                 495

Ser Ser Ser Glu Val Gly Tyr Asp Ala Met Ala Gly Asp Phe Val Asn
                500                 505                 510

Met Val Glu Lys Gly Ile Ile Asp Pro Thr Lys Val Val Arg Thr Ala
            515                 520                 525

Leu Leu Asp Ala Ala Gly Val Ala Ser Leu Leu Thr Thr Ala Glu Val
    530                 535                 540

Val Val Thr Glu Ile Pro Lys Glu Glu Lys Asp Pro Gly Met Gly Ala
```

```
                    545                 550                 555                 560
               Met Gly Gly Met Gly Gly Gly Met Gly Gly Gly Met Phe
                                    565                 570

<210> SEQ ID NO 13
<211> LENGTH: 2376
<212> TYPE: DNA
<213> ORGANISM: Homo sapiens

<400> SEQUENCE: 13
gaggaggagt ggggaccggg cgggggggtgg aggaagaggc ctcgcgcaga ggagggagca      60
attgaatttc aaacacaaac aactcgacga gcgcgcaccc accgcgccgg agccttgccc     120
cgatccgcgc ccgccccgtc cgtgcggcgc cggggcggag acgccgtggc cgcgccggag     180
ctcgggccgg gggccaccat cgaggcgggg gccgcgcgag ggccggagcg gagcggcgcc     240
gccaccgccg cacgcgcaaa cttgggctcg cgcttcccgg cccggcgcgg agcccggggc     300
gcccggagcc ccgccatgtc gcgatccaac cggcagaagg agtacaaatg cggggaccTg     360
gtgttcgcca agatgaaggg ctacccacac tggccggccc ggattgacga gatgcctgag     420
gctgccgtga aatcaacagc caacaaatac caagtctttt ttttcgggac ccacgagacg     480
gcattcctgg cccccaagga cctcttccct tacgaggaat ccaaggagaa gtttggcaag     540
cccaacaaga ggaaagggtt cagcgagggg ctgtgggaga tcgagaacaa ccctactgtc     600
aaggcttccg gctatcagtc ctcccagaaa aagagctgtg tggaagagcc tgaaccagag     660
cccgaagctg cagagggtga cggtgataag aaggggaatg cagagggcag cagcgacgag     720
gaagggaagc tggtcattga tgagccagcc aaggagaaga acgagaaagg agcgttgaag     780
aggagagcag gggacttgct ggaggactct cctaaacgtc ccaaggaggc agaaaaccct     840
gaaggagagg agaaggaggc agccaccttg gaggttgaga ggccccttcc tatggaggtg     900
gaaaagaata gcacccccte tgagcccggc tctggccggg ggcctcccca agaggaagaa     960
gaagaggagg atgaagagga agaggctacc aaggaagatg ctgaggcccc aggcatcaga    1020
gatcatgaga gcctgtagcc accaatgttt caagaggagc ccccaccctg ttcctgctgc    1080
tgtctgggtg ctactgggga aactggccat ggcctgcaaa ctgggaaccc cttttcccacc    1140 ccaacctgct ctcctcttct actcactttt cccactccaa gcccagccca tggagattga    1200
cctggatggg gcaggccacc tggctctcac ctctaggtcc ccatactcct atgatctgag    1260
tcagagccat gtcttctccc tggaatgagt tgaggccact gtgttccttc cgcttggagc    1320 tatttttccag gcttctgctg gggcctggga caactgctcc cacctcctga caccctctc    1380 ccactctcct aggcattctg gacctctggg ttgggatcag gggtaggaat ggaaggatgg    1440
agcatcaaca gcagggtggg cttgtggggc ctgggagggg caatcctcaa atgcggggtg    1500
ggggcagcac aggagggcgg cctccttctg agctcctgtc ccctgctaca cctattatcc    1560
cagctgccta gattcaggga aagtgggaca gcttgtaggg gagggctcc tttccataaa     1620 tccttgatga ttgacaacac ccattttttcc ttttgccgac cccaagagtt tgggagttg    1680 tagttaatca tcaagagaat ttggggcttc caagttgttc gggccaagga cctgagacct    1740
gaagggttga ctttacccat ttgggtggga gtgttgagca tctgtccccc tttagatctc    1800
tgaagccaca aataggatgc ttgggaagac tcctagctgt ccttttttcct ctccacacag    1860 tgctcaaggc cagcttatag tcatatatat cacccagaca taaggaaaaa gacacattt     1920 ttaggaaatg ttttttaataa aagaaaatta caaaaaaaaa ttttaaagac ccctaaccct    1980
```

```
ttgtgtgctc tccattctgc tccttcccca tcgttgcccc catttctgag gtgcactggg    2040
aggctcccct tctatttggg gcttgatgac tttcttttg tagctggggc tttgatgttc     2100
cttccagtgt catttctcat ccacataccc tgacctggcc ccctcagtgt tgtcaccaga    2160
tctgatttgt aacccactga gaggacagag agaaataagt gccctctccc accctcttcc    2220
tactggtctc tctatgcctc tctacagtct cgtctctttt accctggccc ctctcccttg    2280
ggctctgatg aaaaattgct gactgtagct ttggaagttt agctctgaga accgtagatg    2340
atttcagttc taggaaaata aaacccgttg attact                              2376
```

<210> SEQ ID NO 14
<211> LENGTH: 240
<212> TYPE: PRT
<213> ORGANISM: Homo sapiens

<400> SEQUENCE: 14

```
Met Ser Arg Ser Asn Arg Gln Lys Glu Tyr Lys Cys Gly Asp Leu Val
 1               5                  10                  15

Phe Ala Lys Met Lys Gly Tyr Pro His Trp Pro Ala Arg Ile Asp Glu
            20                  25                  30

Met Pro Glu Ala Ala Val Lys Ser Thr Ala Asn Lys Tyr Gln Val Phe
        35                  40                  45

Phe Phe Gly Thr His Glu Thr Ala Phe Leu Gly Pro Lys Asp Leu Phe
    50                  55                  60

Pro Tyr Glu Glu Ser Lys Glu Lys Phe Gly Lys Pro Asn Lys Arg Lys
65                  70                  75                  80

Gly Phe Ser Glu Gly Leu Trp Glu Ile Glu Asn Asn Pro Thr Val Lys
                85                  90                  95

Ala Ser Gly Tyr Gln Ser Ser Gln Lys Lys Ser Cys Val Glu Glu Pro
            100                 105                 110

Glu Pro Glu Pro Glu Ala Ala Glu Gly Asp Gly Asp Lys Lys Gly Asn
        115                 120                 125

Ala Glu Gly Ser Ser Asp Glu Glu Gly Lys Leu Val Ile Asp Glu Pro
    130                 135                 140

Ala Lys Glu Lys Asn Glu Lys Gly Ala Leu Lys Arg Arg Ala Gly Asp
145                 150                 155                 160

Leu Leu Glu Asp Ser Pro Lys Arg Pro Lys Glu Ala Glu Asn Pro Glu
                165                 170                 175

Gly Glu Glu Lys Glu Ala Ala Thr Leu Glu Val Glu Arg Pro Leu Pro
            180                 185                 190

Met Glu Val Glu Lys Asn Ser Thr Pro Ser Glu Pro Gly Ser Gly Arg
        195                 200                 205

Gly Pro Pro Gln Glu Glu Glu Glu Asp Glu Glu Glu Ala
    210                 215                 220

Thr Lys Glu Asp Ala Glu Ala Pro Gly Ile Arg Asp His Glu Ser Leu
225                 230                 235                 240
```

<210> SEQ ID NO 15
<211> LENGTH: 3689
<212> TYPE: DNA
<213> ORGANISM: Homo sapiens

<400> SEQUENCE: 15

```
aagatctcat aaaatctatg ctgaggaatg agcgacagtt caaggaggag aagcttgcag    60
agcagctcaa gcaagctgag gagctcaggc aatataaagt cctggttcac gctcaggaac   120
```

-continued

```
gagagctgac ccagttaagg gagaagttgc gggaagggag agatgcctcc cgctcattga    180
atgagcatct ccaggccctc ctcactccgg atgagccgga caagtcccag ggcaggacc     240 tccaagaaca gctggctgag gggtgtagac tggcacagca ccttgtccaa aagctcagcc    300
cagaaaatga caacgatgac gatgaagatg ttcaagttga ggtggctgag aaagtgcaga    360
aatcgtctgc ccccagggag atgcagaagg ctgaagaaaa ggaagtccct gaggactcac    420
tggaggaatg tgccatcact tgttcaaata gccatggccc ttatgactcc aaccagccac    480
ataggaaaac caaatcaca tttgaggaag acaaagtcga ctcaactctc attggctcat     540
cctctcatgt tgaatgggag gatgctgtac acattattcc agaaaatgaa agtgatgatg    600
aggaagagga agaaaaagga ccagtgtctc ccaggaatct gcaggagtct gaagaggagg    660
aagtccccca ggagtcctgg gatgaaggtt attcgactct ctcaattcct cctgaaatgt    720
tggcctcgta caagtcttac agcagcacat tcactcatt agaggaacag caagtctgca    780
tggctgttga cataggcaga catcggtggg atcaagtgaa aaggaggac cacgaggcaa     840 caggtcccag gctcagcaga gagctgctgg atgagaaagg cctgaagtc ttgcaggact    900 cactggatag atgttattca actccttcag gttgtcttga actgactgac tcatgccagc    960
cctacagaag tgccttttac gtattggagc aacagcgtgt tggcttggct gttaacatgg   1020
atgaaattga aaagtaccaa gaagtggaag aagaccaaga cccatcatgc cccaggctca   1080
gcagggagct gctggatgag aaagagcctg aagtcttgca ggactcactg gtagatgtt    1140 attcgactcc ttcaggttat cttgaactgc ctgacttagg ccagccctac agcagtgctg   1200
tttactcatt ggaggaacag taccttggct tggctcttga cgtggacaga attaaaaagg   1260
accaagaaga ggaagaagac caaggcccac catgccccag gctcagcagg gagctgctgg   1320
aggtagtaga gcctgaagtc ttgcaggact cactggatag atgttattca actccttcca   1380
gttgtcttga acagcctgac tcctgccagc cctatggaag ttccttttat gcattggagg   1440
aaaagcatgt tggcttttct cttgacgtgg agaaattga aaagaagggg aaggggaaga   1500
aaagaagggg aagaagatca agaaggaaa gaagaagggg aagaaaagaa ggggaagaag   1560
atcaaaaccc accatgcccc aggctcagca gggagctgct ggatgagaaa gggcctgaag   1620
tcttgcagga ctcactggat agatgttatt caactccttc aggttgtctt gaactgactg   1680
actcatgcca gccctacaga agtgcctttt acatattgga gcaacagcgt gttggcttgg   1740
ctgttgacat ggatgaaatt gaaaagtacc aagaagtgga agaagaccaa gacccatcat   1800
gccccaggct cagcggggag ctgttggatg agaaagagcc tgaagtcttg caggagtcac   1860
tggatagatg ctattcaact ccttcaggtt gtcttgaact gactgactca tgccagccct   1920
acagaagtgc cttttacata ttggagcaac agcgtgttgg cttggctgtt gacatggatg   1980
aaattgaaaa gtaccaagaa gtggaagaag accaagaccc atcatgcccc aggctcagca   2040
gggagctgct ggatgagaaa gagcctgaag tcttgcagga ctcactgggt agatgttatt   2100
cgactccttc aggttatctt gaactgcctg acttaggcca gccctacagc agtgctgttt   2160
actcattgga ggaacagtac cttggcttgg ctcttgacgt ggacagaatt aaaaaggacc   2220
aagaagagga agaagaccaa ggcccaccat gccccaggct cagcagggag ctgctggagg   2280
tagtagagcc tgaagtcttg caggactcac tggatagatg ttattcaact ccttccagtt   2340
gtcttgaaca gcctgactcc tgccagccct atggaagttc cttttatgca ttggaggaaa   2400
acatgttggg cttttctctt gacgtgggag aaattgaaaa gaaggggaag ggaagaaaa   2460 gaagggaag aagatcaaag aaggaaagaa gaagggaag aaaagaaggg gaagaagatc   2520
```

-continued

```
aaaacccacc atgccccagg ctcaacagca tgctgatgga agtggaagag cctgaagtct     2580
tgcaggactc actggatata tgttattcga ctccgtcaat gtactttgaa ctacctgact     2640
cattccagca ctacagaagt gtgttttact catttgagga agagcatatc agcttcgccc     2700
tttacgtgga caataggttt tttactttga cggtgacaag tctccacctg gtgttccaga     2760
tgggagtcat attcccacaa taagcagccc ttactaagcc gagaggtgtc attcctgcag     2820
gcaggaccta taggcacgtg aagatttgaa tgaaagtaca gttccatttg aagcccaga     2880 cataggatgg gtcagtgggc atggctctat tcctattctc aaaccatgcc agtggcaacc     2940
tgtgctcagt ctgaagacaa tggacccacg ttaggtgtga cacgttcaca taactgtgca     3000
gcacatgccg ggagtgatca gtcagacatt ttaatttgaa ccacgtatct ctgggtagct     3060
acaaaattcc tcagggatgt catttttgcag gcatgtctct gagcttctat acctgctcaa     3120
ggtcattgtc atctttgtgt ttagctcatc caaaggtgtt accctggttt caatgaacct     3180
aacctcattc tttgtgtctt cagtgttggc ttgttttagc tgatccatct gtaacacagg     3240
agggatcctt ggctgaggat tgtatttcag aaccaccaac tgctcttgac aattgttaac     3300
ccgctaggct cctttggtta gagaagccac agtccttcag cctccaattg gtgtcagtac     3360
ttaggaagac cacagctaga tggacaaaca gcattgggag gccttagccc tgctcctctc     3420
aattccatcc tgtagagaac aggagtcagg agccgctggc aggagacagc atgtcaccca     3480
ggactctgcc ggtgcagaat atgagcaatg ccatgttctt gcagaaaacg cttaacctga     3540
gtttcatagg aggtaatcac cagacaactg cagaatgtag aacactgagc aggacaactg     3600
acctgtctcc ttcacatagt ccatatcacc acaaatcaca caacaaaaag gagaagagat     3660
attttcggtt gaaaaaaagt aaaagata                                       3689
```

<210> SEQ ID NO 16
<211> LENGTH: 921
<212> TYPE: PRT
<213> ORGANISM: Homo sapiens

<400> SEQUENCE: 16

```
Met Leu Arg Asn Glu Arg Gln Phe Lys Glu Glu Lys Leu Ala Glu Gln
  1               5                  10                  15

Leu Lys Gln Ala Glu Glu Leu Arg Gln Tyr Lys Val Leu Val His Ala
             20                  25                  30

Gln Glu Arg Glu Leu Thr Gln Leu Arg Glu Lys Leu Arg Glu Gly Arg
         35                  40                  45

Asp Ala Ser Arg Ser Leu Asn Glu His Leu Gln Ala Leu Leu Thr Pro
     50                  55                  60

Asp Glu Pro Asp Lys Ser Gln Gly Gln Asp Leu Gln Glu Gln Leu Ala
 65                  70                  75                  80

Glu Gly Cys Arg Leu Ala Gln His Leu Val Gln Lys Leu Ser Pro Glu
                 85                  90                  95

Asn Asp Asn Asp Asp Glu Asp Val Gln Val Glu Val Ala Glu Lys
            100                 105                 110

Val Gln Lys Ser Ser Ala Pro Arg Glu Met Gln Lys Ala Glu Glu Lys
        115                 120                 125

Glu Val Pro Glu Asp Ser Leu Glu Glu Cys Ala Ile Thr Cys Ser Asn
    130                 135                 140

Ser His Gly Pro Tyr Asp Ser Asn Gln Pro His Arg Lys Thr Lys Ile
145                 150                 155                 160
```

```
Thr Phe Glu Glu Asp Lys Val Asp Ser Thr Leu Ile Gly Ser Ser Ser
                165                 170                 175

His Val Glu Trp Glu Asp Ala Val His Ile Ile Pro Glu Asn Glu Ser
            180                 185                 190

Asp Asp Glu Glu Glu Glu Lys Gly Pro Val Ser Pro Arg Asn Leu
        195                 200             205

Gln Glu Ser Glu Glu Glu Val Pro Gln Glu Ser Trp Asp Glu Gly
    210                 215                 220

Tyr Ser Thr Leu Ser Ile Pro Pro Glu Met Leu Ala Ser Tyr Lys Ser
225                 230                 235                 240

Tyr Ser Ser Thr Phe His Ser Leu Glu Glu Gln Gln Val Cys Met Ala
                245                 250                 255

Val Asp Ile Gly Arg His Arg Trp Asp Gln Val Lys Lys Glu Asp His
            260                 265                 270

Glu Ala Thr Gly Pro Arg Leu Ser Arg Glu Leu Leu Asp Glu Lys Gly
            275                 280                 285

Pro Glu Val Leu Gln Asp Ser Leu Asp Arg Cys Tyr Ser Thr Pro Ser
    290                 295                 300

Gly Cys Leu Glu Leu Thr Asp Ser Cys Gln Pro Tyr Arg Ser Ala Phe
305                 310                 315                 320

Tyr Val Leu Glu Gln Gln Arg Val Gly Leu Ala Val Asn Met Asp Glu
                325                 330                 335

Ile Glu Lys Tyr Gln Glu Val Glu Glu Asp Gln Asp Pro Ser Cys Pro
            340                 345                 350

Arg Leu Ser Arg Glu Leu Leu Asp Glu Lys Glu Pro Glu Val Leu Gln
            355                 360                 365

Asp Ser Leu Gly Arg Cys Tyr Ser Thr Pro Ser Gly Tyr Leu Glu Leu
    370                 375                 380

Pro Asp Leu Gly Gln Pro Tyr Ser Ser Ala Val Tyr Ser Leu Glu Glu
385                 390                 395                 400

Gln Tyr Leu Gly Leu Ala Leu Asp Val Asp Arg Ile Lys Lys Asp Gln
                405                 410                 415

Glu Glu Glu Glu Asp Gln Gly Pro Pro Cys Pro Arg Leu Ser Arg Glu
            420                 425                 430

Leu Leu Glu Val Val Glu Pro Glu Val Leu Gln Asp Ser Leu Asp Arg
            435                 440                 445

Cys Tyr Ser Thr Pro Ser Ser Cys Leu Glu Gln Pro Asp Ser Cys Gln
    450                 455                 460

Pro Tyr Gly Ser Ser Phe Tyr Ala Leu Glu Glu Lys His Val Gly Phe
465                 470                 475                 480

Ser Leu Asp Val Gly Glu Ile Glu Lys Lys Gly Lys Gly Lys Lys Arg
                485                 490                 495

Arg Gly Arg Arg Ser Lys Lys Glu Arg Arg Gly Arg Lys Glu Gly
            500                 505                 510

Glu Glu Asp Gln Asn Pro Pro Cys Pro Arg Leu Ser Arg Glu Leu Leu
            515                 520                 525

Asp Glu Lys Gly Pro Glu Val Leu Gln Asp Ser Leu Asp Arg Cys Tyr
    530                 535                 540

Ser Thr Pro Ser Gly Cys Leu Glu Leu Thr Asp Ser Cys Gln Pro Tyr
545                 550                 555                 560

Arg Ser Ala Phe Tyr Ile Leu Glu Gln Gln Arg Val Gly Leu Ala Val
                565                 570                 575

Asp Met Asp Glu Ile Glu Lys Tyr Gln Glu Val Glu Glu Asp Gln Asp
```

```
                    580             585             590
Pro Ser Cys Pro Arg Leu Ser Gly Glu Leu Leu Asp Glu Lys Glu Pro
        595                 600                 605

Glu Val Leu Gln Glu Ser Leu Asp Arg Cys Tyr Ser Thr Pro Ser Gly
    610                 615                 620

Cys Leu Glu Leu Thr Asp Ser Cys Gln Pro Tyr Arg Ser Ala Phe Tyr
625                 630                 635                 640

Ile Leu Glu Gln Gln Arg Val Gly Leu Ala Val Asp Met Asp Glu Ile
                645                 650                 655

Glu Lys Tyr Gln Glu Val Glu Asp Gln Asp Pro Ser Cys Pro Arg
            660                 665                 670

Leu Ser Arg Glu Leu Leu Asp Glu Lys Glu Pro Glu Val Leu Gln Asp
        675                 680                 685

Ser Leu Gly Arg Cys Tyr Ser Thr Pro Ser Gly Tyr Leu Glu Leu Pro
    690                 695                 700

Asp Leu Gly Gln Pro Tyr Ser Ser Ala Val Tyr Ser Leu Glu Glu Gln
705                 710                 715                 720

Tyr Leu Gly Leu Ala Leu Asp Val Asp Arg Ile Lys Lys Asp Gln Glu
                725                 730                 735

Glu Glu Glu Asp Gln Gly Pro Pro Cys Pro Arg Leu Ser Arg Glu Leu
            740                 745                 750

Leu Glu Val Val Glu Pro Glu Val Leu Gln Asp Ser Leu Asp Arg Cys
        755                 760                 765

Tyr Ser Thr Pro Ser Ser Cys Leu Glu Gln Pro Asp Ser Cys Gln Pro
770                 775                 780

Tyr Gly Ser Ser Phe Tyr Ala Leu Glu Glu Lys His Val Gly Phe Ser
785                 790                 795                 800

Leu Asp Val Gly Glu Ile Glu Lys Lys Gly Lys Gly Lys Arg Arg
                805                 810                 815

Gly Arg Arg Ser Lys Lys Glu Arg Arg Gly Arg Lys Glu Gly Glu
            820                 825                 830

Glu Asp Gln Asn Pro Pro Cys Pro Arg Leu Asn Ser Met Leu Met Glu
        835                 840                 845

Val Glu Glu Pro Glu Val Leu Gln Asp Ser Leu Asp Ile Cys Tyr Ser
850                 855                 860

Thr Pro Ser Met Tyr Phe Glu Leu Pro Asp Ser Phe Gln His Tyr Arg
865                 870                 875                 880

Ser Val Phe Tyr Ser Phe Glu Glu Glu His Ile Ser Phe Ala Leu Tyr
                885                 890                 895

Val Asp Asn Arg Phe Phe Thr Leu Thr Val Thr Ser Leu His Leu Val
            900                 905                 910

Phe Gln Met Gly Val Ile Phe Pro Gln
            915                 920

<210> SEQ ID NO 17
<211> LENGTH: 664
<212> TYPE: DNA
<213> ORGANISM: Homo sapiens

<400> SEQUENCE: 17
aacccaatga tcctgcagca gcccttgcag cgaggccccc agggaggggc ccagcgcctc    60
ccgcgggccg ccttgggggt gacttggggc ctggacgcca gctcccctct ccgaggagct   120
gtgcccatga gcaccaagcg gcgcctggag gaggagcagg agcctctgcg caagcagttt   180
```

```
ctgtctgagg agaacatggc cacccacttc tctcaactca gcctgcacaa tgaccacccc      240
tactgcagcc cccccatgac cttctcccca gccctgcccc cactcaggag cccttgctct      300
gagctgcttc tctggcgcta tcctggcagc ctcatccctg aggccctccg tctgctgagg      360
ctgggggaca cccccagtcc ccctacccct gcaaccccag ctgggacat aatggagctc       420 tgagtgctgg tggacagtgc cctcccacc ttccttcttc cccacaacag aagagaccag       480
cgactcccgc aaagggacaa ggttcctccc tctcctgcag gtaggcatc tgggcaccaa       540 gaccttccct caacagagga cactgagccc aacggagttc tgggatggga gggtgggag      600 catgggaagg gaggcatccc accccaaga gaactgaat aaagattgct gagcaaagga       660
aggc                                                                  664
```

```
<210> SEQ ID NO 18
<211> LENGTH: 138
<212> TYPE: PRT
<213> ORGANISM: Homo sapiens

<400> SEQUENCE: 18

Met Ile Leu Gln Gln Pro Leu Gln Arg Gly Pro Gln Gly Gly Ala Gln
 1               5                  10                  15

Arg Leu Pro Arg Ala Ala Leu Gly Val Thr Trp Gly Leu Asp Ala Ser
             20                  25                  30

Ser Pro Leu Arg Gly Ala Val Pro Met Ser Thr Lys Arg Arg Leu Glu
         35                  40                  45

Glu Glu Gln Glu Pro Leu Arg Lys Gln Phe Leu Ser Glu Glu Asn Met
     50                  55                  60

Ala Thr His Phe Ser Gln Leu Ser Leu His Asn Asp His Pro Tyr Cys
 65                  70                  75                  80

Ser Pro Pro Met Thr Phe Ser Pro Ala Leu Pro Pro Leu Arg Ser Pro
                 85                  90                  95

Cys Ser Glu Leu Leu Leu Trp Arg Tyr Pro Gly Ser Leu Ile Pro Glu
            100                 105                 110

Ala Leu Arg Leu Leu Arg Leu Gly Asp Thr Pro Ser Pro Pro Tyr Pro
        115                 120                 125

Ala Thr Pro Ala Gly Asp Ile Met Glu Leu
    130                 135
```

```
<210> SEQ ID NO 19
<211> LENGTH: 2056
<212> TYPE: DNA
<213> ORGANISM: Homo sapiens

<400> SEQUENCE: 19
ggaaccgcgg ctgctggaca agaggggtgc ggtggatact gacctttgct ccggcctcgt       60
cgtgaagaca cagcgcatct ccccgctgta ggcttctccc acagaacccg tttcgggcct      120
cagagcgtct ggtgagatgc tgttgccgct gctgctgctg ctacccatgt gctgggccgt      180
ggaggtcaag aggcccccggg gcgtctccct caccaatcat cacttctacg atgagtccaa    240
gcctttcacc tgcctggacg gttcggccac catcccattt gatcaggtca acgatgacta    300
ttgcgactgc aaagatggct ctgacgagcc aggcacggct gcctgtccta atggcagctt   360
ccactgcacc aacactggct ataagcccct gtatatcccc tccaaccggg tcaacgatgg    420
tgtttgtgac tgctgcgatg aacagacga gtacaacagc ggcgtcatct gtagaacac    480 ctgcaaagag aagggccgta aggagagaga gtccctgcag cagatggccg aggtcacccg    540
```

```
cgaaggggttc cgtctgaaga agatccttat tgaggactgg aagaaggcac gggaggagaa    600
gcagaaaaag ctcattgagc tacaggctgg gaagaagtct ctggaagacc aggtggagat    660
gctgcggaca gtgaaggagg aagctgagaa gccagagaga gaggccaaag agcagcacca    720
gaagctgtgg gaagagcagc tggctgctgc caaggcccaa caggagcagg agctggcggc    780
tgatgccttc aaggagctgg atgatgacat ggacgggacg gtctcggtga ctgagctgca    840
gactcacccg gagctggaca cagatgggga tggggcgttg tcagaagcgg aagctcaggc    900
cctcctcagt ggggacacac agacagacgc cacctctttc tacgaccgcg tctgggccgc    960
catcagggac aagtaccggt ccgaggcact gcccaccgac cttccagcac cttctgcccc   1020
tgacttgacg gagcccaagg aggagcagcc gccagtgccc tcgtcgccca cagaggagga   1080
ggaggaggag gaggaggagg aagaagaggc tgaagaagag gaggaggagg aggattccga   1140
ggaggcccca ccgccactgt cacccccgca gccggccagc cctgctgagg aagacaaaat   1200
gccgccctac gacgagcaga cgcaggcctt catcgatgct gcccaggagg cccgcaacaa   1260
gttcgaggag gccgagcggt cgctgaagga catggaggag tccatcagga acctggagca   1320
agagatttct tttgactttg gccccaacgg ggagtttgct tacctgtaca gccagtgcta   1380
cgagctcacc accaacgaat acgtctaccg cctctgcccc ttcaagcttg tctcgcagaa   1440
acccaaactc gggggctctc ccaccagcct tggcacctgg ggctcatgga ttggccccga   1500
ccacgacaag ttcagtgcca tgaagtatga gcaaggcacg ggctgctggc agggcccaa    1560
ccgctccacc accgtgcgcc tcctgtgcgg gaaagagacc atggtgacca gcaccacaga   1620
gcccagtcgc tgcgagtacc tcatggagct gatgacgcca gccgcctgcc ggagccacc    1680
gcctgaagca cccaccgaag acgaccatga cgagctctag ctggatgggc gcagagaacc   1740
tcaagaaggc atgaagccag cccctgcagt gccgtccacc cgcccctctg ggcctgcctg   1800
tggctctgtt gccctcctct gtggcggcag gacctttgtg gggcttcgtg ccctgctctg   1860
gggcccaggc ggggctggtc cacattccca ggccccaaca gcctccaaag atgggtaaag   1920
gagcttgccc tccctgggcc ccccaccttg gtgactcgcc ccaccacccc cagccctgtc   1980
cctgccaccc ctcctagtgg ggactagtga atgacttgac ctgtgacctc aatacaataa   2040
atgtgatccc ccaccc                                                   2056
```

<210> SEQ ID NO 20
<211> LENGTH: 527
<212> TYPE: PRT
<213> ORGANISM: Homo sapiens

<400> SEQUENCE: 20

```
Met Leu Leu Pro Leu Leu Leu Leu Pro Met Cys Trp Ala Val Glu
 1               5                  10                  15

Val Lys Arg Pro Arg Gly Val Ser Leu Thr Asn His His Phe Tyr Asp
                20                  25                  30

Glu Ser Lys Pro Phe Thr Cys Leu Asp Gly Ser Ala Thr Ile Pro Phe
            35                  40                  45

Asp Gln Val Asn Asp Tyr Cys Asp Cys Lys Asp Gly Ser Asp Glu
        50                  55                  60

Pro Gly Thr Ala Ala Cys Pro Asn Gly Ser Phe His Cys Thr Asn Thr
    65                  70                  75                  80

Gly Tyr Lys Pro Leu Tyr Ile Pro Ser Asn Arg Val Asn Asp Gly Val
                85                  90                  95

Cys Asp Cys Cys Asp Gly Thr Asp Glu Tyr Asn Ser Gly Val Ile Cys
```

-continued

```
                    100                 105                 110
Glu Asn Thr Cys Lys Glu Lys Gly Arg Lys Glu Arg Glu Ser Leu Gln
            115                 120                 125
Gln Met Ala Glu Val Thr Arg Glu Gly Phe Arg Leu Lys Lys Ile Leu
        130                 135                 140
Ile Glu Asp Trp Lys Lys Ala Arg Glu Glu Lys Gln Lys Lys Leu Ile
145                 150                 155                 160
Glu Leu Gln Ala Gly Lys Lys Ser Leu Glu Asp Gln Val Glu Met Leu
                165                 170                 175
Arg Thr Val Lys Glu Glu Ala Glu Lys Pro Glu Arg Glu Ala Lys Glu
            180                 185                 190
Gln His Gln Lys Leu Trp Glu Glu Gln Leu Ala Ala Lys Ala Gln
        195                 200                 205
Gln Glu Gln Glu Leu Ala Ala Asp Ala Phe Lys Glu Leu Asp Asp Asp
        210                 215                 220
Met Asp Gly Thr Val Ser Val Thr Glu Leu Gln Thr His Pro Glu Leu
225                 230                 235                 240
Asp Thr Asp Gly Asp Gly Ala Leu Ser Glu Ala Glu Ala Gln Ala Leu
                245                 250                 255
Leu Ser Gly Asp Thr Gln Thr Asp Ala Thr Ser Phe Tyr Asp Arg Val
            260                 265                 270
Trp Ala Ala Ile Arg Asp Lys Tyr Arg Ser Glu Ala Leu Pro Thr Asp
        275                 280                 285
Leu Pro Ala Pro Ser Ala Pro Asp Leu Thr Glu Pro Lys Glu Glu Gln
        290                 295                 300
Pro Pro Val Pro Ser Ser Pro Thr Glu Glu Glu Glu Glu Glu Glu Glu
305                 310                 315                 320
Glu Glu Glu Glu Ala Glu Glu Glu Glu Glu Asp Ser Glu Glu
                325                 330                 335
Ala Pro Pro Pro Leu Ser Pro Gln Pro Ala Ser Pro Ala Glu Glu
            340                 345                 350
Asp Lys Met Pro Pro Tyr Asp Glu Gln Thr Gln Ala Phe Ile Asp Ala
        355                 360                 365
Ala Gln Glu Ala Arg Asn Lys Phe Glu Glu Ala Glu Arg Ser Leu Lys
        370                 375                 380
Asp Met Glu Glu Ser Ile Arg Asn Leu Glu Gln Glu Ile Ser Phe Asp
385                 390                 395                 400
Phe Gly Pro Asn Gly Glu Phe Ala Tyr Leu Tyr Ser Gln Cys Tyr Glu
                405                 410                 415
Leu Thr Thr Asn Glu Tyr Val Tyr Arg Leu Cys Pro Phe Lys Leu Val
            420                 425                 430
Ser Gln Lys Pro Lys Leu Gly Gly Ser Pro Thr Ser Leu Gly Thr Trp
        435                 440                 445
Gly Ser Trp Ile Gly Pro Asp His Asp Lys Phe Ser Ala Met Lys Tyr
        450                 455                 460
Glu Gln Gly Thr Gly Cys Trp Gln Gly Pro Asn Arg Ser Thr Thr Val
465                 470                 475                 480
Arg Leu Leu Cys Gly Lys Glu Thr Met Val Thr Ser Thr Thr Glu Pro
                485                 490                 495
Ser Arg Cys Glu Tyr Leu Met Glu Leu Met Thr Pro Ala Ala Cys Pro
            500                 505                 510
Glu Pro Pro Pro Glu Ala Pro Thr Glu Asp Asp His Asp Glu Leu
        515                 520                 525
```

<210> SEQ ID NO 21
<211> LENGTH: 384
<212> TYPE: DNA
<213> ORGANISM: Homo sapiens

<400> SEQUENCE: 21

```
atgcctaaat caaaggaact tgtttcttca agctcttctg gcagtgattc tgacagtgag      60
gttgacaaaa agttaaagag gaaaaagcaa gttgctccag aaaaacctgt aaagaaacaa     120
aagacaggtg agacttcgag agccctgtca tcttctaaac agagcagcag cagcagagat     180
gataacatgt ttcagattgg gaaaatgagg tacgttagtg ttcgcgattt taaaggcaaa     240
gtgctaattg atattagaga atattggatg gatcctgaag gtgaaatgaa accaggaaga     300
aaaggtattt ctttaaatcc agaacaatgg agccagctga aggaacagat ctctgatata     360
gatgacgcag taagaaagct gtga                                            384
```

<210> SEQ ID NO 22
<211> LENGTH: 127
<212> TYPE: PRT
<213> ORGANISM: Homo sapiens

<400> SEQUENCE: 22

```
Met Pro Lys Ser Lys Glu Leu Val Ser Ser Ser Ser Gly Ser Asp
 1               5                  10                  15

Ser Asp Ser Glu Val Asp Lys Lys Leu Lys Arg Lys Lys Gln Val Ala
            20                  25                  30

Pro Glu Lys Pro Val Lys Lys Gln Lys Thr Gly Glu Thr Ser Arg Ala
        35                  40                  45

Leu Ser Ser Ser Lys Gln Ser Ser Ser Arg Asp Asp Asn Met Phe
    50                  55                  60

Gln Ile Gly Lys Met Arg Tyr Val Ser Val Arg Asp Phe Lys Gly Lys
 65                  70                  75                  80

Val Leu Ile Asp Ile Arg Glu Tyr Trp Met Asp Pro Glu Gly Glu Met
                85                  90                  95

Lys Pro Gly Arg Lys Gly Ile Ser Leu Asn Pro Glu Gln Trp Ser Gln
            100                 105                 110

Leu Lys Glu Gln Ile Ser Asp Ile Asp Asp Ala Val Arg Lys Leu
        115                 120                 125
```

<210> SEQ ID NO 23
<211> LENGTH: 1554
<212> TYPE: DNA
<213> ORGANISM: Homo sapiens

<400> SEQUENCE: 23

```
gaccacaatg gcggccgcca ccctgctgcg cgcgacgccc cacttcagcg gtctcgccgc      60
cggccggacc ttcctgctgc agggtctgtt gcggctgctg aaagcccggg cattgcctct     120
cttgtgccgc ggcctggccg tggaggccaa gaagacttac gtgcgcgaca gccacatgt     180
gaatgtgggt accatcggcc atgtggacca cgggaagacc acgctgactg cagccatcac     240
gaagattcta gctgagggag gtgggggtaa gttcaagaag tacgaggaga ttgacaatgc     300
cccggaggag cgagctcggg gtatcaccat caatgcggct catgtggagt atagcactgc     360
cgcccgccac tacgcccaca cagactgccc gggtcatgca gattatgtta agaatatgat     420
cacaggcact gcaccctcg acggctgcat cctggtggta gcagccaatg acggccccat     480
```

-continued

```
gccccagacc cgagagcact tattactggc cagacagatt ggggtggagc atgtggtggt    540
gtatgtgaac aaggctgacg ctgtccagga ctctgagatg gtggaactgg tggaactgga    600
gatccgggag ctgctcaccg agtttggcta taaaggggag gagacccag tcatcgtagg     660 ctctgctctc tgtgcccttg agggtcggga ccctgagtta ggcctgaagt ctgtgcagaa    720
gctactggat gctgtggaca cttacatccc agtgcccgcc cgggacctgg agaagccttt    780
cctgctgcct gtggaggcgg tgtactccgt ccctggccgt ggcaccgtgg tgacaggtac    840
actagagcgt ggcatttta agaagggaga cgagtgtgag ctcctaggac atagcaagaa     900
catccgcact gtggtgacag gcattgagat gttccacaag agcctggaga gggccgaggc    960
cggagataac ctcggggccc tggtccgagg cttgaagcgg gaggacttgc ggcggggcct   1020
ggtcatggtc aagccaggtt ccatcaagcc ccaccgaaag gtggaggccc aggtttacat   1080
cctcagcaag gaggaaggtg gccgccacaa gcccttgtg tcccacttca tgcctgtcat    1140
gttctccctg acttggaaca tggcctgtcg gattatcctg ccccagaga aggagcttgc    1200 catgcccggg gaggacctga agttcaacct aatcttgcgg cagccaatga tcttagagaa   1260
aggccagcgt ttcaccctgc gagatggcaa ccggactatt ggcaccggtc tagtcaccaa   1320
cacgctggcc atgactgagg aggagaagaa tatcaaatgg ggttgagtgt gcagatctct   1380
gctcagcttc ccttgcgttt aaggcctgcc ctagccaggg ctccctcctg cttccagtac   1440
cctctcatgg cataggctgc aacccagcag agggcagcta gatggacatt tccctgctc    1500 ggaagggttg gcctgcctgg ctggggaggt cagtaaactt tgaatagtaa gcca          1554
```

<210> SEQ ID NO 24
<211> LENGTH: 452
<212> TYPE: PRT
<213> ORGANISM: Homo sapiens

<400> SEQUENCE: 24

```
Met Ala Ala Ala Thr Leu Leu Arg Ala Thr Pro His Phe Ser Gly Leu
 1               5                  10                  15

Ala Ala Gly Arg Thr Phe Leu Leu Gln Gly Leu Leu Arg Leu Leu Lys
            20                  25                  30

Ala Pro Ala Leu Pro Leu Leu Cys Arg Gly Leu Ala Val Glu Ala Lys
        35                  40                  45

Lys Thr Tyr Val Arg Asp Lys Pro His Val Asn Val Gly Thr Ile Gly
     50                  55                  60

His Val Asp His Gly Lys Thr Thr Leu Thr Ala Ala Ile Thr Lys Ile
 65                  70                  75                  80

Leu Ala Glu Gly Gly Gly Ala Lys Phe Lys Lys Tyr Glu Glu Ile Asp
                85                  90                  95

Asn Ala Pro Glu Glu Arg Ala Arg Gly Ile Thr Ile Asn Ala Ala His
            100                 105                 110

Val Glu Tyr Ser Thr Ala Ala Arg His Tyr Ala His Thr Asp Cys Pro
        115                 120                 125

Gly His Ala Asp Tyr Val Lys Asn Met Ile Thr Gly Thr Ala Pro Leu
    130                 135                 140

Asp Gly Cys Ile Leu Val Val Ala Ala Asn Asp Gly Pro Met Pro Gln
145                 150                 155                 160

Thr Arg Glu His Leu Leu Leu Ala Arg Gln Ile Gly Val Glu His Val
                165                 170                 175

Val Val Tyr Val Asn Lys Ala Asp Ala Val Gln Asp Ser Glu Met Val
            180                 185                 190
```

```
Glu Leu Val Glu Leu Glu Ile Arg Glu Leu Leu Thr Glu Phe Gly Tyr
            195                 200                 205
Lys Gly Glu Glu Thr Pro Val Ile Val Gly Ser Ala Leu Cys Ala Leu
        210                 215                 220
Glu Gly Arg Asp Pro Glu Leu Gly Leu Lys Ser Val Gln Lys Leu Leu
225                 230                 235                 240
Asp Ala Val Asp Thr Tyr Ile Pro Val Pro Ala Arg Asp Leu Glu Lys
            245                 250                 255
Pro Phe Leu Leu Pro Val Glu Ala Val Tyr Ser Val Pro Gly Arg Gly
        260                 265                 270
Thr Val Thr Gly Thr Leu Glu Arg Gly Ile Leu Lys Lys Gly Asp
275                 280                 285
Glu Cys Glu Leu Leu Gly His Ser Lys Asn Ile Arg Thr Val Val Thr
    290                 295                 300
Gly Ile Glu Met Phe His Lys Ser Leu Glu Arg Ala Glu Ala Gly Asp
305                 310                 315                 320
Asn Leu Gly Ala Leu Val Arg Gly Leu Lys Arg Glu Asp Leu Arg Arg
            325                 330                 335
Gly Leu Val Met Val Lys Pro Gly Ser Ile Lys Pro His Gln Lys Val
        340                 345                 350
Glu Ala Gln Val Tyr Ile Leu Ser Lys Glu Gly Gly Arg His Lys
355                 360                 365
Pro Phe Val Ser His Phe Met Pro Val Met Phe Ser Leu Thr Trp Asn
        370                 375                 380
Met Ala Cys Arg Ile Ile Leu Pro Pro Glu Lys Glu Leu Ala Met Pro
385                 390                 395                 400
Gly Glu Asp Leu Lys Phe Asn Leu Ile Leu Arg Gln Pro Met Ile Leu
            405                 410                 415
Glu Lys Gly Gln Arg Phe Thr Leu Arg Asp Gly Asn Arg Thr Ile Gly
        420                 425                 430
Thr Gly Leu Val Thr Asn Thr Leu Ala Met Thr Glu Glu Lys Asn
435                 440                 445
Ile Lys Trp Gly
    450

<210> SEQ ID NO 25
<211> LENGTH: 2201
<212> TYPE: DNA
<213> ORGANISM: Homo sapiens

<400> SEQUENCE: 25 ttttttttt   cgtcttagcc acgcagaagt cgcgtgtcta gtttgtttcg acgccggacc      60
gcgtaagaga cgatgatgtt gggcacggaa ggtggagagg gattcgtggt gaaggtccgg     120
ggcttgccct ggtcttgctc ggccgatgaa gtgcagaggt ttttttctga ctgcaaaatt     180
caaaatgggg ctcaaggtat tcgtttcatc tacaccagag aaggcagacc aagtggcgag     240
gcttttgttg aacttgaatc agaagatgaa gtcaaattgg ccctgaaaaa agacagagaa     300
actatgggac acagatatgt tgaagtattc aagtcaaaca cgttgaaat ggattgggtg     360 ttgaagcata ctggtccaaa tagtcctgac acgccaatg atggctttgt acggcttaga     420
ggacttccct ttggatgtag caaggaagaa attgttcagt tcttctcagg gttggaaatc     480
gtgccaaatg ggataacatt gccggtggac ttcagggga ggagtacggg ggaggccttc     540
gtgcagtttg cttcacagga aatagctgaa aaggctctaa agaaacacaa ggaaagaata     600
```

```
gggcacaggt atattgaaat ctttaagagc agtagagctg aagttagaac tcattatgat    660
ccaccacgaa agcttatggc catgcagcgg ccaggtcctt atgacagacc tggggctggt    720
agagggtata acagcattgg cagaggagct ggctttgaga ggatgaggcg tggtgcttat    780
ggtggaggct atggaggcta tgatgattac aatggctata atgatggcta tggatttggg    840
tcagatagat ttggaagaga cctcaattac tgttttttcag gaatgtctga tcacagatac   900
ggggatggtg gctctacttt ccagagcaca acaggacact gtgtacacat gcggggatta    960
ccttacagag ctactgagaa tgacatttat aattttttt caccgctcaa ccctgtgaga    1020
gtacacattg aaattggtcc tgatggcaga gtaactggtg aagcagatgt cgagttcgca   1080
actcatgaag atgctgtggc agctatgtca aagacaaag caaatatgca acacagatat    1140
gtagaactct tcttgaattc tacagcagga gcaagcggtg gtgcttacga acacagatat   1200
gtagaactct tcttgaattc tacagcagga gcaagcggtg gtgcttatgg tagccaaatg   1260
atgggaggca tgggcttgtc aaaccagtcc agctacgggg cccagccag ccagcagctg    1320
agtgggggtt acgaggcgg ctacggtggc cagagcagca tgagtggata cgaccaagtt    1380
ttacaggaaa actccagtga ttttcaatca aacattgcat aggtaaccaa ggagcagtga   1440
acagcagcta ctacagtagt ggaagccgtg catctatggg cgtgaacgga atggagggt    1500
tgtctagcat gtccagtatg agtggtggat ggggaatgta attgatcgat cctgatcact   1560
gactcttggt caacctttt tttttttttt tttctttaa gaaaacttca gtttaacagt    1620
ttctgcaata caagcttgtg atttatgctt actctaagtg gaaatcagga ttgttatgaa   1680
gacttaaggc ccagtatttt tgaatacaat actcatctag gatgtaacag tgaagctgag   1740
taaactataa ctgttaaact taagttccag cttttctcaa gttagttata ggatgtactt   1800
aagcagtaag cgtatttagg taaaagcagt tgaattatgt taaatgttgc cctttgccac   1860
gttaaattga acactgtttt ggatgcatgt tgaaagacat gctttatttt ttttttgtaaa  1920
acaatatagg agctgtgtct actattaaaa gtgaaacatt ttggcatgtt tgttaattct   1980
agtttcattt aataacctgt aaggcacgta agtttaagct ttttttttt ttaagttaat    2040
gggaaaaatt tgagacgcaa taccaatact taggattttg gtcttggtgt ttgtatgaaa   2100
ttctgaggcc ttgattttaaa tctttcattg tattgtgatt ccttttagg tatattgcgc    2160
taagtgaaac ttgtcaaata aatcctcctt ttaaaaactg c                        2201
```

<210> SEQ ID NO 26
<211> LENGTH: 449
<212> TYPE: PRT
<213> ORGANISM: Homo sapiens

<400> SEQUENCE: 26

```
Met Met Leu Gly Thr Glu Gly Gly Gly Phe Val Val Lys Val Arg
 1               5                   10                  15

Gly Leu Pro Trp Ser Cys Ser Ala Asp Glu Val Gln Arg Phe Phe Ser
                20                  25                  30

Asp Cys Lys Ile Gln Asn Gly Ala Gln Gly Ile Arg Phe Ile Tyr Thr
            35                  40                  45

Arg Glu Gly Arg Pro Ser Gly Glu Ala Phe Val Glu Leu Glu Ser Glu
        50                  55                  60

Asp Glu Val Lys Leu Ala Leu Lys Lys Asp Arg Glu Thr Met Gly His
65                  70                  75                  80

Arg Tyr Val Glu Val Phe Lys Ser Asn Asn Val Glu Met Asp Trp Val
```

-continued

```
                      85                  90                  95
Leu Lys His Thr Gly Pro Asn Ser Pro Asp Thr Ala Asn Asp Gly Phe
                100                 105                 110
Val Arg Leu Arg Gly Leu Pro Phe Gly Cys Ser Lys Glu Glu Ile Val
                115                 120                 125
Gln Phe Phe Ser Gly Leu Glu Ile Val Pro Asn Gly Ile Thr Leu Pro
                130                 135                 140
Val Asp Phe Gln Gly Arg Ser Thr Gly Glu Ala Phe Val Gln Phe Ala
145                 150                 155                 160
Ser Gln Glu Ile Ala Glu Lys Ala Leu Lys Lys His Lys Glu Arg Ile
                165                 170                 175
Gly His Arg Tyr Ile Glu Ile Phe Lys Ser Arg Ala Glu Val Arg
                180                 185                 190
Thr His Tyr Asp Pro Pro Arg Lys Leu Met Ala Met Gln Arg Pro Gly
                195                 200                 205
Pro Tyr Asp Arg Pro Gly Ala Gly Arg Gly Tyr Asn Ser Ile Gly Arg
                210                 215                 220
Gly Ala Gly Phe Glu Arg Met Arg Arg Gly Ala Tyr Gly Gly Gly Tyr
225                 230                 235                 240
Gly Gly Tyr Asp Asp Tyr Asn Gly Tyr Asn Asp Gly Tyr Gly Phe Gly
                245                 250                 255
Ser Asp Arg Phe Gly Arg Asp Leu Asn Tyr Cys Phe Ser Gly Met Ser
                260                 265                 270
Asp His Arg Tyr Gly Asp Gly Ser Thr Phe Gln Ser Thr Thr Gly
                275                 280                 285
His Cys Val His Met Arg Gly Leu Pro Tyr Arg Ala Thr Glu Asn Asp
290                 295                 300
Ile Tyr Asn Phe Phe Ser Pro Leu Asn Pro Val Arg Val His Ile Glu
305                 310                 315                 320
Ile Gly Pro Asp Gly Arg Val Thr Gly Glu Ala Asp Val Glu Phe Ala
                325                 330                 335
Thr His Glu Asp Ala Val Ala Ala Met Ser Lys Asp Lys Ala Asn Met
                340                 345                 350
Gln His Arg Tyr Val Glu Leu Phe Leu Asn Ser Thr Ala Gly Ala Ser
                355                 360                 365
Gly Gly Ala Tyr Glu His Arg Tyr Val Glu Leu Phe Leu Asn Ser Thr
                370                 375                 380
Ala Gly Ala Ser Gly Gly Ala Tyr Gly Ser Gln Met Met Gly Met
385                 390                 395                 400
Gly Leu Ser Asn Gln Ser Ser Tyr Gly Gly Pro Ala Ser Gln Gln Leu
                405                 410                 415
Ser Gly Gly Tyr Gly Gly Gly Tyr Gly Gly Gln Ser Ser Met Ser Gly
                420                 425                 430
Tyr Asp Gln Val Leu Gln Glu Asn Ser Ser Asp Phe Gln Ser Asn Ile
                435                 440                 445
Ala
```

<210> SEQ ID NO 27
<211> LENGTH: 1852
<212> TYPE: DNA
<213> ORGANISM: Homo sapiens

<400> SEQUENCE: 27
acagcccttc gtggggccct gggcaccctg caccagctgg gcatcgtcgt cggcatcctc    60

-continued

```
atcgcccagg tgttcggcct ggactccatc atgggcaaca aggacctgtg gccccctgctg    120 ctgagcatca tcttcatccc ggccctgctg cagtgcatcg tgctgccctt ctgccccgag    180
agtccccgct tcctgctcat caaccgcaac gaggagaacc gggccaagag tgtgctaaag    240
aagctgcgcg ggacagctga cgtgacccat gacctgcagg agatgaagga agagagtcgg    300
cagatgatgc gggagaagaa ggtcaccatc ctggagctgt tccgctcccc cgcctaccgc    360
cagcccatcc tcatcgctgt ggtgctgcag ctgtcccagc agctgtctgg catcaacgct    420
gtcttctatt actccacgag catcttcgag aaggcggggg tgcagcagcc tgtgtatgcc    480
accattggct ccggtatcgt caacacggcc ttcactgtcg tgtcgctgtt tgtggtggag    540
cgagcaggcc ggcggaccct gcacctcata ggcctcgctg gcatggcggg ttgtgccata    600
ctcatgacca tcgcgctagc actgctggag cagctaccct ggatgtccta tctgagcatc    660
gtggccatct ttggctttgt ggccttcttt gaagtgggtc ctggcccccat ccatggttc    720 atcgtggctg aactcttcag ccagggtcca cgtccagctg ccattgccgt tgcaggcttc    780
tccaactgga cctcaaattt cattgtgggc atgtgcttcc agtatgtgga gcaactgtgt    840
ggtccctacg tcttcatcat cttcactgtg ctcctggttc tgttcttcat cttcacctac    900
ttcaaagttc ctgagactaa aggccggacc ttcgatgaga tcgcttccgg cttccggcag    960
gggggagcca gccaaagtga caagacaccc gaggagctgt ccatcccct gggggctgat   1020 tcccaagtgt gagtcgcccc agatcaccag cccggcctgc tcccagcagc cctaaggatc   1080
tctcaggagc acaggcagct ggatgagact tccaaacctg acagatgtca gccgagccgg   1140
gcctggggct ccttctcca gccagcaatg atgtccagaa gaatattcag gacttaacgg   1200
ctccaggatt ttaacaaaag caagactgtt gctcaaatct attcagacaa gcaacaggtt   1260
ttataatttt tttattactg attttgttat ttttatatca gcctgagtct cctgtgccca   1320
catcccaggc ttcaccctga atggttccat gcctgagggt ggagactaag ccctgtcgag   1380
acacttgcct tcttcaccca gctaatctgt agggctggac ctatgtccta aggacacact   1440
aatcgaacta tgaactacaa agcttctatc caggaggtg gctatggcca cccgttctgc    1500
tggcctggat ctccccactc tagggggtcag gctccattag gatttgcccc ttcccatctc   1560
ttcctaccca accactcaaa ttaatctttc tttacctgag accagttggg agcactggag   1620
tgcagggagg agaggggaag ggccagtctg ggctgccggg ttctagtctc ctttgcactg   1680
agggccacac tattaccatg agaagagggc ctgtgggagc ctgcaaactc actgctcaag   1740
aagacatgga gactcctgcc ctgttgtgta tagatgcaag atatttatat atattttttgg   1800 ttgtcaatat taaatacaga cactaagtta tagtaaaaaa aaaaaaaaaa aa            1852
```

<210> SEQ ID NO 28
<211> LENGTH: 343
<212> TYPE: PRT
<213> ORGANISM: Homo sapiens

<400> SEQUENCE: 28

Thr Ala Leu Arg Gly Ala Leu Gly Thr Leu His Gln Leu Gly Ile Val
 1               5                  10                  15

Val Gly Ile Leu Ile Ala Gln Val Phe Gly Leu Asp Ser Ile Met Gly
            20                  25                  30

Asn Lys Asp Leu Trp Pro Leu Leu Leu Ser Ile Ile Phe Ile Pro Ala
        35                  40                  45

Leu Leu Gln Cys Ile Val Leu Pro Phe Cys Pro Glu Ser Pro Arg Phe

```
                    50                  55                  60
Leu Leu Ile Asn Arg Asn Glu Glu Asn Arg Ala Lys Ser Val Leu Lys
 65                  70                  75                  80

Lys Leu Arg Gly Thr Ala Asp Val Thr His Asp Leu Gln Glu Met Lys
                 85                  90                  95

Glu Glu Ser Arg Gln Met Met Arg Glu Lys Lys Val Thr Ile Leu Glu
            100                 105                 110

Leu Phe Arg Ser Pro Ala Tyr Arg Gln Pro Ile Leu Ile Ala Val Val
            115                 120                 125

Leu Gln Leu Ser Gln Gln Leu Ser Gly Ile Asn Ala Val Phe Tyr Tyr
        130                 135                 140

Ser Thr Ser Ile Phe Glu Lys Ala Gly Val Gln Gln Pro Val Tyr Ala
145                 150                 155                 160

Thr Ile Gly Ser Gly Ile Val Asn Thr Ala Phe Thr Val Val Ser Leu
                165                 170                 175

Phe Val Val Glu Arg Ala Gly Arg Arg Thr Leu His Leu Ile Gly Leu
            180                 185                 190

Ala Gly Met Ala Gly Cys Ala Ile Leu Met Thr Ile Ala Leu Ala Leu
            195                 200                 205

Leu Glu Gln Leu Pro Trp Met Ser Tyr Leu Ser Ile Val Ala Ile Phe
        210                 215                 220

Gly Phe Val Ala Phe Phe Glu Val Gly Pro Gly Pro Ile Pro Trp Phe
225                 230                 235                 240

Ile Val Ala Glu Leu Phe Ser Gln Gly Pro Arg Pro Ala Ala Ile Ala
                245                 250                 255

Val Ala Gly Phe Ser Asn Trp Thr Ser Asn Phe Ile Val Gly Met Cys
            260                 265                 270

Phe Gln Tyr Val Glu Gln Leu Cys Gly Pro Tyr Val Phe Ile Ile Phe
            275                 280                 285

Thr Val Leu Leu Val Leu Phe Phe Ile Phe Thr Tyr Phe Lys Val Pro
        290                 295                 300

Glu Thr Lys Gly Arg Thr Phe Asp Glu Ile Ala Ser Gly Phe Arg Gln
305                 310                 315                 320

Gly Gly Ala Ser Gln Ser Asp Lys Thr Pro Glu Glu Leu Phe His Pro
                325                 330                 335

Leu Gly Ala Asp Ser Gln Val
            340

<210> SEQ ID NO 29
<211> LENGTH: 5368
<212> TYPE: DNA
<213> ORGANISM: Homo sapiens

<400> SEQUENCE: 29
ggaatcagag aagatcattg ctgagttgaa tgaaacttgg gaagagaagc ttcgtaaaac     60
agaggccatc agaatggaga gagaggcttt gttggctgag atgggagttg ccattcggga    120
agatggagga acccgagggg tttctcacc taaaaagacc ccacatcttg ttaacctcaa     180
tgaagaccca ctaatgtctg agtgcctact ttattacatc aaagatggaa ttacaagggt    240
tggccaagca gatgctgagc ggcgccagga catagtgctg agcggggctc acattaaaga    300
agagcattgt atcttccgga gtgagagaag caacagcggg gaagttatcg tgaccttaga    360
gccctgtgag cgctcagaaa cctacgtaaa tggcaagagg gtgtcccagc ctgttcagct    420
gcgctcagga aaccgtatca tcatgggtaa aaaccatgtt ttccgcttta accacccgga    480
```

```
acaagcacga gctgagcgag agaagactcc ttctgctgag acccctctg agcctgtgga    540
ctggacattt gcccagaggg agcttctgga aaaacaagga attgatatga acaagagat    600
ggagaaaagg ctacaggaaa tggagatctt atacaaaaag gagaaggaag aagcagatct    660
tcttttggag cagcagagac tggactatga gagtaaattg caggccttgc agaagcaggt    720
tgaaacccga tctctggctg cagaaacaac tgaagaggag gaagaagagg aagaagttcc    780
ttggacacag catgaatttg agttggccca atgggccttc cggaaatgga agtctcatca    840
gtttacttca ttacgggact tactctgggg caatgccgtg tacctaaagg aggccaatgc    900
catcagtgtg gaactgaaaa agaaggtgca gtttcagttt gttctgctga ctgacacact    960
gtactcccct ttgcctcctg aattacttcc cactgagatg gaaaaaactc atgaggacag   1020
gcctttccct cgcacagtgg tagcagtaga agtccaggat ttgaagaatg gagcaacaca   1080
ctattggtct ttggagaaac tcaagcagag gctggatttg atgcgagaga tgtatgatag   1140
ggcaggggag atggcctcca gtgcccaaga cgaaagcgaa accactgtga ctggcagcga   1200
tcccttctat gatcggttcc actggttcaa acttgtgggg agctccccca ttttccacgg   1260
ctgtgtgaac gagcgccttg ccgaccgcac accctccccc actttttcca cggccgattc   1320
cgacatcact gagctggctg acgagcagca agatgagatg gaggattttg atgatgaggc   1380
attcgtggat gacgccggct ctgacgcagg gacggaggag ggatcagatc tcttcagtga   1440
cgggcatgac ccgtttttacg accgatcccc ttggttcatt ttagtgggaa gggcatttgt   1500
ttacctgagc aatctgctgt atcccgtgcc cctgatccac agggtggcca tcgtcagtga   1560
gaaaggtgaa gtgcggggat ttctgcgtgt ggctgtacag gccatcgcag cggatgaaga   1620
agctcctgat tatggctctg gaattcgaca gtcaggaaca gctaaaatat cttttgataa   1680
tgaatacttt aatcagagtg acttttcgtc tgttgcaatg actcgttctg gtctgtcctt   1740
ggaggagttg aggattgtgg aaggacaggg tcagagttct gaggtcatca ctcctccaga   1800
agaaatcagt cgaattaatg acttggattt gaagtcaagc actttgctgg atggtaagat   1860
ggtaatggaa gggttttctg aagagattgg caaccacctg aaactgggca gtgccttcac   1920
tttccgagta acagtgttgc aggccagtgg aatcctccca gagtatgcag atatcttctg   1980
tcagttcaac tttttgcatc gccatgatga agcattctcc acggagcccc tcaaaaacaa   2040
tggcagagga agtcccctgg cctttttatca tgtgcagaat attgcagtgg agatcactga   2100
atcatttgtg gattacatca aaaccaagcc tattgtattt gaagtctttg ggcattatca   2160
gcagcaccca cttcatctgc aaggacagga gcttaacagt ccgcctcagc cgtgccgccg   2220
attcttccct ccacccatgc cactgtccaa gccagttcca gccaccaagt taaacacgat   2280
gagcaaaacc agccttggcc agagcatgag caagtatgac ctcctggttt ggtttgagat   2340
cagtgaactg gagcctacag gagagtatat cccagctgtg gttgaccaca cagcaggctt   2400
gccttgccag gggacatttt tgcttcatca gggcatccag cgaaggatca cagtgaccat   2460
tatccatgag aaggggagcg agctccattg gaaagatgtt cgtgaactgg tggtaggtcg   2520
tattcggaat aagcctgagg tggatgaagc tgcagttgat gccatcctct ccctaaatat   2580
tatttctgcc aagtacctga agtcttccca caactctagc aggaccttct accgctttga   2640
ggctgtgtgg gatagctctc tgcataactc ccttcttctg aaccgagtga caccctatgg   2700
agaaaagatc tacatgacct tgtcggccta cctagagctg atcattgca tccagccggc   2760
tgtcatcacc aaggatgtgt gcatggtctt ctactcccga gatgccaaga tctcaccacc   2820
```

```
acgctctctg cgtagcctct ttggcagcgg ctactcaaag tcaccagatt cgaatcgagt    2880
cactggcatt tacgaactca gcttatgcaa aatgtcagac acaggtagtc caggtatgca    2940
gagaaggaga agaaaaatct tagatacgtc agtggcatat gtgcggggag aagagaactt    3000
agcaggctgg cggccccgtg gagacagcct catccttgag caccagtggg agctggagaa    3060
gctggagctc ctacatgagg tggaaaaaac ccgccacttt ttgctgctgc gtgagagact    3120
tggtgacagc atccccaaat ccctgagcga ctcgttatcc cccagcctca gcagtgggac    3180
cctcagcacc tccaccagta tctcctctca gatctcaacc actacctttg aaagcgccat    3240
cacacctagc gagagcagtg gctatgattc aggagacatc gaaagcctgg tggaccgaga    3300
gaaagagctg gctaccaagt gcctgcaact tctcacccac actttcaaca gagaattcag    3360
ccaggtgcac ggcagcgtca gtgactgtaa gttgtctgat atctctccaa ttggacggga    3420
tccctctgag tccagtttca gcagtgccac cctcactccc tcctccacct gtccctctct    3480
ggtagactct aggagcaact ctctggatca gaagaccccca gaagccaatt cccgggcctc    3540
tagtccctgc ccagaatttg aacagtttca gattgtccca gctgtggaaa caccatattt    3600
ggcccgagca ggaaaaaacg aatttctcaa tcttgttcca gatattgaag aaattagacc    3660
aagctcagtg gtctctaaga aaggatacct tcatttcaag gagcctcttt acagtaactg    3720
ggctaaacat tttgttgtcg tccgtcggcc ttatgtcttc atctataaca gtgacaaaga    3780
ccctgtggag cgtggaatca ttaacctgtc cacagcacag gtggagtaca gtgaggacca    3840
gcaggccatg gtgaagacac caaacacctt tgctgtctgc acaaagcacc gtggggtcct    3900
tttgcaggcc ctcaatgaca aagacatgaa cgactggttg tatgccttca acccacttct    3960
agctggcaca atacggtcaa agctttcccg cagatgcccg agccagtcga aatactaagt    4020
gactctgccg agtgccctca ctcgccttcg agagataaag aaagcgttac ctctcatttc    4080
tctttgtgat tcttgacggt gactcttgta tgtaatcctg tggcttaact acttctccct    4140
ccttgtccag cacttttcta gctctcccgt tccccatctc cattgctctg tactcttttc    4200
ttttttcttg tgctgagaat ctcgttagta gcatgtggcc taacaaaagg aaaaaatgtt    4260
tttaaacaca cacacacaca cacacacaca cacacacata cacagacaaa aacacaaaaa    4320
ctctgagggg atctggtgaa tctccaaatt attgtgggtg tactttggct tccttttgta    4380
tgataggtcc ccatcatgac cacctctgat gtctgtgctg ctgtcaccag gcacctttgt    4440
ttttcaagac aacatacttt ttttttcttt tctctgtttg tgatatcact ttaattttc     4500 ttgggtggct tagagactaa gggaggagac atctggcctt tttagaacct gagaggaaaa    4560
aaagagtctt ttttccccct ctgtctcttt ttgccatggc taatccctgc atttccattc    4620
agggaaaagg tggtagtgag catagaactg caacagttat attctgagtc aaagttgggg    4680 cttttacgg cataattatg gaattttat ttactggtag agaggagacg agaggctttt     4740
tcagtgggcc tgggacagtg gctgctcttg actttgtgtg aagggaaatg ccaaggatgc    4800
ttctggtgga cttcagggga ccccagggtt tggccgtggg ccgtgatggc agcaggcggt    4860
gggatgcttg tagctcctca cagcaggatt cctgcccact gttttttctc tgttgggagg    4920
gaagctcttt tctaggagtg tctcagttct gcttttggca ttagtgatgg tggtggtaca    4980
gttggaatta gtgccatgtc atacacaaat gttccacaag gcgggagtgt ttcactttct    5040
ggtgataaac ttgatggtca ttgttatgat taagataatg ccgggcaggc gggcacagt     5100 ggctcacgcc tgtaatccaa gcacttgggg aggccgaggc gggcagatca cgagatcagg    5160
agttcaagac cagcctggcc aatgtgatga accccgtct ctactaaaaa tacaaaatta     5220
```

```
gtcgggtatg gtggcacatg cctgtaattc cagctgcttg ggagcctgag gcaggagaac     5280
tgcttgaacc caggaggcag aggttgcagt gagccaagat cgcgctattg cactccagcc     5340
tgggtgacag agcaagactc tgcctcag                                        5368
```

<210> SEQ ID NO 30
<211> LENGTH: 1338
<212> TYPE: PRT
<213> ORGANISM: Homo sapiens

<400> SEQUENCE: 30

```
Glu Ser Glu Lys Ile Ile Ala Glu Leu Asn Glu Thr Trp Glu Glu Lys
 1               5                  10                  15

Leu Arg Lys Thr Glu Ala Ile Arg Met Glu Arg Glu Ala Leu Leu Ala
            20                  25                  30

Glu Met Gly Val Ala Ile Arg Glu Asp Gly Thr Leu Gly Val Phe
        35                  40                  45

Ser Pro Lys Lys Thr Pro His Leu Val Asn Leu Asn Glu Asp Pro Leu
    50                  55                  60

Met Ser Glu Cys Leu Leu Tyr Tyr Ile Lys Asp Gly Ile Thr Arg Val
65                  70                  75                  80

Gly Gln Ala Asp Ala Glu Arg Arg Gln Asp Ile Val Leu Ser Gly Ala
                85                  90                  95

His Ile Lys Glu Glu His Cys Ile Phe Arg Ser Glu Arg Ser Asn Ser
            100                 105                 110

Gly Glu Val Ile Val Thr Leu Glu Pro Cys Glu Arg Ser Glu Thr Tyr
        115                 120                 125

Val Asn Gly Lys Arg Val Ser Gln Pro Val Gln Leu Arg Ser Gly Asn
    130                 135                 140

Arg Ile Ile Met Gly Lys Asn His Val Phe Arg Phe Asn His Pro Glu
145                 150                 155                 160

Gln Ala Arg Ala Glu Arg Glu Lys Thr Pro Ser Ala Glu Thr Pro Ser
                165                 170                 175

Glu Pro Val Asp Trp Thr Phe Ala Gln Arg Glu Leu Leu Glu Lys Gln
            180                 185                 190

Gly Ile Asp Met Lys Gln Glu Met Glu Lys Arg Leu Gln Glu Met Glu
        195                 200                 205

Ile Leu Tyr Lys Lys Glu Lys Glu Glu Ala Asp Leu Leu Leu Glu Gln
    210                 215                 220

Gln Arg Leu Asp Tyr Glu Ser Lys Leu Gln Ala Leu Gln Lys Gln Val
225                 230                 235                 240

Glu Thr Arg Ser Leu Ala Ala Glu Thr Thr Glu Glu Glu Glu Glu Glu
                245                 250                 255

Glu Glu Val Pro Trp Thr Gln His Glu Phe Glu Leu Ala Gln Trp Ala
            260                 265                 270

Phe Arg Lys Trp Lys Ser His Gln Phe Thr Ser Leu Arg Asp Leu Leu
        275                 280                 285

Trp Gly Asn Ala Val Tyr Leu Lys Glu Ala Asn Ala Ile Ser Val Glu
    290                 295                 300

Leu Lys Lys Lys Val Gln Phe Gln Phe Val Leu Leu Thr Asp Thr Leu
305                 310                 315                 320

Tyr Ser Pro Leu Pro Pro Glu Leu Leu Pro Thr Glu Met Glu Lys Thr
                325                 330                 335

His Glu Asp Arg Pro Phe Pro Arg Thr Val Val Ala Val Glu Val Gln
```

```
                340             345             350
Asp Leu Lys Asn Gly Ala Thr His Tyr Trp Ser Leu Glu Lys Leu Lys
            355                 360                 365
Gln Arg Leu Asp Leu Met Arg Glu Met Tyr Asp Arg Ala Gly Glu Met
        370                 375                 380
Ala Ser Ser Ala Gln Asp Glu Ser Glu Thr Thr Val Thr Gly Ser Asp
385                 390                 395                 400
Pro Phe Tyr Asp Arg Phe His Trp Phe Lys Leu Val Gly Ser Ser Pro
                405                 410                 415
Ile Phe His Gly Cys Val Asn Glu Arg Leu Ala Asp Arg Thr Pro Ser
            420                 425                 430
Pro Thr Phe Ser Thr Ala Asp Ser Asp Ile Thr Glu Leu Ala Asp Glu
        435                 440                 445
Gln Gln Asp Glu Met Glu Asp Phe Asp Glu Ala Phe Val Asp Asp
450                 455                 460
Ala Gly Ser Asp Ala Gly Thr Glu Glu Gly Ser Asp Leu Phe Ser Asp
465                 470                 475                 480
Gly His Asp Pro Phe Tyr Asp Arg Ser Pro Trp Phe Ile Leu Val Gly
                485                 490                 495
Arg Ala Phe Val Tyr Leu Ser Asn Leu Leu Tyr Pro Val Pro Leu Ile
            500                 505                 510
His Arg Val Ala Ile Val Ser Glu Lys Gly Glu Val Arg Gly Phe Leu
        515                 520                 525
Arg Val Ala Val Gln Ala Ile Ala Ala Asp Glu Ala Pro Asp Tyr
            530                 535                 540
Gly Ser Gly Ile Arg Gln Ser Gly Thr Ala Lys Ile Ser Phe Asp Asn
545                 550                 555                 560
Glu Tyr Phe Asn Gln Ser Asp Phe Ser Ser Val Ala Met Thr Arg Ser
                565                 570                 575
Gly Leu Ser Leu Glu Glu Leu Arg Ile Val Glu Gly Gln Gly Gln Ser
            580                 585                 590
Ser Glu Val Ile Thr Pro Pro Glu Glu Ile Ser Arg Ile Asn Asp Leu
        595                 600                 605
Asp Leu Lys Ser Ser Thr Leu Leu Asp Gly Lys Met Val Met Glu Gly
610                 615                 620
Phe Ser Glu Glu Ile Gly Asn His Leu Lys Leu Gly Ser Ala Phe Thr
625                 630                 635                 640
Phe Arg Val Thr Val Leu Gln Ala Ser Gly Ile Leu Pro Glu Tyr Ala
                645                 650                 655
Asp Ile Phe Cys Gln Phe Asn Phe Leu His Arg His Asp Glu Ala Phe
            660                 665                 670
Ser Thr Glu Pro Leu Lys Asn Asn Gly Arg Gly Ser Pro Leu Ala Phe
        675                 680                 685
Tyr His Val Gln Asn Ile Ala Val Glu Ile Thr Glu Ser Phe Val Asp
            690                 695                 700
Tyr Ile Lys Thr Lys Pro Ile Val Phe Glu Val Phe Gly His Tyr Gln
705                 710                 715                 720
Gln His Pro Leu His Leu Gln Gly Gln Glu Leu Asn Ser Pro Pro Gln
                725                 730                 735
Pro Cys Arg Arg Phe Phe Pro Pro Met Pro Leu Ser Lys Pro Val
            740                 745                 750
Pro Ala Thr Lys Leu Asn Thr Met Ser Lys Thr Ser Leu Gly Gln Ser
755                 760                 765
```

```
Met Ser Lys Tyr Asp Leu Leu Val Trp Phe Glu Ile Ser Glu Leu Glu
    770                 775                 780

Pro Thr Gly Glu Tyr Ile Pro Ala Val Val Asp His Thr Ala Gly Leu
785                 790                 795                 800

Pro Cys Gln Gly Thr Phe Leu Leu His Gln Gly Ile Gln Arg Arg Ile
                805                 810                 815

Thr Val Thr Ile Ile His Glu Lys Gly Ser Glu Leu His Trp Lys Asp
                820                 825                 830

Val Arg Glu Leu Val Val Gly Arg Ile Arg Asn Lys Pro Glu Val Asp
        835                 840                 845

Glu Ala Ala Val Asp Ala Ile Leu Ser Leu Asn Ile Ile Ser Ala Lys
    850                 855                 860

Tyr Leu Lys Ser Ser His Asn Ser Ser Arg Thr Phe Tyr Arg Phe Glu
865                 870                 875                 880

Ala Val Trp Asp Ser Ser Leu His Asn Ser Leu Leu Asn Arg Val
                885                 890                 895

Thr Pro Tyr Gly Glu Lys Ile Tyr Met Thr Leu Ser Ala Tyr Leu Glu
                900                 905                 910

Leu Asp His Cys Ile Gln Pro Ala Val Ile Thr Lys Asp Val Cys Met
        915                 920                 925

Val Phe Tyr Ser Arg Asp Ala Lys Ile Ser Pro Arg Ser Leu Arg
    930                 935                 940

Ser Leu Phe Gly Ser Gly Tyr Ser Lys Ser Pro Asp Ser Asn Arg Val
945                 950                 955                 960

Thr Gly Ile Tyr Glu Leu Ser Leu Cys Lys Met Ser Asp Thr Gly Ser
                965                 970                 975

Pro Gly Met Gln Arg Arg Arg Arg Lys Ile Leu Asp Thr Ser Val Ala
                980                 985                 990

Tyr Val Arg Gly Glu Glu Asn Leu Ala Gly Trp Arg Pro Arg Gly Asp
        995                 1000                1005

Ser Leu Ile Leu Glu His Gln Trp Glu Leu Glu Lys Leu Glu Leu Leu
    1010                1015                1020

His Glu Val Glu Lys Thr Arg His Phe Leu Leu Arg Glu Arg Leu
1025                1030                1035                1040

Gly Asp Ser Ile Pro Lys Ser Leu Ser Asp Ser Leu Ser Pro Ser Leu
                1045                1050                1055

Ser Ser Gly Thr Leu Ser Thr Ser Thr Ser Ile Ser Ser Gln Ile Ser
                1060                1065                1070

Thr Thr Thr Phe Glu Ser Ala Ile Thr Pro Ser Glu Ser Ser Gly Tyr
            1075                1080                1085

Asp Ser Gly Asp Ile Glu Ser Leu Val Asp Arg Glu Lys Glu Leu Ala
    1090                1095                1100

Thr Lys Cys Leu Gln Leu Leu Thr His Thr Phe Asn Arg Glu Phe Ser
1105                1110                1115                1120

Gln Val His Gly Ser Val Ser Asp Cys Lys Leu Ser Asp Ile Ser Pro
                1125                1130                1135

Ile Gly Arg Asp Pro Ser Glu Ser Ser Phe Ser Ser Ala Thr Leu Thr
                1140                1145                1150

Pro Ser Ser Thr Cys Pro Ser Leu Val Asp Ser Arg Ser Asn Ser Leu
            1155                1160                1165

Asp Gln Lys Thr Pro Glu Ala Asn Ser Arg Ala Ser Ser Pro Cys Pro
    1170                1175                1180
```

| Glu | Phe | Glu | Gln | Phe | Gln | Ile | Val | Pro | Ala | Val | Glu | Thr | Pro | Tyr | Leu |
|---|---|---|---|---|---|---|---|---|---|---|---|---|---|---|---|
| 1185 | | | | 1190 | | | | | 1195 | | | | | 1200 | |

Ala Arg Ala Gly Lys Asn Glu Phe Leu Asn Leu Val Pro Asp Ile Glu
                  1205                      1210                      1215

Glu Ile Arg Pro Ser Ser Val Val Ser Lys Lys Gly Tyr Leu His Phe
            1220                      1225                      1230

Lys Glu Pro Leu Tyr Ser Asn Trp Ala Lys His Phe Val Val Arg
          1235                      1240                      1245

Arg Pro Tyr Val Phe Ile Tyr Asn Ser Asp Lys Asp Pro Val Glu Arg
    1250                      1255                      1260

Gly Ile Ile Asn Leu Ser Thr Ala Gln Val Glu Tyr Ser Glu Asp Gln
1265                1270                      1275                      1280

Gln Ala Met Val Lys Thr Pro Asn Thr Phe Ala Val Cys Thr Lys His
                  1285                      1290                      1295

Arg Gly Val Leu Leu Gln Ala Leu Asn Asp Lys Asp Met Asn Asp Trp
              1300                      1305                      1310

Leu Tyr Ala Phe Asn Pro Leu Leu Ala Gly Thr Ile Arg Ser Lys Leu
        1315                      1320                      1325

Ser Arg Arg Cys Pro Ser Gln Ser Lys Tyr
    1330                      1335

<210> SEQ ID NO 31
<211> LENGTH: 3094
<212> TYPE: DNA
<213> ORGANISM: Homo sapiens

<400> SEQUENCE: 31

| | | | | |
|---|---|---|---|---|
| tttgactggc cgtagagtct gcgcagttgg tgaatggcgt tggtggcggg aaagttgagt | 60 |
| ctctcctgcg ccgagccttc ggggcgatgt gtagtgcctt ccatagggct gagtctggga | 120 |
| ccgagctcct tgcccgactt gaaggtagaa gttccttgaa agaaatagaa ccaaatctgt | 180 |
| ttgctgatga agattcacct gtgcatggtg atattcttga atttcatggc ccagaaggaa | 240 |
| caggaaaaac agaaatgctt tatcacctaa cagcacgatg tatacttccc aaatcagaag | 300 |
| gtggcctgga agtagaagtc ttatttattg atacagatta ccactttgat atgctccggc | 360 |
| tagttacaat tcttgagcac agactatccc aaagctctga gaaataatc aaatactgcc | 420 |
| tgggaagatt ttttttggtg tactgcagta gtagcaccca cttacttctt acactttact | 480 |
| cactagaaag tatgttttgt agtcacccat ctctctgcct tttgattttg gatagcctgt | 540 |
| cagctttta ctggatagac cgcgtcaatg gaggagaaag tgtgaactta caggagtcta | 600 |
| ctctgaggaa atgttctcag tgcttagaga agcttgtaaa tgactatcgc ctggttcttt | 660 |
| ttgcaacgac acaaactata atgcagaaag cctcgagctc atcagaagaa ccttctcatg | 720 |
| cctctcgacg actgtgtgat gtggacatag actacagacc ttatctctgt aaggcatggc | 780 |
| agcaactggt gaagcacagg atgttttct ccaaacaaga tgattctcaa gcagcaacc | 840 |
| aattttcatt agtttcacgt tgtttaaaaa gtaacagttt aaaaaaacat tttttatta | 900 |
| ttggagaaag tggggttgaa ttttgttgat atacatcata aaatagtctt ttgcagggta | 960 |
| ctacgcaagc cttaaaattt ttcttaagac agagtcttgc tctgtctccc aggctggagt | 1020 |
| gcagtggcac aatcatggct cactgcagcc ttgaactcct ggcctcaagg gatcctccta | 1080 |
| tgtgtgcctc ctagagtgca gggattacag gcgtgagcca ctgctcgtgg ccaaaagttt | 1140 |
| tctttttttt tttttttctt tttgaaacag tcttactctg tctcccaggc tgctggagtg | 1200 |
| cagtggcaca atctcggccc gctgcagcct ctgcctcttg ggttcaagtg attcttccac | 1260 |

-continued

```
ctcagcctcc caggtagctg ggattacagg cacccaccac cacgcctggc taattttgt    1320 atttttaata gagacggggt ttcaccatgt tggccaggct ggtctcgaac tcctgacctc    1380
aagtgatcca cccacctcgg cctcccaaag tgctaggatt acaggcccgt gcccagccct    1440
aaagttttaa actctagggg aattaacagt atttctttac agaatggatt tgttaaacta    1500
gcacagtaaa agtaaagact attctgtttc taggctgttg aatcaaagtg attttagcaa    1560
ttaaactttg tattaattta ccaccaatat ttcttcacaa aggaactttt aaaagattat    1620
ctcagaaagt aaatctgaga ggtaagaagt aataatgagt aaatggtaag tacttgagta    1680
aatctaaaga aatattgata gtaaggcaat cctaagcaaa aagaacaaag ctggaggcat    1740
cacgctaccc agcttcaaac tatactacaa ggctacagta accaaaacag catagtactg    1800
gcacaaaaac acacgtagac tgatggaaca gaatagagaa tttagaaatg agaccacaca    1860
cctataattt ttttgatctt cgatgaacct gacaaaaaca agcaatgggc aatggattct    1920
ctattcaata aatcgtgctg ggataactgg ccagccatat ggaaaagatt gaaaatggac    1980
gccttcctta tgccatatac aaaaattaac tcaagatgga ttaaagactt aatgtaaaac    2040
ccaaaacagt aaaaatcctg gaagacaacc caggcagtac cattcaggac ataggcacag    2100
gcaaagattt catgacgaag acgccaaaaa caattgcaac agaagcaaaa attcacaaat    2160
gggatctaat taaactaaag agctgcacag caaaagaaac tatcaagaga gtaaacagac    2220
agcttacaga atgggagaaa attgttgcaa actatgcatc tgagaaaggt ctgaaatcca    2280
gcatctatac gtaatttaaa caaatttaga agaaaaaacc accccattaa aaagtgggca    2340
aaggacatga acagacactt ttcaaaagaa gacatctgtg gccaacaatc ctatggaaaa    2400
aagcccagca tcactgatca ttagagaaat gcaaatcgaa acaacaacga gataccatct    2460
cacaccagtc caaatggcta ttataaaaat gtcagaaaat aacagatgct ggtgaggttg    2520
tggagaaaaa gatatgctta tacactgttg gtggaaatgt aaattaaatt agttcagcca    2580
ttgtggaaga cagtgtgggg ataaagacag agataccatt caacccagca atctcattac    2640
tgggtatata cccaaaggaa tagaaatcat tgttataaag acacatgcac gcgtatgttc    2700
gttgcagcac tgcccatcag tgacagactg gattaaaaaa atgtggtaca tacacaccag    2760
ggaatactat acagccataa aaaggaacaa gactgactgg gcgtggtggc tcatgcctgt    2820
gatcctagca ctttgcgagg ccgaggtggg tggattgccc gcgctcagga ggtcaagacc    2880
agcctgggca acacggtgaa accccatctc tattaaaata caaaaaatta gctgggcatg    2940
gtggtgcgtg cctgtagtgc cagctactca ggaggccgag gcaggagaat gctggaacc    3000 caggaggtgg aggttgcagt gagctgagat cgcgccattg cactcccgcc tgggcgactc    3060
catctctaaa aaaaaaaaa aaaaaaaaa aaaa                                  3094
```

<210> SEQ ID NO 32
<211> LENGTH: 280
<212> TYPE: PRT
<213> ORGANISM: Homo sapiens

<400> SEQUENCE: 32

Met Cys Ser Ala Phe His Arg Ala Glu Ser Gly Thr Glu Leu Leu Ala
1               5                   10                  15

Arg Leu Glu Gly Arg Ser Ser Leu Lys Glu Ile Glu Pro Asn Leu Phe
            20                  25                  30

Ala Asp Glu Asp Ser Pro Val His Gly Asp Ile Leu Glu Phe His Gly
        35                  40                  45

```
Pro Glu Gly Thr Gly Lys Thr Glu Met Leu Tyr His Leu Thr Ala Arg
 50                  55                  60
Cys Ile Leu Pro Lys Ser Gly Gly Leu Glu Val Glu Val Leu Phe
 65                  70                  75                  80
Ile Asp Thr Asp Tyr His Phe Asp Met Leu Arg Leu Val Thr Ile Leu
                 85                  90                  95
Glu His Arg Leu Ser Gln Ser Ser Glu Ile Ile Lys Tyr Cys Leu
                100                 105                 110
Gly Arg Phe Phe Leu Val Tyr Cys Ser Ser Thr His Leu Leu Leu
            115                 120                 125
Thr Leu Tyr Ser Leu Glu Ser Met Phe Cys Ser His Pro Ser Leu Cys
        130                 135                 140
Leu Leu Ile Leu Asp Ser Leu Ser Ala Phe Tyr Trp Ile Asp Arg Val
145                 150                 155                 160
Asn Gly Gly Glu Ser Val Asn Leu Gln Glu Ser Thr Leu Arg Lys Cys
                165                 170                 175
Ser Gln Cys Leu Glu Lys Leu Val Asn Asp Tyr Arg Leu Val Leu Phe
                180                 185                 190
Ala Thr Thr Gln Thr Ile Met Gln Lys Ala Ser Ser Ser Glu Glu
            195                 200                 205
Pro Ser His Ala Ser Arg Arg Leu Cys Asp Val Asp Ile Asp Tyr Arg
        210                 215                 220
Pro Tyr Leu Cys Lys Ala Trp Gln Gln Leu Val Lys His Arg Met Phe
225                 230                 235                 240
Phe Ser Lys Gln Asp Asp Ser Gln Ser Ser Asn Gln Phe Ser Leu Val
                245                 250                 255
Ser Arg Cys Leu Lys Ser Asn Ser Leu Lys Lys His Phe Phe Ile Ile
                260                 265                 270
Gly Glu Ser Gly Val Glu Phe Cys
            275                 280

<210> SEQ ID NO 33
<211> LENGTH: 691
<212> TYPE: DNA
<213> ORGANISM: Homo sapiens

<400> SEQUENCE: 33
gtcctcctcg ccctccaggc cgcccgcgcc gcgccggagt ccgctgtccg ccagctaccc    60
gcttcctgcc gcccgccgct gccatgctgc ccgccgcgct gctccgccgc ccgggacttg   120
gccgcctcgt ccgccacgcc cgtgcctatg ccgaggccgc cgccgccccg gctgccgcct   180
ctggccccaa ccagatgtcc ttcaccttcg cctctcccac gcaggtgttc ttcaacggtg   240
ccaacgtccg gcaggtggac gtgcccacgc tgaccggagc cttcggcatc ctggcggccc   300
acgtgcccac gctgcaggtc ctgcggccgg ggctggtcgt ggtgcatgca gaggacggca   360
ccacctccaa atactttgtg agcagcggtt ccatcgcagt gaacgccgac tcttcggtgc   420
agttgttggc cgaagaggcc gtgacgctgg acatgttgga cctgggggca gccaaggcaa   480
acttggagaa ggcccaggcg gagctggtgg ggacagctga cgaggccacg cgggcagaga   540
tccagatccg aatcgaggcc aacgaggccc tggtgaaggc cctggagtag gcagccagc    600
cgccaaggtt gacctcagct tcggagccac ctctggatga actgccccca gccccgccc    660
cattaaagac ccggaagcct gaaaaaaaaa a                                  691
```

<210> SEQ ID NO 34
<211> LENGTH: 168
<212> TYPE: PRT
<213> ORGANISM: Homo sapiens

<400> SEQUENCE: 34

```
Met Leu Pro Ala Ala Leu Leu Arg Arg Pro Gly Leu Gly Arg Leu Val
 1               5                  10                  15
Arg His Ala Arg Ala Tyr Ala Glu Ala Ala Ala Pro Ala Ala Ala
            20                  25                  30
Ser Gly Pro Asn Gln Met Ser Phe Thr Phe Ala Ser Pro Thr Gln Val
            35                  40                  45
Phe Phe Asn Gly Ala Asn Val Arg Gln Val Asp Val Pro Thr Leu Thr
    50                  55                  60
Gly Ala Phe Gly Ile Leu Ala Ala His Val Pro Thr Leu Gln Val Leu
65                  70                  75                  80
Arg Pro Gly Leu Val Val His Ala Glu Asp Gly Thr Thr Ser Lys
                85                  90                  95
Tyr Phe Val Ser Ser Gly Ser Ile Ala Val Asn Ala Asp Ser Ser Val
                100                 105                 110
Gln Leu Leu Ala Glu Glu Ala Val Thr Leu Asp Met Leu Asp Leu Gly
            115                 120                 125
Ala Ala Lys Ala Asn Leu Glu Lys Ala Gln Ala Glu Leu Val Gly Thr
    130                 135                 140
Ala Asp Glu Ala Thr Arg Ala Glu Ile Gln Ile Arg Ile Glu Ala Asn
145                 150                 155                 160
Glu Ala Leu Val Lys Ala Leu Glu
                165
```

<210> SEQ ID NO 35
<211> LENGTH: 1378
<212> TYPE: DNA
<213> ORGANISM: Homo sapiens

<400> SEQUENCE: 35

| | | | | | |
|---|---|---|---|---|---|
| gcgcggcccg | ctgcaatccg | tggaggaacg | cgccgccgag | ccaccatcat | gcctgggcac | 60 |
| ttacaggaag | gcttcggctg | cgtggtcacc | aaccgattcg | accagttatt | tgacgacgaa | 120 |
| tcggacccct | tcgaggtgct | gaaggcagca | gagaacaaga | aaaagaagc | cggcggggc | 180 |
| ggcgttgggg | gccctgggc | caagagcgca | gctcaggccg | cggcccagac | caactccaac | 240 |
| gcggcaggca | aacagctgcg | caaggagtcc | cagaaagacc | gcaagaaccc | gctgccccc | 300 |
| agcgttggcg | tggttgacaa | gaaagaggag | acgcagccgc | ccgtggcgct | taagaaagaa | 360 |
| ggaataagac | gagttggaag | aagacctgat | caacaacttc | agggtgaagg | gaaaataatt | 420 |
| gatagaagac | cagaaaggcg | accacctcgt | gaacgaagat | tcgaaaagcc | acttgaagaa | 480 |
| aagggtgaag | gaggcgaatt | ttcagttgat | agaccgatta | ttgaccgacc | tattcgaggt | 540 |
| cgtggtggtc | ttggaagagg | tcgaggggc | cgtggacgtg | gaatgggccg | aggagatgga | 600 |
| tttgattctc | gtggcaaacg | tgaatttgat | aggcatagtg | gaagtgatag | atcttctttt | 660 |
| tcacattaca | gtggcctgaa | gcacgaggac | aaacgtggag | gtagcggatc | tcacaactgg | 720 |
| ggaactgtca | agacgaatt | aacagagtcc | cccaaataca | ttcagaaaca | aatatcttat | 780 |
| aattacagtg | acttggatca | atcaaatgtg | actgaggaaa | cacctgaagg | tgaagaacat | 840 |
| catccagtgg | cagacactga | aaataaggag | aatgaagttg | aagaggtaaa | agaggagggt | 900 |
| ccaaaagaga | tgactttgga | tgagtggaag | gctattcaaa | ataaggaccg | ggcaaaagta | 960 |

| | |
|---|---:|
| gaatttaata tccgaaaacc aaatgaaggt gctgatgggc agtggaagaa gggatttgtt | 1020 |
| cttcataaat caaagagtga agaggctcat gctgaagatt cggttatgga ccatcatttc | 1080 |
| cggaagccag caaatgatat aacgtctcag ctggagatca attttggaga ccttggccgc | 1140 |
| ccaggacgtg gcggcagggg aggacgaggt ggacgtgggc gtggtgggcg cccaaaccgt | 1200 |
| ggcagcagga ccgacaagtc aagtgcttct gctcctgatg tggatgaccc agaggcattc | 1260 |
| ccagctctgg cttaactgga tgccataaga caaccctggt tcctttgtga acccttctgt | 1320 |
| tcaaagcttt tgcatgctta aggattccaa acgactaaga aaaaaaaaaa aaaaaaa | 1378 |

<210> SEQ ID NO 36
<211> LENGTH: 2896
<212> TYPE: DNA
<213> ORGANISM: Homo sapiens

<400> SEQUENCE: 36

| | |
|---|---:|
| gggcgcgcca gctcgtagca ggggagcgcc cgcggcgtcg ggtttgggct ggaggtcgcc | 60 |
| atggggcgag gcagcggcac cttcgagcgt ctcctagaca aggcgaccag ccagctcctg | 120 |
| ttggagacag attgggagtc cattttgcag atctgcgacc tgatccgcca aggggacaca | 180 |
| caagcaaaat atgctgtgaa ttccatcaag aagaaagtca acgacaagaa cccacacgtc | 240 |
| gccttgtatg ccctggaggt catggaatct gtggtaaaga actgtggcca gacagttcat | 300 |
| gatgaggtgg ccaacaagca gaccatggag gagctgaagg acctgctgaa gagacaagtg | 360 |
| gaggtaaacg tccgtaacaa gatcctgtac ctgatccagg cctgggcgca tgccttccgg | 420 |
| aacgagccca gtacaaggt ggtccaggac acctaccaga tcatgaaggt ggaggggcac | 480 |
| gtctttccag aattcaaaga gagcgatgcc atgtttgctg ccgagagagc cccagactgg | 540 |
| gtggacgctg aggaatgcca ccgctgcagg gtgcagttcg gggtgatgac ccgtaagcac | 600 |
| cactgccggg cgtgtgggca gatattctgt ggaaagtgtt cttccaagta ctccaccatc | 660 |
| cccaagtttg gcatcgagaa ggaggtgcgc gtgtgtgagc cctgctacga gcagctgaac | 720 |
| aggaaagcgg agggaaaggc cacttccacc actgagctgc ccccgagta cctgaccagc | 780 |
| cccctgtctc agcagtccca gctgccccc aagagggacg agacggccct gcaggaggag | 840 |
| gaggagctgc agctggccct ggcgctgtca cagtcagagg cggaggagaa ggagaggctg | 900 |
| agacagaagt ccacgtacac ttcgtacccc aaggcggagc ccatgccctc ggcctcctca | 960 |
| gcgccccccg ccagcagcct gtactcttca cctgtgaact cgtcggcgcc tctggctgag | 1020 |
| gacatcgacc ctgagctcgc acggtatctc aaccggaact actgggagaa gaagcaggag | 1080 |
| gaggctcgca gagccccac gccatctgcg cccgtgcccc tgacgagcc ggctgcacag | 1140 |
| cctgggggaag ggcacgcagc ccccaccaac gtggtggaga ccccctccc ggagacagac | 1200 |
| tctcagccca ttcctccctc tggtggcccc tttagtgagc acagttcca caatggcgag | 1260 |
| tctgaggaga gccacgagca gttcctgaag gcgctgcaga acgccgtcac caccttcgtg | 1320 |
| aaccgcatga agagtaacca catgcggggc cgcagcatca ccaatgactc ggccgtgctc | 1380 |
| tcactcttcc agtccatcaa cggcatgcac ccgcagctgc tggagctgct caaccagctg | 1440 |
| gacgagcgca gctgtactac tgaggggctg caggacaagc tggcacagat cgcgatgcc | 1500 |
| cgggggggcgc tgagtgccct gcgcgaagag caccgggaga agcttcgccg ggcagccgag | 1560 |
| gaggcagagc gccagcgcca gatccagctg gcccagaagc tggagataat gcggcagaag | 1620 |
| aagcaggagt acctggaggt gcagaggcag ctggccatcc agagcgcctg ggagcaggag | 1680 |

-continued

```
aaggagcggc agatgcggct ggagcagcag aagcagacgg tccagatgcg cgcgcagatg   1740
cccgccttcc ccctgcccta cgcccagctc caggccatgc ccgcagccgg aggtgtgctc   1800
taccagccct cgggaccagc cagcttcccc agcaccttca gccctgccgg ctcggtggag   1860
ggctccccaa tgcacggcgt gtacatgagc cagccggccc ctgccgctgg cccctacccc   1920
agcatgccca gcactgcggc tgatcccagc atggtgagtg cctacatgta cccagcaggg   1980
gccactgggg cgcaggcggc ccccaggcc caggccggac ccaccgccag cccgcttac    2040 tcatcctacc agcctactcc cacagcgggc taccagaacg tggcctccca ggccccacag   2100
agcctcccgg ccatctctca gcctccgcag tccagcacca tgggctacat ggggagccag   2160
tcagtctcca tgggctacca gccttacaac atgcagaatc tcatgaccac cctcccaagc   2220
caggatgcgt ctctgccacc ccagcagccc tacatcgcgg ggcagcagcc catgtaccag   2280
cagatggcac cctctggcgg tcccccccag cagcagcccc ccgtggccca gcaaccgcag   2340
gcacaggggc cgccggcaca gggcagcgag gcccagctca tttcattcga ctgacccagg   2400
ccatgctcac gtccggagta acactacata cagttcacct gaaacgcctc gtctctaact   2460
gccgtcgtcc tgcctccctg tcctctactg ccggtagtgt cccttctctg cgagtgaggg   2520
ggggccttca ccccaagccc acctcccttg tcctcagcct actgcagtcc ctgagttagt   2580 ctctgctttc ттcccагg gctgggccat ggggagggaa ggactttctc ccaggggaag   2640
cccccagccc tgtgggtcat ggtctgtgag aggtggcagg aatggggacc ctcacccccc   2700
aagcagcctg tgccctctgg ccgcactgtg agctggctgt ggtgtctggg tgtggcctgg   2760
ggctccctct gcagggcct ctctcggcag ccacagccaa gggtggaggc ttcaggtctc   2820
cagcttctct gcttctcagc tgccatctcc agtgccccag aatggtacag cgataataaa   2880
atgtatttca gaaagg                                                   2896
```

<210> SEQ ID NO 37
<211> LENGTH: 777
<212> TYPE: PRT
<213> ORGANISM: Homo sapiens

<400> SEQUENCE: 37

```
Met Gly Arg Gly Ser Gly Thr Phe Glu Arg Leu Leu Asp Lys Ala Thr
 1               5                  10                  15

Ser Gln Leu Leu Leu Glu Thr Asp Trp Glu Ser Ile Leu Gln Ile Cys
             20                  25                  30

Asp Leu Ile Arg Gln Gly Asp Thr Gln Ala Lys Tyr Ala Val Asn Ser
         35                  40                  45

Ile Lys Lys Lys Val Asn Asp Lys Asn Pro His Val Ala Leu Tyr Ala
     50                  55                  60

Leu Glu Val Met Glu Ser Val Val Lys Asn Cys Gly Gln Thr Val His
 65                  70                  75                  80

Asp Glu Val Ala Asn Lys Gln Thr Met Glu Glu Leu Lys Asp Leu Leu
                 85                  90                  95

Lys Arg Gln Val Glu Val Asn Val Arg Asn Lys Ile Leu Tyr Leu Ile
            100                 105                 110

Gln Ala Trp Ala His Ala Phe Arg Asn Glu Pro Lys Tyr Lys Val Val
        115                 120                 125

Gln Asp Thr Tyr Gln Ile Met Lys Val Glu Gly His Val Phe Pro Glu
    130                 135                 140

Phe Lys Glu Ser Asp Ala Met Phe Ala Ala Glu Arg Ala Pro Asp Trp
145                 150                 155                 160
```

```
Val Asp Ala Glu Glu Cys His Arg Cys Arg Val Gln Phe Gly Val Met
            165                 170                 175

Thr Arg Lys His His Cys Arg Ala Cys Gly Gln Ile Phe Cys Gly Lys
            180                 185                 190

Cys Ser Ser Lys Tyr Ser Thr Ile Pro Lys Phe Gly Ile Glu Lys Glu
            195                 200                 205

Val Arg Val Cys Glu Pro Cys Tyr Gln Leu Asn Arg Lys Ala Glu
            210                 215                 220

Gly Lys Ala Thr Ser Thr Thr Glu Leu Pro Glu Tyr Leu Thr Ser
225                 230                 235                 240

Pro Leu Ser Gln Gln Ser Gln Leu Pro Pro Lys Arg Asp Glu Thr Ala
            245                 250                 255

Leu Gln Glu Glu Glu Glu Leu Gln Leu Ala Leu Ala Leu Ser Gln Ser
            260                 265                 270

Glu Ala Glu Glu Lys Glu Arg Leu Arg Gln Lys Ser Thr Tyr Thr Ser
            275                 280                 285

Tyr Pro Lys Ala Glu Pro Met Pro Ser Ala Ser Ser Ala Pro Pro Ala
            290                 295                 300

Ser Ser Leu Tyr Ser Ser Pro Val Asn Ser Ser Ala Pro Leu Ala Glu
305                 310                 315                 320

Asp Ile Asp Pro Glu Leu Ala Arg Tyr Leu Asn Arg Asn Tyr Trp Glu
            325                 330                 335

Lys Lys Gln Glu Glu Ala Arg Lys Ser Pro Thr Pro Ser Ala Pro Val
            340                 345                 350

Pro Leu Thr Glu Pro Ala Ala Gln Pro Gly Glu Gly His Ala Ala Pro
            355                 360                 365

Thr Asn Val Val Glu Asn Pro Leu Pro Glu Thr Asp Ser Gln Pro Ile
            370                 375                 380

Pro Pro Ser Gly Gly Pro Phe Ser Glu Pro Gln Phe His Asn Gly Glu
385                 390                 395                 400

Ser Glu Glu Ser His Glu Gln Phe Leu Lys Ala Leu Gln Asn Ala Val
            405                 410                 415

Thr Thr Phe Val Asn Arg Met Lys Ser Asn His Met Arg Gly Arg Ser
            420                 425                 430

Ile Thr Asn Asp Ser Ala Val Leu Ser Leu Phe Gln Ser Ile Asn Gly
            435                 440                 445

Met His Pro Gln Leu Leu Glu Leu Leu Asn Gln Leu Asp Glu Arg Arg
            450                 455                 460

Leu Tyr Tyr Glu Gly Leu Gln Asp Lys Leu Ala Gln Ile Arg Asp Ala
465                 470                 475                 480

Arg Gly Ala Leu Ser Ala Leu Arg Glu Glu His Arg Glu Lys Leu Arg
            485                 490                 495

Arg Ala Ala Glu Glu Ala Glu Arg Gln Arg Gln Ile Gln Leu Ala Gln
            500                 505                 510

Lys Leu Glu Ile Met Arg Gln Lys Gln Glu Tyr Leu Glu Val Gln
            515                 520                 525

Arg Gln Leu Ala Ile Gln Arg Leu Gln Glu Gln Glu Lys Glu Arg Gln
            530                 535                 540

Met Arg Leu Glu Gln Gln Lys Gln Thr Val Gln Met Arg Ala Gln Met
545                 550                 555                 560

Pro Ala Phe Pro Leu Pro Tyr Ala Gln Leu Gln Ala Met Pro Ala Ala
            565                 570                 575
```

-continued

Gly Gly Val Leu Tyr Gln Pro Ser Gly Pro Ala Ser Phe Pro Ser Thr
                580                 585                 590
Phe Ser Pro Ala Gly Ser Val Glu Gly Ser Pro Met His Gly Val Tyr
            595                 600                 605
Met Ser Gln Pro Ala Pro Ala Ala Gly Pro Tyr Pro Ser Met Pro Ser
        610                 615                 620
Thr Ala Ala Asp Pro Ser Met Val Ser Ala Tyr Met Tyr Pro Ala Gly
625                 630                 635                 640
Ala Thr Gly Ala Gln Ala Ala Pro Gln Ala Gln Ala Gly Pro Thr Ala
                645                 650                 655
Ser Pro Ala Tyr Ser Ser Tyr Gln Pro Thr Pro Thr Ala Gly Tyr Gln
            660                 665                 670
Asn Val Ala Ser Gln Ala Pro Gln Ser Leu Pro Ala Ile Ser Gln Pro
        675                 680                 685
Pro Gln Ser Ser Thr Met Gly Tyr Met Gly Ser Gln Ser Val Ser Met
    690                 695                 700
Gly Tyr Gln Pro Tyr Asn Met Gln Asn Leu Met Thr Thr Leu Pro Ser
705                 710                 715                 720
Gln Asp Ala Ser Leu Pro Pro Gln Pro Tyr Ile Ala Gly Gln Gln
                725                 730                 735
Pro Met Tyr Gln Gln Met Ala Pro Ser Gly Gly Pro Gln Gln Gln
            740                 745                 750
Pro Pro Val Ala Gln Gln Pro Gln Ala Gln Gly Pro Pro Ala Gln Gly
        755                 760                 765
Ser Glu Ala Gln Leu Ile Ser Phe Asp
    770                 775

<210> SEQ ID NO 38
<211> LENGTH: 2569
<212> TYPE: DNA
<213> ORGANISM: Homo sapiens

<400> SEQUENCE: 38

```
tccctcgtct ctctcgggca acatggcggg cgtggaggag gtagcggcct ccgggagcca    60
cctgaatggc gacctggatc agacgacag ggaagaagga gctgcctcta cggctgagga   120
agcagccaag aaaaaagac gaaagaagaa gaagagcaaa gggccttctg cagcagggga   180
acaggaacct gataaagaat caggagcctc agtggatgaa gtagcaagac agttggaaag   240
atcagcattg gaagataaag aaagagatga agatgatgaa gatggagatg gcgatggaga   300
tggagcaact ggaaagaaga gaaaaagaa gaagaagaag agaggaccaa aagttcaaac   360
agaccctccc tcagttccaa tatgtgacct gtatcctaat ggtgtatttc ccaaaggaca   420
agaatgcgaa tacccaccca cacaagatgg gcgaacagct gcttggagaa ctacaagtga   480
agaaaagaaa gcattagatc aggcaagtga agagatttgg aatgattttc gagaagctgc   540
agaagcacat cgacaagtta gaaatacgt aatgagctgg atcaagcctg ggatgacaat   600
gatagaaatc tgtgaaaagt tggaagactg ttcacgcaag ttaataaaag agaatggatt   660
aaatgcaggc ctggcatttc ctactggatg ttctctcaat aattgtgctg cccattatac   720
tcccaatgcc ggtgacacaa cagtattaca gtatgatgac atctgtaaaa tagactttgg   780
aacacatata agtggtagga ttattgactg tgcttttact gtcacttta atcccaaata   840
tgatacgtta ttaaaagctg taaagatgc tactaaacact ggaataaagt gtgctggaat   900
tgatgttcgt ctgtgtgatg ttggtgaggc catccaagaa gttatggagt cctatgaagt   960
```

```
tgaaatagat gggaagacat atcaagtgaa accaatccgt aatctaaatg gacattcaat    1020
tgggcaatat agaatacatg ctggaaaaac agtgccgatt gtgaaaggag gggaggcaac    1080
aagaatggag gaaggagaag tatatgcaat tgaaaccttt ggtagtacag gaaaaggtgt    1140
tgttcatgat gatatggaat gttcacatta catgaaaaat tttgatgttg gacatgtgcc    1200 ataaggctt ccaagaacaa aacacttgtt aaatgtcatc aatgaaaact ttggaaccct     1260
tgccttctgc cgcagatggc tggatcgctt gggagaaagt aaatacttga tggctctgaa    1320
gaatctgtgt gacttgggca ttgtagatcc atatccacca ttatgtgaca ttaaaggatc    1380
atatacagcg caatttgaac ataccatcct gttgcgtcca acatgtaaag aagttgtcag    1440
cagaggagat gactattaaa cttagtccaa agccacctca acacctttat tttctgagct    1500
ttgttggaaa acatgatacc agaattaatt tgccacatgt tgtctgtttt aacagtggac    1560
ccatgtaata cttttatcca tgtttaaaaa agaaggaatt tggacaaagg caaaccgtct    1620
aatgtaatta accaacgaaa aagctttccg gactttttaaa tgctaactgt ttttcccctt    1680
cctgtctagg aaaatgctat aaagctcaaa ttagttagga atgacttata cgttttgttt    1740
tgaataccta agagatactt tttggatatt tatattgcca tattcttact tgaatgcttt    1800
gaatgactac atccagttct gcacctatac cctctggtgt tgcttttttaa ccttcctgga    1860 atccattttc taaaaaataa agacacattc ttctcagcac cacacaacac ctattccaaa    1920
atcgaccaca tatttggaag taaagctctc ctcagcaaat gtaaagaac agaaattata     1980 acaaactgtc tctcagacca cagtataacc aaactagaac tcaggattaa gaaactcact    2040
caaaaccaca caactacatg gaaactgaac aacctgctcc tgaatgacta ctggatacat    2100
aacaaaatga aggcagaaat aaagatgttc tttaaaacca atgagaacaa agacacaaca    2160
taccagaatc tctgggacac attcaaagca gtgtgtagag ggaaatttat agcactaaat    2220
gcccacaaga gaaagcagga aatatctaaa attgacaccc taacatcaca attaaaagaa    2280
ctagagaagc aagagcaaac acattgaaaa gctaagagaa ggcaagaaat aactaagatc    2340
agagcagaac tgaaggaaat agagacacaa aaaactcttc aaaaaatcaa tgaatccagg    2400
agctggtttt ttgaaacgat caacaaaatt gatagacact agcaagacta ataaagaaga    2460
aaggagagaa gaatcaaata gaagcaataa aaaatgataa aggggatatc accaccaatc    2520
ccacagaaat aaaccaccat cagagaatac tacaaacacc tctacgcaa                2569
```

<210> SEQ ID NO 39
<211> LENGTH: 478
<212> TYPE: PRT
<213> ORGANISM: Homo sapiens

<400> SEQUENCE: 39

```
Met Ala Gly Val Glu Val Ala Ala Ser Gly Ser His Leu Asn Gly
  1               5                  10                  15

Asp Leu Asp Pro Asp Asp Arg Glu Gly Ala Ala Ser Thr Ala Glu
                 20                  25                  30

Glu Ala Ala Lys Lys Lys Arg Lys Lys Lys Ser Lys Gly Pro
             35                  40                  45

Ser Ala Ala Gly Glu Gln Glu Pro Asp Lys Glu Ser Gly Ala Ser Val
         50                  55                  60

Asp Glu Val Ala Arg Gln Leu Glu Arg Ser Ala Leu Glu Asp Lys Glu
 65                  70                  75                  80

Arg Asp Glu Asp Glu Asp Gly Asp Gly Asp Gly Asp Gly Ala Thr
                 85                  90                  95
```

```
Gly Lys Lys Lys Lys Lys Lys Lys Arg Gly Lys Val Gln
        100                 105                 110

Thr Asp Pro Pro Ser Val Pro Ile Cys Asp Leu Tyr Pro Asn Gly Val
        115                 120                 125

Phe Pro Lys Gly Gln Glu Cys Glu Tyr Pro Pro Thr Gln Asp Gly Arg
        130                 135                 140

Thr Ala Ala Trp Arg Thr Thr Ser Glu Glu Lys Lys Ala Leu Asp Gln
145                 150                 155                 160

Ala Ser Glu Glu Ile Trp Asn Asp Phe Arg Glu Ala Ala Glu Ala His
                165                 170                 175

Arg Gln Val Arg Lys Tyr Val Met Ser Trp Ile Lys Pro Gly Met Thr
                180                 185                 190

Met Ile Glu Ile Cys Glu Lys Leu Glu Asp Cys Ser Arg Lys Leu Ile
            195                 200                 205

Lys Glu Asn Gly Leu Asn Ala Gly Leu Ala Phe Pro Thr Gly Cys Ser
        210                 215                 220

Leu Asn Asn Cys Ala Ala His Tyr Thr Pro Asn Ala Gly Asp Thr Thr
225                 230                 235                 240

Val Leu Gln Tyr Asp Asp Ile Cys Lys Ile Asp Phe Gly Thr His Ile
                245                 250                 255

Ser Gly Arg Ile Ile Asp Cys Ala Phe Thr Val Thr Phe Asn Pro Lys
                260                 265                 270

Tyr Asp Thr Leu Leu Lys Ala Val Lys Asp Ala Thr Asn Thr Gly Ile
                275                 280                 285

Lys Cys Ala Gly Ile Asp Val Arg Leu Cys Asp Val Gly Glu Ala Ile
        290                 295                 300

Gln Glu Val Met Glu Ser Tyr Glu Val Glu Ile Asp Gly Lys Thr Tyr
305                 310                 315                 320

Gln Val Lys Pro Ile Arg Asn Leu Asn Gly His Ser Ile Gly Gln Tyr
                325                 330                 335

Arg Ile His Ala Gly Lys Thr Val Pro Ile Val Lys Gly Gly Glu Ala
                340                 345                 350

Thr Arg Met Glu Glu Gly Glu Val Tyr Ala Ile Glu Thr Phe Gly Ser
            355                 360                 365

Thr Gly Lys Gly Val Val His Asp Asp Met Glu Cys Ser His Tyr Met
        370                 375                 380

Lys Asn Phe Asp Val Gly His Val Pro Ile Arg Leu Pro Arg Thr Lys
385                 390                 395                 400

His Leu Leu Asn Val Ile Asn Glu Asn Phe Gly Thr Leu Ala Phe Cys
                405                 410                 415

Arg Arg Trp Leu Asp Arg Leu Gly Glu Ser Lys Tyr Leu Met Ala Leu
                420                 425                 430

Lys Asn Leu Cys Asp Leu Gly Ile Val Asp Pro Tyr Pro Pro Leu Cys
        435                 440                 445

Asp Ile Lys Gly Ser Tyr Thr Ala Gln Phe Glu His Thr Ile Leu Leu
        450                 455                 460

Arg Pro Thr Cys Lys Glu Val Val Ser Arg Gly Asp Asp Tyr
465                 470                 475

<210> SEQ ID NO 40
<211> LENGTH: 1183
<212> TYPE: DNA
<213> ORGANISM: Homo sapiens
<220> FEATURE:
```

```
<221> NAME/KEY: misc_feature
<222> LOCATION: (0)...(0)
<223> OTHER INFORMATION: n = a, t, c or g

<400> SEQUENCE: 40
cgcccaagaa gaaaatggcc ataagtggag tccctgtgct aggattttc atcatagctg      60
tgctgatgag cgctcaggaa tcatgggcta tcaaagaaga acatgtgatc atccaggccg    120
agttctatct gaatcctgac caatcaggcg agtttatgtt tgactttgat ggtgatgaga    180
ttttccatgt ggatatggca agaaggaga cggtctggcg gcttgaagaa tttggacgat     240
ttgccagctt tgaggctcaa ggtgcattgg ccaacatagc tgtggacaaa gccaacttgg    300
aaatcatgac aaagcgctcc aactatactc cgatcaccaa tgtacctcca gaggtaactg    360
tgctcacgaa cagccctgtg gaactgagag agcccaacgt cctcatctgt ttcatcgaca    420
agttcacccc accagtggtc aatgtcacgt ggcttcgaaa tggaaaacct gtcaccacag    480
gagtgtcaga gacagtcttc ctgcccaggg aagaccacct tttccgcaag ttccactatc    540
tccccttcct gccctcaact gaggacgttt acgactgcag ggtggagcac tgggcttgg    600
atgagcctct tctcaagcac tgggagtttg atgctccaag ccctctccca gagactacag    660
agaacgtggt gtgtgccctg ggcctgactg tgggtctggt gggcatcatt attgggacca    720
tcttcatcat caagggagtg cgcaaaagca atgcagcaga acgcagggg cctctgtaag    780
gcacatggag gtgatgatgt tcttagaga aagatcact gaagaaactt ctgctttaat     840
gactttacaa agctggcaat attacaatcc ttgacctcag tgaaagcagt catcttcagc    900
gttttccagc cctatagcca ccccaagtgt ggttatgcct cctcgattgc tccgtactct    960
aacatctagc tggcttccct gtctattgcc ttttcctgta tctattttcc tctatttcct   1020
atcattttat tatcaccatg caatgcctct ggaataaaac atacaggagt ctgtctctgc   1080
tatggaatgc cccatggggc atctcttgtg tacttattgt ttaaggtttc ctcaaactgn   1140
gattcttctg aacacaataa actattttga tgatcttggg tgg                     1183

<210> SEQ ID NO 41
<211> LENGTH: 254
<212> TYPE: PRT
<213> ORGANISM: Homo sapiens

<400> SEQUENCE: 41

Met Ala Ile Ser Gly Val Pro Val Leu Gly Phe Phe Ile Ile Ala Val
  1               5                  10                  15

Leu Met Ser Ala Gln Glu Ser Trp Ala Ile Lys Glu His Val Ile
             20                  25                  30

Ile Gln Ala Glu Phe Tyr Leu Asn Pro Asp Gln Ser Gly Glu Phe Met
         35                  40                  45

Phe Asp Phe Asp Gly Asp Glu Ile Phe His Val Asp Met Ala Lys Lys
     50                  55                  60

Glu Thr Val Trp Arg Leu Glu Glu Phe Gly Arg Phe Ala Ser Phe Glu
 65                  70                  75                  80

Ala Gln Gly Ala Leu Ala Asn Ile Ala Val Asp Lys Ala Asn Leu Glu
                 85                  90                  95

Ile Met Thr Lys Arg Ser Asn Tyr Thr Pro Ile Thr Asn Val Pro Pro
            100                 105                 110

Glu Val Thr Val Leu Thr Asn Ser Pro Val Glu Leu Arg Glu Pro Asn
        115                 120                 125

Val Leu Ile Cys Phe Ile Asp Lys Phe Thr Pro Pro Val Val Asn Val
```

-continued

```
            130                 135                 140
Thr Trp Leu Arg Asn Gly Lys Pro Val Thr Thr Gly Val Ser Glu Thr
145                 150                 155                 160

Val Phe Leu Pro Arg Glu Asp His Leu Phe Arg Lys Phe His Tyr Leu
                165                 170                 175

Pro Phe Leu Pro Ser Thr Glu Asp Val Tyr Asp Cys Arg Val Glu His
                180                 185                 190

Trp Gly Leu Asp Glu Pro Leu Leu Lys His Trp Glu Phe Asp Ala Pro
            195                 200                 205

Ser Pro Leu Pro Glu Thr Thr Glu Asn Val Val Cys Ala Leu Gly Leu
        210                 215                 220

Thr Val Gly Leu Val Gly Ile Ile Ile Gly Thr Ile Phe Ile Ile Lys
225                 230                 235                 240

Gly Val Arg Lys Ser Asn Ala Ala Glu Arg Arg Gly Pro Leu
                245                 250
```

<210> SEQ ID NO 42
<211> LENGTH: 266
<212> TYPE: DNA
<213> ORGANISM: Homo sapiens

<400> SEQUENCE: 42

```
atgcccaagt gtcccaagtg caacaaggag gtgtacttcg ccgagagggt gacctctctg    60
ggcaaggact ggcatcggcc ctgcctgaag tgcgagaaat gtgggaagac gctgacctct   120
gggggccacg ctgagcacga aggcaaaccc tactgcaacc accctgcta cgcagccatg    180
tttgggccta aaggctttgg gcggggcgga gccgagagcc acactttcaa gtaaaccagg   240
tggtggagac ccatccttgg ctgctt                                        266
```

<210> SEQ ID NO 43
<211> LENGTH: 77
<212> TYPE: PRT
<213> ORGANISM: Homo sapiens

<400> SEQUENCE: 43

```
Met Pro Lys Cys Pro Lys Cys Asn Lys Glu Val Tyr Phe Ala Glu Arg
1               5                   10                  15

Val Thr Ser Leu Gly Lys Asp Trp His Arg Pro Cys Leu Lys Cys Glu
            20                  25                  30

Lys Cys Gly Lys Thr Leu Thr Ser Gly Gly His Ala Glu His Glu Gly
        35                  40                  45

Lys Pro Tyr Cys Asn His Pro Cys Tyr Ala Ala Met Phe Gly Pro Lys
    50                  55                  60

Gly Phe Gly Arg Gly Gly Ala Glu Ser His Thr Phe Lys
65                  70                  75
```

<210> SEQ ID NO 44
<211> LENGTH: 1665
<212> TYPE: DNA
<213> ORGANISM: Homo sapiens

<400> SEQUENCE: 44

```
gaaggaactg gttctgctca cacttgctgg cttgcgcatc aggactggct ttatctcctg    60
actcacggtg caaaggtgca ctctgcgaac gttaagtccg tccccagcgc ttggaatcct   120
acggccccca cagccggatc ccctcagcct tccaggtcct caactcccgt ggacgctgaa   180
caatggcctc catgggcta caggtaatgg gcatcgcgct ggccgtcctg ggctggctgg   240
```

-continued

```
ccgtcatgct gtgctgcgcg ctgcccatgt ggcgcgtgac ggccttcatc ggcagcaaca    300
ttgtcacctc gcagaccatc tgggagggcc tatggatgaa ctgcgtggtg cagagcaccg    360
gccagatgca gtgcaaggtg tacgactcgc tgctggcact gccgcaggac ctgcaggcgg    420
cccgcgccct cgtcatcatc agcatcatcg tggctgctct gggcgtgctg ctgtccgtgg    480
tggggggcaa gtgtaccaac tgcctggagg atgaaagcgc caaggccaag accatgatcg    540
tggcgggcgt ggtgttcctg ttggccggcc ttatggtgat agtgccggtg tcctggacgg    600
cccacaacat catccaagac ttctacaatc cgctggtggc ctccgggcag aagcgggaga    660
tgggtgcctc gctctacgtc ggctgggccg cctccggcct gctgctcctt ggcggggggc    720
tgctttgctg caactgtcca ccccgcacag acaagcctta ctccgccaag tattctgctg    780
cccgctctgc tgctgccagc aactacgtgt aaggtgccac ggctccactc tgttcctctc    840
tgctttgttc ttccctggac tgagctcagc gcaggctgtg accccaggag ggccctgcca    900
cgggccactg gctgctgggg actggggact gggcagagac tgagccaggc aggaaggcag    960
cagccttcag cctctctggc ccactcggac aacttcccaa ggccgcctcc tgctagcaag   1020
aacagagtcc accctcctct ggatattggg gagggacgga agtgacaggg tgtggtggtg   1080
gagtggggag ctggcttctg ctggccagga tagcttaacc ctgactttgg gatctgcctg   1140
catcggcgtt ggccactgtc cccatttaca ttttccccac tctgtctgcc tgcatctcct   1200
ctgttccggg taggccttga tatcacctct gggactgtgc cttgctcacc gaaacccgcg   1260
cccaggagta tggctgaggc cttgcccacc cacctgcctg ggaagtgcag agtggatgga   1320
cgggtttaga ggggaggggc gaaggtgctg taaacaggtt tgggcagtgg tgggggaggg   1380
ggccagagag gcggctcagg ttgcccagct ctgtggcctc aggactctct gcctcacccg   1440
cttcagccca gggcccctgg agactgatcc cctctgagtc ctctgcccct tccaaggaca   1500
ctaatgagcc tgggagggtg gcagggagga ggggacagct tcacccttgg aagtcctggg   1560
gttttttcctc ttccttcttt gtggtttctg ttttgtaatt taagaagagc tattcatcac   1620
tgtaattatt attattttct acaataaatg ggacctgtgc acagg                   1665
```

<210> SEQ ID NO 45
<211> LENGTH: 209
<212> TYPE: PRT
<213> ORGANISM: Homo sapiens

<400> SEQUENCE: 45

```
Met Ala Ser Met Gly Leu Gln Val Met Gly Ile Ala Leu Ala Val Leu
  1               5                  10                  15

Gly Trp Leu Ala Val Met Leu Cys Cys Ala Leu Pro Met Trp Arg Val
             20                  25                  30

Thr Ala Phe Ile Gly Ser Asn Ile Val Thr Ser Gln Thr Ile Trp Glu
         35                  40                  45

Gly Leu Trp Met Asn Cys Val Val Gln Ser Thr Gly Gln Met Gln Cys
     50                  55                  60

Lys Val Tyr Asp Ser Leu Leu Ala Leu Pro Gln Asp Leu Gln Ala Ala
 65                  70                  75                  80

Arg Ala Leu Val Ile Ile Ser Ile Ile Val Ala Ala Leu Gly Val Leu
                 85                  90                  95

Leu Ser Val Val Gly Gly Lys Cys Thr Asn Cys Leu Glu Asp Glu Ser
            100                 105                 110

Ala Lys Ala Lys Thr Met Ile Val Ala Gly Val Val Phe Leu Leu Ala
```

```
                    115                 120                 125
Gly Leu Met Val Ile Val Pro Val Ser Trp Thr Ala His Asn Ile Ile
    130                 135                 140

Gly Asp Phe Tyr Asn Pro Leu Val Ala Ser Gly Gln Lys Arg Glu Met
145                 150                 155                 160

Gly Ala Ser Leu Tyr Val Gly Trp Ala Ala Ser Gly Leu Leu Leu Leu
                165                 170                 175

Gly Gly Gly Leu Leu Cys Cys Asn Cys Pro Pro Arg Thr Asp Lys Pro
                180                 185                 190

Tyr Ser Ala Lys Tyr Ser Ala Ala Arg Ser Ala Ala Ala Ser Asn Tyr
                195                 200                 205

Val
```

<210> SEQ ID NO 46
<211> LENGTH: 1009
<212> TYPE: DNA
<213> ORGANISM: Homo sapiens

<400> SEQUENCE: 46

```
ggcagtagct tgctgatgct cccagctgaa taaagccctt ccttctacaa tttggtgtct      60
gaggggtttt gtctgcggct cgtcctgcta catttcttgg ttccctgacc aggaaacgag     120
gtaactgatg gacagccgag gcagcccctt aggcggctta ggcctcccct gtggagcatc     180
cctgaggcgg actccggcca gcccgagtga tgcgatccaa agagcactcc cgggtaggaa     240
attgccccgg tggaatgcct caccagagca gcgtgtagca gttccctgtg gaggattaac     300
acagtggctg aacaccggga aggaactggc acttggagtc cggacatctg aaacttggta     360
agactagtct ttgaacttg ccccactcca tctaggtgga agtgtggcct gatcacccac     420
gacatgcctg cattggcact tctgttctgg ttttgacttg acttagattg tgtgatactt     480
tggttttggt tttggtttga cctggcttgg attctagata ctctgatttg gttttgatt      540
tggtttggtg taaactgcaa gagtgtgtat gcccttttta cctgttttt gtttgtggc       600
atgtgtgtgt gtgggtgtg gtgttttgtc tcgaagaagc atgggtcagg tacaaataag      660
cccaccccac taggaactat gttaaaaaaa aattcaagaa agaatttaag ggagattaca     720
gtgttactgt gacaccagga aaacttagaa ctttgtgtga aatagactgg ccagcattag     780
aggtgggttg gccatcagaa ggaagcctgg acaggtccct tgtttcaaag gtatgacaca     840
aggtaacacc aattctaagt taatttgaag tttgcttaaa gttaacagtg taacatgtat     900
tatggtaact tctaatcttg tggccttaga cagtctagtc caaaggcata agaaagttt      960
gctttaaaaa aaaaaaaaag gaatggttat cttcaaaaaa aaaaaaaa                 1009
```

<210> SEQ ID NO 47
<211> LENGTH: 1250
<212> TYPE: DNA
<213> ORGANISM: Homo sapiens

<400> SEQUENCE: 47

```
aattcggcac gagggcaggt gcaggcgcac gcggcgagag cgtatggagc cgagccgtta      60
gcgcgcgccg tcggtgagtc agtccgtccg tccgtccgtc gtcggggcg ccgcagctcc     120
cgccaggccc agcggcccg gccccctcgtc tccccgcacc cggagccacc cggtggagcg     180
ggccttgccg cggcagccat gtccatgggc ctggagatca cgggcaccgc gctggccgtg     240
ctgggctggc tgggcaccat cgtgtgctgc gcgttgccca tgtggcgcgt gtcggccttc     300
```

-continued

| | |
|---|---|
| atcggcagca acatcatcac gtcgcagaac atctgggagg gcctgtggat gaactgcgtg | 360 |
| gtgcagagca ccggccagat gcagtgcaag gtgtacgact cgctgctggc actgccacag | 420 |
| gaccttcagg cggcccgcgc cctcatcgtg gtggccatcc tgctggccgc cttcgggctg | 480 |
| ctagtggcgc tggtgggcgc ccagtgcacc aactgcgtgc aggacgacac ggccaaggcc | 540 |
| aagatcacca tcgtggcagg cgtgctgttc cttctcgccg ccctgctcac cctcgtgccg | 600 |
| gtgtcctggt cggccaacac cattatccgg gacttctaca accccgtggt gcccgaggcg | 660 |
| cagaagcgcg agatgggcgc gggcctgtac gtgggctggg cggccgcggc gctgcagctg | 720 |
| ctgggggcg cgctgctctg ctgctcgtgt cccccacgcg agaagaagta cacggccacc | 780 |
| aaggtcgtct actccgcgcc gcgctccacc ggcccgggag ccagcctggg cacaggctac | 840 |
| gaccgcaagg actacgtcta agggacagac gcagggagac cccaccacca ccaccaccac | 900 |
| caacaccacc accaccaccg cgagctggag cgcgcaccag gccatccagc gtgcagcctt | 960 |
| gcctcggagg ccagcccacc cccagaagcc aggaagcccc cgcgctggac tggggcagct | 1020 |
| tccccagcag ccacggcttt cggggccggg cagtcgactt cggggcccag ggaccaacct | 1080 |
| gcatggactg tgaaacctca cccttctgga gcacggggcc tgggtgaccg ccaatacttg | 1140 |
| accacccccgt cgagccccat cgggccgctg ccccatgtc gcgctgggca gggaccggca | 1200 |
| gccctggaag gggcacttga tatttttcaa taaaagcctc tcgttttagc | 1250 |

<210> SEQ ID NO 48
<211> LENGTH: 220
<212> TYPE: PRT
<213> ORGANISM: Homo sapiens

<400> SEQUENCE: 48

Met Ser Met Gly Leu Glu Ile Thr Gly Thr Ala Leu Ala Val Leu Gly
1               5                   10                  15

Trp Leu Gly Thr Ile Val Cys Cys Ala Leu Pro Met Trp Arg Val Ser
            20                  25                  30

Ala Phe Ile Gly Ser Asn Ile Ile Thr Ser Gln Asn Ile Trp Glu Gly
        35                  40                  45

Leu Trp Met Asn Cys Val Val Gln Ser Thr Gly Gln Met Gln Cys Lys
    50                  55                  60

Val Tyr Asp Ser Leu Leu Ala Leu Pro Gln Asp Leu Gln Ala Ala Arg
65                  70                  75                  80

Ala Leu Ile Val Val Ala Ile Leu Leu Ala Ala Phe Gly Leu Leu Val
                85                  90                  95

Ala Leu Val Gly Ala Gln Cys Thr Asn Cys Val Gln Asp Asp Thr Ala
            100                 105                 110

Lys Ala Lys Ile Thr Ile Val Ala Gly Val Leu Phe Leu Leu Ala Ala
        115                 120                 125

Leu Leu Thr Leu Val Pro Val Ser Trp Ser Ala Asn Thr Ile Ile Arg
    130                 135                 140

Asp Phe Tyr Asn Pro Val Val Pro Glu Ala Gln Lys Arg Glu Met Gly
145                 150                 155                 160

Ala Gly Leu Tyr Val Gly Trp Ala Ala Ala Ala Leu Gln Leu Leu Gly
                165                 170                 175

Gly Ala Leu Leu Cys Cys Ser Cys Pro Pro Arg Glu Lys Lys Tyr Thr
            180                 185                 190

Ala Thr Lys Val Val Tyr Ser Ala Pro Arg Ser Thr Gly Pro Gly Ala
        195                 200                 205

```
Ser Leu Gly Thr Gly Tyr Asp Arg Lys Asp Tyr Val
    210                 215                 220
```

<210> SEQ ID NO 49
<211> LENGTH: 3321
<212> TYPE: DNA
<213> ORGANISM: Homo sapiens

<400> SEQUENCE: 49

| | | | | | |
|---|---|---|---|---|---|
| atgaagattt | tgatacttgg | tatttttctg | tttttatgta | gtaccccagc | ctgggcgaaa | 60 |
| gaaaagcatt | attacattgg | aattattgaa | acgacttggg | attatgcctc | tgaccatggg | 120 |
| gaaaagaaac | ttatttctgt | tgacacggaa | cattccaata | tctatcttca | aaatggccca | 180 |
| gatagaattg | ggagactata | taagaaggcc | ctttatcttc | agtacacaga | tgaaaccttt | 240 |
| aggacaacta | tagaaaaacc | ggtctggctt | gggttttag | gccctattat | caaagctgaa | 300 |
| actggagata | agtttatgt | acacttaaaa | aaccttgcct | ctaggcccta | caccttcat | 360 |
| tcacatggaa | taacttacta | taaggaacat | gagggggcca | tctaccctga | taacaccaca | 420 |
| gattttcaaa | gagcagatga | caaagtatat | ccaggagagc | agtatacata | catgttgctt | 480 |
| gccactgaag | aacaaagtcc | tggggaagga | gatggcaatt | gtgtgactag | gatttaccat | 540 |
| tcccacattg | atgctccaaa | agatattgcc | tcaggactca | tcggaccttt | aataatctgt | 600 |
| aaaaaagatt | ctctagataa | agaaaaagaa | aaacatattg | accgagaatt | tgtggtgatg | 660 |
| ttttctgtgg | tggatgaaaa | tttcagctgg | tacctagaag | acaacattaa | aacctactgc | 720 |
| tcagaaccag | agaagttga | caaagacaac | gaagacttcc | aggagagtaa | cagaatgtat | 780 |
| tctgtgaatg | gatacacttt | tggaagtctc | ccaggactct | ccatgtgtgc | tgaagacaga | 840 |
| gtaaaatggt | acctttttgg | tatgggtaat | gaagttgatg | tgcacgcagc | tttctttcac | 900 |
| gggcaagcac | tgactaacaa | gaactaccgt | attgacacaa | tcaacctctt | cctgctacc | 960 |
| ctgtttgatg | cttatatggt | ggcccagaac | cctggagaat | ggatgctcag | ctgtcagaat | 1020 |
| ctaaaccatc | tgaaagccgg | tttgcaagcc | ttttccagg | tccaggagtg | taacaagtct | 1080 |
| tcatcaaagg | ataatatccg | tgggaagcat | gttagacact | actacattgc | cgctgaggaa | 1140 |
| atcatctgga | actatgctcc | ctctggtata | gacatcttca | ctaaagaaaa | cttaacagca | 1200 |
| cctggaagtg | actcagcggt | gttttttgaa | caaggtacca | aagaattgg | aggctcttat | 1260 |
| aaaaagctgg | tttatcgtga | gtacacagat | gcctccttca | caaatcgaaa | ggagagaggc | 1320 |
| cctgaagaag | agcatcttgg | catcctgggt | cctgtcattt | gggcagaggt | gggagacacc | 1380 |
| atcagagtaa | ccttccataa | caaggagca | tatcccctca | gtattgagcc | gattggggtg | 1440 |
| agattcaata | gaacaacga | gggcacatac | tattcccaa | attacaaccc | ccagagcaga | 1500 |
| agtgtgcctc | cttcagcctc | ccatgtggca | cccacagaaa | cattcaccta | tgaatggact | 1560 |
| gtccccaaag | aagtaggacc | cactaatgca | gatcctgtgt | gtctagctaa | gatgtattat | 1620 |
| tctgctgtgg | atcccactaa | agatatattc | actgggctta | ttgggccaat | gaaaatatgc | 1680 |
| aagaaaggaa | gttacatgc | aaatgggaga | cagaaagatg | tagacaagga | attctatttg | 1740 |
| tttcctacag | tatttgatga | gaatgagagt | ttactcctgg | aagataatat | tagaatgttt | 1800 |
| acaactgcac | ctgatcaggt | ggataaggaa | gatgaagact | tcaggaatc | taataaaatg | 1860 |
| cactccatga | atggattcat | gtatgggaat | cagccgggtc | tcactatgtg | caaaggagat | 1920 |
| tcggtcgtgt | ggtacttatt | cagcgccgga | aatgaggccg | atgtacatgg | aatatacttt | 1980 |
| tcaggaaaca | catatctgtg | gagaggagaa | cggagagaca | cagcaaacct | cttccctcaa | 2040 |

-continued

```
acaagtctta cgctccacat gtggcctgac acagagggga cttttaatgt tgaatgcctt    2100
acaactgatc attacacagg cggcatgaag caaaaatata ctgtgaacca atgcaggcgg    2160
cagtctgagg attccacctt ctacctggga gagaggacat actatatcgc agcagtggag    2220
gtggaatggg attattcccc acaaagggag tgggaaaagg agctgcatca tttacaagag    2280
cagaatgttt caaatgcatt tttagataag ggagagtttt acataggctc aaagtacaag    2340
aaagttgtgt atcggcagta tactgatagc acattccgtg ttccagtgga gagaaaagct    2400
gaagaagaac atctgggaat tctaggtcca caacttcatg cagatgttgg agacaaagtc    2460
aaaattatct ttaaaaacat ggccacaagg ccctactcaa tacatgccca tggggtacaa    2520
acagagagtt ctacagttac tccaacatta ccaggtgaaa ctctcactta cgtatggaaa    2580
atcccagaaa gatctggagc tggaacagag gattctgctt gtattccatg ggcttattat    2640
tcaactgtgg atcaagttaa ggacctctac agtggattaa ttggcccct gattgtttgt    2700 cgaagacctt acttgaaagt attcaatccc agaaggaagc tggaatttgc ccttctgttt    2760 ctagttttg atgagaatga atcttggtac ttagatgaca acatcaaaac atactctgat    2820 cacccccgaga agtaaacaa agatgatgag gaattcatag aaagcaataa aatgcatgct    2880
attaatggaa gaatgtttgg aaacctacaa ggcctcacaa tgcacgtggg agatgaagtc    2940
aactggtatc tgatgggaat gggcaatgaa atagacttac acactgtaca ttttcacggc    3000
catagcttcc aatacaagca caggggagtt tatagttctg atgtctttga cattttccct    3060
ggaacatacc aaaccctaga aatgtttcca agaacacctg gaatttggtt actccactgc    3120
catgtgaccg accacattca tgctggaatg gaaaccactt acaccgttct acaaaatgaa    3180
gacaccaaat ctggctgaat gaaataaatt ggtgataagt ggaaaaaaga gaaaaaccaa    3240
tgattcataa caatgtatgt gaaagtgtaa aatagaatgt tactttggaa tgactataaa    3300
cattaaaaga gactggagca t                                              3321
```

<210> SEQ ID NO 50
<211> LENGTH: 1065
<212> TYPE: PRT
<213> ORGANISM: Homo sapiens

<400> SEQUENCE: 50

```
Met Lys Ile Leu Ile Leu Gly Ile Phe Leu Phe Leu Cys Ser Thr Pro
 1               5                  10                  15

Ala Trp Ala Lys Glu Lys His Tyr Tyr Ile Gly Ile Ile Glu Thr Thr
            20                  25                  30

Trp Asp Tyr Ala Ser Asp His Gly Glu Lys Lys Leu Ile Ser Val Asp
        35                  40                  45

Thr Glu His Ser Asn Ile Tyr Leu Gln Asn Gly Pro Asp Arg Ile Gly
    50                  55                  60

Arg Leu Tyr Lys Lys Ala Leu Tyr Leu Gln Tyr Thr Asp Glu Thr Phe
65                  70                  75                  80

Arg Thr Thr Ile Glu Lys Pro Val Trp Leu Gly Phe Leu Gly Pro Ile
                85                  90                  95

Ile Lys Ala Glu Thr Gly Asp Lys Val Tyr Val His Leu Lys Asn Leu
            100                 105                 110

Ala Ser Arg Pro Tyr Thr Phe His Ser His Gly Ile Thr Tyr Tyr Lys
        115                 120                 125

Glu His Glu Gly Ala Ile Tyr Pro Asp Asn Thr Thr Asp Phe Gln Arg
    130                 135                 140
```

-continued

```
Ala Asp Asp Lys Val Tyr Pro Gly Glu Gln Tyr Thr Tyr Met Leu Leu
145                 150                 155                 160

Ala Thr Glu Glu Gln Ser Pro Gly Glu Gly Asp Gly Asn Cys Val Thr
                165                 170                 175

Arg Ile Tyr His Ser His Ile Asp Ala Pro Lys Asp Ile Ala Ser Gly
                180                 185                 190

Leu Ile Gly Pro Leu Ile Ile Cys Lys Lys Asp Ser Leu Asp Lys Glu
            195                 200                 205

Lys Glu Lys His Ile Asp Arg Glu Phe Val Val Met Phe Ser Val Val
        210                 215                 220

Asp Glu Asn Phe Ser Trp Tyr Leu Glu Asp Asn Ile Lys Thr Tyr Cys
225                 230                 235                 240

Ser Glu Pro Glu Lys Val Asp Lys Asp Asn Glu Asp Phe Gln Glu Ser
                245                 250                 255

Asn Arg Met Tyr Ser Val Asn Gly Tyr Thr Phe Gly Ser Leu Pro Gly
                260                 265                 270

Leu Ser Met Cys Ala Glu Asp Arg Val Lys Trp Tyr Leu Phe Gly Met
            275                 280                 285

Gly Asn Glu Val Asp Val His Ala Ala Phe Phe His Gly Gln Ala Leu
        290                 295                 300

Thr Asn Lys Asn Tyr Arg Ile Asp Thr Ile Asn Leu Phe Pro Ala Thr
305                 310                 315                 320

Leu Phe Asp Ala Tyr Met Val Ala Gln Asn Pro Gly Glu Trp Met Leu
                325                 330                 335

Ser Cys Gln Asn Leu Asn His Leu Lys Ala Gly Leu Gln Ala Phe Phe
                340                 345                 350

Gln Val Gln Glu Cys Asn Lys Ser Ser Lys Asp Asn Ile Arg Gly
            355                 360                 365

Lys His Val Arg His Tyr Tyr Ile Ala Ala Glu Ile Ile Trp Asn
        370                 375                 380

Tyr Ala Pro Ser Gly Ile Asp Ile Phe Thr Lys Glu Asn Leu Thr Ala
385                 390                 395                 400

Pro Gly Ser Asp Ser Ala Val Phe Phe Glu Gln Gly Thr Thr Arg Ile
                405                 410                 415

Gly Gly Ser Tyr Lys Lys Leu Val Tyr Arg Glu Tyr Thr Asp Ala Ser
                420                 425                 430

Phe Thr Asn Arg Lys Glu Arg Gly Pro Glu Glu Glu His Leu Gly Ile
            435                 440                 445

Leu Gly Pro Val Ile Trp Ala Glu Val Gly Asp Thr Ile Arg Val Thr
        450                 455                 460

Phe His Asn Lys Gly Ala Tyr Pro Leu Ser Ile Glu Pro Ile Gly Val
465                 470                 475                 480

Arg Phe Asn Lys Asn Asn Glu Gly Thr Tyr Tyr Ser Pro Asn Tyr Asn
                485                 490                 495

Pro Gln Ser Arg Ser Val Pro Pro Ser Ala Ser His Val Ala Pro Thr
                500                 505                 510

Glu Thr Phe Thr Tyr Glu Trp Thr Val Pro Lys Glu Val Gly Pro Thr
            515                 520                 525

Asn Ala Asp Pro Val Cys Leu Ala Lys Met Tyr Tyr Ser Ala Val Asp
530                 535                 540

Pro Thr Lys Asp Ile Phe Thr Gly Leu Ile Gly Pro Met Lys Ile Cys
545                 550                 555                 560

Lys Lys Gly Ser Leu His Ala Asn Gly Arg Gln Lys Asp Val Asp Lys
```

-continued

```
                565                 570                 575
Glu Phe Tyr Leu Phe Pro Thr Val Phe Asp Glu Asn Glu Ser Leu Leu
            580                 585                 590
Leu Glu Asp Asn Ile Arg Met Phe Thr Thr Ala Pro Asp Gln Val Asp
        595                 600                 605
Lys Glu Asp Glu Asp Phe Gln Glu Ser Asn Lys Met His Ser Met Asn
    610                 615                 620
Gly Phe Met Tyr Gly Asn Gln Pro Gly Leu Thr Met Cys Lys Gly Asp
625                 630                 635                 640
Ser Val Val Trp Tyr Leu Phe Ser Ala Gly Asn Glu Ala Asp Val His
            645                 650                 655
Gly Ile Tyr Phe Ser Gly Asn Thr Tyr Leu Trp Arg Gly Glu Arg Arg
            660                 665                 670
Asp Thr Ala Asn Leu Phe Pro Gln Thr Ser Leu Thr Leu His Met Trp
        675                 680                 685
Pro Asp Thr Glu Gly Thr Phe Asn Val Glu Cys Leu Thr Thr Asp His
        690                 695                 700
Tyr Thr Gly Gly Met Lys Gln Lys Tyr Thr Val Asn Gln Cys Arg Arg
705                 710                 715                 720
Gln Ser Glu Asp Ser Thr Phe Tyr Leu Gly Glu Arg Thr Tyr Tyr Ile
            725                 730                 735
Ala Ala Val Glu Val Glu Trp Asp Tyr Ser Pro Gln Arg Glu Trp Glu
            740                 745                 750
Lys Glu Leu His His Leu Gln Glu Gln Asn Val Ser Asn Ala Phe Leu
        755                 760                 765
Asp Lys Gly Glu Phe Tyr Ile Gly Ser Lys Tyr Lys Lys Val Val Tyr
    770                 775                 780
Arg Gln Tyr Thr Asp Ser Thr Phe Arg Val Pro Val Glu Arg Lys Ala
785                 790                 795                 800
Glu Glu Glu His Leu Gly Ile Leu Gly Pro Gln Leu His Ala Asp Val
            805                 810                 815
Gly Asp Lys Val Lys Ile Ile Phe Lys Asn Met Ala Thr Arg Pro Tyr
        820                 825                 830
Ser Ile His Ala His Gly Val Gln Thr Glu Ser Ser Thr Val Thr Pro
        835                 840                 845
Thr Leu Pro Gly Glu Thr Leu Thr Tyr Val Trp Lys Ile Pro Glu Arg
    850                 855                 860
Ser Gly Ala Gly Thr Glu Asp Ser Ala Cys Ile Pro Trp Ala Tyr Tyr
865                 870                 875                 880
Ser Thr Val Asp Gln Val Lys Asp Leu Tyr Ser Gly Leu Ile Gly Pro
            885                 890                 895
Leu Ile Val Cys Arg Arg Pro Tyr Leu Lys Val Phe Asn Pro Arg Arg
            900                 905                 910
Lys Leu Glu Phe Ala Leu Leu Phe Leu Val Phe Asp Glu Asn Glu Ser
        915                 920                 925
Trp Tyr Leu Asp Asp Asn Ile Lys Thr Tyr Ser Asp His Pro Glu Lys
    930                 935                 940
Val Asn Lys Asp Asp Glu Glu Phe Ile Glu Ser Asn Lys Met His Ala
945                 950                 955                 960
Ile Asn Gly Arg Met Phe Gly Asn Leu Gln Gly Leu Thr Met His Val
            965                 970                 975
Gly Asp Glu Val Asn Trp Tyr Leu Met Gly Met Gly Asn Glu Ile Asp
            980                 985                 990
```

Leu His Thr Val His Phe His Gly His Ser Phe Gln Tyr Lys His Arg
    995                1000                1005

Gly Val Tyr Ser Ser Asp Val Phe Asp Ile Phe Pro Gly Thr Tyr Gln
    1010               1015                1020

Thr Leu Glu Met Phe Pro Arg Thr Pro Gly Ile Trp Leu Leu His Cys
1025                1030                1035                1040

His Val Thr Asp His Ile His Ala Gly Met Glu Thr Thr Tyr Thr Val
                1045                1050                1055

Leu Gln Asn Glu Asp Thr Lys Ser Gly
            1060                1065

<210> SEQ ID NO 51
<211> LENGTH: 1603
<212> TYPE: DNA
<213> ORGANISM: Homo sapiens

<400> SEQUENCE: 51

| | | | | | |
|---|---|---|---|---|---|
| ggccagggat | caggcagcgg | ctcaggcgac | cctgagtgtg | cccccacccc | gccatggccc | 60 |
| ggctgctgca | ggcgtcctgc | ctgctttccc | tgctcctggc | cggcttcgtc | tcgcagagcc | 120 |
| ggggacaaga | gaagtcgaag | atggactgcc | atggtggcat | aagtggcacc | atttacgagt | 180 |
| acggagccct | caccattgat | ggggaggagt | acatcccctt | caagcagtat | gctggcaaat | 240 |
| acgtcctctt | tgtcaacgtg | gccagctact | gaggcctgac | gggccagtac | attgaactga | 300 |
| atgcactaca | ggaagagctt | gcaccattcg | gtctggtcat | tctgggcttt | ccctgcaacc | 360 |
| aatttggaaa | acaggaacca | ggagagaact | cagagatcct | tcctaccctc | aagtatgtcc | 420 |
| gaccaggtgg | aggctttgtc | cctaatttcc | agctctttga | gaaagggggat | gtcaatggag | 480 |
| agaaagagca | gaaattctac | actttcctaa | agaactcctg | tcctcccacc | tcggagctcc | 540 |
| tgggtacatc | tgaccgcctc | ttctgggaac | ccatgaaggt | tcacgacatc | cgctggaact | 600 |
| ttgagaagtt | cctggtgggg | ccagatggta | tacccatcat | gcgctggcac | caccggacca | 660 |
| cggtcagcaa | cgtcaagatg | gacatcctgt | cctacatgag | gcggcaggca | gccctggggg | 720 |
| tcaagaggaa | gtaactgaag | gccgtctcat | cccatgtcca | ccatgtaggg | gagggacttt | 780 |
| gttcaggaag | aaatccgtgt | ctccaaccac | actatctacc | catcacagac | ccctttccta | 840 |
| tcactcaagg | ccccagcctg | gcacaaatgg | atgcatacag | ttctgtgtac | tgccaggcat | 900 |
| gtgggtgtgg | gtgcatgtgg | gtgtttacac | acatgcctac | aggtatgcgt | gattgtgtgt | 960 |
| gtgtgcatgg | gtgtacagcc | acgtgtccta | cctatgtgtc | tttctgggaa | tgtgtaccat | 1020 |
| ctgtgtgcct | gcagctgtgt | agtgctggac | agtgacaacc | ctttctctcc | agttctccac | 1080 |
| tccaatgata | atagttcact | tacacctaaa | cccaaaggaa | aaaccagctc | taggtccaat | 1140 |
| tgttctgctc | taactgatac | ctcaaccttg | gggccagcat | ctcccactgc | ctccaaatat | 1200 |
| tagtaactat | gactgacgtc | cccagaagtt | tctgggtcta | ccacactccc | caaccccca | 1260 |
| ctcctacttc | ctgaagggcc | ctcccaaggc | tacatcccca | ccccacagtt | ctccctgaga | 1320 |
| gagatcaacc | tccctagatc | aaccaaggca | gatgtgacaa | gcaagggcca | cggacccat | 1380 |
| aggcagggt | ggcgtcttca | tgagggaggg | gcccaaagcc | cttgtgggcg | gacctcccct | 1440 |
| gagcctgtct | gaggggccag | cccttagtgc | attcaggcta | aggcccctgg | gcagggatgc | 1500 |
| caccctgctc | cttcggagga | cgtgccctca | ccctcactg | gtccactggc | ttgagactca | 1560 |
| ccccgtctgc | ccagtaaaag | cctttctgca | gcaaaaaacc | ccc | | 1603 |

-continued

```
<210> SEQ ID NO 52
<211> LENGTH: 226
<212> TYPE: PRT
<213> ORGANISM: Homo sapiens
<220> FEATURE:
<221> NAME/KEY: VARIANT
<222> LOCATION: 0-00
<223> OTHER INFORMATION: Xaa = any amino acid

<400> SEQUENCE: 52

Met Ala Arg Leu Leu Gln Ala Ser Cys Leu Leu Ser Leu Leu Leu Ala
  1               5                  10                  15

Gly Phe Val Ser Gln Ser Arg Gly Gln Glu Lys Ser Lys Met Asp Cys
             20                  25                  30

His Gly Gly Ile Ser Gly Thr Ile Tyr Glu Tyr Gly Ala Leu Thr Ile
         35                  40                  45

Asp Gly Glu Glu Tyr Ile Pro Phe Lys Gln Tyr Ala Gly Lys Tyr Val
     50                  55                  60

Leu Phe Val Asn Val Ala Ser Tyr Xaa Gly Leu Thr Gly Gln Tyr Ile
 65                  70                  75                  80

Glu Leu Asn Ala Leu Gln Glu Glu Leu Ala Pro Phe Gly Leu Val Ile
                 85                  90                  95

Leu Gly Phe Pro Cys Asn Gln Phe Gly Lys Gln Glu Pro Gly Glu Asn
            100                 105                 110

Ser Glu Ile Leu Pro Thr Leu Lys Tyr Val Arg Pro Gly Gly Gly Phe
        115                 120                 125

Val Pro Asn Phe Gln Leu Phe Glu Lys Gly Asp Val Asn Gly Glu Lys
    130                 135                 140

Glu Gln Lys Phe Tyr Thr Phe Leu Lys Asn Ser Cys Pro Pro Thr Ser
145                 150                 155                 160

Glu Leu Leu Gly Thr Ser Asp Arg Leu Phe Trp Glu Pro Met Lys Val
                165                 170                 175

His Asp Ile Arg Trp Asn Phe Glu Lys Phe Leu Val Gly Pro Asp Gly
            180                 185                 190

Ile Pro Ile Met Arg Trp His His Arg Thr Thr Val Ser Asn Val Lys
        195                 200                 205

Met Asp Ile Leu Ser Tyr Met Arg Arg Gln Ala Ala Leu Gly Val Lys
    210                 215                 220

Arg Lys
225

<210> SEQ ID NO 53
<211> LENGTH: 399
<212> TYPE: DNA
<213> ORGANISM: Homo sapiens

<400> SEQUENCE: 53
atgaagtcca gcggcctctt cccttcctg gtgctgcttg ccctgggaac tctggcacct    60
tgggctgtgg aaggctctgg aaagtccttc aaagctggag tctgtcctcc taagaaatct   120
gcccagtgcc ttagatacaa gaaacctgag tgccagagtg actggcagtg tccaggaag   180 aagagatgtt gtcctgacac ttgtggcatc aaatgcctgg atcctgttga caccccaaac   240
ccaacaagga ggaagcctgg gaagtgccca gtgacttatg ccaatgtttt gatgcttaac   300
ccccccaatt tctgtgagat ggatggccag tgcaagcgtg acttgaagtg ttgcatgggc   360
atgtgtggga atcctgcgt ttccctgtg aaagcttga                          399
```

<210> SEQ ID NO 54
<211> LENGTH: 132
<212> TYPE: PRT
<213> ORGANISM: Homo sapiens

<400> SEQUENCE: 54

```
Met Lys Ser Ser Gly Leu Phe Pro Phe Leu Val Leu Leu Ala Leu Gly
1               5                   10                  15
Thr Leu Ala Pro Trp Ala Val Glu Gly Ser Gly Lys Ser Phe Lys Ala
            20                  25                  30
Gly Val Cys Pro Pro Lys Lys Ser Ala Gln Cys Leu Arg Tyr Lys Lys
        35                  40                  45
Pro Glu Cys Gln Ser Asp Trp Gln Cys Pro Gly Lys Lys Arg Cys Cys
    50                  55                  60
Pro Asp Thr Cys Gly Ile Lys Cys Leu Asp Pro Val Asp Thr Pro Asn
65                  70                  75                  80
Pro Thr Arg Arg Lys Pro Gly Lys Cys Pro Val Thr Tyr Gly Gln Cys
                85                  90                  95
Leu Met Leu Asn Pro Pro Asn Phe Cys Glu Met Asp Gly Gln Cys Lys
            100                 105                 110
Arg Asp Leu Lys Cys Cys Met Gly Met Cys Gly Lys Ser Cys Val Ser
        115                 120                 125
Pro Val Lys Ala
    130
```

<210> SEQ ID NO 55
<211> LENGTH: 3557
<212> TYPE: DNA
<213> ORGANISM: Homo sapiens

<400> SEQUENCE: 55

| | | | | | |
|---|---|---|---|---|---|
| gagagggtcc | ttcagggtct | gcttatgccc | ttgttcaaga | acaccagtgt | cagctctctg | 60 |
| tactctggtt | gcagactgac | cttgctcagg | cctgagaagg | atggggcagc | caccagagtg | 120 |
| gatgctgtct | gcacccatcg | tcctgacccc | aaaagccctg | gactggacag | agagcggctg | 180 |
| tactggaagc | tgagccagct | gacccacggc | atcactgagc | tgggccccta | caccctggac | 240 |
| aggcacagtc | tctatgtcaa | tggtttcacc | catcagagct | ctatgacgac | caccagaact | 300 |
| cctgatacct | ccacaatgca | cctggcaacc | tcgagaactc | cagcctccct | gtctggacct | 360 |
| acgaccgcca | gccctctcct | ggtgctattc | acaattaact | tcaccatcac | taacctgcgg | 420 |
| tatgaggaga | catgcatca | ccctggctct | agaaagttta | acaccacgga | gagagtcctt | 480 |
| cagggtctgc | tcaggcctgt | gttcaagaac | accagtgttg | ccctctgta | ctctggctgc | 540 |
| agactgacct | tgctcaggcc | caagaaggat | ggggcagcca | caaagtgga | tgccatctgc | 600 |
| acctaccgcc | tgatcccaa | agccctgga | ctggacagag | agcagctata | ctgggagctg | 660 |
| agccagctaa | cccacagcat | cactgagctg | gcccctaca | ccctggacag | ggacagtctc | 720 |
| tatgtcaatg | gtttcacaca | gcggagctct | gtgcccacca | ctagcattcc | tgggaccccc | 780 |
| acagtggacc | tggaacatc | tgggactcca | gtttctaaac | ctggtccctc | ggctgccagc | 840 |
| cctctcctgg | tgctattcac | tctcaacttc | accatcacca | acctgcggta | tgaggagaac | 900 |
| atgcagcacc | ctggctccag | gaagttcaac | accacgagag | gggtccttca | gggcctgctc | 960 |
| aggtccctgt | tcaagagcac | cagtgttggc | cctctgtact | ctggctgcag | actgactttg | 1020 |
| ctcaggcctg | aaaaggatgg | gacagccact | ggagtggatg | ccatctgcac | ccaccaccct | 1080 |
| gaccccaaaa | gccctaggct | ggacagagag | cagctgtatt | gggagctgag | ccagctgacc | 1140 |

-continued

```
cacaatatca ctgagctggg ccactatgcc ctggacaacg acagcctctt tgtcaatggt      1200
ttcactcatc ggagctctgt gtccaccacc agcactcctg gaccccac agtgtatctg        1260 ggagcatcta agactccagc ctcgatattt ggcccttcag ctgccagcca tctcctgata      1320
ctattcaccc tcaacttcac catcactaac ctgcggtatg aggagaacat gtggcctggc      1380
tccaggaagt tcaacactac agagagggtc cttcagggcc tgctaaggcc cttgttcaag      1440
aacaccagtg ttggccctct gtactctggc tccaggctga ccttgctcag gccagagaaa     1500
gatggggaag ccaccggagt ggatgccatc tgcacccacc gccctgaccc cacaggccct      1560
gggctggaca gagagcagct gtatttggag ctgagccagc tgacccacag catcactgag      1620
ctggccccct acacactgga caggacagt ctctatgtca atggtttcac ccatcggagc       1680
tctgtaccca ccaccagcac cggggtggtc agcgaggagc cattcacact gaacttcacc      1740
atcaacaacc tgcgctacat ggcggacatg gccaaccccg ctccctcaa gttcaacatc       1800 acagacaacg tcatgaagca cctgctcagt cctttgttcc agaggagcag cctgggtgca      1860
cggtacacag gctgcaggt catcgcacta aggtctgtga agaacggtgc tgagacacgg       1920
gtggacctcc tctgcaccta cctgcagccc ctcagcggcc caggtctgcc tatcaagcag      1980
gtgttccatg agctgagcca gcagacccat ggcatcaccc ggctgggccc ctactctctg      2040
gacaaagaca gcctctacct taacggttac aatgaacctg gtctagatga gcctcctaca      2100
actcccaagc cagccaccac attcctgcct cctctgtcag aagccacaac agccatgggg      2160
taccacctga agaccctcac actcaacttc accatctcca atctccagta ttcaccagat      2220
atgggcaagg gctcagctac attcaactcc accgaggggg tccttcagca cctgctcaga      2280 ccccttgttcc agaagagcag catgggcccc ttctacttgg gttgccaact gatctccctc      2340
aggcctgaga aggatggggc agccactggt gtggacacca cctgcaccta ccaccctgac      2400
cctgtgggcc ccgggctgga catacagcag ctttactggg agctgagtca gctgacccat      2460
ggtgtcaccc aactgggctt ctatgtcctg acagggata gcctcttcat caatggctat      2520
gcaccccaga atttatcaat ccggggcgag taccagataa atttccacat tgtcaactgg      2580
aacctcagta atccagaccc cacatcctca gagtacatca ccctgctgag ggacatccag      2640
gacaaggtca ccacactcta caaaggcagt caactacatg acacattccg cttctgcctg      2700
gtcaccaact tgacgatgga ctccgtgttg gtcactgtca aggcattgtt ctcctccaat      2760
ttggacccca gctggtgga gcaagtcttt ctagataaga cctgaatgc ctcattccat       2820 tggctgggct ccacctacca gttggtggac atccatgtga cagaaatgga gtcatcagtt      2880
tatcaaccaa caagcagctc cagcacccag cacttctacc cgaatttcac catcaccaac      2940
ctaccatatt cccaggacaa agcccagcca ggcaccacca attaccagag gaacaaaagg      3000
aatattgagg atgcgctcaa ccaactcttc gaaacagca gcatcaagag ttatttttct      3060
gactgtcaag tttcaacatt caggtctgtc cccaacaggc accacaccgg ggtggactcc      3120
ctgtgtaact ctcgccact ggctcggaga gtagacagag ttgccatcta tgaggaattt      3180
ctgcggatga cccggaatgg tacccagctg cagaacttca ccctggacag gagcagtgtc      3240
cttgtggatg gtattctcc caacagaaat gagcccttaa ctgggaattc tgaccttccc      3300
ttctgggctg tcatcttcat cggcttggca ggactcctgg gactcatcac atgcctgatc      3360
tgcggtgtcc tggtgaccac ccgcggcgg aagaaggaag gagaatacaa cgtccagcaa      3420
cagtgcccag gctactacca gtcacaccta gacctggagg atctgcaatg actggaactt      3480
```

```
gccggtgcct ggggtgcctt tcccccagcc agggtccaaa gaagcttggc tggggcagaa    3540
ataaaccata ttggtcg                                                   3557
```

<210> SEQ ID NO 56
<211> LENGTH: 1148
<212> TYPE: PRT
<213> ORGANISM: Homo sapiens

<400> SEQUENCE: 56

```
Met Pro Leu Phe Lys Asn Thr Ser Val Ser Ser Leu Tyr Ser Gly Cys
 1               5                  10                  15

Arg Leu Thr Leu Leu Arg Pro Glu Lys Asp Gly Ala Ala Thr Arg Val
             20                  25                  30

Asp Ala Val Cys Thr His Arg Pro Asp Pro Lys Ser Pro Gly Leu Asp
         35                  40                  45

Arg Glu Arg Leu Tyr Trp Lys Leu Ser Gln Leu Thr His Gly Ile Thr
 50                  55                  60

Glu Leu Gly Pro Tyr Thr Leu Asp Arg His Ser Leu Tyr Val Asn Gly
 65                  70                  75                  80

Phe Thr His Gln Ser Ser Met Thr Thr Thr Arg Thr Pro Asp Thr Ser
                 85                  90                  95

Thr Met His Leu Ala Thr Ser Arg Thr Pro Ala Ser Leu Ser Gly Pro
            100                 105                 110

Thr Thr Ala Ser Pro Leu Leu Val Leu Phe Thr Ile Asn Phe Thr Ile
        115                 120                 125

Thr Asn Leu Arg Tyr Glu Glu Asn Met His His Pro Gly Ser Arg Lys
    130                 135                 140

Phe Asn Thr Thr Glu Arg Val Leu Gln Gly Leu Leu Arg Pro Val Phe
145                 150                 155                 160

Lys Asn Thr Ser Val Gly Pro Leu Tyr Ser Gly Cys Arg Leu Thr Leu
                165                 170                 175

Leu Arg Pro Lys Lys Asp Gly Ala Ala Thr Lys Val Asp Ala Ile Cys
            180                 185                 190

Thr Tyr Arg Pro Asp Pro Lys Ser Pro Gly Leu Asp Arg Glu Gln Leu
        195                 200                 205

Tyr Trp Glu Leu Ser Gln Leu Thr His Ser Ile Thr Glu Leu Gly Pro
    210                 215                 220

Tyr Thr Leu Asp Arg Asp Ser Leu Tyr Val Asn Gly Phe Thr Gln Arg
225                 230                 235                 240

Ser Ser Val Pro Thr Thr Ser Ile Pro Gly Thr Pro Thr Val Asp Leu
                245                 250                 255

Gly Thr Ser Gly Thr Pro Val Ser Lys Pro Gly Pro Ser Ala Ala Ser
            260                 265                 270

Pro Leu Leu Val Leu Phe Thr Leu Asn Phe Thr Ile Thr Asn Leu Arg
        275                 280                 285

Tyr Glu Glu Asn Met Gln His Pro Gly Ser Arg Lys Phe Asn Thr Thr
    290                 295                 300

Glu Arg Val Leu Gln Gly Leu Leu Arg Ser Leu Phe Lys Ser Thr Ser
305                 310                 315                 320

Val Gly Pro Leu Tyr Ser Gly Cys Arg Leu Thr Leu Leu Arg Pro Glu
                325                 330                 335

Lys Asp Gly Thr Ala Thr Gly Val Asp Ala Ile Cys Thr His His Pro
            340                 345                 350

Asp Pro Lys Ser Pro Arg Leu Asp Arg Glu Gln Leu Tyr Trp Glu Leu
```

```
                355                 360                 365
Ser Gln Leu Thr His Asn Ile Thr Glu Leu Gly His Tyr Ala Leu Asp
    370                 375                 380

Asn Asp Ser Leu Phe Val Asn Gly Phe Thr His Arg Ser Ser Val Ser
385                 390                 395                 400

Thr Thr Ser Thr Pro Gly Thr Pro Thr Val Tyr Leu Gly Ala Ser Lys
                405                 410                 415

Thr Pro Ala Ser Ile Phe Gly Pro Ser Ala Ala Ser His Leu Leu Ile
                420                 425                 430

Leu Phe Thr Leu Asn Phe Thr Ile Thr Asn Leu Arg Tyr Glu Glu Asn
            435                 440                 445

Met Trp Pro Gly Ser Arg Lys Phe Asn Thr Thr Glu Arg Val Leu Gln
        450                 455                 460

Gly Leu Leu Arg Pro Leu Phe Lys Asn Thr Ser Val Gly Pro Leu Tyr
465                 470                 475                 480

Ser Gly Ser Arg Leu Thr Leu Leu Arg Pro Glu Lys Asp Gly Glu Ala
                485                 490                 495

Thr Gly Val Asp Ala Ile Cys Thr His Arg Pro Asp Pro Thr Gly Pro
                500                 505                 510

Gly Leu Asp Arg Glu Gln Leu Tyr Leu Glu Leu Ser Gln Leu Thr His
            515                 520                 525

Ser Ile Thr Glu Leu Gly Pro Tyr Thr Leu Asp Arg Asp Ser Leu Tyr
        530                 535                 540

Val Asn Gly Phe Thr His Arg Ser Ser Val Pro Thr Thr Ser Thr Gly
545                 550                 555                 560

Val Val Ser Glu Glu Pro Phe Thr Leu Asn Phe Thr Ile Asn Asn Leu
                565                 570                 575

Arg Tyr Met Ala Asp Met Gly Gln Pro Gly Ser Leu Lys Phe Asn Ile
                580                 585                 590

Thr Asp Asn Val Met Lys His Leu Leu Ser Pro Leu Phe Gln Arg Ser
            595                 600                 605

Ser Leu Gly Ala Arg Tyr Thr Gly Cys Arg Val Ile Ala Leu Arg Ser
        610                 615                 620

Val Lys Asn Gly Ala Glu Thr Arg Val Asp Leu Leu Cys Thr Tyr Leu
625                 630                 635                 640

Gln Pro Leu Ser Gly Pro Gly Leu Pro Ile Lys Gln Val Phe His Glu
                645                 650                 655

Leu Ser Gln Gln Thr His Gly Ile Thr Arg Leu Gly Pro Tyr Ser Leu
            660                 665                 670

Asp Lys Asp Ser Leu Tyr Leu Asn Gly Tyr Asn Glu Pro Gly Leu Asp
        675                 680                 685

Glu Pro Pro Thr Thr Pro Lys Pro Ala Thr Thr Phe Leu Pro Pro Leu
    690                 695                 700

Ser Glu Ala Thr Thr Ala Met Gly Tyr His Leu Lys Thr Leu Thr Leu
705                 710                 715                 720

Asn Phe Thr Ile Ser Asn Leu Gln Tyr Ser Pro Asp Met Gly Lys Gly
                725                 730                 735

Ser Ala Thr Phe Asn Ser Thr Glu Gly Val Leu Gln His Leu Leu Arg
                740                 745                 750

Pro Leu Phe Gln Lys Ser Ser Met Gly Pro Phe Tyr Leu Gly Cys Gln
            755                 760                 765

Leu Ile Ser Leu Arg Pro Glu Lys Asp Gly Ala Ala Thr Gly Val Asp
        770                 775                 780
```

```
Thr Thr Cys Thr Tyr His Pro Asp Pro Val Gly Pro Gly Leu Asp Ile
785                 790                 795                 800

Gln Gln Leu Tyr Trp Glu Leu Ser Gln Leu Thr His Gly Val Thr Gln
            805                 810                 815

Leu Gly Phe Tyr Val Leu Asp Arg Asp Ser Leu Phe Ile Asn Gly Tyr
            820                 825                 830

Ala Pro Gln Asn Leu Ser Ile Arg Gly Glu Tyr Gln Ile Asn Phe His
            835                 840                 845

Ile Val Asn Trp Asn Leu Ser Asn Pro Asp Pro Thr Ser Ser Glu Tyr
850                 855                 860

Ile Thr Leu Leu Arg Asp Ile Gln Asp Lys Val Thr Thr Leu Tyr Lys
865                 870                 875                 880

Gly Ser Gln Leu His Asp Thr Phe Arg Phe Cys Leu Val Thr Asn Leu
                885                 890                 895

Thr Met Asp Ser Val Leu Val Thr Val Lys Ala Leu Phe Ser Ser Asn
                900                 905                 910

Leu Asp Pro Ser Leu Val Glu Gln Val Phe Leu Asp Lys Thr Leu Asn
            915                 920                 925

Ala Ser Phe His Trp Leu Gly Ser Thr Tyr Gln Leu Val Asp Ile His
930                 935                 940

Val Thr Glu Met Glu Ser Ser Val Tyr Gln Pro Thr Ser Ser Ser Ser
945                 950                 955                 960

Thr Gln His Phe Tyr Pro Asn Phe Thr Ile Thr Asn Leu Pro Tyr Ser
                965                 970                 975

Gln Asp Lys Ala Gln Pro Gly Thr Thr Asn Tyr Gln Arg Asn Lys Arg
            980                 985                 990

Asn Ile Glu Asp Ala Leu Asn Gln Leu Phe Arg Asn Ser Ser Ile Lys
            995                 1000                1005

Ser Tyr Phe Ser Asp Cys Gln Val Ser Thr Phe Arg Ser Val Pro Asn
    1010                1015                1020

Arg His His Thr Gly Val Asp Ser Leu Cys Asn Phe Ser Pro Leu Ala
1025                1030                1035                1040

Arg Arg Val Asp Arg Val Ala Ile Tyr Glu Glu Phe Leu Arg Met Thr
            1045                1050                1055

Arg Asn Gly Thr Gln Leu Gln Asn Phe Thr Leu Asp Arg Ser Ser Val
            1060                1065                1070

Leu Val Asp Gly Tyr Ser Pro Asn Arg Asn Glu Pro Leu Thr Gly Asn
            1075                1080                1085

Ser Asp Leu Pro Phe Trp Ala Val Ile Phe Ile Gly Leu Ala Gly Leu
    1090                1095                1100

Leu Gly Leu Ile Thr Cys Leu Ile Cys Gly Val Leu Val Thr Thr Arg
1105                1110                1115                1120

Arg Arg Lys Lys Glu Gly Glu Tyr Asn Val Gln Gln Cys Pro Gly
            1125                1130                1135

Tyr Tyr Gln Ser His Leu Asp Leu Glu Asp Leu Gln
            1140                1145

<210> SEQ ID NO 57
<211> LENGTH: 853
<212> TYPE: DNA
<213> ORGANISM: Homo sapiens

<400> SEQUENCE: 57
ctagtcctga cttcacttct gatgaggaag cctctctcct tagccttcag cctttcctcc    60
```

```
caccctgcca taagtaattt gatcctcaag aagttaaacc acacctcatt ggtccctggc      120
taattcacca atttacaaac agcaggaaat agaaacttaa gagaaataca cacttctgag      180
aaactgaaac gacaggggaa aggaggtctc actgagcacc gtcccagcat ccggacacca      240
cagcggccct tcgctccacg cagaaaacca cacttctcaa accttcactc aacacttcct      300
tccccaaagc cagaagatgc acaaggagga acatgaggtg gctgtgctgg ggcaccccc      360 cagcaccatc cttccaaggt ccaccgtgat caacatccac agcgagacct ccgtgcccga      420
ccatgtcgtc tggtccctgt tcaacaccct cttcttgaac tggtgctgtc tgggcttcat      480
agcattcgcc tactccgtga agtctaggga caggaagatg gttggcgacg tgaccggggc      540
ccaggcctat gcctccaccg ccaagtgcct gaacatctgg gccctgattc tgggcatcct      600
catgaccatt ggattcatcc tgtcactggt attcggctct gtgacagtct accatattat      660
gttacagata atacaggaaa aacgggggtta ctagtagccg cccatagcct gcaacctttg      720
cactccactg tgcaatgctg gccctgcacg ctggggctgt tgcccctgcc ccttggtcc      780 tgcccctaga tacagcagtt tatacccaca cacctgtcta cagtgtcatt caataaagtg      840
cacgtgcttg tga                                                        853
```

<210> SEQ ID NO 58
<211> LENGTH: 125
<212> TYPE: PRT
<213> ORGANISM: Homo sapiens

<400> SEQUENCE: 58

```
Met His Lys Glu Glu His Glu Val Ala Val Leu Gly Ala Pro Pro Ser
 1               5                  10                  15

Thr Ile Leu Pro Arg Ser Thr Val Ile Asn Ile His Ser Glu Thr Ser
            20                  25                  30

Val Pro Asp His Val Val Trp Ser Leu Phe Asn Thr Leu Phe Leu Asn
        35                  40                  45

Trp Cys Cys Leu Gly Phe Ile Ala Phe Ala Tyr Ser Val Lys Ser Arg
    50                  55                  60

Asp Arg Lys Met Val Gly Asp Val Thr Gly Ala Gln Ala Tyr Ala Ser
65                  70                  75                  80

Thr Ala Lys Cys Leu Asn Ile Trp Ala Leu Ile Leu Gly Ile Leu Met
                85                  90                  95

Thr Ile Gly Phe Ile Leu Ser Leu Val Phe Gly Ser Val Thr Val Tyr
            100                 105                 110

His Ile Met Leu Gln Ile Ile Gln Glu Lys Arg Gly Tyr
        115                 120                 125
```

<210> SEQ ID NO 59
<211> LENGTH: 1512
<212> TYPE: DNA
<213> ORGANISM: Homo sapiens

<400> SEQUENCE: 59

```
ttccggtccc ccaggacatg tccaatcagg gaagtaagta cgtcaataag gaaattcaaa       60
atgctgtcaa cggggtgaaa cagataaaga ctctcataga aaaacaaac gaagagcgca      120 agacactgct cagcaaccta gaagaagcca agaagaagaa agaggatgcc ctaaatgaga      180
ccagggaatc agagacaaag ctgaaggagc tcccaggagt gtgcaatgag accatgatgg      240
ccctctggga agagtgtaag ccctgcctga acagacctg catgaagttc tacgcacgcg      300
```

-continued

```
tctgcagaag tggctcaggc ctggttggcc gccagcttga ggagttcctg aaccagagct   360
cgcccttcta cttctggatg aatggtgacc gcatcgactc cctgctggag aacgaccggc   420
agcagacgca catgctggat gtcatgcagg accacttcag ccgcgcgtcc agcatcatag   480
acgagctctt ccaggacagg ttcttcaccc gggagcccca ggatacctac cactacctgc   540
ccttcagcct gccccaccgg aggcctcact tcttctttcc caagtcccgc atcgtccgca   600
gcttgatgcc cttctctccg tacgagcccc tgaacttcca cgccatgttc cagcccttcc   660
ttgagatgat acacgaggct cagcaggcca tggacatcca cttccacagc ccggccttcc   720
agcacccgcc aacagaattc atacgagaag gcgacgatga ccggactgtg tgccgggaga   780
tccgccacaa ctccacgggc tgcctgcgga tgaaggacca gtgtgacaag tgccgggaga   840
tcttgtctgt ggactgttcc accaacaacc cctcccaggc taagctgcgg cgggagctcg   900
acgaatccct ccaggtcgct gagaggttga ccaggaaata caacgagctg ctaaagtcct   960
accagtggaa gatgctcaac acctcctcct gctggagcag gctgaacgag cagtttaact  1020
gggtgtcccg gctggcaaac ctcacgcaag gcgaagacca gtactatctg cgggtcacca  1080
cggtggcttc ccacacttct gactcggacg ttccttccgg tgtcactgag gtggtcgtga  1140
agctctttga ctctgatccc atcactgtga cggtccctgt agaagtctcc aggaagaacc  1200
ctaaatttat ggagaccgtg gcggagaaag cgctgcagga ataccgcaaa aagcaccggg  1260
aggagtgaga tgtggatgtt gcttttgcac ctacggggc atctgagtcc agctcccccc   1320
aagatgagct gcagccccc agagagagct ctgcacgtca ccaagtaacc aggccccagc   1380
ctccaggccc ccaactccgc ccagcctctc cccgctctgg atcctgcact ctaacactcg  1440
actctgctgc tcatgggaag aacagaattg ctcctgcatg caactaattc aataaaactg  1500
tcttgtgagc tg                                                     1512
```

<210> SEQ ID NO 60
<211> LENGTH: 416
<212> TYPE: PRT
<213> ORGANISM: Homo sapiens

<400> SEQUENCE: 60

```
Met Ser Asn Gln Gly Ser Lys Tyr Val Asn Lys Glu Ile Gln Asn Ala
1               5                   10                  15

Val Asn Gly Val Lys Gln Ile Lys Thr Leu Ile Glu Lys Thr Asn Glu
            20                  25                  30

Glu Arg Lys Thr Leu Leu Ser Asn Leu Glu Glu Ala Lys Lys Lys Lys
        35                  40                  45

Glu Asp Ala Leu Asn Glu Thr Arg Glu Ser Thr Lys Leu Lys Glu
    50                  55                  60

Leu Pro Gly Val Cys Asn Glu Thr Met Met Ala Leu Trp Glu Glu Cys
65                  70                  75                  80

Lys Pro Cys Leu Lys Gln Thr Cys Met Lys Phe Tyr Ala Arg Val Cys
                85                  90                  95

Arg Ser Gly Ser Gly Leu Val Gly Arg Gln Leu Glu Glu Phe Leu Asn
            100                 105                 110

Gln Ser Ser Pro Phe Tyr Phe Trp Met Asn Gly Asp Arg Ile Asp Ser
        115                 120                 125

Leu Leu Glu Asn Asp Arg Gln Gln Thr His Met Leu Asp Val Met Gln
    130                 135                 140

Asp His Phe Ser Arg Ala Ser Ser Ile Ile Asp Glu Leu Phe Gln Asp
145                 150                 155                 160
```

```
Arg Phe Phe Thr Arg Glu Pro Gln Asp Thr Tyr His Tyr Leu Pro Phe
            165                 170                 175

Ser Leu Pro His Arg Pro His Phe Phe Pro Lys Ser Arg Ile
        180                 185                 190

Val Arg Ser Leu Met Pro Phe Ser Pro Tyr Glu Pro Leu Asn Phe His
        195                 200                 205

Ala Met Phe Gln Pro Phe Leu Glu Met Ile His Glu Ala Gln Gln Ala
    210                 215                 220

Met Asp Ile His Phe His Ser Pro Ala Phe Gln His Pro Pro Thr Glu
225                 230                 235                 240

Phe Ile Arg Glu Gly Asp Asp Arg Thr Val Cys Arg Glu Ile Arg
                245                 250                 255

His Asn Ser Thr Gly Cys Leu Arg Met Lys Asp Gln Cys Asp Lys Cys
            260                 265                 270

Arg Glu Ile Leu Ser Val Asp Cys Ser Thr Asn Asn Pro Ser Gln Ala
        275                 280                 285

Lys Leu Arg Arg Glu Leu Asp Glu Ser Leu Gln Val Ala Glu Arg Leu
    290                 295                 300

Thr Arg Lys Tyr Asn Glu Leu Leu Lys Ser Tyr Gln Trp Lys Met Leu
305                 310                 315                 320

Asn Thr Ser Ser Leu Leu Glu Gln Leu Asn Glu Gln Phe Asn Trp Val
                325                 330                 335

Ser Arg Leu Ala Asn Leu Thr Gln Gly Glu Asp Gln Tyr Tyr Leu Arg
            340                 345                 350

Val Thr Thr Val Ala Ser His Thr Ser Asp Ser Asp Val Pro Ser Gly
        355                 360                 365

Val Thr Glu Val Val Val Lys Leu Phe Asp Ser Asp Pro Ile Thr Val
    370                 375                 380

Thr Val Pro Val Glu Val Ser Arg Lys Asn Pro Lys Phe Met Glu Thr
385                 390                 395                 400

Val Ala Glu Lys Ala Leu Gln Glu Tyr Arg Lys Lys His Arg Glu Glu
                405                 410                 415
```

<210> SEQ ID NO 61
<211> LENGTH: 1564
<212> TYPE: DNA
<213> ORGANISM: Homo sapiens

<400> SEQUENCE: 61

| | | | | | |
|---|---|---|---|---|---|
| cggacgcgtg | ggcggacgcg | tgggcgaggg | cgcgagtgag | gagcagaccc | aggcatcgcg | 60 |
| cgccgagaag | gccggagcgt | cggcacctga | acgcgaggcg | ctccattgcg | cgtgcgcgtt | 120 |
| gagggcttc | ccgcacctga | tcgcgagacc | ccaacggctg | gtggcgtcgc | ctgcgcgggc | 180 |
| gtccccacac | tgccggtccg | gaaaggcgac | ttccgggggc | tttggcacct | ggcggacgct | 240 |
| cccggagcgt | cggcacctga | acgcgaggcg | ctccattgcg | cgtgcgcgtt | gagggcttc | 300 |
| ccgcacctga | tcgcgagacc | ccaacggctg | gtggcgtcgc | ctgcgcgtct | cggctgagct | 360 |
| ggccatggcg | cacctgtgcg | ggctgaggcg | gagccgggcg | tttctcgccc | tgctgggatc | 420 |
| gctgctcctc | tctggggtcc | tggcggccga | ccgagaacgc | agcatccacg | acttctgcct | 480 |
| ggtgtcgaag | gtggtgggca | gatgccgggc | ctccatgcct | aagtggtggt | acaatgtcac | 540 |
| tgacggatcc | tgccagctgt | ttgtgtatgg | gggctgtgac | ggaaacagca | ataattacct | 600 |
| gaccaaggag | gagtgcctca | agaaatgtgc | cactgtcaca | gagaatgcca | cgggtgacct | 660 |

-continued

| | |
|---|---|
| ggccaccagc aggaatgcag cggattcctc tgtcccaagt gctcccagaa ggcaggattc | 720 |
| tgaagaccac tccagcgata tgttcaacta tgaagaatac tgcaccgcca acgcagtcac | 780 |
| tgggccttgc cgtgcatcct tcccacgctg gtactttgac gtggagagga actcctgcaa | 840 |
| taacttcatc tatggaggct gccggggcaa taagaacagc taccgctctg aggaggcctg | 900 |
| catgctccgc tgcttccgcc agcaggagaa tcctcccctg ccccttggct caaaggtggt | 960 |
| ggttctggcg gggctgttcg tgatggtgtt gatcctcttc ctgggagcct ccatggtcta | 1020 |
| cctgatccgg gtggcacgga ggaaccagga gcgtgccctg cgcaccgtct ggagctccgg | 1080 |
| acatgacaag gagcagctgg tgaagaacac atatgtcctg tgaccgccct gtcgccaaga | 1140 |
| ggactgggga agggagggga gactatgtgt gagctttttt taaatagcgg gattgactcg | 1200 |
| gatttgagtg atcattaggg ctgaggtgtg tttctctggg aggtaggacg gctgcttcct | 1260 |
| ggtctggcag ggatgggttt gctttggaaa tcctctagga ggctcctcct cgcatggcct | 1320 |
| gcagtctggc agcagccccg agttgtttcc tcgctgatcg atttctttcc tccaggtaga | 1380 |
| gttttctttg cttatgttga attccattgc ctctttctc atcacagaag tgatgttgga | 1440 |
| atcgtttctt ttgtttgtct gatttatggt tttttttaagt ataaacaaaa gttttttatt | 1500 |
| aacatctgaa agaaggaaag taaaatgtac aagtttaata aaaggggcc ttccccttta | 1560 |
| gaat | 1564 |

<210> SEQ ID NO 62
<211> LENGTH: 252
<212> TYPE: PRT
<213> ORGANISM: Homo sapiens

<400> SEQUENCE: 62

Met Ala His Leu Cys Gly Leu Arg Arg Ser Arg Ala Phe Leu Ala Leu
1               5                   10                  15

Leu Gly Ser Leu Leu Leu Ser Gly Val Leu Ala Ala Asp Arg Glu Arg
            20                  25                  30

Ser Ile His Asp Phe Cys Leu Val Ser Lys Val Val Gly Arg Cys Arg
        35                  40                  45

Ala Ser Met Pro Lys Trp Trp Tyr Asn Val Thr Asp Gly Ser Cys Gln
    50                  55                  60

Leu Phe Val Tyr Gly Gly Cys Asp Gly Asn Ser Asn Asn Tyr Leu Thr
65                  70                  75                  80

Lys Glu Glu Cys Leu Lys Lys Cys Ala Thr Val Thr Glu Asn Ala Thr
                85                  90                  95

Gly Asp Leu Ala Thr Ser Arg Asn Ala Ala Asp Ser Ser Val Pro Ser
            100                 105                 110

Ala Pro Arg Arg Gln Asp Ser Glu Asp His Ser Ser Asp Met Phe Asn
        115                 120                 125

Tyr Glu Glu Tyr Cys Thr Ala Asn Ala Val Thr Gly Pro Cys Arg Ala
    130                 135                 140

Ser Phe Pro Arg Trp Tyr Phe Asp Val Glu Arg Asn Ser Cys Asn Asn
145                 150                 155                 160

Phe Ile Tyr Gly Gly Cys Arg Gly Asn Lys Asn Ser Tyr Arg Ser Glu
                165                 170                 175

Glu Ala Cys Met Leu Arg Cys Phe Arg Gln Gln Glu Asn Pro Pro Leu
            180                 185                 190

Pro Leu Gly Ser Lys Val Val Val Leu Ala Gly Leu Phe Val Met Val
        195                 200                 205

-continued

```
Leu Ile Leu Phe Leu Gly Ala Ser Met Val Tyr Leu Ile Arg Val Ala
    210                 215                 220

Arg Arg Asn Gln Glu Arg Ala Leu Arg Thr Val Trp Ser Ser Gly His
225                 230                 235                 240

Asp Lys Glu Gln Leu Val Lys Asn Thr Tyr Val Leu
                245                 250

<210> SEQ ID NO 63
<211> LENGTH: 1147
<212> TYPE: DNA
<213> ORGANISM: Homo sapiens

<400> SEQUENCE: 63
ggacgtcctt ccccaggagc cgactggcca atcacaggca ggaagatgaa ggttctgtgg      60
gctgcgttgc tggtcacatt cctggcagga tgccaggcca aggtggagca agcggtggag     120
acagagccgg agcccgagct cgccagcag accgagtggc agagcggcca gcgctgggaa     180
ctggcactgg gtcgcttttg ggattacctg cgctgggtgc agacactgtc tgagcaggtg     240
caggaggagc tgctcagctc ccaggtcacc caggaactga gggcgctgat ggacgagacc     300
atgaaggagt tgaaggccta caatcggaa ctggaggaac aactgacccc ggtggcggag     360
gagacgcggg cacggctgtc caaggagctg caggcggcgc aggcccggct gggcgcggac     420
atggaggacg tgtgcggccg cctggtgcag taccgcggcg aggtgcaggc catgctcggc     480
cagagcaccg aggagctgcg ggtgcgcctc gcctcccacc tgcgcaagct gcgtaagcgg     540
ctcctccgcg atgccgatga cctgcagaag cgcctgcag tgtaccaggc cggggcccgc     600
gagggcgccg agcgcggcct cagcgccatc cgcgagcgcc tggggcccct ggtggaacag     660
ggccgcgtgc gggccgccac tgtgggctcc ctggccggcc agccgctaca ggagcgggcc     720
caggcctggg gcgagcggct gcgcgcgcgg atggaggaga tgggcagccg acccgcgac     780 cgcctggacg aggtgaagga gcaggtggcg gaggtgcgcg ccaagctgga ggagcaggcc     840
cagcagatac gcctgcaggc cgaggccttc caggcccgcc tcaagagctg gttcgagccc     900
ctggtggaag acatgcagcg ccagtgggcc gggctggtgg agaaggtgca ggctgccgtg     960
ggcaccagcg ccgcccctgt gcccagcgac aatcactgaa cgccgaagcc tgcagccatg    1020
cgaccccacg ccacccgtg cctcctgcct ccgcgcagcc tgcagcggga gaccctgtcc    1080
ccgccccagc cgtcctcctg gggtggaccc tagtttaata aagattcacc aagtttcacg    1140
caaaaaa                                                              1147

<210> SEQ ID NO 64
<211> LENGTH: 317
<212> TYPE: PRT
<213> ORGANISM: Homo sapiens

<400> SEQUENCE: 64

Met Lys Val Leu Trp Ala Ala Leu Leu Val Thr Phe Leu Ala Gly Cys
  1               5                  10                  15

Gln Ala Lys Val Glu Gln Ala Val Glu Thr Glu Pro Glu Pro Glu Leu
                 20                  25                  30

Arg Gln Gln Thr Glu Trp Gln Ser Gly Gln Arg Trp Glu Leu Ala Leu
             35                  40                  45

Gly Arg Phe Trp Asp Tyr Leu Arg Trp Val Gln Thr Leu Ser Glu Gln
         50                  55                  60

Val Gln Glu Glu Leu Leu Ser Ser Gln Val Thr Gln Glu Leu Arg Ala
 65                  70                  75                  80
```

-continued

```
Leu Met Asp Glu Thr Met Lys Glu Leu Lys Ala Tyr Lys Ser Glu Leu
                 85                  90                  95

Glu Glu Gln Leu Thr Pro Val Ala Glu Thr Arg Ala Arg Leu Ser
            100                 105                 110

Lys Glu Leu Gln Ala Ala Gln Ala Arg Leu Gly Ala Asp Met Glu Asp
            115                 120                 125

Val Cys Gly Arg Leu Val Gln Tyr Arg Gly Glu Val Gln Ala Met Leu
        130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Leu Gln Lys Arg
                165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
            195                 200                 205

Arg Ala Ala Thr Val Gly Ser Leu Ala Gly Gln Pro Leu Gln Glu Arg
        210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
            260                 265                 270

Glu Ala Phe Gln Ala Arg Leu Lys Ser Trp Phe Glu Pro Leu Val Glu
            275                 280                 285

Asp Met Gln Arg Gln Trp Ala Gly Leu Val Glu Lys Val Gln Ala Ala
            290                 295                 300

Val Gly Thr Ser Ala Ala Pro Val Pro Ser Asp Asn His
305                 310                 315
```

<210> SEQ ID NO 65
<211> LENGTH: 2493
<212> TYPE: DNA
<213> ORGANISM: Homo sapiens

<400> SEQUENCE: 65

```
ggatcgattt gagtaagagc atagctgtcg ggagagccca ggattcaaca cgggccttga    60
gaaatgtggc tcttgtacct cctggtgccg gccctgttct gcagggcagg aggctccatt   120
cccatccctc agaagttatt tggggaggtg acttcccctc tgttccccaa gccttacccc   180
aacaactttg aaacaaccac tgtgatcaca gtccccacgg gatacagggt gaagctcgtc   240
ttccagcagt ttgacctgga gccttctgaa ggctgcttct atgattatgt caagatctct   300
gctgataaga aaagcctggg gaggttctgt gggcaactgg ttctccact gggcaacccc    360 ccgggaaaga aggaatttat gtcccaaggg aacaagatgc tgctgacctt ccacacagac   420
ttctccaacg aggagaatgg gaccatcatg ttctacaagg cttcctggc ctactaccaa     480 gctgtggacc ttgatgaatg tgcttcccgg agcaaatcag gggaggagga tccccagccc   540
cagtgccagc acctgtgtca aactacgtt ggaggctact ctgttcctg ccgtccaggc      600 tatgagcttc aggaagacag gcattcctgc caggctgagt gcagcagcga gctgtacacg   660
gaggcatcag gctacatctc cagcctggag taccctcggt cctacccccc tgacctgcgc   720
tgcaactaca gcatccgggt ggagcggggc ctcaccctgc acctcaagtt cctggagcct   780
```

```
tttgatattg atgaccacca gcaagtacac tgcccctatg accagctaca gatctatgcc    840
aacgggaaga acattggcga gttctgtggg aagcaaaggc cccccgacct cgacaccagc    900
agcaatgctg tggatctgct gttcttcaca gatgagtcgg gggacagccg gggctggaag    960
ctgcgctaca ccaccgagat catcaagtgc ccccagccca agaccctaga cgagttcacc   1020
atcatccaga acctgcagcc tcagtaccag ttccgtgact acttcattgc tacctgcaag   1080
caaggctacc agctcataga ggggaaccag gtgctgcatt ccttcacagc tgtctgccag   1140
gatgatggca cgtggcatcg tgccatgccc agatgcaaga tcaaggactg tgggcagccc   1200
cgaaacctgc ctaatggtga cttccgttac accaccacaa tgggagtgaa cacctacaag   1260
gcccgtatcc agtactactg ccatgagcca tattacaaga tgcagaccag agctggcagc   1320
agggagtctg agcaagggt gtacacctgc acagcacagg gcatttggaa gaatgaacag   1380
aagggagaga agattcctcg gtgcttgcca gtgtgtggga agcccgtgaa ccccgtggaa   1440
cagaggcagc gcataatcgg agggcaaaaa gccaagatgg gcaacttccc ctggcaggtg   1500
ttcaccaaca tccacgggcg cggggcggg gccctgctgg gcgaccgctg gatcctcaca   1560
gctgcccaca ccctgtatcc caaggaacac gaagcgcaaa gcaacgcctc tttggatgtg   1620
ttcctgggcc acacaaatgt ggaagagctc atgaagctag aaatcaccc catccgcagg   1680
gtcagcgtcc acccggacta ccgtcaggat gagtcctaca ttttgaggg ggacatcgcc   1740
ctgctggagc tggaaaatag tgtcacccctg gtcccaacc tcctcccat ctgcctccct   1800
gacaacgata ccttctacga cctgggcttg atgggctatg tcagtggctt cggggtcatg   1860
gaggagaaga ttgctcatga cctcaggttt gtccgtctgc ccgtagctaa tccacaggcc   1920
tgtgagaact ggctccgggg aaagaatagg atggatgtgt tctctcaaaa catgttctgt   1980
gctggacacc catctctaaa gcaggacgcc tgccagggg atagtggggg cgttttttgca   2040
gtaagggacc cgaacactga tcgctgggtg ccacgggca tcgtgtcctg gggcatcggg   2100
tgcagcaggg gctatggctt ctacaccaaa gtgctcaact acgtggactg gatcaagaaa   2160
gagatggagg aggaggactg agcccagaat tcactaggtt cgaatccaga gagcagtgtg   2220
gaaaaaaaaa aaacaaaaaa caactgacca gttgttgata accactaaga gtctctatta   2280
aaattactga tgcagaaaga ccgtgtgtga aattctcttt cctgtagtcc cattgatgta   2340
ctttacctga aacaacccaa aggccccttt ctttcttctg aggattgcag aggatatagt   2400
tatcaatctc tagttgtcac tttcctcttc cactttgata ccattgggtc attgaatata   2460
actttttcca aataaagttt tatgagaaat gcc                                2493
```

<210> SEQ ID NO 66
<211> LENGTH: 705
<212> TYPE: PRT
<213> ORGANISM: Homo sapiens
<400> SEQUENCE: 66

```
Met Trp Leu Leu Tyr Leu Leu Val Pro Ala Leu Phe Cys Arg Ala Gly
 1               5                  10                  15

Gly Ser Ile Pro Ile Pro Gln Lys Leu Phe Gly Glu Val Thr Ser Pro
            20                  25                  30

Leu Phe Pro Lys Pro Tyr Pro Asn Asn Phe Glu Thr Thr Thr Val Ile
        35                  40                  45

Thr Val Pro Thr Gly Tyr Arg Val Lys Leu Val Phe Gln Gln Phe Asp
    50                  55                  60
```

-continued

```
Leu Glu Pro Ser Glu Gly Cys Phe Tyr Asp Tyr Val Lys Ile Ser Ala
 65                  70                  75                  80

Asp Lys Lys Ser Leu Gly Arg Phe Cys Gly Gln Leu Gly Ser Pro Leu
                 85                  90                  95

Gly Asn Pro Pro Gly Lys Lys Glu Phe Met Ser Gln Gly Asn Lys Met
            100                 105                 110

Leu Leu Thr Phe His Thr Asp Phe Ser Asn Glu Glu Asn Gly Thr Ile
            115                 120                 125

Met Phe Tyr Lys Gly Phe Leu Ala Tyr Tyr Gln Ala Val Asp Leu Asp
130                 135                 140

Glu Cys Ala Ser Arg Ser Lys Ser Gly Glu Glu Asp Pro Gln Pro Gln
145                 150                 155                 160

Cys Gln His Leu Cys His Asn Tyr Val Gly Gly Tyr Phe Cys Ser Cys
                165                 170                 175

Arg Pro Gly Tyr Glu Leu Gln Glu Asp Arg His Ser Cys Gln Ala Glu
            180                 185                 190

Cys Ser Ser Glu Leu Tyr Thr Glu Ala Ser Gly Tyr Ile Ser Ser Leu
            195                 200                 205

Glu Tyr Pro Arg Ser Tyr Pro Pro Asp Leu Arg Cys Asn Tyr Ser Ile
210                 215                 220

Arg Val Glu Arg Gly Leu Thr Leu His Leu Lys Phe Leu Glu Pro Phe
225                 230                 235                 240

Asp Ile Asp Asp His Gln Val His Cys Pro Tyr Asp Gln Leu Gln
                245                 250                 255

Ile Tyr Ala Asn Gly Lys Asn Ile Gly Glu Phe Cys Gly Lys Gln Arg
            260                 265                 270

Pro Pro Asp Leu Asp Thr Ser Ser Asn Ala Val Asp Leu Leu Phe Phe
            275                 280                 285

Thr Asp Glu Ser Gly Asp Ser Arg Gly Trp Lys Leu Arg Tyr Thr Thr
290                 295                 300

Glu Ile Ile Lys Cys Pro Gln Pro Lys Thr Leu Asp Glu Phe Thr Ile
305                 310                 315                 320

Ile Gln Asn Leu Gln Pro Gln Tyr Gln Phe Arg Asp Tyr Phe Ile Ala
            325                 330                 335

Thr Cys Lys Gln Gly Tyr Gln Leu Ile Glu Gly Asn Gln Val Leu His
            340                 345                 350

Ser Phe Thr Ala Val Cys Gln Asp Asp Gly Thr Trp His Arg Ala Met
            355                 360                 365

Pro Arg Cys Lys Ile Lys Asp Cys Gly Gln Pro Arg Asn Leu Pro Asn
370                 375                 380

Gly Asp Phe Arg Tyr Thr Thr Met Gly Val Asn Thr Tyr Lys Ala
385                 390                 395                 400

Arg Ile Gln Tyr Tyr Cys His Glu Pro Tyr Tyr Lys Met Gln Thr Arg
            405                 410                 415

Ala Gly Ser Arg Glu Ser Glu Gln Gly Val Tyr Thr Cys Thr Ala Gln
            420                 425                 430

Gly Ile Trp Lys Asn Glu Gln Lys Gly Glu Lys Ile Pro Arg Cys Leu
            435                 440                 445

Pro Val Cys Gly Lys Pro Val Asn Pro Val Glu Gln Arg Gln Arg Ile
450                 455                 460

Ile Gly Gly Gln Lys Ala Lys Met Gly Asn Phe Pro Trp Gln Val Phe
465                 470                 475                 480

Thr Asn Ile His Gly Arg Gly Gly Gly Ala Leu Leu Gly Asp Arg Trp
```

```
                485                 490                 495
Ile Leu Thr Ala Ala His Thr Leu Tyr Pro Lys Glu His Glu Ala Gln
            500                 505                 510
Ser Asn Ala Ser Leu Asp Val Phe Leu Gly His Thr Asn Val Glu Glu
            515                 520                 525
Leu Met Lys Leu Gly Asn His Pro Ile Arg Arg Val Ser Val His Pro
            530                 535                 540
Asp Tyr Arg Gln Asp Glu Ser Tyr Asn Phe Glu Gly Asp Ile Ala Leu
545                 550                 555                 560
Leu Glu Leu Glu Asn Ser Val Thr Leu Gly Pro Asn Leu Leu Pro Ile
            565                 570                 575
Cys Leu Pro Asp Asn Asp Thr Phe Tyr Asp Leu Gly Leu Met Gly Tyr
            580                 585                 590
Val Ser Gly Phe Gly Val Met Glu Glu Lys Ile Ala His Asp Leu Arg
            595                 600                 605
Phe Val Arg Leu Pro Val Ala Asn Pro Gln Ala Cys Glu Asn Trp Leu
            610                 615                 620
Arg Gly Lys Asn Arg Met Asp Val Phe Ser Gln Asn Met Phe Cys Ala
625                 630                 635                 640
Gly His Pro Ser Leu Lys Gln Asp Ala Cys Gln Gly Asp Ser Gly Gly
            645                 650                 655
Val Phe Ala Val Arg Asp Pro Asn Thr Asp Arg Trp Val Ala Thr Gly
            660                 665                 670
Ile Val Ser Trp Gly Ile Gly Cys Ser Arg Gly Tyr Gly Phe Tyr Thr
            675                 680                 685
Lys Val Leu Asn Tyr Val Asp Trp Ile Lys Lys Glu Met Glu Glu Glu
            690                 695                 700
Asp
705

<210> SEQ ID NO 67
<211> LENGTH: 777
<212> TYPE: DNA
<213> ORGANISM: Homo sapiens

<400> SEQUENCE: 67
gctccgggct gaagattgct tctcttctct cctccaaggt ctagtgacgg agcccgcgcg    60
cgcgccacca tgcggcagaa ggcggtatcc gttttcttgt gctacctgct gctcttcact   120
tgcagtgggg tggaggcagg taagaaaaag tgctcggaga gctcggacag cggctccggg   180
ttctggaagg ccctgacctt catggccgtc ggaggaggac tcgcagtcgc cgggctgccc   240
gcgctgggct tcaccggcgc cggcatcgcg gccaactcgg tggctgcctc gctgatgagc   300
tggtctgcga tcctgaatgg gggcggcgtg cccgccgggg gctagtggca cgctgcag    360 agcctcgggg ctggtggcag cagcgtcgtc ataggtaata ttggtgccct gatgcggtac   420
gccacccaca gtatctcga tagtgaggag gatgaggagt agccagcagc tcccagaacc   480
tcttcttcct tcttggccta actcttccag ttaggatcta gaactttgcc ttttttttt   540 ttttttttt tttgagatgg gttctcacta tattgtccag gctagagtgc agtggctatt   600
cacagatgcg aacatagtac actgcagcct ccaactccta gcctcaagtg atcctcctgt   660
ctcaacctcc caagtaggat tacaagcatg cgccgacgat gcccagaatc agaactttg   720 tctatcactc tccccaacaa cctagatgtg aaaacagaat aaacttcacc cagaaaa     777
```

<210> SEQ ID NO 68
<211> LENGTH: 130
<212> TYPE: PRT
<213> ORGANISM: Homo sapiens

<400> SEQUENCE: 68

```
Met Arg Gln Lys Ala Val Ser Val Phe Leu Cys Tyr Leu Leu Leu Phe
1               5                   10                  15
Thr Cys Ser Gly Val Glu Ala Gly Lys Lys Cys Ser Glu Ser Ser
            20                  25                  30
Asp Ser Gly Ser Gly Phe Trp Lys Ala Leu Thr Phe Met Ala Val Gly
        35                  40                  45
Gly Gly Leu Ala Val Ala Gly Leu Pro Ala Leu Gly Phe Thr Gly Ala
    50                  55                  60
Gly Ile Ala Ala Asn Ser Val Ala Ala Ser Leu Met Ser Trp Ser Ala
65                  70                  75                  80
Ile Leu Asn Gly Gly Gly Val Pro Ala Gly Gly Leu Val Ala Thr Leu
                85                  90                  95
Gln Ser Leu Gly Ala Gly Gly Ser Ser Val Val Ile Gly Asn Ile Gly
            100                 105                 110
Ala Leu Met Arg Tyr Ala Thr His Lys Tyr Leu Asp Ser Glu Glu Asp
        115                 120                 125
Glu Glu
    130
```

<210> SEQ ID NO 69
<211> LENGTH: 2402
<212> TYPE: DNA
<213> ORGANISM: Homo sapiens

<400> SEQUENCE: 69

| | | | | | |
|---|---|---|---|---|---|
| agtctccgcc | gccgccgtga | acatggagcc | cccggacgca | ccggcccagg | cgcgcggggc | 60 |
| cccgcggctg | ctgttgctcg | cagtcctgct | ggcggcgcac | ccagatgccc | aggcggaggt | 120 |
| gcgcttgtct | gtaccccgc | tggtggaggt | gatgcgagga | aagtctgtca | ttctggactg | 180 |
| cacccctacg | ggaacccacg | accattatat | gctggaatgg | ttccttaccg | accgtcggg | 240 |
| agctcgcccc | cgcctagcct | cggctgagat | gcagggctct | gagctccagg | tcacaatgca | 300 |
| cgacacccgg | ggccgcagtc | ccccatacca | gctggactcc | caggggcgcc | tggtgctggc | 360 |
| tgaggcccag | gtgggcgacg | agcgagacta | cgtgtgcgtg | gtgagggcag | gggcggcagg | 420 |
| cactgctgag | gccactgcgc | ggctcaacgt | gtttgcaaag | ccagaggcca | ctgaggtctc | 480 |
| ccccaacaaa | gggacactgt | ctgtgatgga | ggactctgcc | caggagatcg | ccacctgcaa | 540 |
| cagccggaac | gggaacccgg | ccccaagat | acgtggtat | cgcaacgggc | agcgcctgga | 600 |
| ggtgcccgta | gagatgaacc | cagagggcta | catgaccagc | cgcacggtcc | gggaggcctc | 660 |
| gggcctgctc | tccctcacca | gcaccctcta | cctgcggctc | cgcaaggatg | accgagacgc | 720 |
| cagcttccac | tgcgccgccc | actacagcct | gcccgagggc | cgccacggcc | gcctggacag | 780 |
| ccccaccttc | cacctcaccc | tgcactatcc | cacggagcac | gtgcagttct | gggtgggcag | 840 |
| cccgtccacc | ccagcaggct | gggtacgcga | gggtgacact | gtccagctgc | tctgccgggg | 900 |
| ggacggcagc | cccagcccgg | agtatacgct | tttccgcctt | caggatgagc | aggaggaagt | 960 |
| gctgaatgtg | aatctcgagg | ggaacttgac | cctggaggga | gtgacccggg | gccagagcgg | 1020 |
| gacctatggc | tgcagagtgg | aggattacga | cgcggcagat | gacgtgcagc | tctccaagac | 1080 |
| gctggagctg | cgcgtggcct | atctggacc | cctggagctc | agcgagggga | aggtgctttc | 1140 |

-continued

```
cttacctcta aacagcagtg cagtcgtgaa ctgctccgtg cacggcctgc ccacccctgc    1200
cctacgctgg accaaggact ccactcccct gggcgatggc cccatgctgt cgctcagttc    1260
tatcaccttc gattccaatg caccctacgt atgtgaggcc tccctgccca cagtcccggt    1320
cctcagccgc acccagaact tcacgctgct ggtccaaggc tcgccagagc taaagacagc    1380
ggaaatagag cccaaggcag atggcagctg gagggaagga gacgaagtca cactcatctg    1440
ctctgcccgc ggccatccag accccaaact cagctggagc caattggggg gcagccccgc    1500
agagccaatc cccggacggc agggttgggt gagcagctct ctgaccctga aagtgaccag    1560
cgccctgagc cgcgatggca tctcctgtga agcctccaac ccccacggga acaagcgcca    1620
tgtcttccac ttcggcgccg tgagccccca gacctcccag gctggagtgg ccgtcatggc    1680
cgtggccgtc agcgtgggcc tcctgctcct cgtcgttgct gtcttctact gcgtgagacg    1740 caaaggggc ccctgctgcc gccagcggcg ggagaagggg gctccgccgc caggggagcc    1800
agggctgagc cactcggggt cggagcaacc agagcagacc ggccttctca tgggaggtgc    1860
ctccggagga gccaggggtg gcagcggggg cttcggagac gagtgctgag ccaagaacct    1920
cctagaggct gtccctggac ctggagctgc aggcatcaga gaaccagccc tgctcacgcc    1980
atgcccgccc ccgccttccc tcttccctct ccctctcccc tgcccagccc tcccttcctt    2040
cctctgccgg caaggcaggg acccacagtg gctgcctgcc tccgggaggg aaggagaggg    2100
agggtgggtg ggtgggaggg ggccttcctc cagggaatgt gactctccca ggccccagaa    2160
tagctcctgg acccaagccc aaggcccagc ctgggacaag gctccgaggg tcggctggcc    2220
ggagctattt ttacctcccg cctcccctgc tggtccccccc acctgacgtc ttgctgcaga    2280
gtctgacact ggattccccc ccctcacccc gcccctggtc ccactcctgc ccccgcccta    2340
cctccgcccc accccatcat ctgtggacac tggagtctgg aataaatgct gtttgtcaca    2400
tc                                                                    2402
```

<210> SEQ ID NO 70
<211> LENGTH: 628
<212> TYPE: PRT
<213> ORGANISM: Homo sapiens

<400> SEQUENCE: 70

Met Glu Pro Pro Asp Ala Pro Ala Gln Ala Arg Gly Ala Pro Arg Leu
1               5                   10                  15

Leu Leu Leu Ala Val Leu Leu Ala Ala His Pro Asp Ala Gln Ala Glu
            20                  25                  30

Val Arg Leu Ser Val Pro Pro Leu Val Glu Val Met Arg Gly Lys Ser
        35                  40                  45

Val Ile Leu Asp Cys Thr Pro Thr Gly Thr His Asp His Tyr Met Leu
    50                  55                  60

Glu Trp Phe Leu Thr Asp Arg Ser Gly Ala Arg Pro Arg Leu Ala Ser
65                  70                  75                  80

Ala Glu Met Gln Gly Ser Glu Leu Gln Val Thr Met His Asp Thr Arg
                85                  90                  95

Gly Arg Ser Pro Pro Tyr Gln Leu Asp Ser Gln Gly Arg Leu Val Leu
            100                 105                 110

Ala Glu Ala Gln Val Gly Asp Glu Arg Asp Tyr Val Cys Val Val Arg
        115                 120                 125

Ala Gly Ala Ala Gly Thr Ala Glu Ala Thr Ala Arg Leu Asn Val Phe
    130                 135                 140

```
Ala Lys Pro Glu Ala Thr Glu Val Ser Pro Asn Lys Gly Thr Leu Ser
145                 150                 155                 160

Val Met Glu Asp Ser Ala Gln Glu Ile Ala Thr Cys Asn Ser Arg Asn
                165                 170                 175

Gly Asn Pro Ala Pro Lys Ile Thr Trp Tyr Arg Asn Gly Gln Arg Leu
            180                 185                 190

Glu Val Pro Val Glu Met Asn Pro Glu Gly Tyr Met Thr Ser Arg Thr
        195                 200                 205

Val Arg Glu Ala Ser Gly Leu Leu Ser Leu Thr Ser Thr Leu Tyr Leu
210                 215                 220

Arg Leu Arg Lys Asp Asp Arg Asp Ala Ser Phe His Cys Ala Ala His
225                 230                 235                 240

Tyr Ser Leu Pro Glu Gly Arg His Gly Arg Leu Asp Ser Pro Thr Phe
                245                 250                 255

His Leu Thr Leu His Tyr Pro Thr Glu His Val Gln Phe Trp Val Gly
            260                 265                 270

Ser Pro Ser Thr Pro Ala Gly Trp Val Arg Glu Gly Asp Thr Val Gln
        275                 280                 285

Leu Leu Cys Arg Gly Asp Gly Ser Pro Ser Pro Glu Tyr Thr Leu Phe
290                 295                 300

Arg Leu Gln Asp Glu Gln Glu Glu Val Leu Asn Val Asn Leu Glu Gly
305                 310                 315                 320

Asn Leu Thr Leu Glu Gly Val Thr Arg Gly Gln Ser Gly Thr Tyr Gly
                325                 330                 335

Cys Arg Val Glu Asp Tyr Asp Ala Ala Asp Val Gln Leu Ser Lys
            340                 345                 350

Thr Leu Glu Leu Arg Val Ala Tyr Leu Asp Pro Leu Glu Leu Ser Glu
        355                 360                 365

Gly Lys Val Leu Ser Leu Pro Leu Asn Ser Ser Ala Val Val Asn Cys
370                 375                 380

Ser Val His Gly Leu Pro Thr Pro Ala Leu Arg Trp Thr Lys Asp Ser
385                 390                 395                 400

Thr Pro Leu Gly Asp Gly Pro Met Leu Ser Leu Ser Ser Ile Thr Phe
                405                 410                 415

Asp Ser Asn Gly Thr Tyr Val Cys Glu Ala Ser Leu Pro Thr Val Pro
            420                 425                 430

Val Leu Ser Arg Thr Gln Asn Phe Thr Leu Leu Val Gln Gly Ser Pro
        435                 440                 445

Glu Leu Lys Thr Ala Glu Ile Glu Pro Lys Ala Asp Gly Ser Trp Arg
450                 455                 460

Glu Gly Asp Glu Val Thr Leu Ile Cys Ser Ala Arg Gly His Pro Asp
465                 470                 475                 480

Pro Lys Leu Ser Trp Ser Gln Leu Gly Gly Ser Pro Ala Glu Pro Ile
                485                 490                 495

Pro Gly Arg Gln Gly Trp Val Ser Ser Ser Leu Thr Leu Lys Val Thr
            500                 505                 510

Ser Ala Leu Ser Arg Asp Gly Ile Ser Cys Glu Ala Ser Asn Pro His
        515                 520                 525

Gly Asn Lys Arg His Val Phe His Phe Gly Ala Val Ser Pro Gln Thr
530                 535                 540

Ser Gln Ala Gly Val Ala Val Met Ala Val Ala Val Ser Val Gly Leu
545                 550                 555                 560
```

-continued

```
Leu Leu Leu Val Val Ala Val Phe Tyr Cys Val Arg Arg Lys Gly Gly
            565                 570                 575
Pro Cys Cys Arg Gln Arg Arg Glu Lys Gly Ala Pro Pro Pro Gly Glu
        580                 585                 590
Pro Gly Leu Ser His Ser Gly Ser Glu Gln Pro Glu Gln Thr Gly Leu
    595                 600                 605
Leu Met Gly Gly Ala Ser Gly Gly Ala Arg Gly Gly Ser Gly Gly Phe
610                 615                 620
Gly Asp Glu Cys
625

<210> SEQ ID NO 71
<211> LENGTH: 5460
<212> TYPE: DNA
<213> ORGANISM: Homo sapiens

<400> SEQUENCE: 71
cgggcccggt gctgaagggc aggaacaac ttgatggtgc tactttgaac tgcttttctt      60 ttctccttt tgcacaaaga gtctcatgtc tgatatttag acatgatgag ctttgtgcaa     120
aaggggagct ggctacttct cgctctgctt catcccacta ttattttggc acaacaggaa    180
gctgttgaag aggatgttc ccatcttggt cagtcctatg cggatagaga tgtctggaag     240
ccagaaccat gccaaatatg tgtctgtgac tcaggatccg ttctctgcga tgacataata    300
tgtgacgatc aagaattaga ctgccccaac ccagaaattc catttggaga atgttgtgca    360
gtttgcccac agcctccaac tgctcctact cgccctccta atggtcaagg acctcaaggc    420
cccaagggag atccaggccc tcctggtatt cctgggagaa atggtgaccc tggtattcca    480
ggacaaccag ggtcccctgg ttctcctggc ccccctggaa tctgtgaatc atgccctact    540
ggtcctcaga actattctcc ccagtatgat tcatatgatg tcaagtctgg agtagcagta    600
ggaggactcg caggctatcc tggaccagct ggcccccag gccctcccgg tcccctggt      660 acatctggtc atcctggttc ccctggatct ccaggatacc aaggaccccc tggtgaacct    720
gggcaagctg gtccttcagg ccctccagga cctcctggtg ctataggtcc atctggtcct    780 gctggaaag atggagaatc aggtagaccc ggacgacctg gagagcgagg attgcctgga    840
cctccaggta tcaaaggtcc agctgggata cctggattcc ctggtatgaa aggacagaga    900
ggcttcgatg gacgaaatgg agaaaagggt gaaacaggtg ctcctggatt aaagggtgaa    960
aatggtcttc aggcgaaaa tggagctcct ggacccatgg gtccaagagg gctcctggt    1020 gagcgaggac ggccaggact tcctggggct gcaggtgctc ggggtaatga cggtgctcga    1080
ggcagtgatg gtcaaccagg ccctcctggt cctcctggaa ctgccggatt ccctggatcc    1140
cctggtgcta agggtgaagt tggacctgca gggtctcctg gttcaaatgg tgcccctgga    1200
caaagaggaa aacctggacc tcagggacac gctggtgctc aaggtcctcc tggccctcct    1260
gggattaatg gtagtcctgg tggtaaaggc gaaatgggtc ccgctggcat tcctggagct    1320
cctggactga tgggagcccg gggtcctcca ggaccagccg gtgctaatgg tgctcctgga    1380
ctgcgaggtg gtgcaggtga gcctggtaag aatggtgcca aggagagcc cggaccacgt    1440 ggtgaacgcg gtgaggctgg tattccaggt gttccaggag ctaaaggcga agatggcaag    1500
gatggatcac ctggagaacc tggtgcaaat gggcttccag gagctgcagg agaaaggggt    1560 gccctgggt ccgaggacc tgctggacca aatggcatcc aggagaaaa gggtcctgct    1620 ggagagcgtg gtgctccagg ccctgcaggg cccagaggag ctgctggaga acctggcaga    1680
```

```
gatggcgtcc ctggaggtcc aggaatgagg ggcatgcccg gaagtccagg aggaccagga    1740
agtgatggga aaccagggcc tcccggaagt caaggagaaa gtggtcgacc aggtcctcct    1800
gggccatctg gtccccgagg tcagcctggt gtcatgggct tccccggtcc taaaggaaat    1860
gatggtgctc ctggtaagaa tggagaacga ggtggccctg gaggacctgg ccctcagggt    1920
cctcctggaa agaatggtga aactggacct caaggacccc cagggcctac tgggcctggt    1980
ggtgacaaag gagacacagg accccctggt ccacaaggat acaaggcttg gcctggtaca    2040
ggtggtcctc caggagaaaa tggaaaacct ggggaaccag gtccaaaggg tgatgccggt    2100
gcacctggag ctccaggagg caaggtgat gctggtgccc ctggtgaacg tggacctcct    2160
ggattggcag gggccccagg acttagaggt ggagctggtc ccctggtcc cgaaggagga    2220 aagggtgctg ctggtcctcc tgggccacct ggtgctgctg gtactcctgg tctgcaagga    2280
atgcctggag aaagaggagg tcttggaagt cctggtccaa agggtgacaa gggtgaacca    2340
ggcggcccag gtgctgatgg tgtcccaggg aaagatggcc caaggggtcc tactggtcct    2400
attggtcctc ctggcccagc tggccagcct ggagataagg gtgaaggtgg tgcccccgga    2460
cttccaggta tagctggacc tcgtggtagc cctggtgaga gaggtgaaac tggccctcca    2520
ggacctgctg gtttccctgg tgctcctgga cagaatggtg aacctggtgg taaaggagaa    2580 agagggctc cgggtgagaa aggtgaagga ggccctcctg gagttgcagg accccctgga    2640
ggttctggac ctgctggtcc tcctggtccc aaggtgtca aggtgaacg tggcagtcct    2700 ggtggacctg gtgctgctgg cttccctggt gctcgtggtc ttcctggtcc tcctggtagt    2760
aatggtaacc aggaccccc aggtcccagc ggttctccag gcaaggatgg gcccccaggt    2820
cctgcgggta acactggtgc tcctggcagc cctggagtgt ctggaccaaa aggtgatgct    2880
ggccaaccag gagagaaggg atcgcctggt gcccagggcc caccaggagc tccaggccca    2940
cttgggattg ctgggatcac tggagcacgg ggtcttgcag gaccaccagg catgccaggt    3000
cctagggaaa gccctggccc tcagggtgtc aagggtgaaa gtgggaaacc aggagctaac    3060
ggtctcagtg gagaacgtgg tcccccctgga ccccagggtc ttcctggtct ggctggtaca    3120
gctggtgaac ctggaagaga tggaaaccct ggatcagatg gtcttccagg ccgagatgga    3180
tctcctggtg gcaagggtga tcgtggtgaa aatggctctc ctggtgcccc tggcgctcct    3240
ggtcatccag gcccacctgg tcctgtcggt ccagctggaa agagtggtga cagaggagaa    3300
agtggccctg ctggccctgc tggtgctccc ggtcctgctg gttccgagg tgctcctggt    3360 cctcaaggcc cacgtggtga caaaggtgaa acaggtgaac gtggagctgc tggcatcaaa    3420
ggacatcgag gattccctgg taatccaggt gccccaggtt ctccaggccc tgctggtcag    3480
cagggtgcaa tcggcagtcc aggacctgca ggccccagag gacctgttgg acccagtgga    3540
cctcctggca agatggaac cagtggacat ccaggtccca ttggaccacc agggcctcga    3600
ggtaacagag gtgaaagagg atctgagggc tccccaggcc acccagggca accaggcccct    3660 cctggaccctc ctggtgcccc tggtccttgc tgtggtggtg ttggagccgc tgccattgct    3720
gggattggag gtgaaaaagc tggcggtttt gccccgtatt atggagatga accaatggat    3780
ttcaaaatca acaccgatga gattatgact tcactcaagt ctgttaatgg acaaatagaa    3840
agcctcatta gtcctgatgg ttctcgtaaa acccccgcta gaaactgcag agacctgaaa    3900
ttctgccatc ctgaactcaa gagtggagaa tactgggttg accctaacca aggatgcaaa    3960
ttggatgcta tcaaggtatt ctgtaatatg gaaactgggg aaacatgcat aagtgccaat    4020
cctttgaatg ttccacggaa acactggtgg acagattcta gtgctgagaa gaaacacgtt    4080
```

```
tggtttggag agtccatgga tggtggtttt cagtttagct acggcaatcc tgaacttcct     4140
gaagatgtcc ttgatgtgca gctggcattc cttcgacttc tctccagccg agcttcccag     4200
aacatcacat atcactgcaa aaatagcatt gcatacatgg atcaggccag tggaaatgta     4260
aagaaggccc tgaagctgat ggggtcaaat gaaggtgaat tcaaggctga aggaaatagc     4320
aaattcacct acacagttct ggaggatggt tgcacgaaac acactgggga atggagcaaa     4380
acagtctttg aatatcgaac acgcaaggct gtgagactac ctattgtaga tattgcaccc     4440
tatgacattg tggtcctga tcaagaattt ggtgtggacg ttggccctgt ttgcttttta      4500
taaaccaaac tctatctgaa atcccaacaa aaaaaattta actccatatg tgttcctctt     4560
gttctaatct tgtcaaccag tgcaagtgac cgacaaaatt ccagttattt atttccaaaa     4620
tgtttggaaa cagtataatt tgacaaagaa aaatgatact tctctttttt tgctgttcca     4680
ccaaatacaa ttcaaatgct ttttgtttta ttttttttacc aattccaatt tcaaaatgtc    4740
tcaatggtgc tataataaat aaacttcaac actctttatg ataacaacac tgtgttatat    4800
tctttgaatc ctagcccatc tgcagagcaa tgactgtgct caccagtaaa agataacctt     4860
tctttctgaa atagtcaaat acgaaattag aaaagccctc cctattttaa ctacctcaac     4920
tggtcagaaa cacagattgt attctatgag tcccagaaga tgaaaaaaat tttatacgtt    4980
gataaaactt ataaatttca ttgattaatc tcctggaaga ttggtttaaa aagaaaagtg    5040
taatgcaaga atttaaagaa atattttttaa agccacaatt attttaatat tggatatcaa   5100
ctgcttgtaa aggtgctcct cttttttctt gtcattgctg gtcaagatta ctaatatttg    5160
ggaaggcttt aaagacgcat gttatggtgc taatgtactt tcacttttaa actctagatc    5220
agaattgttg acttgcattc agaacataaa tgcacaaaat ctgtacatgt ctcccatcag    5280
aaagattcat tggcatgcca cagggattct cctccttcat cctgtaaagg tcaacaataa    5340
aaaccaaatt atgggctgc ttttgtcaca ctagcataga gaatgtgttg aaatttaact     5400
ttgtaagctt gtatgtggtt gttgatcttt ttttccctta cagacaccca taataaaata    5460
```

<210> SEQ ID NO 72
<211> LENGTH: 1466
<212> TYPE: PRT
<213> ORGANISM: Homo sapiens

<400> SEQUENCE: 72

```
Met Met Ser Phe Val Gln Lys Gly Ser Trp Leu Leu Ala Leu Leu
 1               5                  10                  15

His Pro Thr Ile Ile Leu Ala Gln Gln Glu Ala Val Glu Gly Gly Cys
                20                  25                  30

Ser His Leu Gly Gln Ser Tyr Ala Asp Arg Asp Val Trp Lys Pro Glu
            35                  40                  45

Pro Cys Gln Ile Cys Val Cys Asp Ser Gly Ser Val Leu Cys Asp Asp
        50                  55                  60

Ile Ile Cys Asp Asp Gln Glu Leu Asp Cys Pro Asn Pro Glu Ile Pro
65                  70                  75                  80

Phe Gly Glu Cys Cys Ala Val Cys Pro Gln Pro Thr Ala Pro Thr
                85                  90                  95

Arg Pro Pro Asn Gly Gln Gly Pro Gln Gly Pro Lys Gly Asp Pro Gly
            100                 105                 110

Pro Pro Gly Ile Pro Gly Arg Asn Gly Asp Pro Gly Ile Pro Gly Gln
        115                 120                 125
```

-continued

```
Pro Gly Ser Pro Gly Ser Pro Gly Pro Pro Gly Ile Cys Glu Ser Cys
        130                 135                 140
Pro Thr Gly Pro Gln Asn Tyr Ser Pro Gln Tyr Asp Ser Tyr Asp Val
145                 150                 155                 160
Lys Ser Gly Val Ala Val Gly Gly Leu Ala Gly Tyr Pro Gly Pro Ala
                165                 170                 175
Gly Pro Pro Gly Pro Pro Gly Pro Pro Gly Thr Ser Gly His Pro Gly
                180                 185                 190
Ser Pro Gly Ser Pro Gly Tyr Gln Gly Pro Pro Gly Glu Pro Gly Gln
                195                 200                 205
Ala Gly Pro Ser Gly Pro Pro Gly Pro Pro Gly Ala Ile Gly Pro Ser
    210                 215                 220
Gly Pro Ala Gly Lys Asp Gly Glu Ser Gly Arg Pro Gly Arg Pro Gly
225                 230                 235                 240
Glu Arg Gly Leu Pro Gly Pro Pro Gly Ile Lys Gly Pro Ala Gly Ile
                245                 250                 255
Pro Gly Phe Pro Gly Met Lys Gly His Arg Gly Phe Asp Gly Arg Asn
                260                 265                 270
Gly Glu Lys Gly Glu Thr Gly Ala Pro Gly Leu Lys Gly Glu Asn Gly
                275                 280                 285
Leu Pro Gly Glu Asn Gly Ala Pro Gly Pro Met Gly Pro Arg Gly Ala
    290                 295                 300
Pro Gly Glu Arg Gly Arg Pro Gly Leu Pro Gly Ala Ala Gly Ala Arg
305                 310                 315                 320
Gly Asn Asp Gly Ala Arg Gly Ser Asp Gly Gln Pro Gly Pro Pro Gly
                325                 330                 335
Pro Pro Gly Thr Ala Gly Phe Pro Gly Ser Pro Gly Ala Lys Gly Glu
                340                 345                 350
Val Gly Pro Ala Gly Ser Pro Gly Ser Asn Gly Ala Pro Gly Gln Arg
                355                 360                 365
Gly Glu Pro Gly Pro Gln Gly His Ala Gly Ala Gln Gly Pro Pro Gly
                370                 375                 380
Pro Pro Gly Ile Asn Gly Ser Pro Gly Gly Lys Gly Glu Met Gly Pro
385                 390                 395                 400
Ala Gly Ile Pro Gly Ala Pro Gly Leu Met Gly Ala Arg Gly Pro Pro
                405                 410                 415
Gly Pro Ala Gly Ala Asn Gly Ala Pro Gly Leu Arg Gly Gly Ala Gly
                420                 425                 430
Glu Pro Gly Lys Asn Gly Ala Lys Gly Glu Pro Gly Pro Arg Gly Glu
                435                 440                 445
Arg Gly Glu Ala Gly Ile Pro Gly Val Pro Gly Ala Lys Gly Glu Asp
    450                 455                 460
Gly Lys Asp Gly Ser Pro Gly Glu Pro Gly Ala Asn Gly Leu Pro Gly
465                 470                 475                 480
Ala Ala Gly Glu Arg Gly Ala Pro Gly Phe Arg Gly Pro Ala Gly Pro
                485                 490                 495
Asn Gly Ile Pro Gly Glu Lys Gly Pro Ala Gly Glu Arg Gly Ala Pro
                500                 505                 510
Gly Pro Ala Gly Pro Arg Gly Ala Ala Gly Glu Pro Gly Arg Asp Gly
                515                 520                 525
Val Pro Gly Gly Pro Gly Met Arg Gly Met Pro Gly Ser Pro Gly Gly
                530                 535                 540
Pro Gly Ser Asp Gly Lys Pro Gly Pro Pro Gly Ser Gln Gly Glu Ser
```

```
          545                 550                 555                 560
Gly Arg Pro Gly Pro Pro Gly Pro Ser Gly Pro Arg Gly Gln Pro Gly
                    565                 570                 575
Val Met Gly Phe Pro Gly Pro Lys Gly Asn Asp Gly Ala Pro Gly Lys
                580                 585                 590
Asn Gly Glu Arg Gly Gly Pro Gly Gly Pro Gly Pro Gln Gly Pro Pro
            595                 600                 605
Gly Lys Asn Gly Glu Thr Gly Pro Gln Gly Pro Pro Gly Pro Thr Gly
        610                 615                 620
Pro Gly Gly Asp Lys Gly Asp Thr Gly Pro Pro Gly Pro Gln Gly Leu
625                 630                 635                 640
Gln Gly Leu Pro Gly Thr Gly Gly Pro Pro Gly Glu Asn Gly Lys Pro
                645                 650                 655
Gly Glu Pro Gly Pro Lys Gly Asp Ala Gly Ala Pro Gly Ala Pro Gly
                660                 665                 670
Gly Lys Gly Asp Ala Gly Ala Pro Gly Glu Arg Gly Pro Pro Gly Leu
            675                 680                 685
Ala Gly Ala Pro Gly Leu Arg Gly Gly Ala Gly Pro Pro Gly Pro Glu
        690                 695                 700
Gly Gly Lys Gly Ala Ala Gly Pro Pro Gly Pro Pro Gly Ala Ala Gly
705                 710                 715                 720
Thr Pro Gly Leu Gln Gly Met Pro Gly Glu Arg Gly Gly Leu Gly Ser
                725                 730                 735
Pro Gly Pro Lys Gly Asp Lys Gly Glu Pro Gly Gly Pro Gly Ala Asp
                740                 745                 750
Gly Val Pro Gly Lys Asp Gly Pro Arg Gly Pro Thr Gly Pro Ile Gly
            755                 760                 765
Pro Pro Gly Pro Ala Gly Gln Pro Gly Asp Lys Gly Glu Gly Gly Ala
        770                 775                 780
Pro Gly Leu Pro Gly Ile Ala Gly Pro Arg Gly Ser Pro Gly Glu Arg
785                 790                 795                 800
Gly Glu Thr Gly Pro Pro Gly Pro Ala Gly Phe Pro Gly Ala Pro Gly
                805                 810                 815
Gln Asn Gly Glu Pro Gly Gly Lys Gly Glu Arg Gly Ala Pro Gly Glu
                820                 825                 830
Lys Gly Glu Gly Gly Pro Pro Gly Val Ala Gly Pro Pro Gly Gly Ser
            835                 840                 845
Gly Pro Ala Gly Pro Pro Gly Pro Gln Gly Val Lys Gly Glu Arg Gly
        850                 855                 860
Ser Pro Gly Gly Pro Gly Ala Ala Gly Phe Pro Gly Ala Arg Gly Leu
865                 870                 875                 880
Pro Gly Pro Pro Gly Ser Asn Gly Asn Pro Gly Pro Pro Gly Pro Ser
                885                 890                 895
Gly Ser Pro Gly Lys Asp Gly Pro Pro Gly Pro Ala Gly Asn Thr Gly
                900                 905                 910
Ala Pro Gly Ser Pro Gly Val Ser Gly Pro Lys Gly Asp Ala Gly Gln
            915                 920                 925
Pro Gly Glu Lys Gly Ser Pro Gly Ala Gln Gly Pro Pro Gly Ala Pro
        930                 935                 940
Gly Pro Leu Gly Ile Ala Gly Ile Thr Gly Ala Arg Gly Leu Ala Gly
945                 950                 955                 960
Pro Pro Gly Met Pro Gly Pro Arg Gly Ser Pro Gly Pro Gln Gly Val
                965                 970                 975
```

```
Lys Gly Glu Ser Gly Lys Pro Gly Ala Asn Gly Leu Ser Gly Glu Arg
            980                 985                 990

Gly Pro Pro Gly Pro Gln Gly Leu Pro Gly Leu Ala Gly Thr Ala Gly
            995                1000                1005

Glu Pro Gly Arg Asp Gly Asn Pro Gly Ser Asp Gly Leu Pro Gly Arg
           1010                1015                1020

Asp Gly Ser Pro Gly Gly Lys Gly Asp Arg Gly Glu Asn Gly Ser Pro
1025                1030                1035                1040

Gly Ala Pro Gly Ala Pro Gly His Pro Gly Pro Pro Gly Pro Val Gly
               1045                1050                1055

Pro Ala Gly Lys Ser Gly Asp Arg Gly Glu Ser Gly Pro Ala Gly Pro
           1060                1065                1070

Ala Gly Ala Pro Gly Pro Ala Gly Ser Arg Gly Ala Pro Gly Pro Gln
           1075                1080                1085

Gly Pro Arg Gly Asp Lys Gly Glu Thr Gly Glu Arg Gly Ala Ala Gly
           1090                1095                1100

Ile Lys Gly His Arg Gly Phe Pro Gly Asn Pro Gly Ala Pro Gly Ser
1105                1110                1115                1120

Pro Gly Pro Ala Gly Gln Gln Gly Ala Ile Gly Ser Pro Gly Pro Ala
           1125                1130                1135

Gly Pro Arg Gly Pro Val Gly Pro Ser Gly Pro Pro Gly Lys Asp Gly
           1140                1145                1150

Thr Ser Gly His Pro Gly Pro Ile Gly Pro Pro Gly Pro Arg Gly Asn
           1155                1160                1165

Arg Gly Glu Arg Gly Ser Glu Gly Ser Pro Gly His Pro Gly Gln Pro
           1170                1175                1180

Gly Pro Pro Gly Pro Pro Gly Ala Pro Gly Pro Cys Cys Gly Gly Val
1185                1190                1195                1200

Gly Ala Ala Ala Ile Ala Gly Ile Gly Gly Glu Lys Ala Gly Gly Phe
               1205                1210                1215

Ala Pro Tyr Tyr Gly Asp Glu Pro Met Asp Phe Lys Ile Asn Thr Asp
           1220                1225                1230

Glu Ile Met Thr Ser Leu Lys Ser Val Asn Gly Gln Ile Glu Ser Leu
           1235                1240                1245

Ile Ser Pro Asp Gly Ser Arg Lys Asn Pro Ala Arg Asn Cys Arg Asp
           1250                1255                1260

Leu Lys Phe Cys His Pro Glu Leu Lys Ser Gly Glu Tyr Trp Val Asp
1265                1270                1275                1280

Pro Asn Gln Gly Cys Lys Leu Asp Ala Ile Lys Val Phe Cys Asn Met
           1285                1290                1295

Glu Thr Gly Glu Thr Cys Ile Ser Ala Asn Pro Leu Asn Val Pro Arg
           1300                1305                1310

Lys His Trp Trp Thr Asp Ser Ser Ala Glu Lys His Val Trp Phe
           1315                1320                1325

Gly Glu Ser Met Asp Gly Gly Phe Gln Phe Ser Tyr Gly Asn Pro Glu
           1330                1335                1340

Leu Pro Glu Asp Val Leu Asp Val Gln Leu Ala Phe Leu Arg Leu Leu
1345                1350                1355                1360

Ser Ser Arg Ala Ser Gln Asn Ile Thr Tyr His Cys Lys Asn Ser Ile
           1365                1370                1375

Ala Tyr Met Asp Gln Ala Ser Gly Asn Val Lys Lys Ala Leu Lys Leu
           1380                1385                1390
```

-continued

```
Met Gly Ser Asn Glu Gly Glu Phe Lys Ala Glu Gly Asn Ser Lys Phe
        1395                1400                1405

Thr Tyr Thr Val Leu Glu Asp Gly Cys Thr Lys His Thr Gly Glu Trp
    1410                1415                1420

Ser Lys Thr Val Phe Glu Tyr Arg Thr Arg Lys Ala Val Arg Leu Pro
1425                1430                1435                1440

Ile Val Asp Ile Ala Pro Tyr Asp Ile Gly Gly Pro Asp Gln Glu Phe
            1445                1450                1455

Gly Val Asp Val Gly Pro Val Cys Phe Leu
            1460                1465

<210> SEQ ID NO 73
<211> LENGTH: 1051
<212> TYPE: DNA
<213> ORGANISM: Homo sapiens

<400> SEQUENCE: 73
cgcggagtct gagcggcgct cgtcccgtcc caaggccgac gccagcacgc cgtcatggcc      60
cccgcagcgg cgacgggggg cagcacccct cccagtggct tctcggtctt caccaccttg     120
cccgacttgc tcttcatctt tgagtttatc ttcgggggcc tggtgtggat cctggtggcc     180
tcctccctgg tgccctggcc cctggtccag ggctgggtga tgttcgtgtc tgtgttctgc     240
ttcgtggcca ccaccacctt gatcatcctg tacataattg agcccacgg tggagagact      300 tcctgggtca ccttggacgc agcctaccac tgcaccgctg ccctctttta cctcagcgcc     360
tcagtcctgg aggccctggc caccatcacg atgcaagacg gcttcaccta caggcactac     420
catgaaaaca ttgctgccgt ggtgttctcc tacatagcca ctctgctcta cgtggtccat     480
gcggtgttct ctttaatcag atggaagtct tcataaagcc gcagtagaac ttgagctgaa     540
aacccagatg gtgttaactg gccgccccac tttccggcat aacttttag aaaacagaaa     600 tgcccttgat ggtggaaaaa agaaaacaac cacccccca ctgcccaaaa aaaaaagccc      660
tgccctgttg ctcgtgggtg ctgtgtttac tctcccgtgt gccttcgcgt ccgggttggg     720
agcttgctgt gtctaacctc caactgctgt gctgtctgct agggtcacct cctgtttgtg     780 aaagggggacc ttcttgttcg ggggtgggaa gtggcgaccg tgacctgaga aggaaagaaa    840
gatcctctgc tgaccctctgg agcagctctc gagaactacc tgttggtatt gtccacaagc    900
tctcccgagc gccccatctt gtgccatgtt ttaagtcttc atggatgttc tgcatgtcat     960
ggggactaaa actcacccaa cagatctttc cagaggtcca tggtggaaga cgataaccct    1020
gtgaaatact ttataaaatg tcttaatgtt c                                    1051

<210> SEQ ID NO 74
<211> LENGTH: 153
<212> TYPE: PRT
<213> ORGANISM: Homo sapiens

<400> SEQUENCE: 74

Met Ala Pro Ala Ala Ala Thr Gly Gly Ser Thr Leu Pro Ser Gly Phe
  1               5                  10                  15

Ser Val Phe Thr Thr Leu Pro Asp Leu Leu Phe Ile Phe Glu Phe Ile
                20                  25                  30

Phe Gly Gly Leu Val Trp Ile Leu Val Ala Ser Ser Leu Val Pro Trp
            35                  40                  45

Pro Leu Val Gln Gly Trp Val Met Phe Val Ser Val Phe Cys Phe Val
        50                  55                  60
```

```
Ala Thr Thr Thr Leu Ile Ile Leu Tyr Ile Ile Gly Ala His Gly Gly
 65                  70                  75                  80

Glu Thr Ser Trp Val Thr Leu Asp Ala Ala Tyr His Cys Thr Ala Ala
             85                  90                  95

Leu Phe Tyr Leu Ser Ala Ser Val Leu Glu Ala Leu Ala Thr Ile Thr
            100                 105                 110

Met Gln Asp Gly Phe Thr Tyr Arg His Tyr His Glu Asn Ile Ala Ala
        115                 120                 125

Val Val Phe Ser Tyr Ile Ala Thr Leu Leu Tyr Val Val His Ala Val
    130                 135                 140

Phe Ser Leu Ile Arg Trp Lys Ser Ser
145                 150

<210> SEQ ID NO 75
<211> LENGTH: 5416
<212> TYPE: DNA
<213> ORGANISM: Homo sapiens

<400> SEQUENCE: 75
gtgtcccata gtgtttccaa acttggaaag ggcgggggag ggcgggagga tgcggagggc    60
ggaggtatgc agacaacgag tcagagtttc cccttgaaag cctcaaaagt gtccacgtcc   120
tcaaaaagaa tggaaccaat ttaagaagcc agccccgtgg ccacgtccct tcccccattc   180
gggccctcct ctgcgccccc gcaggctcct cccagctgtg gctgcccggg cccccagccc   240
cagcccctcc attggtggag gccctttttgg aggcacccta gggccaggga aacttttgcc   300
gtataaatag ggcagatccg ggatttgtta ttttagcacc acggcagcag gaggtttcgg   360
ctaagttgga ggtactggcc acgactgcat gcccgcgccc gccatgtgat acctccgccg   420
gtgacccagg gctctgcgac acaaggagtc gcatgtctaa gtgctagaca tgctcagctt   480
tgtggatacg cggactttgt tgctgcttgc agtaacctta tgcctagcaa catgccaatc   540
tttacaagag gaaactgtaa gaaagggccc agccggagat agaggaccac gtggagaaag   600
gggtccacca ggccccccag gcagagatgg tgaagatggt cccacaggcc tcctggtcc    660
acctggtcct cctggccccc ctggtctcgg tgggaacttt gctgctcagt atgatggaaa   720
aggagttgga cttggccctg gaccaatggg cttaatggga cctagaggcc cacctggtgc   780
agctggagcc ccaggccctc aaggtttcca aggacctgct ggtgagcctg gtgaacctgg   840
tcaaactggt cctgcaggtg tcgtggtcc agctggccct cctggcaagg ctggtgaaga   900
tggtcaccct ggaaaacccg gacgacctgg tgagagagga gttgttggac acagggtgc    960
tcgtggtttc cctggaactc ctggacttcc tggcttcaaa ggcattaggg gacacaatgg  1020
tctggatgga ttgaagggac agcccggtgc tcctggtgtg aagggtgaac ctggtgcccc  1080
tggtgaaaat ggaactccag gtcaaacagg agcccgtggt cttcctggtg agagaggacg  1140
tgttggtgcc cctggtccag ctggtgcccg tggaagtgat ggaagtgtgg gtcccgtagg  1200
tcctgctggt cctaatgggt ctgctggccc tccaggtttc ccaggtgccc tggtcccaa   1260
gggtgaaatt ggagctgttg gtaacgctgg tcctactgga cccgccggtc ccgtggtga   1320
agtgggtctt ccaggcctct ccggccccgt tggacctcct ggtaatcctg gagcaaacgg  1380
ccttactggt gccaagggtg ctgctggcct tccggcgtt gctggggctc ccggcctccc   1440
tggaccccgc ggtattcctg gccctcctgg tgctgccggt actactggtg ccagaggact  1500
tgttggtgag cctggtccag ctggctcaa aggagagagc ggtaacaagg gtgagcccgg  1560
ctccgctggt ccccaaggtc ctcctggtcc cagtggtgaa gaaggaaaga gaggccctaa  1620
```

-continued

```
tggggaagct ggatctgccg gccctccagg acctcctggg ctgagaggta gtcctggttc    1680
tcgtggtctt cctggagctg atggcagagc tggcgtcatg ggccctcctg gtagtcgtgg    1740
tgcaagtggc cctgctggag tccgaggacc taatggagat gctggtcgcc ctggggagcc    1800
tggtctcatg ggacccagag gtcttcctgg ttcccctgga aatatcggcc ccgctggaaa    1860
agaaggtcct gtcggcctcc ctggcatcga cggcaggcct ggcccaattg gccccgttgg    1920
agcaagagga gagcctggca acattggatt ccctggaccc aaaggcccca ctggtgaccc    1980
tggcaaaaac ggtgataaag gtcatgctgg tcttgctggt gctcgggtgc tccaggtcc     2040 tgatggaaac aatggtgctc agggacctcc tggaccacag ggtgttcaag gtggaaaagg    2100
tgaacagggt cccgctggtc ctccaggctt ccagggtctg cctggcccct caggtcccgc    2160
tggtgaagtt ggcaaaccag agaaagggg tctccatggt gagtttggtc tccctggtcc     2220
tgctggtcca agaggggaac gcggtccccc aggtgagagt ggtgctgccg gtcctactgg    2280
tcctattgga agccgaggtc cttctggacc cccagggcct gatggaaaca gggtgaacc     2340 tggtgtggtt ggtgctgtgg gcactgctgg tccatctggt cctagtggac tcccaggaga    2400 gagggtgct gctggcatac ctggaggcaa gggagaaaag ggtgaacctg gtctcagagg     2460
tgaaattggt aaccctggca gagatggtgc tcgtggtgct catggtgctg taggtgcccc    2520
tggtcctgct ggagccacag gtgaccgggg cgaagctggg gctgctggtc ctgctggtcc    2580
tgctggtcct cggggaagcc ctggtgaacg tggcgaggtc ggtcctgctg ccccaacgg     2640 atttgctggt ccggctggtg ctgctggtca accgggtgct aaaggagaaa gaggaggcaa    2700
agggcctaag ggtgaaaacg tgttgttgg tcccacaggc cccgttggag ctgctggccc     2760
agctggtcca aatggtcccc ccggtcctgc tggaagtcgt ggtgatggag gcccccctgg    2820
tatgactggt ttccctggtg ctgctggacg gactggtccc ccaggaccct ctggtatttc    2880
tggccctcct ggtcccctg gtcctgctgg gaaagaaggg cttcgtggtc ctcgtggtga     2940
ccaaggtcca gttggccgaa ctggagaagt aggtgcagtt ggtcccctg gcttcgctgg     3000 tgagaagggt ccctctggag aggctggtac tgctggacct cctggcactc caggtcctca    3060
gggtcttctt ggtgctcctg gtattctggg tctccctggc tcgagaggtg aacgtggtct    3120
acctggtgtt gctggtgctg tgggtgaacc tggtcctctt ggcattgccg gccctcctgg    3180
ggcccgtggt cctcctggtg ctgtgggtag tcctggagtc aacggtgctc ctggtgaagc    3240
tggtcgtgat ggcaaccctg ggaacgatgg tcccccaggt cgcgatggtc aacccggaca    3300
caagggagag cgcggttacc ctggcaatat tggtcccgtt ggtgctgcag gtgcacctgg    3360
tcctcatggc cccgtgggtc ctgctggcaa acatggaaac cgtggtgaaa ctggtccttc    3420
tggtcctgtt ggtcctgctg gtgctgttgg cccaagaggt cctagtggcc cacaaggcat    3480
tcgtggcgat aagggagagc ccggtgaaaa ggggcccaga ggtcttcctg gcttcaaggg    3540
acacaatgga ttgcaaggtc tgcctggtat cgctggtcac catggtgatc aaggtgctcc    3600
tggctccgtg ggtcctgctg gtcctagggg ccctgctggt ccttctggcc ctgctggaaa    3660
agatggtcgc actggacatc ctggtacggt tggacctgct ggcattcgag ccctcagggg    3720
tcaccaaggc cctgctggcc ccctggtcc cctggccct cctggacctc caggtgtaag      3780
cggtggtggt tatgactttg gttacgatgg agacttctac agggctgacc agcctcgctc    3840
agcaccttct ctcagaccca aggactatga agttgatgct actctgaagt ctctcaacaa    3900
ccagattgag acccttctta ctcctgaagg ctctagaaag aacccagctc gcacatgccg    3960
```

```
tgacttgaga ctcagccacc cagagtggag cagcggttac tactggattg accccaacca      4020
aggatgcact atggaagcca tcaaagtata ctgtgatttc cctaccggcg aaacctgtat      4080
ccgggcccaa cctgaaaaca tcccagccaa gaactggtat aggagctcca aggacaagaa      4140
acacgtctgg ctaggagaaa ctatcaatgc tggcagccag tttgaatata atgttgaagg      4200
agtgacttcc aaggaaatgg ctacccaact tgccttcatg cgcctgctgg ccaactatgc      4260
ctctcagaac atcacctacc actgcaagaa cagcattgca tacatggatg aggagactgg      4320
caacctgaaa aaggctgtca ttctacaggg ctctaatgat gttgaacttg ttgctgaggg      4380
caacagcagg ttcacttaca ctgttcttgt agatggctgc tctaaaaaga caaatgaatg      4440
gggaaagaca atcattgaat acaaaacaaa taagccatca cgcctgccct tccttgatat      4500
tgcacctttg gacatcggtg gtgctgacca tgaattcttt gtggacattg cccagtctg       4560 tttcaaataa atgaactcaa tctaaattaa aaagaaaga aatttgaaaa aactttctct       4620
ttgccatttc ttcttcttct tttttaactg aaagctgaat ccttccattt cttctgcaca      4680
tctacttgct taaattgtgg gcaaaagaga aaagaagga ttgatcagag cattgtgcaa       4740
tacagtttca ttaactcctt ccccgctcc cccaaaaatt tgaatttttt tttcaacact       4800
cttacacctg ttatggaaaa tgtcaacctt tgtaagaaaa ccaaaataaa aattgaaaaa      4860
taaaaaccat aaacatttgc accacttgtg gcttttgaat atcttccaca gagggaagtt      4920
taaaacccaa acttccaaag gtttaaacta cctcaaaaca ctttcccatg agtgtgatcc      4980
acattgttag gtgctgacct agacagagat gaactgaggt ccttgttttg ttttgttcat      5040
aatacaaagg tgctaattaa tagtatttca gatacttgaa gaatgttgat ggtgctagaa      5100
gaatttgaga agaaatactc ctgtattgag ttgtatcgtg tggtgtattt tttaaaaaat      5160
ttgatttagc attcatattt tccatcttat tcccaattaa aagtatgcag attatttgcc      5220
caaagttgtc ctcttcttca gattcagcat ttgttctttg ccagtctcat tttcatcttc      5280
ttccatggtt ccacagaagc tttgtttctt gggcaagcag aaaaattaaa ttgtacctat      5340
tttgtatatg tgagatgttt aaataaattg tgaaaaaat gaaataaagc atgtttggtt      5400
ttccaaaaga acatat                                                     5416
```

<210> SEQ ID NO 76
<211> LENGTH: 1366
<212> TYPE: PRT
<213> ORGANISM: Homo sapiens

<400> SEQUENCE: 76

```
Met Leu Ser Phe Val Asp Thr Arg Thr Leu Leu Leu Ala Val Thr
 1               5                  10                  15

Leu Cys Leu Ala Thr Cys Gln Ser Leu Gln Glu Glu Thr Val Arg Lys
                20                  25                  30

Gly Pro Ala Gly Asp Arg Gly Pro Arg Gly Glu Arg Gly Pro Pro Gly
            35                  40                  45

Pro Pro Gly Arg Asp Gly Glu Asp Gly Pro Thr Gly Pro Pro Gly Pro
        50                  55                  60

Pro Gly Pro Pro Gly Pro Gly Leu Gly Gly Asn Phe Ala Ala Gln
65                  70                  75                  80

Tyr Asp Gly Lys Gly Val Gly Leu Gly Pro Gly Pro Met Gly Leu Met
                85                  90                  95

Gly Pro Arg Gly Pro Pro Gly Ala Ala Gly Ala Pro Gly Pro Gln Gly
            100                 105                 110
```

```
Phe Gln Gly Pro Ala Gly Glu Pro Gly Glu Pro Gly Gln Thr Gly Pro
        115                 120                 125
Ala Gly Ala Arg Gly Pro Ala Gly Pro Pro Gly Lys Ala Gly Glu Asp
130                 135                 140
Gly His Pro Gly Lys Pro Gly Arg Pro Gly Glu Arg Gly Val Val Gly
145                 150                 155                 160
Pro Gln Gly Ala Arg Gly Phe Pro Gly Thr Pro Gly Leu Pro Gly Phe
                165                 170                 175
Lys Gly Ile Arg Gly His Asn Gly Leu Asp Gly Leu Lys Gly Gln Pro
            180                 185                 190
Gly Ala Pro Gly Val Lys Gly Glu Pro Gly Ala Pro Gly Glu Asn Gly
        195                 200                 205
Thr Pro Gly Gln Thr Gly Ala Arg Gly Leu Pro Gly Glu Arg Gly Arg
210                 215                 220
Val Gly Ala Pro Gly Pro Ala Gly Ala Arg Gly Ser Asp Gly Ser Val
225                 230                 235                 240
Gly Pro Val Gly Pro Ala Gly Pro Asn Gly Ser Ala Gly Pro Pro Gly
                245                 250                 255
Phe Pro Gly Ala Pro Gly Pro Lys Gly Glu Ile Gly Ala Val Gly Asn
            260                 265                 270
Ala Gly Pro Thr Gly Pro Ala Gly Pro Arg Gly Glu Val Gly Leu Pro
        275                 280                 285
Gly Leu Ser Gly Pro Val Gly Pro Pro Gly Asn Pro Gly Ala Asn Gly
        290                 295                 300
Leu Thr Gly Ala Lys Gly Ala Ala Gly Leu Pro Gly Val Ala Gly Ala
305                 310                 315                 320
Pro Gly Leu Pro Gly Pro Arg Gly Ile Pro Gly Pro Pro Gly Ala Ala
                325                 330                 335
Gly Thr Thr Gly Ala Arg Gly Leu Val Gly Glu Pro Gly Pro Ala Gly
            340                 345                 350
Ser Lys Gly Glu Ser Gly Asn Lys Gly Glu Pro Gly Ser Ala Gly Pro
        355                 360                 365
Gln Gly Pro Pro Gly Pro Ser Gly Glu Glu Gly Lys Arg Gly Pro Asn
370                 375                 380
Gly Glu Ala Gly Ser Ala Gly Pro Pro Gly Pro Pro Gly Leu Arg Gly
385                 390                 395                 400
Ser Pro Gly Ser Arg Gly Leu Pro Gly Ala Asp Gly Arg Ala Gly Val
                405                 410                 415
Met Gly Pro Pro Gly Ser Arg Gly Ala Ser Gly Pro Ala Gly Val Arg
            420                 425                 430
Gly Pro Asn Gly Asp Ala Gly Arg Pro Gly Glu Pro Gly Leu Met Gly
        435                 440                 445
Pro Arg Gly Leu Pro Gly Ser Pro Gly Asn Ile Gly Pro Ala Gly Lys
450                 455                 460
Glu Gly Pro Val Gly Leu Pro Gly Ile Asp Gly Arg Pro Gly Pro Ile
465                 470                 475                 480
Gly Pro Val Gly Ala Arg Gly Glu Pro Gly Asn Ile Gly Phe Pro Gly
                485                 490                 495
Pro Lys Gly Pro Thr Gly Asp Pro Gly Lys Asn Gly Asp Lys Gly His
            500                 505                 510
Ala Gly Leu Ala Gly Ala Arg Gly Ala Pro Gly Pro Asp Gly Asn Asn
        515                 520                 525
Gly Ala Gln Gly Pro Pro Gly Pro Gln Gly Val Gln Gly Gly Lys Gly
```

```
            530                 535                 540
Glu Gln Gly Pro Ala Gly Pro Gly Phe Gln Gly Leu Pro Gly Pro
545                 550                 555                 560

Ser Gly Pro Ala Gly Glu Val Gly Lys Pro Gly Glu Arg Gly Leu His
                565                 570                 575

Gly Glu Phe Gly Leu Pro Gly Pro Ala Gly Pro Arg Gly Glu Arg Gly
            580                 585                 590

Pro Pro Gly Glu Ser Gly Ala Ala Gly Pro Thr Gly Pro Ile Gly Ser
                595                 600                 605

Arg Gly Pro Ser Gly Pro Pro Gly Pro Asp Gly Asn Lys Gly Glu Pro
            610                 615                 620

Gly Val Val Gly Ala Val Gly Thr Ala Gly Pro Ser Gly Pro Ser Gly
625                 630                 635                 640

Leu Pro Gly Glu Arg Gly Ala Ala Gly Ile Pro Gly Gly Lys Gly Glu
                645                 650                 655

Lys Gly Glu Pro Gly Leu Arg Gly Glu Ile Gly Asn Pro Gly Arg Asp
                660                 665                 670

Gly Ala Arg Gly Ala His Gly Ala Val Gly Ala Pro Gly Pro Ala Gly
            675                 680                 685

Ala Thr Gly Asp Arg Gly Glu Ala Gly Ala Ala Gly Pro Ala Gly Pro
            690                 695                 700

Ala Gly Pro Arg Gly Ser Pro Gly Glu Arg Gly Glu Val Gly Pro Ala
705                 710                 715                 720

Gly Pro Asn Gly Phe Ala Gly Pro Ala Gly Ala Ala Gly Gln Pro Gly
                725                 730                 735

Ala Lys Gly Glu Arg Gly Gly Lys Gly Pro Lys Gly Glu Asn Gly Val
            740                 745                 750

Val Gly Pro Thr Gly Pro Val Gly Ala Ala Gly Pro Ala Gly Pro Asn
            755                 760                 765

Gly Pro Pro Gly Pro Ala Gly Ser Arg Gly Asp Gly Gly Pro Pro Gly
            770                 775                 780

Met Thr Gly Phe Pro Gly Ala Ala Gly Arg Thr Gly Pro Pro Gly Pro
785                 790                 795                 800

Ser Gly Ile Ser Gly Pro Pro Gly Pro Pro Gly Pro Ala Gly Lys Glu
                805                 810                 815

Gly Leu Arg Gly Pro Arg Gly Asp Gln Gly Pro Val Gly Arg Thr Gly
            820                 825                 830

Glu Val Gly Ala Val Gly Pro Pro Gly Phe Ala Gly Glu Lys Gly Pro
            835                 840                 845

Ser Gly Glu Ala Gly Thr Ala Gly Pro Pro Gly Thr Pro Gly Pro Gln
850                 855                 860

Gly Leu Leu Gly Ala Pro Gly Ile Leu Gly Leu Pro Gly Ser Arg Gly
865                 870                 875                 880

Glu Arg Gly Leu Pro Gly Val Ala Gly Ala Val Gly Glu Pro Gly Pro
                885                 890                 895

Leu Gly Ile Ala Gly Pro Pro Gly Ala Arg Gly Pro Pro Gly Ala Val
            900                 905                 910

Gly Ser Pro Gly Val Asn Gly Ala Pro Gly Glu Ala Gly Arg Asp Gly
            915                 920                 925

Asn Pro Gly Asn Asp Gly Pro Pro Gly Arg Asp Gly Gln Pro Gly His
            930                 935                 940

Lys Gly Glu Arg Gly Tyr Pro Gly Asn Ile Gly Pro Val Gly Ala Ala
945                 950                 955                 960
```

-continued

Gly Ala Pro Gly Pro His Gly Pro Val Gly Ala Gly Lys His Gly
            965                 970                 975

Asn Arg Gly Glu Thr Gly Pro Ser Gly Pro Val Gly Pro Ala Gly Ala
            980                 985                 990

Val Gly Pro Arg Gly Pro Ser Gly Pro Gln Gly Ile Arg Gly Asp Lys
            995                 1000                1005

Gly Glu Pro Gly Glu Lys Gly Pro Arg Gly Leu Pro Gly Phe Lys Gly
            1010                1015                1020

His Asn Gly Leu Gln Gly Leu Pro Gly Ile Ala Gly His His Gly Asp
1025                1030                1035                1040

Gln Gly Ala Pro Gly Ser Val Gly Pro Ala Gly Pro Arg Gly Pro Ala
            1045                1050                1055

Gly Pro Ser Gly Pro Ala Gly Lys Asp Gly Arg Thr Gly His Pro Gly
            1060                1065                1070

Thr Val Gly Pro Ala Gly Ile Arg Gly Pro Gln Gly His Gln Gly Pro
            1075                1080                1085

Ala Gly Pro Pro Gly Pro Pro Gly Pro Pro Gly Pro Pro Gly Val Ser
            1090                1095                1100

Gly Gly Gly Tyr Asp Phe Gly Tyr Asp Gly Asp Phe Tyr Arg Ala Asp
1105                1110                1115                1120

Gln Pro Arg Ser Ala Pro Ser Leu Arg Pro Lys Asp Tyr Glu Val Asp
            1125                1130                1135

Ala Thr Leu Lys Ser Leu Asn Asn Gln Ile Glu Thr Leu Leu Thr Pro
            1140                1145                1150

Glu Gly Ser Arg Lys Asn Pro Ala Arg Thr Cys Arg Asp Leu Arg Leu
            1155                1160                1165

Ser His Pro Glu Trp Ser Ser Gly Tyr Tyr Trp Ile Asp Pro Asn Gln
            1170                1175                1180

Gly Cys Thr Met Glu Ala Ile Lys Val Tyr Cys Asp Phe Pro Thr Gly
1185                1190                1195                1200

Glu Thr Cys Ile Arg Ala Gln Pro Glu Asn Ile Pro Ala Lys Asn Trp
            1205                1210                1215

Tyr Arg Ser Ser Lys Asp Lys Lys His Val Trp Leu Gly Glu Thr Ile
            1220                1225                1230

Asn Ala Gly Ser Gln Phe Glu Tyr Asn Val Glu Gly Val Thr Ser Lys
            1235                1240                1245

Glu Met Ala Thr Gln Leu Ala Phe Met Arg Leu Leu Ala Asn Tyr Ala
            1250                1255                1260

Ser Gln Asn Ile Thr Tyr His Cys Lys Asn Ser Ile Ala Tyr Met Asp
1265                1270                1275                1280

Glu Glu Thr Gly Asn Leu Lys Lys Ala Val Ile Leu Gln Gly Ser Asn
            1285                1290                1295

Asp Val Glu Leu Val Ala Glu Gly Asn Ser Arg Phe Thr Tyr Thr Val
            1300                1305                1310

Leu Val Asp Gly Cys Ser Lys Lys Thr Asn Glu Trp Gly Lys Thr Ile
            1315                1320                1325

Ile Glu Tyr Lys Thr Asn Lys Pro Ser Arg Leu Pro Phe Leu Asp Ile
            1330                1335                1340

Ala Pro Leu Asp Ile Gly Gly Ala Asp His Glu Phe Phe Val Asp Ile
1345                1350                1355                1360

Gly Pro Val Cys Phe Lys
            1365

<210> SEQ ID NO 77
<211> LENGTH: 1082
<212> TYPE: DNA
<213> ORGANISM: Homo sapiens

<400> SEQUENCE: 77

| | | | | | |
|---|---|---|---|---|---|
| agctcccttt | agcgagtcct | tcttttcctg | actgcagctc | ttttcatttt | gccatccttt | 60 |
| tccagcacca | tgatggttct | gcaggtttct | gcggccccc | ggacagtggc | tctgacggcg | 120 |
| ttactgatgg | tgctgctcac | atctgtggtc | cagggcaggg | ccactccaga | gaattacctt | 180 |
| ttccagggac | ggcaggaatg | ctacgcgttt | aatgggacac | agcgcttcct | ggagagatac | 240 |
| atctacaacc | gggaggagtt | cgcgcgcttc | gacagcgacg | tgggggagtt | ccgggcggtg | 300 |
| acggagctgg | ggcggcctgc | tgcggagtac | tggaacagcc | agaaggacat | cctggaggag | 360 |
| aagcgggcag | tgccggacag | gatgtgcaga | cacaactacg | agctgggcgg | gcccatgacc | 420 |
| ctgcagcgcc | gagtccagcc | tagggtgaat | gtttcccct | caagaagggg | gcccttgcag | 480 |
| caccacaacc | tgcttgtctg | ccacgtgacg | gatttctacc | caggcagcat | tcaagtccga | 540 |
| tggttcctga | atggacagga | ggaaacagct | gggtcgtgt | ccaccaacct | gatccgtaat | 600 |
| ggagactgga | ccttccagat | cctggtgatg | ctggaaatga | ccccccagca | gggagatgtc | 660 |
| tacacctgcc | aagtggagca | caccagcctg | atagtcctg | tcaccgtgga | gtggaaggca | 720 |
| cagtctgatt | ctgcccggag | taagacattg | acgggagctg | ggggcttcgt | gctggggctc | 780 |
| atcatctgtg | gagtgggcat | cttcatgcac | aggaggagca | agaaagttca | acgaggatct | 840 |
| gcataaacag | ggttcctgag | ctcactgaaa | agactattgt | gccttaggaa | aagcatttgc | 900 |
| tgtgtttcgt | tagcatctgg | ctccaggaca | gaccttcaac | ttccaaattg | atactgctgc | 960 |
| caagaagttg | ctctgaagtc | agtttctatc | attctgctct | ttgattcaaa | gcactgtttc | 1020 |
| tctcactggg | cctccaacca | tgttcccttc | ttcttagcac | cacaaataat | caaaacccaa | 1080 |
| ca | | | | | | 1082 |

<210> SEQ ID NO 78
<211> LENGTH: 258
<212> TYPE: PRT
<213> ORGANISM: Homo sapiens

<400> SEQUENCE: 78

Met Met Val Leu Gln Val Ser Ala Ala Pro Arg Thr Val Ala Leu Thr
1               5                   10                  15

Ala Leu Leu Met Val Leu Leu Thr Ser Val Val Gln Gly Arg Ala Thr
            20                  25                  30

Pro Glu Asn Tyr Leu Phe Gln Gly Arg Gln Glu Cys Tyr Ala Phe Asn
        35                  40                  45

Gly Thr Gln Arg Phe Leu Glu Arg Tyr Ile Tyr Asn Arg Glu Glu Phe
    50                  55                  60

Ala Arg Phe Asp Ser Asp Val Gly Glu Phe Arg Ala Val Thr Glu Leu
65                  70                  75                  80

Gly Arg Pro Ala Ala Glu Tyr Trp Asn Ser Gln Lys Asp Ile Leu Glu
                85                  90                  95

Glu Lys Arg Ala Val Pro Asp Arg Met Cys Arg His Asn Tyr Glu Leu
            100                 105                 110

Gly Gly Pro Met Thr Leu Gln Arg Arg Val Gln Pro Arg Val Asn Val
        115                 120                 125

Ser Pro Ser Lys Lys Gly Pro Leu Gln His His Asn Leu Leu Val Cys

```
                130              135              140
His Val Thr Asp Phe Tyr Pro Gly Ser Ile Gln Val Arg Trp Phe Leu
145              150              155              160

Asn Gly Gln Glu Glu Thr Ala Gly Val Val Ser Thr Asn Leu Ile Arg
            165              170              175

Asn Gly Asp Trp Thr Phe Gln Ile Leu Val Met Leu Glu Met Thr Pro
            180              185              190

Gln Gln Gly Asp Val Tyr Thr Cys Gln Val Glu His Thr Ser Leu Asp
            195              200              205

Ser Pro Val Thr Val Glu Trp Lys Ala Gln Ser Asp Ser Ala Arg Ser
    210              215              220

Lys Thr Leu Thr Gly Ala Gly Gly Phe Val Leu Gly Leu Ile Ile Cys
225              230              235              240

Gly Val Gly Ile Phe Met His Arg Arg Ser Lys Lys Val Gln Arg Gly
                245              250              255

Ser Ala

<210> SEQ ID NO 79
<211> LENGTH: 996
<212> TYPE: DNA
<213> ORGANISM: Homo sapiens

<400> SEQUENCE: 79
gtggaattca tggcatctac ttcgtatgac tattgcagag tgcccatgga agacggggat     60
aagcgctgta agcttctgct ggggatagga attctggtgc tcctgatcat cgtgattctg    120
ggggtgccct tgattatctt caccatcaag gccaacagcg aggcctgccg ggacggcctt    180
cgggcagtga tggagtgtcg caatgtcacc catctcctgc aacaagagct gaccgaggcc    240
cagaagggct ttcaggatgt ggaggcccag gccgccacct gcaaccacac tgtgatggcc    300
ctaatggctt ccctggatgc agagaaggcc caaggacaaa agaaagtgga ggagcttgag    360
ggagagatca ctacattaaa ccataagctt caggacgcgt ctgcagaggt ggagcgactg    420
agaagagaaa accaggtctt aagcgtgaga atcgcggaca gaagtactac ccccagctcc    480
caggactcca gctccgctgc ggcgccccag ctgctgattg tgctgctggg cctcagcgct    540
ctgctgcagt gagatcccag gaagctggca catcttggaa ggtccgtcct gctcggcttt    600
tcgcttgaac attcccttga tctcatcagt tctgagcggg tcatgggca acacggttag    660
cggggagagc acgggtagc cggagaaggg cctctggagc aggtctggag gggccatggg    720
gcagtcctgg gtgtggggac acagtcgggt tgacccaggg ctgtctccct ccagagcctc    780
cctccggaca atgagtcccc cctcttgtct cccaccctga gattgggcat ggggtgcggt    840
gtgggggca tgtgctgcct gttgttatgg gttttttttg cggggggggt tgcttttttc    900
tgggtctttt gagctccaaa aaataaacac ttcctttgag ggagagcaaa aaaaaaaaa    960
aaaaaaaa aaaaaaaaa aaagaattcc accaca                                 996

<210> SEQ ID NO 80
<211> LENGTH: 180
<212> TYPE: PRT
<213> ORGANISM: Homo sapiens

<400> SEQUENCE: 80

Met Ala Ser Thr Ser Tyr Asp Tyr Cys Arg Val Pro Met Glu Asp Gly
1               5                   10                  15

Asp Lys Arg Cys Lys Leu Leu Leu Gly Ile Gly Ile Leu Val Leu Leu
```

```
                20                  25                  30
Ile Ile Val Ile Leu Gly Val Pro Leu Ile Ile Phe Thr Ile Lys Ala
            35                  40                  45
Asn Ser Glu Ala Cys Arg Asp Gly Leu Arg Ala Val Met Glu Cys Arg
        50                  55                  60
Asn Val Thr His Leu Leu Gln Gln Glu Leu Thr Glu Ala Gln Lys Gly
65                  70                  75                  80
Phe Gln Asp Val Glu Ala Gln Ala Ala Thr Cys Asn His Thr Val Met
                85                  90                  95
Ala Leu Met Ala Ser Leu Asp Ala Glu Lys Ala Gln Gly Gln Lys Lys
            100                 105                 110
Val Glu Glu Leu Glu Gly Glu Ile Thr Thr Leu Asn His Lys Leu Gln
            115                 120                 125
Asp Ala Ser Ala Glu Val Glu Arg Leu Arg Arg Glu Asn Gln Val Leu
        130                 135                 140
Ser Val Arg Ile Ala Asp Lys Lys Tyr Tyr Pro Ser Ser Gln Asp Ser
145                 150                 155                 160
Ser Ser Ala Ala Ala Pro Gln Leu Leu Ile Val Leu Leu Gly Leu Ser
                165                 170                 175
Ala Leu Leu Gln
            180

<210> SEQ ID NO 81
<211> LENGTH: 4316
<212> TYPE: DNA
<213> ORGANISM: Homo sapiens

<400> SEQUENCE: 81
ctgcagctaa taaaaaaaaa aaaagaaaga agaaactgg tctctgtcct atttcatatg      60
ctcaggtaca acttttccag agaagaagag gaggggggcg gggaggagca ggaggaggag    120
gaaagaagga ggagaaggag aaggagaaga agaggaagag gaagaggaag aagaagaaga    180
agaagaagag gaagaggaag aggaagaaga agaagaagaa gaagaagaag aagaagaaga    240
agaagaagaa gaagaagaag aagaagaaga ggaagaagag gaagaagaag aaactgtctc    300
tagaccttca ttctcaggac aagttcattg tctggcacca agctccttgg ggtgaatttt    360
cttccaaaag agtccgggga gtccaggtat ggaatgggag gcagaaagtt caatcaaggg    420
actgggattt cggaatgaat aatgaaggga gatggactgg gtccatgccg aaggtttctc    480
cctggtttct cagcccccgg gcgaagactc agggagacat tgagacacac cctgcacagg    540
aggggagggg gaggggggag ggcaaagtcc cagggcccca ggagtggctc tcaagggctc    600
aggccccgag gcggtgtctg gggttggaag gctcagtatt gagaattccc catctcccca    660
gagtttctct ttctctccca acccgtgtca ggtccttcat cctggatact cataacgcgg    720
ccccatttct cactcccatt gggcgtcgcg tttctagaga agccaatcag tgtcgccgca    780
gttcccaggt tctaaagtcc cacgcacccc gcgggactca tattttcccc agacgcggag    840 gttgggtca tggcgcccg aagcctcctc ctgctgctct caggggccct ggccctgacc        900
gatacttggg cggtgagtg cggggtccag agagaaacgg cctctgtggg gaggagtgag       960
gggcccgccc ggtggggggcg caggactcag ggagccgcgc ccggaggagg gtctggcggg  1020
tctcaccccc tcctcgcccc caggctccca ctccttgagg tatttcagca ccgctgtgtc    1080 gcggccgc cgcggggagc cccgctacat cgccgtggag tacgtagacg acacgcaatt       1140
cctgcggttc gacagcgacg ccgcgattcc gaggatggag ccgcgggagc cgtgggtgga   1200
```

```
gcaagagggg ccgcagtatt gggagtggac cacagggtac gccaaggcca acgcacagac  1260
tgaccgagtg gccctgagga acctgctccg ccgctacaac cagagcgagg ctggtgagtg  1320
aacccggccg ggggcgcagg tcacgaccac ccccatccg ccacgaccg cccgggtccc  1380 cccgagtctc cggatccgaa atctaccccg aggcagcgga cccgcccaga ccctccaccc  1440
gggagagtcc caggcgcctt taccgaggtt cattttcagt ttaggccaaa atcccgcgg  1500 gttgggcggg gaggggcgg ggctagctgg gcggggctga ctgcggggac cggctagggt  1560
ctcacaccct ccagggaatg aatggctgcg acatggggcc cgacggacgc ctcctccgcg  1620
ggtatcacca gcacgcgtac gacggcaagg attacatctc cctgaacgag gacctgcgct  1680
cctggaccgc ggcggacacc gtggctcaga tcacccagcg cttctatgag gcagaggaat  1740
atgcagagga gttcaggacc tacctggagg gcgagtgcct ggagttgctc cgcagatact  1800
tggagaatgg gaaggagacg ctacagcgcg caggtaccag gggccatggg cgccttccct  1860
atctcctgta gatctcttgg gatggcctcg cacaaggttg ggaggaaagt gggcccaatg  1920
ctaggatatc gccctccctc tagtcctgag taggaagaat cttcctggct ttcgagatcc  1980
ggtaccagag agtgactgtg agagtccgcc ctgctctctg gacaattaa gggatgaaat  2040 ctctgaggga atggagggaa gacagtccct ggaataccga tccgcggtcc cctttgagcc  2100
ctccaacagc cttgggcccc gtgacttttc tctcaagttt tgttctctgc ctcacactca  2160
atgtgtttgg ggctctgatt ccagtccctc ggcctccact taggtcaggg ccagaagtcc  2220
ctgctcccca ctcagagact cgaactttcc aaggaatagg agatttttccc aggtgtctgt  2280 gtccaggctg gtgtctgggt tctgtgctcc cttccccacc ccaggtgtcc tgtccattct  2340
caggttggtc acatgggtgc tgctggggtt tcccatgagg agtgcaaagt gcctgaattt  2400
tctgactctt ctcagatcct ccaaaggcac acgttgccca ccaccccatc tctgaccatg  2460
aggccaccct gaggtgctgg gccctgggct tctaccctgc ggagatcacg ctgacctggc  2520
agcgggatgg ggaggaacag acccaggaca cagagcttgt ggagaccagg cctgcagggg  2580
atggaacctt ccagaagtgg gccgctgtgg tggtgccttc tggagaggaa cagagataca  2640
catgccatgt gcagcacgag gggctgcccc agcccctcat cctgagatgg ggtaaggagg  2700
gagatgggta aagaggggaa cgaggggtca tgtcttttct cagggaaagc aggagccctt  2760
ctggagctct tcagcagggt cagggctgag gcctggagat cagggcccct caccttccct  2820
tcctttccca gagcagtctc cccagcccac catccccatc gtgggcatcg ttgctggcct  2880
tgttgtcctt ggagctgtgg tcactggagc tgtggtcgct gctgtgatgt ggaggaagaa  2940
gagctcaggt aggaaggggt gaggagtgga gtctgagttt tcttgtccca ctgggggttg  3000 caagcccaa gtagaagtgt gccctgcctc attactggga agcaccatcc acactcatgg  3060
gtctacccag cctgggccct gtgtgccagc acctactcat ttgtaaagct cctgtgaaaa  3120
tgaaggacag attcttcact tcgatgatta tggtggtgat gggacctgat cccagcagtc  3180
acaaatcaca ggggaaggtc cctgctgatg acagacctca ggagggcagt tggtccagga  3240
cccacatctg ctttcttcat atttcttgat cctgccctgg atctacagtt acactttctc  3300
ggaaacttct ctgggatcaa agactagggg ttgctctag gaccttatgg ccctgcctcc  3360
tttctggcct ctcacaggac attttcttcc catagataga aacagaggga gctactctca  3420
ggctgcaggt aagatgaagg aggctgatcc ctgagattgt tgggatattg tggtcaggag  3480
cctatgaggg agctcaccca ccccacagtt cctctagcca catctgtggg ctctgaccag  3540
```

| | | | |
|---|---|---|---|
| gtcctgtttt | tgttctaccc caatcactga cagtgcccag ggctctgggg tgtctctcac | | 3600 |
| agctaataaa | ggtgacactc cagggcaggg gccctgatgt gagtgggtg ttgggggga | | 3660 |
| acagagggga | ctcagctgtg ctattgggtt tctttgactt ggatgtcttg agcatgaaat | | 3720 |
| gggctattta | gagtgttacc tctcactgtg actgatacga atttgttcat gaatattttc | | 3780 |
| tctatagtgt | gagacagctt ccttgtgtgg gactgagaag caagatatca atgtagcaga | | 3840 |
| attgcacttg | tgcctcacga acatacataa attttaaaaa taaagaataa aaatatatct | | 3900 |
| ttttatagat | acaggtagat atgtttttat agcatgcacg taaatgtgtg tgtgtgtgtg | | 3960 |
| tgtgtgtgaa | gagaaagagt gaatagagag attaagattc ttttaatggt gaaaagatat | | 4020 |
| acatatattt | ggaattagcc agcttgactc agtttaggtg atcccaattt tggtggcaac | | 4080 |
| aaccaaagca | tcgtagtcag gagccagtcg aacatatgcc ttcctctctc catcagactg | | 4140 |
| aatcagagtg | ttgactttgg ccacatcaat gtcacaaact tcttcacagc ctgtttgatc | | 4200 |
| tggtgcttgt | tggctttaac atccacagtg aacacaagta ggctgttgtt ttctatcttc | | 4260 |
| ttcacagcct | actcagtggt cagcggaaac ttgatgataa catggtggtc aagctt | | 4316 |

<210> SEQ ID NO 82
<211> LENGTH: 362
<212> TYPE: PRT
<213> ORGANISM: Homo sapiens

<400> SEQUENCE: 82

```
Met Ala Pro Arg Ser Leu Leu Leu Leu Ser Gly Ala Leu Ala Leu
 1               5                  10                  15

Thr Asp Thr Trp Ala Gly Ser His Ser Leu Arg Tyr Phe Ser Thr Ala
            20                  25                  30

Val Ser Arg Pro Gly Arg Gly Glu Pro Arg Tyr Ile Ala Val Glu Tyr
        35                  40                  45

Val Asp Asp Thr Gln Phe Leu Arg Phe Asp Ser Asp Ala Ala Ile Pro
    50                  55                  60

Arg Met Glu Pro Arg Glu Pro Trp Val Glu Gln Glu Gly Pro Gln Tyr
65                  70                  75                  80

Trp Glu Trp Thr Thr Gly Tyr Ala Lys Ala Asn Ala Gln Thr Asp Arg
                85                  90                  95

Val Ala Leu Arg Asn Leu Leu Arg Arg Tyr Asn Gln Ser Glu Ala Gly
            100                 105                 110

Ser His Thr Leu Gln Gly Met Asn Gly Cys Asp Met Gly Pro Asp Gly
        115                 120                 125

Arg Leu Leu Arg Gly Tyr His Gln His Ala Tyr Asp Gly Lys Asp Tyr
    130                 135                 140

Ile Ser Leu Asn Glu Asp Leu Arg Ser Trp Thr Ala Ala Asp Thr Val
145                 150                 155                 160

Ala Gln Ile Thr Gln Arg Phe Tyr Glu Ala Glu Tyr Ala Glu
                165                 170                 175

Phe Arg Thr Tyr Leu Glu Gly Glu Cys Leu Glu Leu Leu Arg Arg Tyr
            180                 185                 190

Leu Glu Asn Gly Lys Glu Thr Leu Gln Arg Ala Asp Pro Pro Lys Ala
        195                 200                 205

His Val Ala His His Pro Ile Ser Asp His Glu Ala Thr Leu Arg Cys
    210                 215                 220

Trp Ala Leu Gly Phe Tyr Pro Ala Glu Ile Thr Leu Thr Trp Gln Arg
225                 230                 235                 240
```

```
Asp Gly Glu Glu Gln Thr Gln Asp Thr Glu Leu Val Glu Thr Arg Pro
                245                 250                 255

Ala Gly Asp Gly Thr Phe Gln Lys Trp Ala Ala Val Val Pro Ser
        260                 265                 270

Gly Glu Glu Gln Arg Tyr Thr Cys His Val Gln His Glu Gly Leu Pro
            275                 280                 285

Gln Pro Leu Ile Leu Arg Trp Glu Gln Ser Pro Gln Pro Thr Ile Pro
        290                 295                 300

Ile Val Gly Ile Val Ala Gly Leu Val Val Leu Gly Ala Val Val Thr
305                 310                 315                 320

Gly Ala Val Val Ala Ala Val Met Trp Arg Lys Lys Ser Ser Asp Arg
                325                 330                 335

Asn Arg Gly Ser Tyr Ser Gln Ala Ala Val Thr Asp Ser Ala Gln Gly
            340                 345                 350

Ser Gly Val Ser Leu Thr Ala Asn Lys Val
        355                 360
```

<210> SEQ ID NO 83
<211> LENGTH: 10
<212> TYPE: DNA
<213> ORGANISM: Homo sapiens

<400> SEQUENCE: 83
tcagacgcag                                                           10

<210> SEQ ID NO 84
<211> LENGTH: 10
<212> TYPE: DNA
<213> ORGANISM: Homo sapiens

<400> SEQUENCE: 84
ttatgggatc                                                           10

<210> SEQ ID NO 85
<211> LENGTH: 10
<212> TYPE: DNA
<213> ORGANISM: Homo sapiens

<400> SEQUENCE: 85
cccgcccccg                                                           10

<210> SEQ ID NO 86
<211> LENGTH: 10
<212> TYPE: DNA
<213> ORGANISM: Homo sapiens

<400> SEQUENCE: 86
gaggaagaag                                                           10

<210> SEQ ID NO 87
<211> LENGTH: 10
<212> TYPE: DNA
<213> ORGANISM: Homo sapiens

<400> SEQUENCE: 87
gaagctttgc                                                           10

<210> SEQ ID NO 88
<211> LENGTH: 10
<212> TYPE: DNA
<213> ORGANISM: Homo sapiens

<400> SEQUENCE: 88
taccagtgta                                                              10

<210> SEQ ID NO 89
<211> LENGTH: 10
<212> TYPE: DNA
<213> ORGANISM: Homo sapiens

<400> SEQUENCE: 89
tcttctccct                                                              10

<210> SEQ ID NO 90
<211> LENGTH: 10
<212> TYPE: DNA
<213> ORGANISM: Homo sapiens

<400> SEQUENCE: 90
ttggcttttc                                                              10

<210> SEQ ID NO 91
<211> LENGTH: 10
<212> TYPE: DNA
<213> ORGANISM: Homo sapiens

<400> SEQUENCE: 91
ggaagggagg                                                              10

<210> SEQ ID NO 92
<211> LENGTH: 10
<212> TYPE: DNA
<213> ORGANISM: Homo sapiens

<400> SEQUENCE: 92
aagccagccc                                                              10

<210> SEQ ID NO 93
<211> LENGTH: 10
<212> TYPE: DNA
<213> ORGANISM: Homo sapiens

<400> SEQUENCE: 93
tttcagattg                                                              10

<210> SEQ ID NO 94
<211> LENGTH: 10
<212> TYPE: DNA
<213> ORGANISM: Homo sapiens

<400> SEQUENCE: 94
gcataggctg                                                              10

<210> SEQ ID NO 95
<211> LENGTH: 10
<212> TYPE: DNA
<213> ORGANISM: Homo sapiens

<400> SEQUENCE: 95
tttgttaatt                                                              10

<210> SEQ ID NO 96
<211> LENGTH: 10
<212> TYPE: DNA

<213> ORGANISM: Homo sapiens

<400> SEQUENCE: 96
gagactcctg                                                          10

<210> SEQ ID NO 97
<211> LENGTH: 10
<212> TYPE: DNA
<213> ORGANISM: Homo sapiens

<400> SEQUENCE: 97
cctgtaattc                                                          10

<210> SEQ ID NO 98
<211> LENGTH: 10
<212> TYPE: DNA
<213> ORGANISM: Homo sapiens

<400> SEQUENCE: 98
gtggtgcgtg                                                          10

<210> SEQ ID NO 99
<211> LENGTH: 10
<212> TYPE: DNA
<213> ORGANISM: Homo sapiens

<400> SEQUENCE: 99
ttggacctgg                                                          10

<210> SEQ ID NO 100
<211> LENGTH: 10
<212> TYPE: DNA
<213> ORGANISM: Homo sapiens

<400> SEQUENCE: 100
cttaaggatt                                                          10

<210> SEQ ID NO 101
<211> LENGTH: 10
<212> TYPE: DNA
<213> ORGANISM: Homo sapiens

<400> SEQUENCE: 101
gtctgtgaga                                                          10

<210> SEQ ID NO 102
<211> LENGTH: 10
<212> TYPE: DNA
<213> ORGANISM: Homo sapiens

<400> SEQUENCE: 102
gaaactgaac                                                          10

<210> SEQ ID NO 103
<211> LENGTH: 10
<212> TYPE: DNA
<213> ORGANISM: Homo sapiens

<400> SEQUENCE: 103
gggcatctct                                                          10

<210> SEQ ID NO 104
<211> LENGTH: 10

```
<212> TYPE: DNA
<213> ORGANISM: Homo sapiens

<400> SEQUENCE: 104
tttgggccta                                                          10

<210> SEQ ID NO 105
<211> LENGTH: 10
<212> TYPE: DNA
<213> ORGANISM: Homo sapiens

<400> SEQUENCE: 105
atcgtggcgg                                                          10

<210> SEQ ID NO 106
<211> LENGTH: 10
<212> TYPE: DNA
<213> ORGANISM: Homo sapiens

<400> SEQUENCE: 106
tattatggta                                                          10

<210> SEQ ID NO 107
<211> LENGTH: 10
<212> TYPE: DNA
<213> ORGANISM: Homo sapiens

<400> SEQUENCE: 107
gcctacccga                                                          10

<210> SEQ ID NO 108
<211> LENGTH: 10
<212> TYPE: DNA
<213> ORGANISM: Homo sapiens

<400> SEQUENCE: 108
ctcgcgctgg                                                          10

<210> SEQ ID NO 109
<211> LENGTH: 10
<212> TYPE: DNA
<213> ORGANISM: Homo sapiens

<400> SEQUENCE: 109
ttgcttgcca                                                          10

<210> SEQ ID NO 110
<211> LENGTH: 10
<212> TYPE: DNA
<213> ORGANISM: Homo sapiens

<400> SEQUENCE: 110
cctgcttgtc                                                          10

<210> SEQ ID NO 111
<211> LENGTH: 10
<212> TYPE: DNA
<213> ORGANISM: Homo sapiens

<400> SEQUENCE: 111
agggaggggc                                                          10

<210> SEQ ID NO 112
```

```
<211> LENGTH: 10
<212> TYPE: DNA
<213> ORGANISM: Homo sapiens

<400> SEQUENCE: 112
tgtgggaaat                                                              10

<210> SEQ ID NO 113
<211> LENGTH: 10
<212> TYPE: DNA
<213> ORGANISM: Homo sapiens

<400> SEQUENCE: 113
cctgatctgc                                                              10

<210> SEQ ID NO 114
<211> LENGTH: 10
<212> TYPE: DNA
<213> ORGANISM: Homo sapiens

<400> SEQUENCE: 114
accattggat                                                              10

<210> SEQ ID NO 115
<211> LENGTH: 10
<212> TYPE: DNA
<213> ORGANISM: Homo sapiens

<400> SEQUENCE: 115
agtttgttag                                                              10

<210> SEQ ID NO 116
<211> LENGTH: 10
<212> TYPE: DNA
<213> ORGANISM: Homo sapiens

<400> SEQUENCE: 116
cctgggaagt                                                              10

<210> SEQ ID NO 117
<211> LENGTH: 10
<212> TYPE: DNA
<213> ORGANISM: Homo sapiens

<400> SEQUENCE: 117
caactaattc                                                              10

<210> SEQ ID NO 118
<211> LENGTH: 10
<212> TYPE: DNA
<213> ORGANISM: Homo sapiens

<400> SEQUENCE: 118
gcctgcagtc                                                              10

<210> SEQ ID NO 119
<211> LENGTH: 10
<212> TYPE: DNA
<213> ORGANISM: Homo sapiens

<400> SEQUENCE: 119
cgaccccacg                                                              10
```

```
<210> SEQ ID NO 120
<211> LENGTH: 10
<212> TYPE: DNA
<213> ORGANISM: Homo sapiens

<400> SEQUENCE: 120
ttctgtgctg                                                                10

<210> SEQ ID NO 121
<211> LENGTH: 10
<212> TYPE: DNA
<213> ORGANISM: Homo sapiens

<400> SEQUENCE: 121
cgccgacgat                                                                10

<210> SEQ ID NO 122
<211> LENGTH: 10
<212> TYPE: DNA
<213> ORGANISM: Homo sapiens

<400> SEQUENCE: 122
cccgcccccg                                                                10

<210> SEQ ID NO 123
<211> LENGTH: 10
<212> TYPE: DNA
<213> ORGANISM: Homo sapiens

<400> SEQUENCE: 123
gatcaggcca                                                                10

<210> SEQ ID NO 124
<211> LENGTH: 10
<212> TYPE: DNA
<213> ORGANISM: Homo sapiens

<400> SEQUENCE: 124
gtggaagacg                                                                10

<210> SEQ ID NO 125
<211> LENGTH: 10
<212> TYPE: DNA
<213> ORGANISM: Homo sapiens

<400> SEQUENCE: 125
gatgaggaga                                                                10

<210> SEQ ID NO 126
<211> LENGTH: 10
<212> TYPE: DNA
<213> ORGANISM: Homo sapiens

<400> SEQUENCE: 126
ttcccttctt                                                                10

<210> SEQ ID NO 127
<211> LENGTH: 10
<212> TYPE: DNA
<213> ORGANISM: Homo sapiens

<400> SEQUENCE: 127
ccccctgcag                                                                10
```

```
<210> SEQ ID NO 128
<211> LENGTH: 10
<212> TYPE: DNA
<213> ORGANISM: Homo sapiens

<400> SEQUENCE: 128
tgctgcctgt                                                          10

<210> SEQ ID NO 129
<211> LENGTH: 10
<212> TYPE: DNA
<213> ORGANISM: Homo sapiens

<400> SEQUENCE: 129
tgcagcacga                                                          10

<210> SEQ ID NO 130
<211> LENGTH: 10
<212> TYPE: DNA
<213> ORGANISM: Homo sapiens

<400> SEQUENCE: 130
ggttattttg                                                          10

<210> SEQ ID NO 131
<211> LENGTH: 10
<212> TYPE: DNA
<213> ORGANISM: Homo sapiens

<400> SEQUENCE: 131
tgtcatcaca                                                          10

<210> SEQ ID NO 132
<211> LENGTH: 10
<212> TYPE: DNA
<213> ORGANISM: Homo sapiens

<400> SEQUENCE: 132
aaaataaaca                                                          10

<210> SEQ ID NO 133
<211> LENGTH: 10
<212> TYPE: DNA
<213> ORGANISM: Homo sapiens

<400> SEQUENCE: 133
taaaaatgtt                                                          10

<210> SEQ ID NO 134
<211> LENGTH: 10
<212> TYPE: DNA
<213> ORGANISM: Homo sapiens

<400> SEQUENCE: 134
gagcttttga                                                          10

<210> SEQ ID NO 135
<211> LENGTH: 10
<212> TYPE: DNA
<213> ORGANISM: Homo sapiens

<400> SEQUENCE: 135
ggctgatgtg                                                          10
```

<210> SEQ ID NO 136
<211> LENGTH: 10
<212> TYPE: DNA
<213> ORGANISM: Homo sapiens

<400> SEQUENCE: 136
cgacgaggag                                                              10

<210> SEQ ID NO 137
<211> LENGTH: 10
<212> TYPE: DNA
<213> ORGANISM: Homo sapiens

<400> SEQUENCE: 137
gcccccaata                                                              10

<210> SEQ ID NO 138
<211> LENGTH: 10
<212> TYPE: DNA
<213> ORGANISM: Homo sapiens

<400> SEQUENCE: 138
gcaacttgga                                                              10

<210> SEQ ID NO 139
<211> LENGTH: 408
<212> TYPE: PRT
<213> ORGANISM: Homo sapiens

<400> SEQUENCE: 139

Met Pro Gly His Leu Gln Glu Gly Phe Gly Cys Val Val Thr Asn Arg
 1               5                  10                  15

Phe Asp Gln Leu Phe Asp Asp Glu Ser Asp Pro Phe Glu Val Leu Lys
            20                  25                  30

Ala Ala Glu Asn Lys Lys Lys Glu Ala Gly Gly Gly Val Gly Gly
        35                  40                  45

Pro Gly Ala Lys Ser Ala Gln Ala Ala Ala Gln Thr Asn Ser Asn
    50                  55                  60

Ala Ala Gly Lys Gln Leu Arg Lys Glu Ser Gln Lys Asp Arg Lys Asn
65                  70                  75                  80

Pro Leu Pro Pro Ser Val Gly Val Asp Lys Lys Glu Glu Thr Gln
                85                  90                  95

Pro Pro Val Ala Leu Lys Lys Glu Gly Ile Arg Arg Val Gly Arg Arg
            100                 105                 110

Pro Asp Gln Gln Leu Gln Gly Glu Gly Lys Ile Ile Asp Arg Arg Pro
        115                 120                 125

Glu Arg Arg Pro Pro Arg Glu Arg Arg Phe Glu Lys Pro Leu Glu Glu
    130                 135                 140

Lys Gly Glu Gly Gly Glu Phe Ser Val Asp Arg Pro Ile Ile Asp Arg
145                 150                 155                 160

Pro Ile Arg Gly Arg Gly Gly Leu Gly Arg Gly Arg Gly Arg Gly
                165                 170                 175

Arg Gly Met Gly Arg Gly Asp Gly Phe Asp Ser Arg Gly Lys Arg Glu
            180                 185                 190

Phe Asp Arg His Ser Gly Ser Asp Arg Ser Ser Phe Ser His Tyr Ser
        195                 200                 205

Gly Leu Lys His Glu Asp Lys Arg Gly Gly Ser Gly Ser His Asn Trp

```
       210                 215                 220
Gly Thr Val Lys Asp Glu Leu Thr Glu Ser Pro Lys Tyr Ile Gln Lys
225                 230                 235                 240

Gln Ile Ser Tyr Asn Tyr Ser Asp Leu Asp Gln Ser Asn Val Thr Glu
                245                 250                 255

Glu Thr Pro Glu Gly Glu His His Pro Val Ala Asp Thr Glu Asn
            260                 265                 270

Lys Asn Glu Val Glu Val Lys Glu Gly Pro Lys Glu Met
        275                 280                 285

Thr Leu Asp Glu Trp Lys Ala Ile Gln Asn Lys Asp Arg Ala Lys Val
290                 295                 300

Glu Phe Asn Ile Arg Lys Pro Asn Glu Gly Ala Asp Gly Gln Trp Lys
305                 310                 315                 320

Lys Gly Phe Val Leu His Lys Ser Lys Ser Glu Ala His Ala Glu
                325                 330                 335

Asp Ser Val Met Asp His His Phe Arg Lys Pro Ala Asn Asp Ile Thr
                340                 345                 350

Ser Gln Leu Glu Ile Asn Phe Gly Asp Leu Gly Arg Pro Gly Arg Gly
                355                 360                 365

Gly Arg Gly Gly Arg Gly Gly Arg Gly Arg Gly Gly Arg Pro Asn Arg
370                 375                 380

Gly Ser Arg Thr Asp Lys Ser Ser Ala Ser Ala Pro Asp Val Asp Asp
385                 390                 395                 400

Pro Glu Ala Phe Pro Ala Leu Ala
                405

<210> SEQ ID NO 140
<211> LENGTH: 10
<212> TYPE: DNA
<213> ORGANISM: Homo sapiens

<400> SEQUENCE: 140
atgataatgg                                                                      10

<210> SEQ ID NO 141
<211> LENGTH: 1024
<212> TYPE: DNA
<213> ORGANISM: Homo sapiens

<400> SEQUENCE: 141
ccccacccga aacacactca gcccttgcac tgacctgcct tctgattgga ggctggttgc       60
ttcggataat gacctccagg accccactgt tggttacagc ctgtttgtat tattcttact      120
gcaactcaag acacctgcag cagggcgtga gaaaaagtaa aagaccagta ttttcacatt      180
gccaggtacc agaaacacag aagactgaca cccgccactt aagtggggcc agggctggtg      240
tctgcccatg ttgccatcct gatgggctgc ttgccacaat gagggatctt cttcaataca      300
tcgcttgctt cttttgccttt ttctctgctg ggttttttgat tgtggccacc tggactgact      360
gttggatggt gaatgctgat gactctctgg aggtgagcac aaaatgccga ggcctctggt      420
gggaatgcgt cacaaatgct tttgatggga ttcgcacctg tgatgagtac gattccatac      480
ttgcggagca tcccttgaag ctggtggtaa ctcgagcgtt gatgattact gcagatattc      540
tagctgggtt tggatttctc accctgctcc ttggtcttga ctgcgtgaaa ttcctccctg      600
atgagccgta cattaaagtc cgcatctgct tgttgctgg agccacgtta ctaatagcag      660
gtaccccagg aatcattggc tctgtgtggt atgctgttga tgtgtatgtg gaacgttcta      720
```

```
cttttggtttt gcacaatata tttcttggta tccaatataa atttggttgg tcctgttggc      780
tcggaatggc tgggtctctg ggttgctttt tggctggagc tgttctcacc tgctgcttat      840
atctttttaa agatgtggga cctgagaaaa ctagccttat cccttgagga aagcctattc      900
agccgcgagg tgtttccatg gccaagtcat actcagcccc tcgcacagag acggccaaaa      960
tgtatgctgt agacacaagg gtgtaaaatg cacgtttcag ggtgtgtttg catatgattt     1020
aatc                                                                  1024
```

<210> SEQ ID NO 142  
<211> LENGTH: 294  
<212> TYPE: PRT  
<213> ORGANISM: Homo sapiens

<400> SEQUENCE: 142

```
Pro Pro Glu Thr His Ser Ala Leu Ala Leu Thr Cys Leu Leu Ile Gly
  1               5                  10                  15

Gly Trp Leu Leu Arg Ile Met Thr Ser Arg Thr Pro Leu Leu Val Thr
             20                  25                  30

Ala Cys Leu Tyr Tyr Ser Tyr Cys Asn Ser Arg His Leu Gln Gln Gly
         35                  40                  45

Val Arg Lys Ser Lys Arg Pro Val Phe Ser His Cys Gln Val Pro Glu
     50                  55                  60

Thr Gln Lys Thr Asp Thr Arg His Leu Ser Gly Ala Arg Ala Gly Val
 65                  70                  75                  80

Cys Pro Cys Cys His Pro Asp Gly Leu Leu Ala Thr Met Arg Asp Leu
                 85                  90                  95

Leu Gln Tyr Ile Ala Cys Phe Phe Ala Phe Phe Ser Ala Gly Phe Leu
            100                 105                 110

Ile Val Ala Thr Trp Thr Asp Cys Trp Met Val Asn Ala Asp Asp Ser
        115                 120                 125

Leu Glu Val Ser Thr Lys Cys Arg Gly Leu Trp Trp Glu Cys Val Thr
    130                 135                 140

Asn Ala Phe Asp Gly Ile Arg Thr Cys Asp Glu Tyr Asp Ser Ile Leu
145                 150                 155                 160

Ala Glu His Pro Leu Lys Leu Val Val Thr Arg Ala Leu Met Ile Thr
                165                 170                 175

Ala Asp Ile Leu Ala Gly Phe Gly Phe Leu Thr Leu Leu Gly Leu
            180                 185                 190

Asp Cys Val Lys Phe Leu Pro Asp Glu Pro Tyr Ile Lys Val Arg Ile
        195                 200                 205

Cys Phe Val Ala Gly Ala Thr Leu Leu Ile Ala Gly Thr Pro Gly Ile
    210                 215                 220

Ile Gly Ser Val Trp Tyr Ala Val Asp Val Tyr Val Glu Arg Ser Thr
225                 230                 235                 240

Leu Val Leu His Asn Ile Phe Leu Gly Ile Gln Tyr Lys Phe Gly Trp
                245                 250                 255

Ser Cys Trp Leu Gly Met Ala Gly Ser Leu Gly Cys Phe Leu Ala Gly
            260                 265                 270

Ala Val Leu Thr Cys Cys Leu Tyr Leu Phe Lys Asp Val Gly Pro Glu
        275                 280                 285

Lys Thr Ser Leu Ile Pro
    290
```

<210> SEQ ID NO 143
<211> LENGTH: 10
<212> TYPE: DNA
<213> ORGANISM: Homo sapiens

<400> SEQUENCE: 143
gtgggcacag                                                              10

<210> SEQ ID NO 144
<211> LENGTH: 1851
<212> TYPE: DNA
<213> ORGANISM: Homo sapiens

<400> SEQUENCE: 144
ggatatcgtc gacccagcgt ccggaccggg acagctcgcg gccccccgag agctctagcc        60
gtcgaggagc tgcctgggga cgtttccctg ggccccagcc tggcccgggt caccctggca       120
tgaggagatg ggcctgttgc tcctggtccc gttgctcctg ctgcccggct cctacggact       180
gcccttctac aacggcttct actactccaa cagcgccaac gaccagaacc taggcaacgg       240
tcatggcaaa gacctcctta atggagtgaa gctggtggtg gagacacccg aggagaccct       300
gttcacctac caaggggcca gtgtgatcct gccctgcgta ccgctacgag ccggccctgg       360
tctccccgcg gcgtgtgcgt gtcaaatggt ggaagctgtc ggagaacggg gccccagaga       420
aggacgtgct ggtggccatc gggctgaggc accgctcctt tgggactacc aaggccgcgt       480
gcactgcggc aggacaaaga gcatgagctc tcgctggaga tccagatctc gctgaggac       540
tatgggcctt accgctgtga ggtcattgac gggctggagg atgaaagcgg tctggtggag       600
ctggagctgc gggtgtggt cttcccttac cagtccccaa cgggcgctac cagttcaact       660
tccacgaggg ccagcaggtc tgtgcagagc aggctgcgt ggtggcctcc tttgagcagc       720
tcttccgggc tgggaggag ggcctggact ggtgcaacgc gggctggctg caggatgcca       780
cggtgcagta ccccatcatg ttgccccggc agccctgcgg tggcccgggc ctggcacctg       840
gcgtgcgaag ctacggcccc cgccaccgcc gcctgcaccg ctatgatgta ttctcgttcg       900
ctactgccct caaggggcgg gtgtactacc tggagcaccc tgagaacgtg acgctgacag       960
aggcaaggga ggcctgccag gaagatgatg ccacgattgc caaggtggac agctctttgc      1020
cgcctggaag ttccatggcc tggaccgctg cgacgctggc tggctggcag atggcagcgt      1080
ccgctaccct gtggttcacc cgcatcctaa ctgtgggccc ccagagcctg ggtccgaag      1140
ctttggcttc cccgacccgc agagccgctt gtacggtgtt tactgtaccg ccagcactag      1200
gacctggggc cctcccctgc cgcattccct cactggctgt gtatttattg agtggttcgt      1260
tttcccttgt gggttggagc cattttaact gtttttatac ttctcaattt aaattttctt      1320
taaacatttt tttactattt tttgtaaagc aaacagaacc caatgcctcc ctttgctcct      1380
ggatgcccca ctccaggaat catgcttgct ccccgggctt ctggagggtt ccccgccatc      1440
caggctggtc tccctccctt aaggaggttg gtgcccagag tgggcggtgg cctgtctaga      1500
atgccgccgg gagtccgggc atggtgggca cagttctccc tgccccctcag cctgggggaa      1560
gaagagggcc tcggggctc cggagctggg ctttgggcct ctcctgccca cctctacttc      1620
tctgtgaagc cgctgacccc agtctgccca ctgaggggct agggctggaa gccagttcta      1680
ggcttccagg cgaaagctga gggaaggaag aaactccctc cccgttcccc ttcccctctc      1740
ggttccaaag aatctgtttg ttgtcatttg tttctcctgt ttccctgtgt gggagggc        1800
cctcaggtgt gtgtactttg gacaataaat ggtgctatga ctgccttccg c                1851

<210> SEQ ID NO 145
<211> LENGTH: 10
<212> TYPE: DNA
<213> ORGANISM: Homo sapiens

<400> SEQUENCE: 145
cctgccccgc                                                              10

<210> SEQ ID NO 146
<211> LENGTH: 4111
<212> TYPE: DNA
<213> ORGANISM: Homo sapiens

<400> SEQUENCE: 146

| | | | | |
|---|---|---|---|---|
| ctcacagccc | agcacctgcg | gagggagcgc | tgaccatggc | tccctggcct gaattgggag | 60 |
| atgcccagcc | caaccccgat | aagtacctcg | aaggggccgc | aggtcagcag cccactgccc | 120 |
| ctgataaaag | caaagagacc | aacaaaaata | acactgaggc | acctgtaacc aagattgaac | 180 |
| ttctgccgtc | ctactccacg | gctacactga | tagatgagcc | cactgaggtg gatgacccct | 240 |
| ggaacctacc | cactcttcag | gactcgggga | tcaagtggtc | agagagagac accaaaggga | 300 |
| agattctctg | tttcttccaa | gggattggga | gattgatttt | acttctcgga tttctctact | 360 |
| ttttcgtgtg | ctccctggat | attcttagta | gcgccttcca | gctggttgga ggaaaaatgg | 420 |
| caggacagtt | cttcagcaac | agctctatta | tgtccaaccc | tttgttgggg ctggtgatcg | 480 |
| gggtgctggt | gaccgtcttg | gtgcagagct | ccagcacctc | aacgtccatc gttgtcagca | 540 |
| tggtgtcctc | ttcattgctc | actgttcggg | ctgccatccc | cattatcatg ggggccaaca | 600 |
| ttggaacgtc | aatcaccaac | actattgttg | cgctcatgca | ggtgggagat cggagtgagt | 660 |
| tcagaagagc | ttttgcagga | gccactgtcc | atgacttctt | caactggctg tccctgttgg | 720 |
| tgctcttgcc | cgtggaggtg | gccacccatt | acctcgagat | cataacccag cttatagtgg | 780 |
| agagcttcca | cttcaagaat | ggagaagatg | ccccagatct | tctgaaagtc atcactaagc | 840 |
| ccttcacaaa | gctcattgtc | cagctggata | aaaagttat | cagccaaatt gcaatgaacg | 900 |
| atgaaaaagc | gaaaaacaag | agtcttgtca | agatttggtg | caaaactttt accaacaaga | 960 |
| cccagattaa | cgtcactgtt | ccctcgactg | ctaactgcac | ctcccctccc tctgttgga | 1020 |
| cggatggcat | ccaaaactgg | accatgaaga | atgtgaccta | caaggagaac atcgccaaat | 1080 |
| gccagcatat | ctttgtgaat | ttccaccctcc | cggatcttgc | tgtgggcacc atcttgctca | 1140 |
| tactctccct | gctggtcctc | tgtggttgcc | tgatcatgat | tgtcaagatc ctgggctctg | 1200 |
| tgctcaaggg | gcaggtcgcc | actgtcatca | agaagaccat caacactgat | ttccccttc | 1260 |
| cctttgcatg | gttgactggc | tacctggcca | tcctcgtcgg | ggcaggcatg accttcatcg | 1320 |
| tacagagcag | ctctgtgttc | acgtcggcct | tgacccccct | gattggaatc ggcgtgataa | 1380 |
| ccattgagag | ggcttatcca | ctcacgctgg | ctccaacat | cggcaccacc accaccgcca | 1440 |
| tcctggccgc | cttagccagc | cctggcaatg | cattgaggag | ttcactccag atcgccctgt | 1500 |
| gccactttt | cttcaacatc | tccggcatct | tgctgtggta | cccgatcccg ttcactcgcc | 1560 |
| tgcccatccg | catggccaag | gggctgggca | acatctctgc | caagtatcgc tggttcgccg | 1620 |
| tcttctacct | gatcatcttc | ttcttcctga | tcccgctgac | ggtgtttggc ctctcgctgg | 1680 |
| ccggctggcg | ggtgctggtt | ggtgtcgggg | ttcccgtcgt | cttcatcatc atcctggtac | 1740 |
| tgtgcctccg | actcctgcag | tctcgctgcc | cacgcgtcct | gccgaagaaa ctccagaact | 1800 |
| ggaacttcct | gccgctgtgg | atgcgctcgc | tgaagccctg ggatgccgtc gtctccaagt | 1860 |

-continued

```
tcaccggctg cttccagatg cgctgctgct gctgctgccg cgtgtgctgc cgcgcgtgct    1920
gcttgctgtg tggctgcccc aagtgctgcc gctgcagcaa gtgctgcgag gacttggagg    1980
aggcgcagga ggggcaggat gtccctgtca aggctcctga gcctttgat aacataacca     2040
ttagcagaga ggctcagggt gaggtccctg cctcggactc aaagaccgaa tgcacggcct    2100
tgtaggggac gccccagatt gtcagggatg ggggatggt ccttgagttt tgcatgctct     2160
cctccctccc acttctgcac cctttcacca cctcgaggag atttgctccc cattagcgaa    2220
tgaaattgat gcagtcctac ctaactcgat tcccttggc ttggtgggta ggcctgcagg     2280
gcacttttat tccaacccct ggtcactcag taatctttta ctccaggaag gcacaggatg    2340
gtacctaaag agaattagag aatgaacctg gcgggacgga tgtctaatcc tgcacctagc    2400
tgggttggtc agtagaacct attttcagac tcaaaaacca tcttcagaaa gaaaaggccc    2460
agggaaggaa tgtatgagag gctctcccag atgaggaagt gtactctcta tgactatcaa    2520
gctcaggcct ctccctttt ttaaaccaaa gtctggcaac caagagcagc agctccatgg     2580
cctccttgcc ccagatcagc ctgggtcagg ggacatagtg tcattgtttg gaaactgcag    2640
accacaaggt gtgggtctat cccacttcct agtgctcccc acattcccca tcagggcttc    2700
ctcacgtgga caggtgtgct agtccaggca gttcacttgc agtttccttg tcctcatgct    2760
tcggggatgg gagccacgcc tgaactagag ttcaggctgg atacatgtgc tcacctgctg    2820
ctcttgtctt cctaagagac agagagtggg gcagatggag gagaagaaag tgaggaatga    2880
gtagcatagc attctgccaa aagggcccca gattcttaat ttagcaaact aagaagccca    2940
attcaaaagc attgtggcta aagtctaacg ctcctctctt ggtcagataa caaaagccct    3000
ccctgttgga tcttttgaaa taaaacgtgc aagttatcca ggctcgtagc ctgcatgctg    3060
ccaccttgaa tcccagggag tatctgcacc tggaatagct ctccacccct ctctgcctcc    3120
ttactttctg tgcaagatga tttcctgggt taacttcctt ctttccatcc acccaccac     3180
tggaatctct ttccaaacat ttttccattt tcccacagat gggctttgat tagctgtcct    3240
ctctccatgc ctgcaaagct ccagattttt ggggaaagct gtacccaact ggactgccca    3300
gtgaactggg atcattgagt acagtcgagc acacgtgtgt gcatgggtca aagggggtgtg   3360
ttccttctca tcctagatgc cttctctgtg ccttccacag cctcctgcct gattacacca    3420
ctgcccccgc cccacccctca gccatcccaa ttcttcctgg ccagtgcgct ccagccttat   3480
ctaggaaagg aggagtgggt gtagccgtgc agcaagattg gggcctcccc catcccagct    3540
tctccaccat cccagcaagt caggatatca gacagtcctc ccctgaccct ccccttgta     3600
gatatcaatt cccaaacaga gccaaatact ctatatctat agtcacagcc ctgtacagca    3660
ttttcataa gttatatagt aaatggtctg catgatttgt gcttctagtg ctctcatttg     3720
gaaatgaggc aggcttcttc tatgaaatgt aaagaaagaa accactttgt atattttgta    3780
ataccacctc tgtggccatg cctgccccgc ccactctgta tatatgtaag ttaaacccgg    3840
gcagggctg tggccgtctt tgtactctgg tgattttta aaattgaatc tttgtacttg      3900
cattgattgt ataataattt tgagaccagg tctcgctgtg ttgctcaggc tggtctcaaa    3960
ctcctgagat caagcaatcc gcccacctca gcctcccaaa gtgctgagat cacaggcgtg    4020
agccaccacc aggcctgatt gtaattttt ttttttttt tactggttat gggaagggag      4080
aaataaaatc atcaaacccc aaaaaaaaa a                                    4111
```

<210> SEQ ID NO 147

-continued

```
<211> LENGTH: 689
<212> TYPE: PRT
<213> ORGANISM: Homo sapiens

<400> SEQUENCE: 147

Met Ala Pro Trp Pro Glu Leu Gly Asp Ala Gln Pro Asn Pro Asp Lys
 1               5                  10                  15

Tyr Leu Glu Gly Ala Ala Gly Gln Gln Pro Thr Ala Pro Asp Lys Ser
             20                  25                  30

Lys Glu Thr Asn Lys Asn Asn Thr Glu Ala Pro Val Thr Lys Ile Glu
         35                  40                  45

Leu Leu Pro Ser Tyr Ser Thr Ala Thr Leu Ile Asp Glu Pro Thr Glu
     50                  55                  60

Val Asp Asp Pro Trp Asn Leu Pro Thr Leu Gln Asp Ser Gly Ile Lys
 65                  70                  75                  80

Trp Ser Glu Arg Asp Thr Lys Gly Lys Ile Leu Cys Phe Phe Gln Gly
                 85                  90                  95

Ile Gly Arg Leu Ile Leu Leu Leu Gly Phe Leu Tyr Phe Val Cys
            100                 105                 110

Ser Leu Asp Ile Leu Ser Ser Ala Phe Gln Leu Val Gly Gly Lys Met
        115                 120                 125

Ala Gly Gln Phe Phe Ser Asn Ser Ser Ile Met Ser Asn Pro Leu Leu
    130                 135                 140

Gly Leu Val Ile Gly Val Leu Val Thr Val Leu Val Gln Ser Ser Ser
145                 150                 155                 160

Thr Ser Thr Ser Ile Val Val Ser Met Val Ser Ser Leu Leu Thr
                165                 170                 175

Val Arg Ala Ala Ile Pro Ile Ile Met Gly Ala Asn Ile Gly Thr Ser
            180                 185                 190

Ile Thr Asn Thr Ile Val Ala Leu Met Gln Val Gly Asp Arg Ser Glu
        195                 200                 205

Phe Arg Arg Ala Phe Ala Gly Ala Thr Val His Asp Phe Asn Trp
    210                 215                 220

Leu Ser Leu Leu Val Leu Leu Pro Val Glu Val Ala Thr His Tyr Leu
225                 230                 235                 240

Glu Ile Ile Thr Gln Leu Ile Val Glu Ser Phe His Phe Lys Asn Gly
                245                 250                 255

Glu Asp Ala Pro Asp Leu Leu Lys Val Ile Thr Lys Pro Phe Thr Lys
            260                 265                 270

Leu Ile Val Gln Leu Asp Lys Lys Val Ile Ser Gln Ile Ala Met Asn
        275                 280                 285

Asp Glu Lys Ala Lys Asn Lys Ser Leu Val Lys Ile Trp Cys Lys Thr
    290                 295                 300

Phe Thr Asn Lys Thr Gln Ile Asn Val Thr Val Pro Ser Thr Ala Asn
305                 310                 315                 320

Cys Thr Ser Pro Ser Leu Cys Trp Thr Asp Gly Ile Gln Asn Trp Thr
                325                 330                 335

Met Lys Asn Val Thr Tyr Lys Glu Asn Ile Ala Lys Cys Gln His Ile
            340                 345                 350

Phe Val Asn Phe His Leu Pro Asp Leu Ala Val Gly Thr Ile Leu Leu
        355                 360                 365

Ile Leu Ser Leu Leu Val Leu Cys Gly Cys Leu Ile Met Ile Val Lys
    370                 375                 380

Ile Leu Gly Ser Val Leu Lys Gly Gln Val Ala Thr Val Ile Lys Lys
```

-continued

```
385                 390                 395                 400
Thr Ile Asn Thr Asp Phe Pro Phe Pro Phe Ala Trp Leu Thr Gly Tyr
                405                 410                 415

Leu Ala Ile Leu Val Gly Ala Gly Met Thr Phe Ile Val Gln Ser Ser
                420                 425                 430

Ser Val Phe Thr Ser Ala Leu Thr Pro Leu Ile Gly Ile Gly Val Ile
                435                 440                 445

Thr Ile Glu Arg Ala Tyr Pro Leu Thr Leu Gly Ser Asn Ile Gly Thr
                450                 455                 460

Thr Thr Thr Ala Ile Leu Ala Ala Leu Ala Ser Pro Gly Asn Ala Leu
465                 470                 475                 480

Arg Ser Ser Leu Gln Ile Ala Leu Cys His Phe Phe Asn Ile Ser
                485                 490                 495

Gly Ile Leu Leu Trp Tyr Pro Ile Pro Phe Thr Arg Leu Pro Ile Arg
                500                 505                 510

Met Ala Lys Gly Leu Gly Asn Ile Ser Ala Lys Tyr Arg Trp Phe Ala
                515                 520                 525

Val Phe Tyr Leu Ile Ile Phe Phe Phe Leu Ile Pro Leu Thr Val Phe
                530                 535                 540

Gly Leu Ser Leu Ala Gly Trp Arg Val Leu Val Gly Val Gly Val Pro
545                 550                 555                 560

Val Val Phe Ile Ile Ile Leu Val Leu Cys Leu Arg Leu Leu Gln Ser
                565                 570                 575

Arg Cys Pro Arg Val Leu Pro Lys Lys Leu Gln Asn Trp Asn Phe Leu
                580                 585                 590

Pro Leu Trp Met Arg Ser Leu Lys Pro Trp Asp Ala Val Val Ser Lys
                595                 600                 605

Phe Thr Gly Cys Phe Gln Met Arg Cys Cys Cys Cys Arg Val Cys
                610             615                 620

Cys Arg Ala Cys Cys Leu Leu Cys Gly Cys Pro Lys Cys Cys Arg Cys
625                 630                 635                 640

Ser Lys Cys Cys Glu Asp Leu Glu Glu Ala Gln Glu Gly Gln Asp Val
                645                 650                 655

Pro Val Lys Ala Pro Glu Thr Phe Asp Asn Ile Thr Ile Ser Arg Glu
                660                 665                 670

Ala Gln Gly Glu Val Pro Ala Ser Asp Ser Lys Thr Glu Cys Thr Ala
                675                 680                 685

Leu
```